(12) United States Patent
Babaoglu et al.

(10) Patent No.: US 9,376,392 B2
(45) Date of Patent: *Jun. 28, 2016

(54) 2-(TERT-BUTOXY)-2-(7-METHYLQUINOLIN-6-YL) ACETIC ACID DERIVATIVES FOR TREATING AIDS

(71) Applicant: Gilead Sciences, Inc., Foster City, CA (US)

(72) Inventors: Kerim Babaoglu, Lansdale, PA (US); Kyla L. Bjornson, San Lorenzo, CA (US); Paul Hrvatin, Davis, CA (US); Eric Lansdon, San Jose, CA (US); John O. Link, San Francisco, CA (US); Hongtao Liu, Cupertino, CA (US); Ryan McFadden, Foster City, CA (US); Michael L. Mitchell, Castro Valley, CA (US); Yingmei Qi, Foster City, CA (US); Paul A. Roethle, San Francisco, CA (US); Lianhong Xu, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/370,464

(22) PCT Filed: Jan. 3, 2013

(86) PCT No.: PCT/US2013/020151
§ 371 (c)(1),
(2) Date: Jul. 2, 2014

(87) PCT Pub. No.: WO2013/103724
PCT Pub. Date: Jul. 11, 2013

(65) Prior Publication Data
US 2015/0045374 A1    Feb. 12, 2015

Related U.S. Application Data

(60) Provisional application No. 61/583,122, filed on Jan. 4, 2012.

(51) Int. Cl.
| | | |
|---|---|---|
| C07D 215/227 | (2006.01) |
| A61K 31/4704 | (2006.01) |
| C07D 519/00 | (2006.01) |
| A61K 31/4745 | (2006.01) |
| C07D 491/06 | (2006.01) |
| A61K 45/06 | (2006.01) |
| A61K 31/4741 | (2006.01) |
| A61K 31/497 | (2006.01) |
| A61K 31/506 | (2006.01) |

(52) U.S. Cl.
CPC ........ *C07D 215/227* (2013.01); *A61K 31/4704* (2013.01); *A61K 31/4741* (2013.01); *A61K 31/4745* (2013.01); *A61K 31/497* (2013.01); *A61K 31/506* (2013.01); *A61K 45/06* (2013.01); *C07D 491/06* (2013.01); *C07D 519/00* (2013.01)

(58) Field of Classification Search
CPC ... C07D 215/227; C07D 491/06; A61K 45/06
USPC .................................. 546/82, 89; 514/255.05
See application file for complete search history.

(56) References Cited

U.S. PATENT DOCUMENTS

| | | |
|---|---|---|
| 3,895,028 A | 7/1975 | Wada et al. |
| 3,900,486 A | 8/1975 | Suzuki et al. |
| 4,816,570 A | 3/1989 | Farquhar |
| 4,968,788 A | 11/1990 | Farquhar |
| 5,434,188 A | 7/1995 | Boschelli et al. |
| 5,663,159 A | 9/1997 | Starrett, Jr. et al. |
| 5,733,906 A | 3/1998 | Jungheim et al. |
| 5,738,985 A | 4/1998 | Miles et al. |
| 5,792,756 A | 8/1998 | Starrett, Jr. et al. |
| 5,798,365 A | 8/1998 | Kirsch et al. |
| 7,514,233 B2 | 4/2009 | Debyser et al. |
| 8,008,470 B2 | 8/2011 | Debyser et al. |
| 2005/0165052 A1 | 7/2005 | Fakhfakh et al. |
| 2005/0239819 A1 | 10/2005 | Satoh et al. |
| 2005/0261336 A1 | 11/2005 | Mousnier et al. |
| 2006/0035926 A1 | 2/2006 | Lee et al. |
| 2006/0094755 A1 | 5/2006 | Rajagopalan et al. |
| 2006/0275748 A1 | 12/2006 | Debyser et al. |
| 2009/0197862 A1 | 8/2009 | Steinig et al. |
| 2009/0203742 A1 | 8/2009 | Surleraux et al. |
| 2010/0311735 A1 | 12/2010 | Tsantrizos et al. |
| 2011/0223131 A1 | 9/2011 | Jin et al. |

(Continued)

FOREIGN PATENT DOCUMENTS

| | | | |
|---|---|---|---|
| CA | 1144556 A1 | 4/1983 |
| CN | 1123275 A | 5/1996 |

(Continued)

OTHER PUBLICATIONS

Al-Mawsawi, L.Q. et al. (Feb. 7, 2011; e-pub. Jan. 12, 2011). "Allosteric inhibitor development targeting HIV-1 integrase," *ChemMedChem.* 6(2):228-241.

(Continued)

*Primary Examiner* — Rita Desai

(57) ABSTRACT

The invention provides compounds and salts thereof as d herein. The invention also provides pharmaceutical compositions comprising a compound disclosed herein, processes for preparing compounds disclosed herein, intermediates useful for preparing compounds disclosed herein and therapeutic methods for treating an HIV infection, treating the proliferation of the HIV virus, treating AIDS or delaying the onset of AIDS or ARC symptoms in a mammal using compounds disclosed herein.

6 Claims, No Drawings

(56) References Cited

U.S. PATENT DOCUMENTS

| | | |
|---|---|---|
| 2012/0329780 A1 | 12/2012 | Thormann et al. |
| 2012/0329785 A1 | 12/2012 | Thormann et al. |
| 2013/0203727 A1 | 8/2013 | Babaoglu et al. |
| 2013/0210801 A1 | 8/2013 | Babaoglu et al. |
| 2013/0231331 A1 | 9/2013 | Pendri et al. |
| 2013/0281433 A1 | 10/2013 | Babaoglu et al. |
| 2013/0281434 A1 | 10/2013 | Babaoglu et al. |
| 2014/0031338 A1 | 1/2014 | Chasset et al. |
| 2014/0045818 A1 | 2/2014 | Mitchell et al. |
| 2014/0120087 A1 | 5/2014 | Schulze et al. |

FOREIGN PATENT DOCUMENTS

| | | |
|---|---|---|
| CN | 1044117 C | 7/1999 |
| CN | 1466576 A | 1/2004 |
| DE | 24 03 682 A1 | 7/1974 |
| EP | 0 017 543 A1 | 10/1980 |
| EP | 1 441 228 A1 | 7/2004 |
| EP | 1 541 558 A1 | 6/2005 |
| EP | 1 565 471 B1 | 10/2006 |
| EP | 1 873 238 A1 | 1/2008 |
| EP | 1 873 238 B1 | 1/2008 |
| GB | 2 154 583 A | 9/1985 |
| JP | 3-287558 A | 12/1991 |
| WO | WO-91/19721 A1 | 12/1991 |
| WO | WO-94/23041 A2 | 10/1994 |
| WO | WO-94/23041 A3 | 10/1994 |
| WO | WO-99/52850 A1 | 10/1999 |
| WO | WO-00/63152 A1 | 10/2000 |
| WO | WO-02/18341 A2 | 3/2002 |
| WO | WO-02/18341 A3 | 3/2002 |
| WO | WO-2004/014371 A1 | 2/2004 |
| WO | WO-2004/046115 A1 | 6/2004 |
| WO | WO-2004/087153 A2 | 10/2004 |
| WO | WO-2004/087153 A3 | 10/2004 |
| WO | WO-2005/120508 A1 | 12/2005 |
| WO | WO-2006/001958 A2 | 1/2006 |
| WO | WO-2006/001958 A3 | 1/2006 |
| WO | WO-2006/002185 A1 | 1/2006 |
| WO | WO-2006/116412 A2 | 11/2006 |
| WO | WO-2006/116412 A3 | 11/2006 |
| WO | WO-2006/124780 A2 | 11/2006 |
| WO | WO-2006/124780 A3 | 11/2006 |
| WO | WO-2007/016392 A2 | 2/2007 |
| WO | WO-2007/016392 A3 | 2/2007 |
| WO | WO-2007/131350 A1 | 11/2007 |
| WO | WO-2007/138472 A2 | 12/2007 |
| WO | WO-2007/138472 A3 | 12/2007 |
| WO | WO-2007/147884 A1 | 12/2007 |
| WO | WO-2008/053478 A2 | 5/2008 |
| WO | WO-2008/053478 A3 | 5/2008 |
| WO | WO-2008/071587 A2 | 6/2008 |
| WO | WO-2008/071587 A3 | 6/2008 |
| WO | WO-2009/062285 A1 | 5/2009 |
| WO | WO-2009/062288 A1 | 5/2009 |
| WO | WO-2009/062289 A1 | 5/2009 |
| WO | WO-2009/062308 A1 | 5/2009 |
| WO | WO-2009/095500 A1 | 8/2009 |
| WO | WO-2010/059658 A1 | 5/2010 |
| WO | WO-2010/130034 A1 | 11/2010 |
| WO | WO-2010/130842 A1 | 11/2010 |
| WO | WO-2011/002635 A1 | 1/2011 |
| WO | WO-2011/015641 A1 | 2/2011 |
| WO | WO-2011/047129 A1 | 4/2011 |
| WO | WO-2011/076765 A1 | 6/2011 |
| WO | WO-2011/106445 A1 | 9/2011 |
| WO | WO-2011/149950 A2 | 12/2011 |
| WO | WO-2011/149950 A3 | 12/2011 |
| WO | WO-2012/003497 A1 | 1/2012 |
| WO | WO-2012/003498 A1 | 1/2012 |
| WO | WO-2012/033735 A1 | 3/2012 |
| WO | WO-2012/065963 A2 | 5/2012 |
| WO | WO-2012/065963 A3 | 5/2012 |
| WO | WO-2012/066442 A1 | 5/2012 |
| WO | WO-2012/088365 A1 | 6/2012 |
| WO | WO-2012/102985 A1 | 8/2012 |
| WO | WO-2012/137181 A1 | 10/2012 |
| WO | WO-2012/138669 A1 | 10/2012 |
| WO | WO-2012/138670 A1 | 10/2012 |
| WO | WO-2012/140243 A1 | 10/2012 |
| WO | WO-2012/145728 A1 | 10/2012 |
| WO | WO-2013/002357 A1 | 1/2013 |
| WO | WO-2013/025584 A1 | 2/2013 |
| WO | WO-2013/043553 A1 | 3/2013 |
| WO | WO-2013/058448 A1 | 4/2013 |
| WO | WO-2013/062028 A1 | 5/2013 |
| WO | WO-2013/103738 A1 | 7/2013 |
| WO | WO-2013/106643 A2 | 7/2013 |
| WO | WO-2013/106643 A3 | 7/2013 |
| WO | WO-2013/123148 A1 | 8/2013 |
| WO | WO-2013/134113 A1 | 9/2013 |
| WO | WO-2013/134142 A1 | 9/2013 |
| WO | WO-2013/157622 A1 | 10/2013 |
| WO | WO-2013/159064 A1 | 10/2013 |
| WO | WO-2014/009794 A1 | 1/2014 |
| WO | WO-2014/028384 A1 | 2/2014 |
| WO | WO-2014/055603 A1 | 4/2014 |
| WO | WO-2014/055618 A1 | 4/2014 |

OTHER PUBLICATIONS

Balakrishnan, M. et al. (Sep. 9, 2013). "Non-catalytic site HIV-1 integrase inhibitors disrupt core maturation and induce a reverse transcription block in target cells," *PloS One* 8(9):e74163, Twelve Total Pages.

Bartholomeeusen, K. et al. (Apr. 24, 2009; e-pub. Feb. 25, 2009). "Lens epithelium-derived growth factor/p75 interacts with the transposase-derived DDE domain of PogZ," *J. Biol. Chem.* 284(17):11467-11477.

Benzaria, S. et al. (Dec. 6, 1996). "Synthesis, In Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," *J. Med. Chem.* 39(25):4958-4965.

Bundgaard, H. (1991). "Design and Application of Prodrugs," Chapter 5 *in A Textbook of Drug Design and Development*, Krogsgaard-Larsen, P. et al. eds., Harwood Academic Publishers, Chur, Switzerland, pp. 113-191.

Busschots, K. et al. (Feb. 2, 2007; e-pub. Nov. 3, 2006). "Identification of the LEDGF/p75 binding site in HIV-1 integrase," *J. Mol. Biol.* 365(5):1480-1492.

Busschots, K. et al. (Jan. 2009; e-pub. Oct. 16, 2008). "In search of small molecules blocking interactions between HIV proteins and intracellular cofactors," *Mol. Biosyst.* 5(1):21-31.

Chakraborty, A. et al. (Mar. 1, 2013; e-pub. Dec. 25, 2012). "Biochemical interactions between HIV-1 integrase and reverse transcriptase," *FEBS Letters* 587(5):425-429.

Chen, S. et al. (2009, e-pub. Jan. 23, 2009). "Design, Synthesis, and Biological Evaluation of Novel Quinoline Derivatives as HIV-1 Tat-TAR Interaction Inhibitors," *Bioorganic & Medicinal Chem.* 17:1948-1956.

Cherepanov, P. et al. (Jun. 2005; e-pub. May 15, 2005). "Solution structure of the HIV-1 integrase-binding domain in LEDGF/p75," *Nat. Struct. Mol. Biol.* 12(6):526-532.

Cherepanov, P. et al. (Nov. 29, 2005; e-pub. Oct. 31, 2005). "Structural basis for the recognition between HIV-1 integrase and transcriptional coactivator p75," *PNAS* 102(48):17308-17313.

Christ, F. et al. (Aug. 2012; e-pub. Jun. 4, 2012). "Small-molecule inhibitors of the LEDGF/p75 binding site of integrase block HIV replication and modulate integrase multimerization," *Antimicrob. Agents Chemother.* 56(8):4365-4374.

Christ, F. et al. (Jun. 2010; e-pub. May 16, 2010). "Rational design of small-molecule inhibitors of the LEDGF/p75-integrase interaction and HIV replication," *Nat. Chem. Biol.*, Twenty-Five Total Pages.

De Lombaert, S. et al. (Feb. 18, 1994). "N-Phosphonomethyl Dipeptides and Their Phosphonate Prodrugs, a New Generation of Neutral Endopeptidase (NEP, EC 3.4.24.11) Inhibitors," *J. Med. Chem.* 37(4):498-511.

(56) References Cited

OTHER PUBLICATIONS

De Luca, L. et al. (Feb. 2011; e-pub. Dec. 21, 2010). "HIV-1 integrase strand-transfer inhibitors: design, synthesis and molecular modeling investigation," *Eur. J. Med. Chem.* 46(2):756-764.

De Luca, L. et al. (Jul. 2011). "Inhibition of the interaction between HIV-1 integrase and its cofactor LEDGF/p75: a promising approach in anti-retroviral therapy," *Mini Rev. Med. Chem.* vol. 11, Fourteen Total Pages.

Desimmie, B.A. et al. (May 30, 2013). "LEDGINs inhibit late stage HIV-1 replication by modulating integrase multimerization in the virions," *Retrovirology* 10:57, Sixteen Total Pages.

Engelman, A. et al. (Mar. 28, 2008). "The lentiviral integrase binding protein LEDGF/p75 and HIV-1 replication," *PloS Pathog.* 4(3):e1000046, Nine Total Pages.

Farquhar, D. et al. (Mar. 1983). "Biologically Reversible Phosphate-Protective Groups," *J. Pharm. Sci.* 72(3):324-325.

Graham, R.L.J. et al. (2011). "Proteomic Analysis of LEDGF/p75 Interactions with Nuclear Proteins," ASMS Poster, one page.

Hauser, F.M. et al. (1978). "New Synthetic Methods for the Regioselective Annelation of Aromatic Rings: 1-Hydroxy-2,3-Disubstituted Naphthalenes and 1,4-Dihydroxy-2,3-Disubstituted Naphthalenes," *J. Org. Chem.* 43(1):178-180.

Hayouka, Z. et al. (2010). "Cyclic Peptide Inhibitors of HIV-1 Integrase Derived from the LEDGF/p75 Protein," *Bioorganic & Medicinal Chemistry* 18:8388-8395.

Hombrouck, A. et al. (Mar. 2007). "Virus Evolution Reveals an Exclusive Role for LEDGF/p75 in Chromosomal Tethering," *PloS* 3(3):e47, Thirteen Total Pages.

Huang, X. et al. (2007). "A Novel Multicomponent Reaction of Arynes, β-Keto Sulfones, and Michael-Type Acceptors: A Direct Synthesis of Polysubstituted Naphthols and Naphthalenes," *J. Org. Chem.* 72:3965-3968.

Johns, B.A. et al. (2013). "HIV Integrase Inhibitors," Chapter 6 *in Successful Strategies for the Discovery of Antiviral Drugs*, Desai, M.C. et al. eds., RSC Publishing, pp. 149-188.

Jurado, K.A. et al. (2013). "Allosteric Integrase Inhibitor Potency is Determined through the Inhibition of HIV-1 Particle Maturation," *PNAS* 110(21):8690-8695.

Kessl, J.J. et al. (2011). "Fret Analysis Reveals Distinct Conformations of IN Tetramers in the Presence of Viral DNA or LEDGF/p75," *Nuc. Acids Res.*, pp. 1-14.

Khamnei, S. et al. (Sep. 27, 1996). "Neighboring Group Catalysis in the Design of Nucleotide Prodrugs," *J. Med. Chem.* 39(20):4109-4115.

Kocienski, P.J. (May 1994). "Protecting Groups: An Overview," Chapter 1 *in Protecting Groups*, Thieme Publishing Group: New York, NY, pp. 1-20.

Kocienski, P.J. (May 1994). "Hydroxyl Protecting Groups," Chapter 2 *in Protecting Groups*, Thieme Publishing Group: New York, NY, pp. 21-94.

Kocienski, P.J. (May 1994). "Diol Protecting Groups," Chapter 3 *in Protecting Groups*, Thieme Publishing Group: New York, NY, pp. 95-117.

Kocienski, P.J. (May 1994). "Carboxyl Protecting Groups," Chapter 4 *in Protecting Groups*, Thieme Publishing Group: New York, NY, pp. 118-154.

Kocienski, P.J. (May 1994). "Carbonyl Protecting Groups," Chapter 5 *in Protecting Groups*, Thieme Publishing Group: New York, NY, pp. 155-184.

Llano, M. et al. (Sep. 2004). "LEDGF/p75 determines cellular trafficking of diverse lentiviral but not murine oncoretroviral integrase proteins and is a component of functional lentiviral preintegration complexes," *J. Virol.* 78(17):9524-9537.

Llano, M. et al. (Oct. 20, 2006; e-pub. Sep. 7, 2006). "An essential role for LEDGF/p75 in HIV integration," *Science* 314(5798):461-464.

McGinnity, D.F. et al. (Nov. 2004, e-pub. Jul. 30, 2004). "Evaluation of Fresh and Cryopreserved Hepatocytes as in Vitro Drug Metabolism Tools for the Prediction of Metabolic Clearance," *Drug Metab. Dispos.* 32(11):1247-1253.

Mekouar, K. et al. (Jul. 16, 1998; e-pub. Jun. 25, 1998). "Styrylquinoline Derivatives: A New Class of Potent HIV-1 Integrase Inhibitors That Block HIV-1 Replication in CEM Cells," *J. Med. Chem.* 41(15):2846-2857.

Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," *J. Chem. Soc. Perkin Trans. 1* 2345-2353.

Obach, R.S. et al. (Oct. 1997). "The Prediction of Human Pharmacokinetic Parameters from Preclinical and in Vitro Metabolism Data," *J. Pharmacol. Exp. Ther.* 283(1):46-58.

Palella, F.J. et al. (Mar. 26, 1998). "Declining Morbidity and Mortality Among Patients with Advanced Human Immunodeficiency Virus Infection," *N. Engl. J. Med.* 338(13):853-860.

Pauwels, R. et al. (Jun. 1987). "Sensitive and Rapid Assay on MT-4 Cells for Detection of Antiviral Compounds Against the AIDS Virus," *J. Virol. Methods* 16(3):171-185.

Pendri, A. et al. (Aug. 2011, e-pub. May 20, 2011). "New First and Second Generation Inhibitors of Human Immunodeficiency Virus-1 Integrase," *Expert Opin. Ther. Pat.* 21(8):1173-1189.

Poeschla, E.M. et al. (2008). "Integrase, LEDGF/p75 and HIV Replication," *Cell. Mol. Life Sci.* 65:1403-1424.

Porto, S. et al. (2007). "Chiral Thiols: The Assignment of Their Absolute Configuration by $^1$H NMR," *Organic Letters* 9(24):5015-5018.

Puech, F. et al. (Oct. 1993). "Intracellular Delivery of Nucleoside Monophosphates Through a Reductase-Mediated Activation Process," *Antiviral Res.* 22(2-3):155-174.

Rain, J.C. et al. (2009). "Yeast-Two Hybrid Detection of Integrase-Host Factor Interactions," *Methods*, Seven Total Pages.

Rhodes, D.I. et al. (Oct. 17, 2011; e-pub. Aug. 17, 2011). "Crystal structures of novel allosteric peptide inhibitors of HIV integrase identify new interactions at the LEDGF binding site," *Chembiochem.* 12(15):2311-2315.

Richman, D.D. (Apr. 19, 2001). "HIV Chemotherapy," *Nature* 410:995-1001.

Sagar, K.S. et al. (Aug. 1, 2004, e-pub. Jun. 19, 2004). "Preparation and Anti-HIV Activities of Retrojusticidin B Analogs and Azalignans," *Bioorg. Med. Chem.* 12(15):4045-4054.

Shun, M.C. et al. (Jul. 15, 2007). "LEDGF/p75 functions downstream from preintegration complex formation to effect gene-specific HIV-1 integration," *Genes Dev.* 21(14):1767-1778.

Spivey, A.C. et al. (1999, e-pub. Dec. 4, 1999). "Configurationally Stable Biaryl Analogues of 4-(Dimethylamino) Pyridine: A Novel Class of Chiral Nucleophilic Catalysts," *J. Org. Chem.* 64(26):9430-9443.

Suzuki, Y. et al. (Mar. 2007). "The road to chromatin—nuclear entry of retroviruses," *Nat. Rev. Microbiol.* 5(3):187-196.

Tsiang, M. et al. (Jun. 15, 2012; e-pub. Apr. 25, 2012). "New class of HIV-1 integrase (IN) inhibitors with a dual mode of action," *J. Biol. Chem.* 287(25):21189-21203.

Vandekerckhove, L. et al. (Feb. 2006). "Transient and stable knockdown of the integrase cofactor LEDGF/p75 reveals its role in the replication cycle of human immunodeficiency virus," *J. Virol.* 80(4):1886-1896.

Walker, M.A. (2009). "New approaches for inhibiting HIV integrase: a journey beyond the active site," *Curr. Opin. Investig. Drugs* 10(2):129-136.

Wang, C.Y. et al. (Dec. 2004). "Pharmacokinetic and Metabolic Studies of Retrojusticidin B, A Potential Anti-Viral Lignan, in Rats," *Planta Medica* 70(12):1161-1165.

Wenhua, Z. et al. (2003). "Advances on Effects of Natural Products Against AIDS Virus," *Chinese Traditional Patent Medicine* 25(9):750-752 (with English Translation).

Willgerodt, C. et al. (1900). "Regarding Quino-α:p-α-Phenyl and Quino-α:p-α Methyl Quinoline-γ-Hydroxy Acid," *Reports of the German Chemical Society* 33(3):2927-2935 (with full English Translation).

Zhan, P. et al. (2009). "Synthesis and Anti-HIV Activity Evaluation of 2-(4-(Naphthalen-yl)-1,2,3-thiadiazol-5-ylthio)-*N*-Acetamides as Novel Non-Nucleoside HIV-1 Reverse Transcriptase Inhibitors," *European Journal of Medicinal Chem.* 44:4648-4653.

(56) References Cited

OTHER PUBLICATIONS

Zouhiri, F. et al. (2001). "HIV-1 Replication Inhibitors of the Styrylquinoline Class: Incorporation of a Masked Diketo Acid Pharmacophore," *Tetrahedron Letters* 42:8189-8192.
Restriction Requirement mailed on Nov. 8, 2013 for U.S. Appl. No. 13/866,997, filed Apr. 19, 2013, eight pages.
Restriction Requirement mailed on Apr. 24, 2014, for U.S. Appl. No. 14/112,473, filed Oct. 17, 2013, eight pages.
Non-Final Office Action mailed on May 23, 2014, for U.S. Appl. No. 13/866,997, filed Apr. 19, 2013, eight pages.
Non-Final Office Action mailed on Nov. 4, 2014, for U.S. Appl. No. 13/867,016, filed Apr. 19, 2013, seven pages.
Notice of Allowance mailed on Aug. 15, 2014, for U.S. Appl. No. 14/112,473, filed Oct. 17, 2013, seven pages.
Notice of Allowance mailed on Nov. 7, 2014, for U.S. Appl. No. 13/866,997, filed Apr. 19, 2013, eight pages.
Australian Office Action mailed on Feb. 26, 2014, for Australian Patent Application No. 2011274323, filed on Jul. 1, 2011, three pages.
Australian Office Action mailed on Mar. 7, 2014, for Australian Patent Application No. 2011274322 filed on Jul. 1, 2011, three pages.
Bolivian Opposition submitted to the Bolivian Patent Office for Bolivian Patent Application No. SP-0194-2011, filed on Jul. 1, 2011, two pages.
Chinese Office Action mailed on Mar. 3, 2014, for Chinese Patent Application No. 201180038442.X filed on Jul. 1, 2011, eight pages.
Chinese Office Action mailed on Mar. 25, 2014 for Chinese Patent Application No. 201180038443.4, filed on Jul. 1, 2011, eight pages.
Costa Rican Opposition filed Apr. 28, 2014 against Costa Rican Patent Application No. 201320102, filed Jul. 1, 2011, sixteen pages.
Bolivian Opposition submitted to the Bolivian Patent Office for Bolivian Patent Application No. SP-0195-2011, filed on Jul. 1, 2011, two pages.
Columbian Office Action mailed on Feb. 20, 2014, for Columbian Patent Application No. 12236161 filed on Jul. 1, 2011, ten pages.
Columbian Office Action mailed on Jun. 12, 2014 for Columbian Patent Application No. 12236158, filed on Jul. 1, 2011, twelve pages.
Columbian Office Action mailed on Oct. 17, 2014 for Columbian Patent Application No. 12236158, filed on Jul. 1, 2011, thirteen pages.
Costa Rican Office Action mailed on Aug. 23, 2013 for Costa Rican Patent Application No. 20130045, filed on Jul. 1, 2011, three pages.
Costa Rican Opposition submitted to the Costa Rican Patent Office for Costa Rican Patent Application No. 20130043, filed on Jul. 1, 2011, three pages.
Eurasian Office Action mailed on Mar. 19, 2014, for Eurasian Patent Application No. 201291300 filed on Jul. 1, 2011, four pages.
Eurasian Office Action mailed in Apr. 9, 2014, for Eurasian Patent Application No. 201291301, filed on Jul. 1, 2011, three pages.
International Search Report mailed on Feb. 21, 2013, for PCT Patent Application No. PCT/US2013/020172 filed on Jan. 3, 2013, four pages.
International Search Report mailed on Sep. 1, 2011, for PCT Patent Application No. PCT/US2011/042880 filed on Jul. 1, 2011, four pages.
International Search Report mailed on Sep. 14, 2011, for PCT Patent Application No. PCT/US2011/042881 filed on Jul. 1, 2011, seven pages.
International Search Report mailed on Mar. 26, 2013, for PCT Patent Application No. PCT/US2013/020151 filed on Jan. 3, 2013, five pages.
International Search Report mailed on Jul. 2, 2012, for PCT Patent Application No. PCT/US2012/034593 filed on Apr. 20, 2012, five pages.
International Search Report mailed on Aug. 5, 2013, for PCT Patent Application No. PCT/US2013/037483 filed on Apr. 19, 2013, three pages.
Israeli Office Action mailed on Mar. 3, 2014 for Israeli Patent Application No. 223558, filed on Jul. 1, 2011, two pages.
New Zealand Office Action mailed on Aug. 22, 2013 for New Zealand Patent Application No. 604598, filed on Jul. 1, 2011, two pages.
Ecuadoran Opposition filed Apr. 23, 2014 against Ecuadoran Patent Application No. SP1312418, filed Jul. 1, 2011, ten pages.
Ecuadoran Opposition from Jun. 2014, against Ecuadoran Patent Application No. SP1312417, filed Jul. 1, 2011, nine pages.
Philippine Office Action mailed on Aug. 1, 2014, for Philippine Patent Application No. 12013500011, filed on Jul. 1, 2011, two pages.
Written Opinion of the International Searching Authority mailed on Sep. 1, 2011, for PCT Patent Application No. PCT/US2011/042880 filed on Jul. 1, 2011, six pages.
Written Opinion of the International Searching Authority mailed on Sep. 14, 2011, for PCT Patent Application No. PCT/US2011/042881 filed on Jul. 1, 2011, twelve pages.
Written Opinion of the International Searching Authority mailed on Jul. 2, 2012, for PCT Patent Application No. PCT/US2012/034593 filed on Apr. 20, 2012, six pages.
Written Opinion of the International Searching Authority mailed on Aug. 5, 2013, for PCT Patent Application No. PCT/US2013/037483 filed on Apr. 19, 2013, seven pages.
Written Opinion of the International Searching Authority mailed on Jul. 17, 2014, for PCT Patent Application No. PCT/US2013/020151 filed on Jan. 3, 2013, six pages.
Written Opinion of the International Searching Authority mailed on Jul. 17, 2014, for PCT Patent Application No. PCT/US2013/020172, filed on Jan. 3, 2013, seven pages.
International Preliminary Report on Patentability mailed on Jan. 17, 2013, for PCT Patent Application No. PCT/US2011/042880 filed on Jul. 1, 2011, seven pages.
European Communication mailed on Oct. 15, 2013 for European Patent Application No. 11738878.5 filed on Jul. 1, 2011, four pages.
European Communication mailed on Feb. 8, 2013 for European Patent Application No. 11738878.5 filed on Jul. 1, 2011, two pages.
European Communication mailed on Mar. 12, 2014 for European Patent Application No. 11738878.5 filed on Jul. 1, 2011, eight pages.
European Communication mailed on Feb. 15, 2013, for European Patent Application No. 11738339.8, filed on Jul. 1, 2011, two pages.
European Office Action mailed on Oct. 20, 2014, for European Patent Application No. 13719355.3, filed on Apr. 19, 2013, four pages.
Pakistani Office Action mailed on Nov. 10, 2012 for Pakistani Patent Application No. 4932011, filed on Jul. 1, 2011, two pages.
Pakistani Office Action mailed on Nov. 10, 2012 for Pakistani Patent Application No. 4942011, filed on Jul. 1, 2011, two pages.
Philippines Office Action mailed on Mar. 14, 2014 for Philippine Patent Application No. 1/2013/500011, filed on Jul. 1, 2011, two pages.
Taiwanese Office Action mailed on Nov. 5, 2013 for Taiwanese Patent Application No. 100123357, filed on Jul. 1, 2011, nine pages.
Mexican Office Action mailed on Mar. 13, 2014 for Mexican Patent Application No. MX/a/2012/015293, filed on Jul. 1, 2011, seven pages.
Vietnamese Office Action mailed on Jul. 28, 2014, for Vietnamese Patent Application No. 1-201300326, filed on Jul. 1, 2011, two pages.

2-(TERT-BUTOXY)-2-(7-METHYLQUINOLIN-6-YL) ACETIC ACID DERIVATIVES FOR TREATING AIDS

CROSS REFERENCE TO RELATED APPLICATIONS

This patent application is a National Phase filing under 35 U.S.C. §371 of International Application No. PCT/US2013/020151, having an international filing date of Jan. 3, 2013, which claims the benefit of priority of U.S. Application Ser. No. 61/583,122, filed Jan. 4, 2012. The contents of these applications are hereby incorporated herein by reference in their entirety.

BACKGROUND OF THE INVENTION

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001). Accordingly, there is a need for new agents that inhibit the replication of HIV. There is also a need for agents that are directed against alternate sites in the viral life cycle including agents that target the inhibition of integrase.

SUMMARY

Compounds and methods for the treatment of an HIV infection are disclosed.

Accordingly, one embodiment provides a compound selected from:

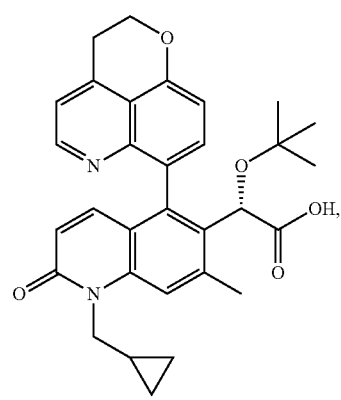

-continued

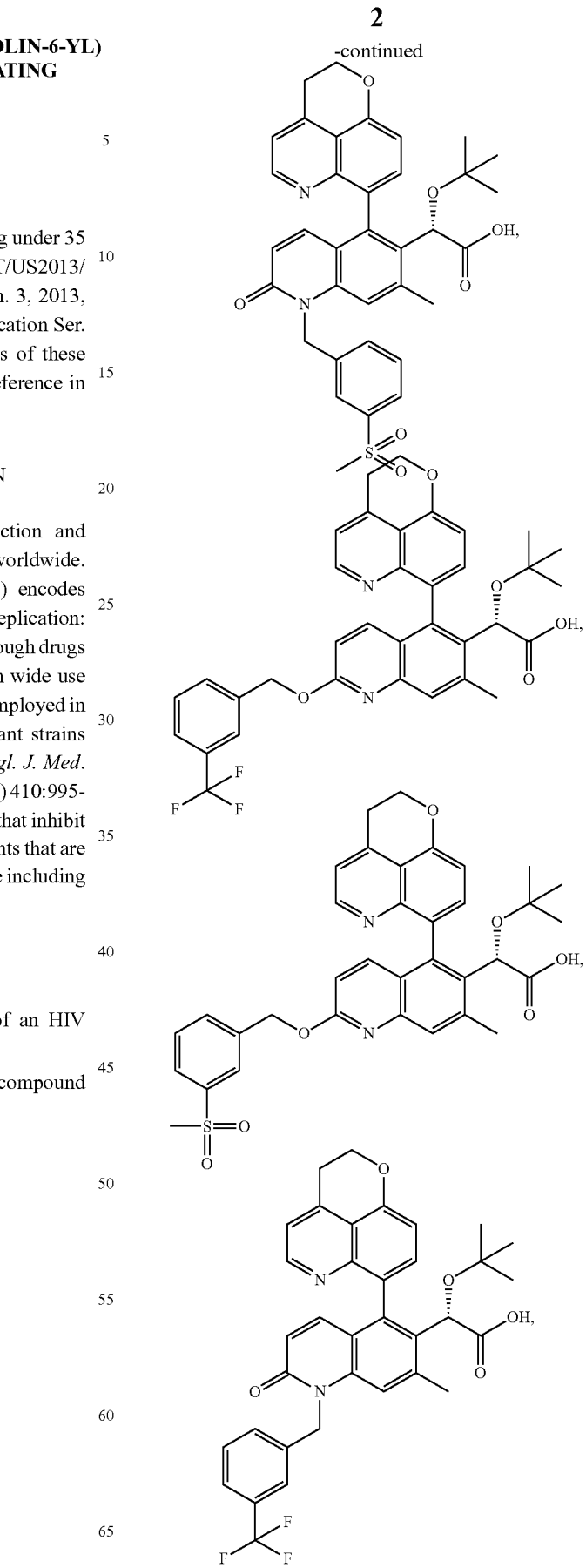

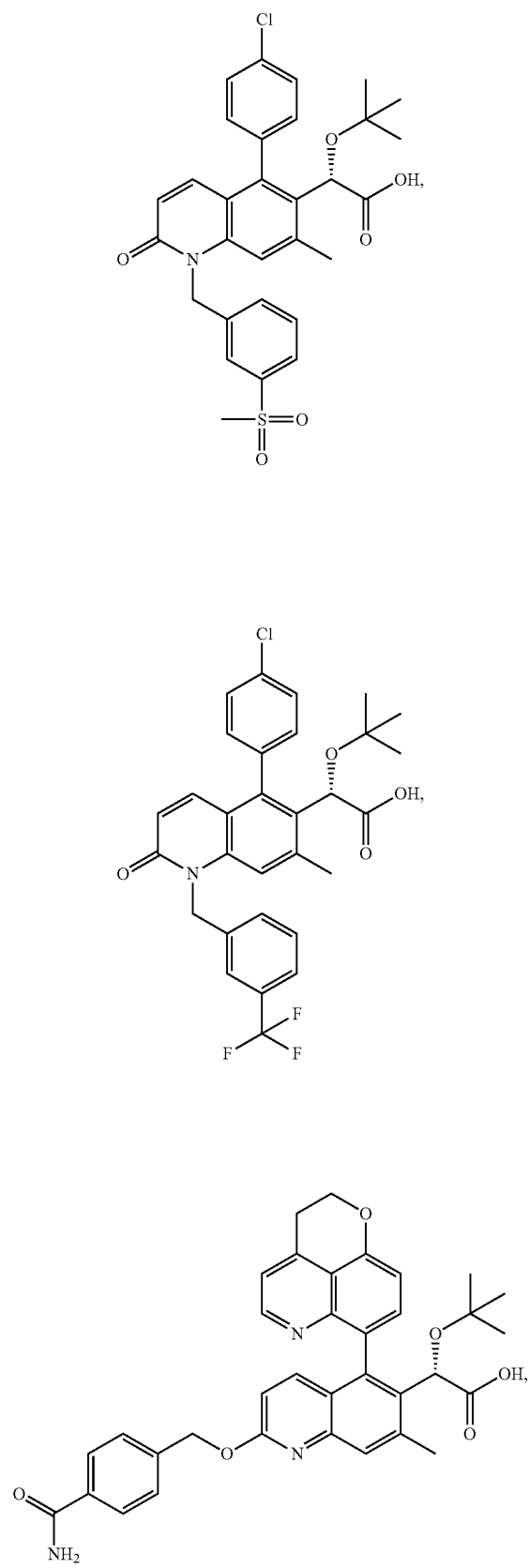
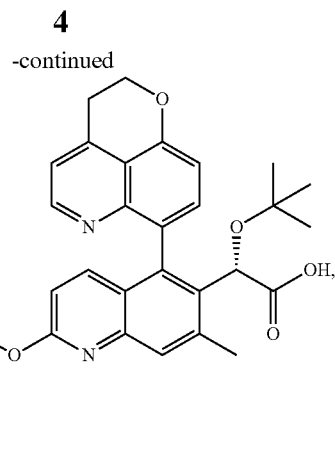
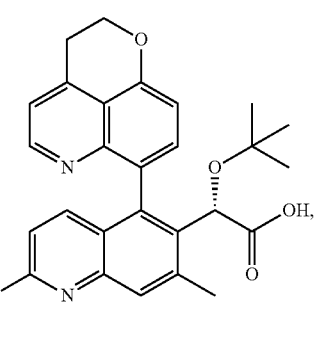
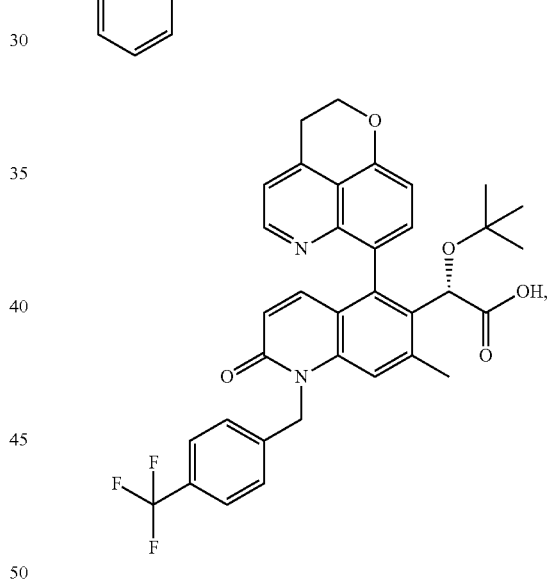
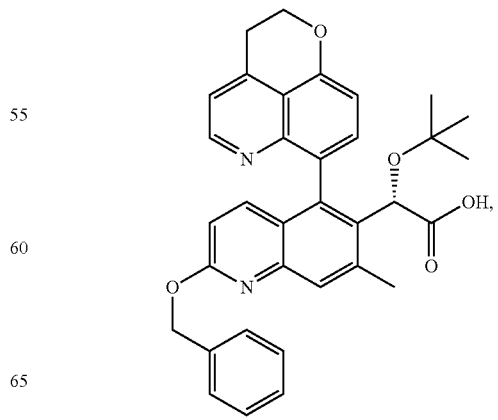

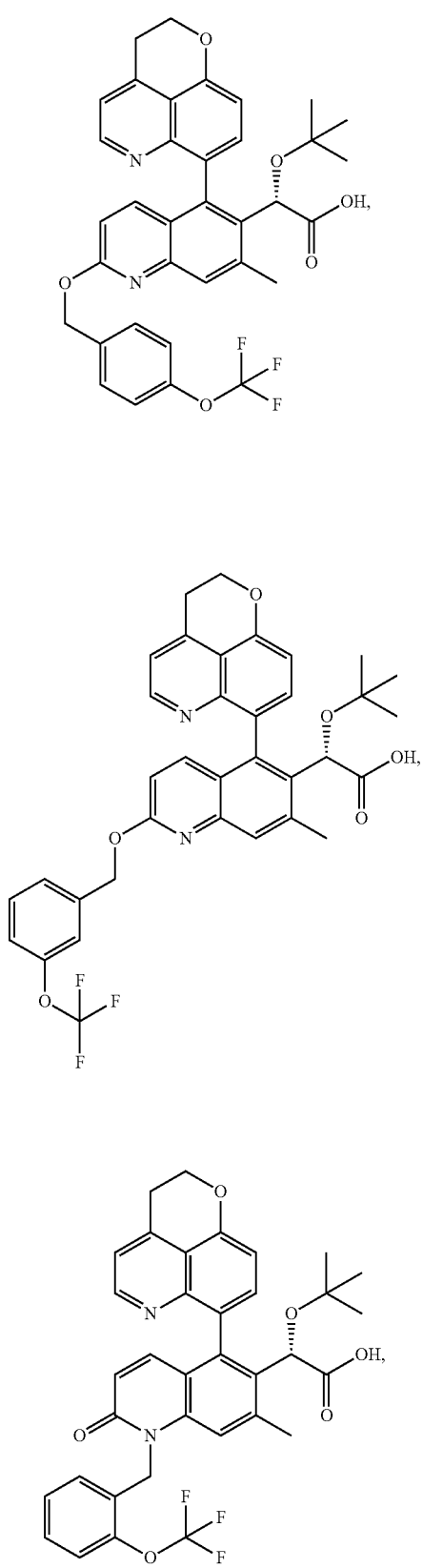
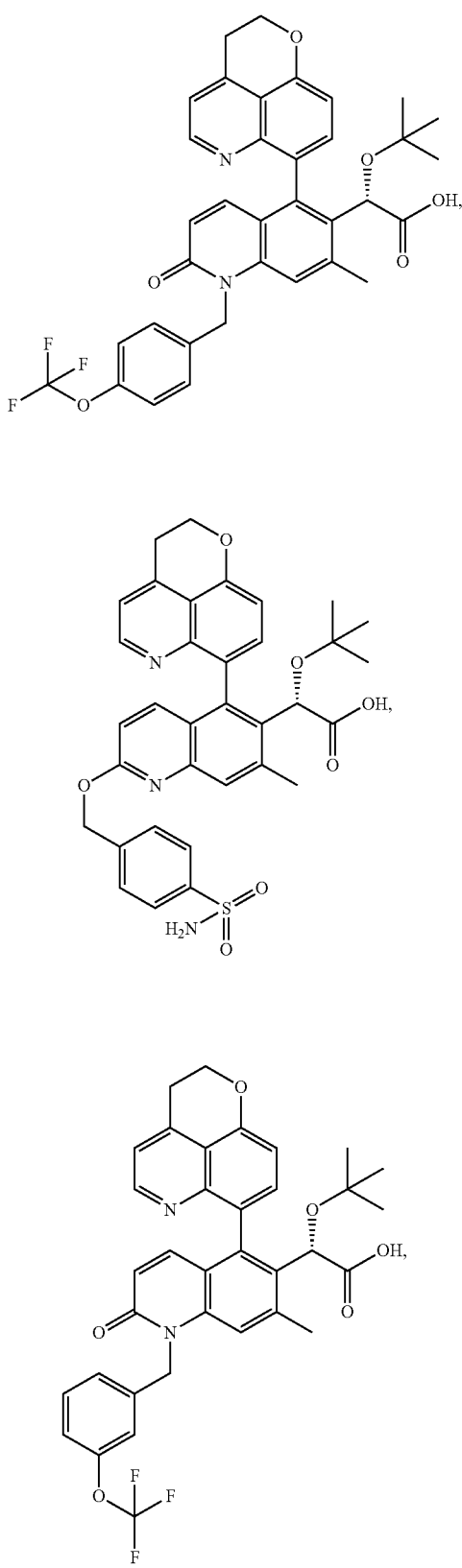

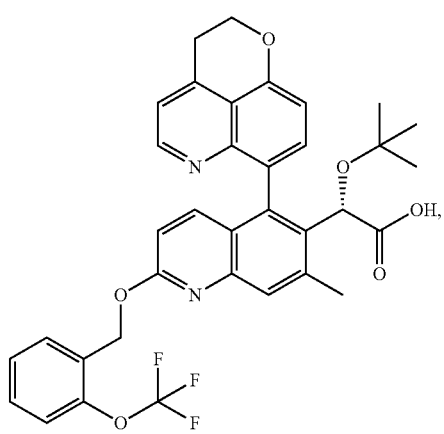
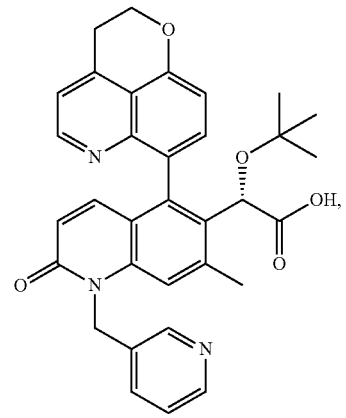
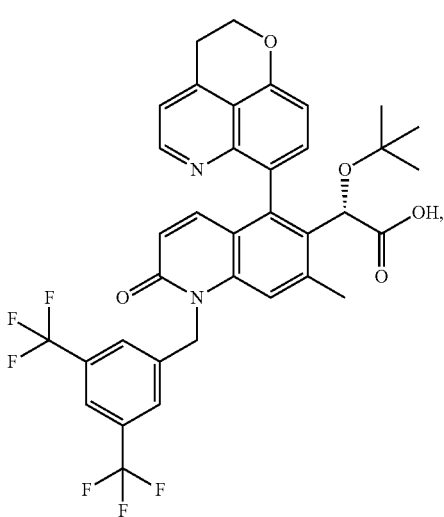
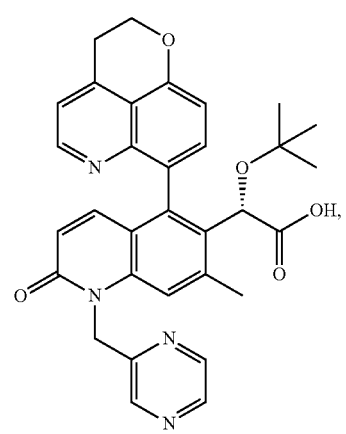
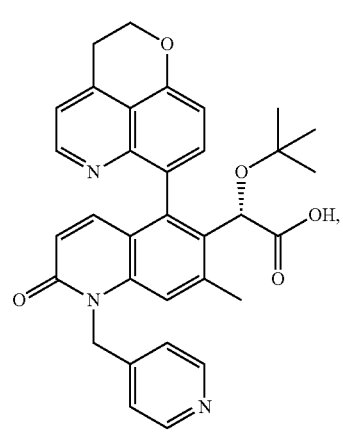

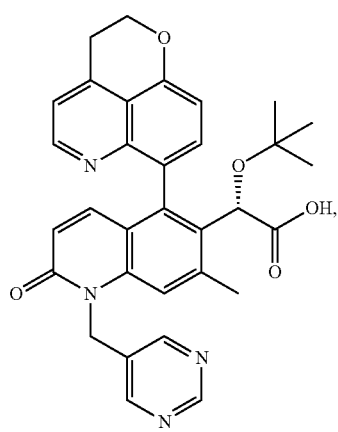
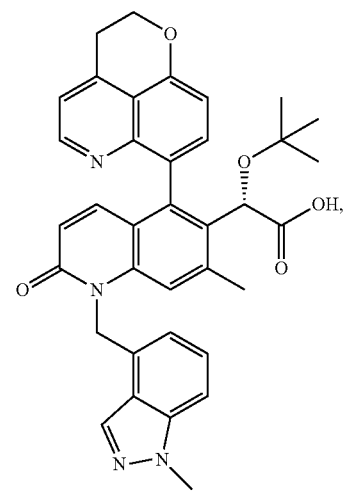
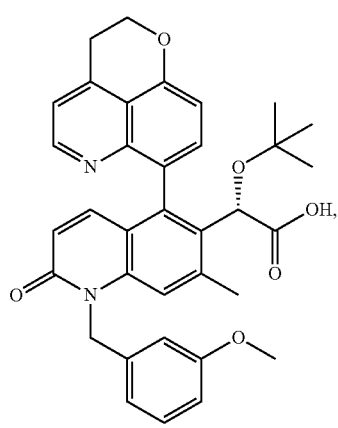
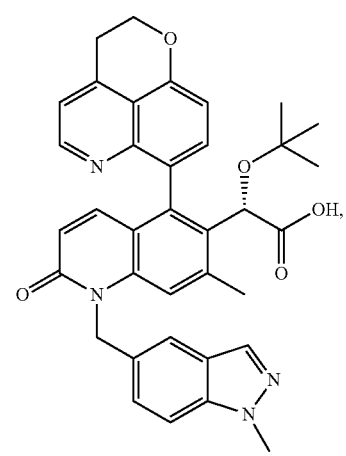
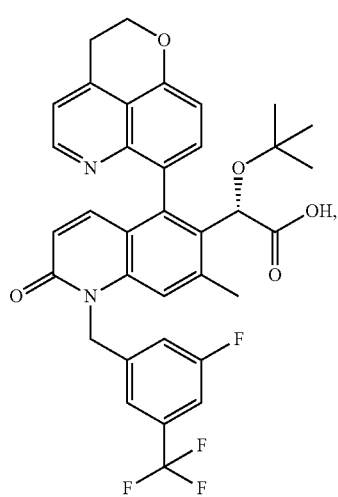
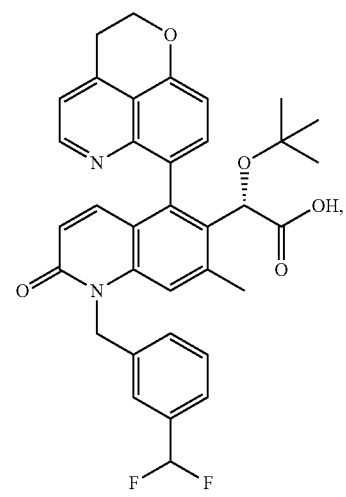

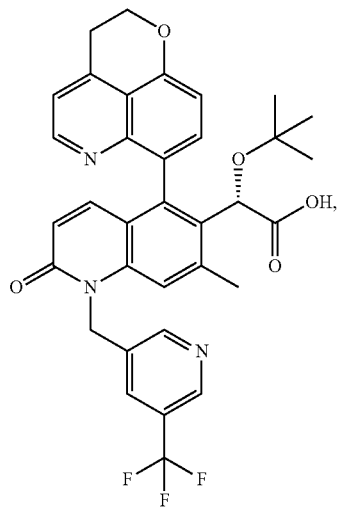
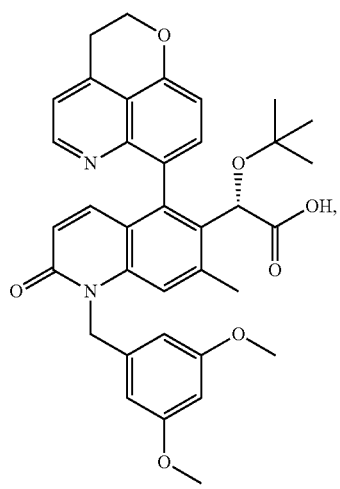
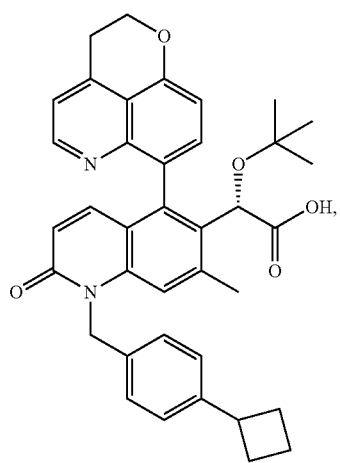
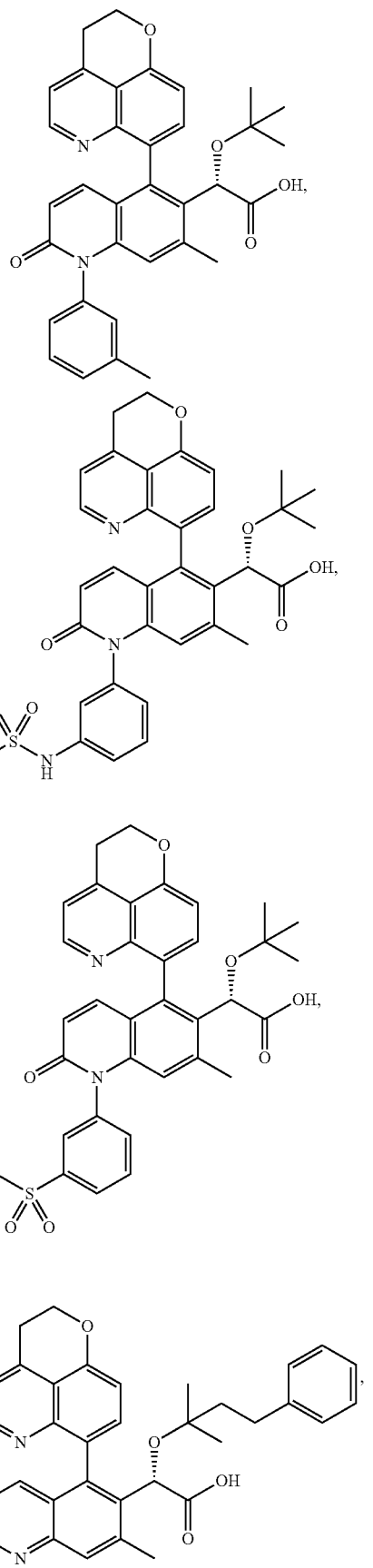

-continued
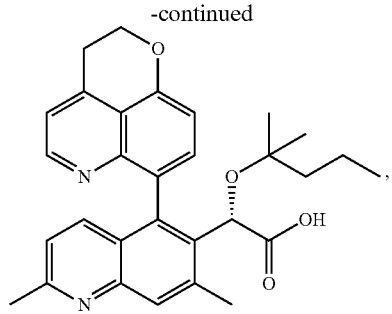
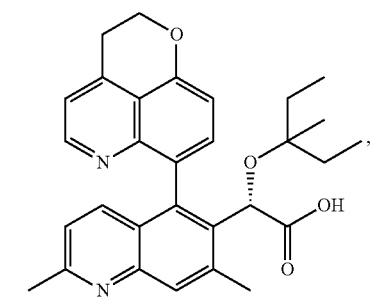
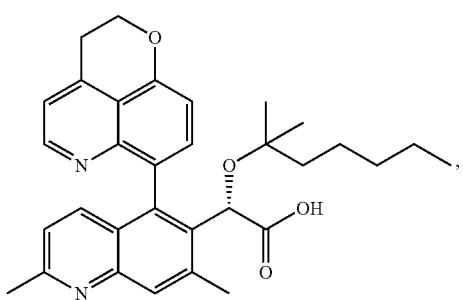
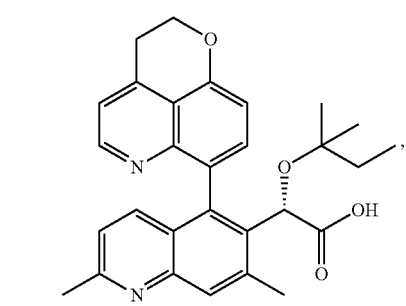
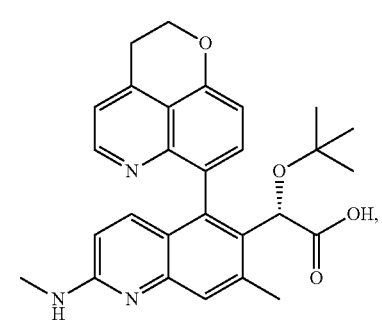
-continued
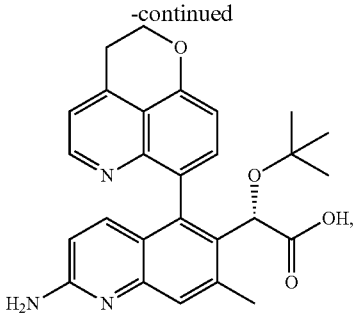
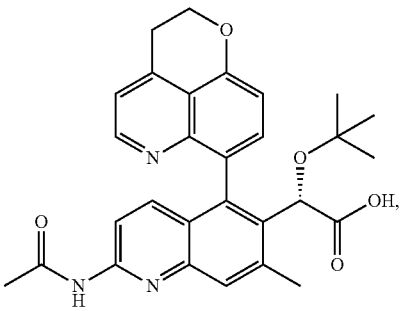
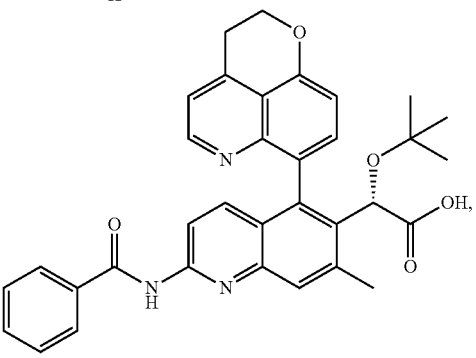
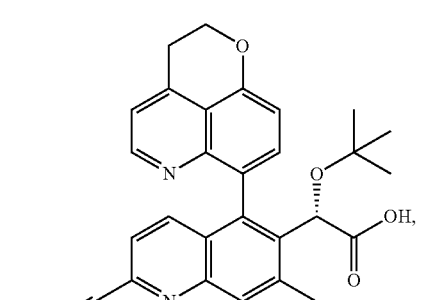
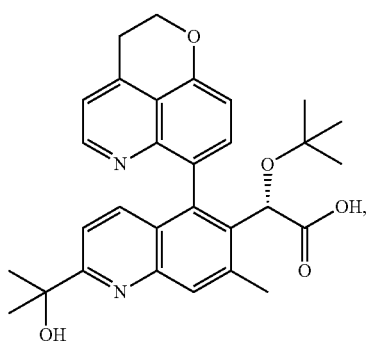

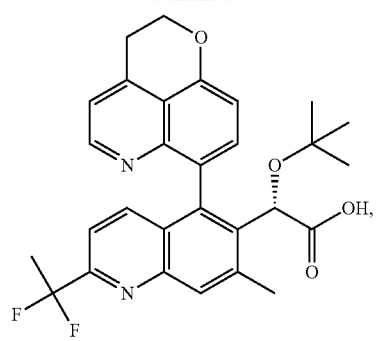
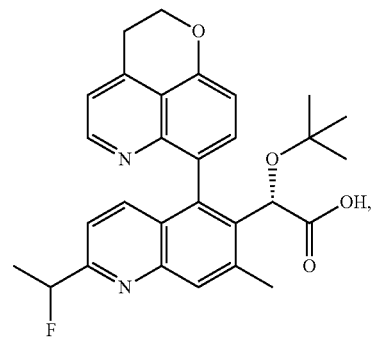
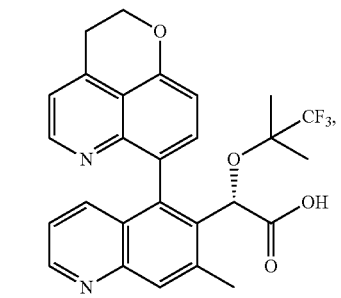
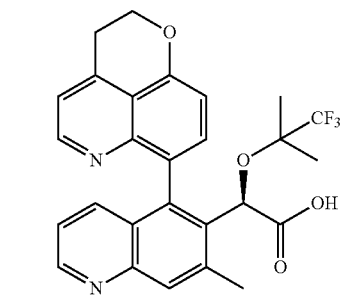
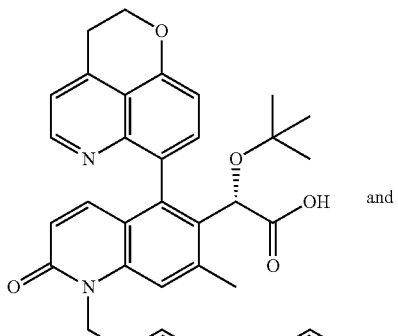
and
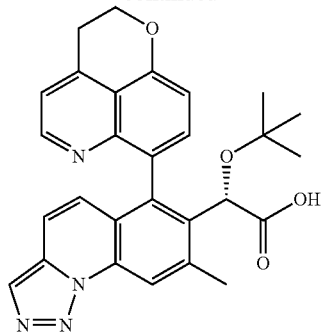 [SMILES: Cc1cc2c(ccc3cnnn32)c(-c2ccc3c4c(ccnc24)CCO3)c1[C@H](OC(C)(C)C)C(=O)O]
and salts thereof.
Another embodiment provides a compound selected from:
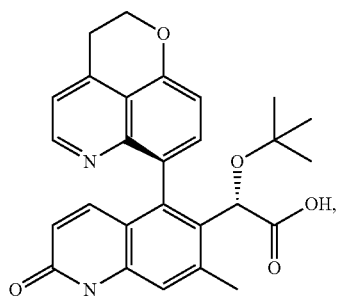
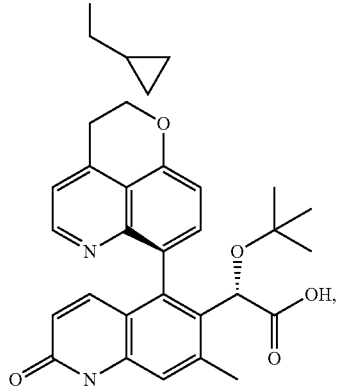
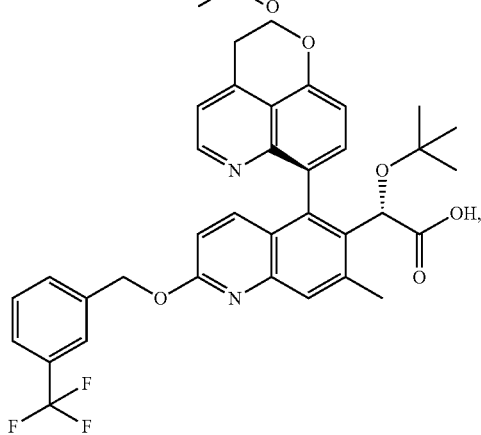

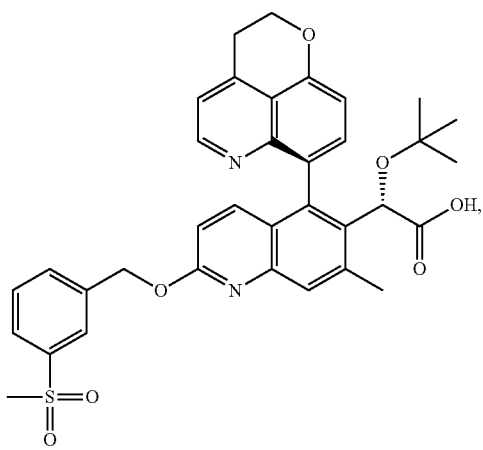
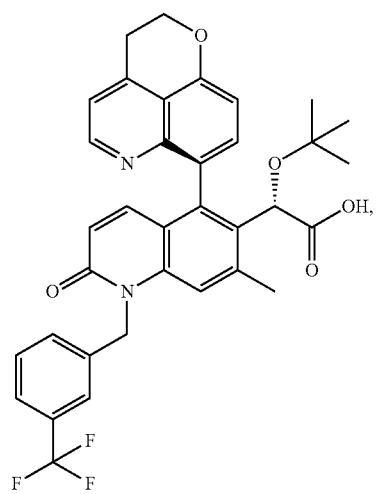
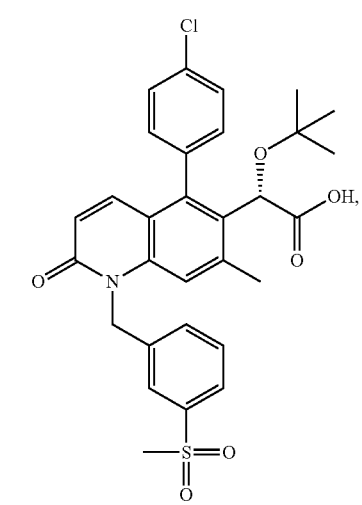
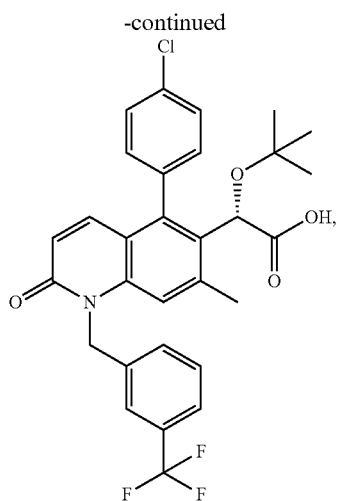
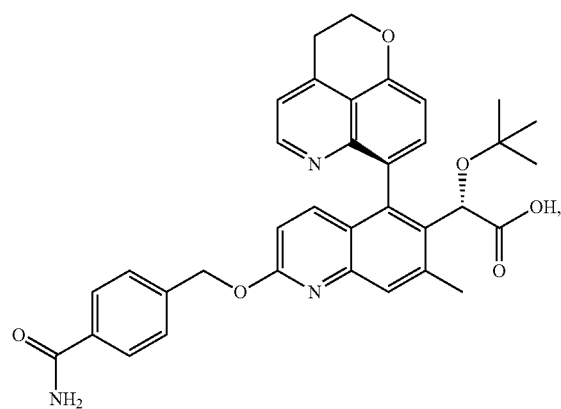
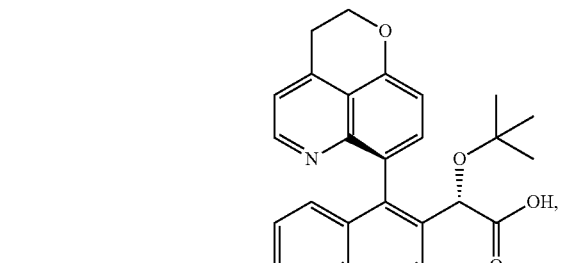
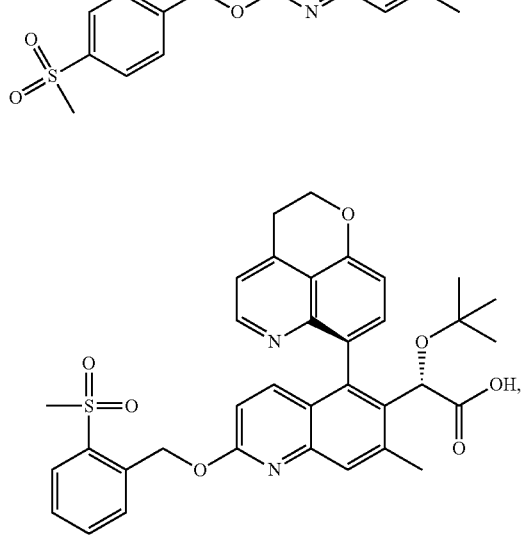

19
-continued
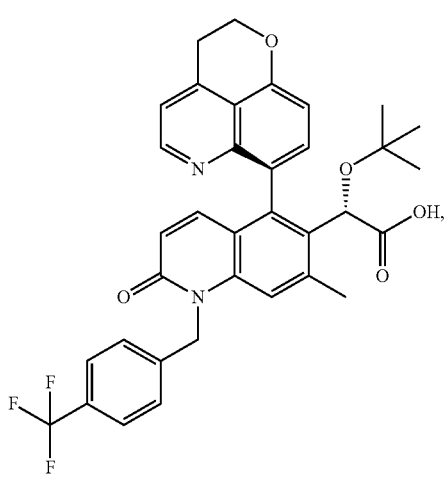
20
-continued
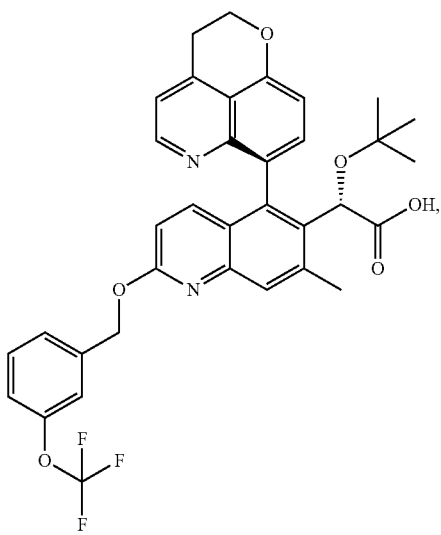
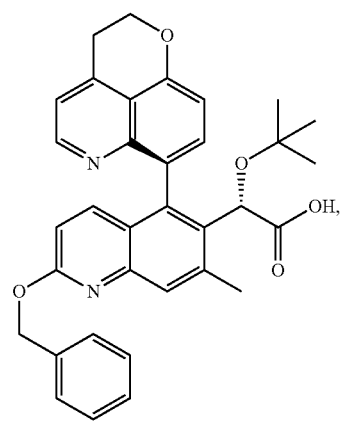
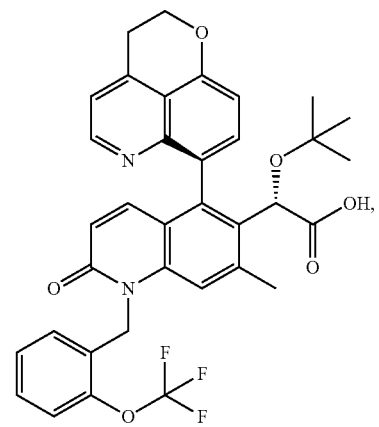
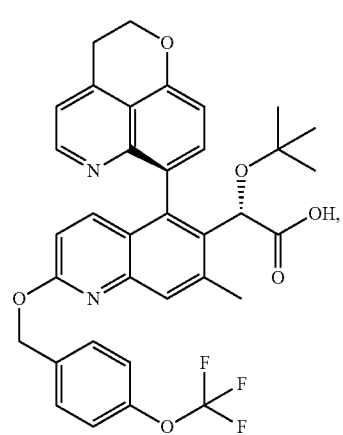

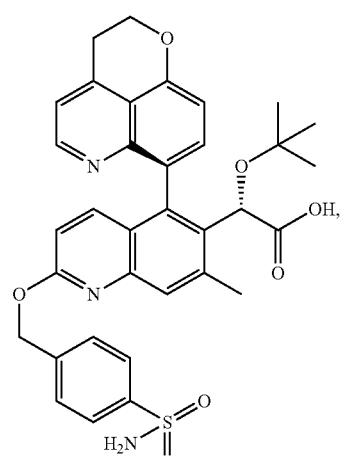
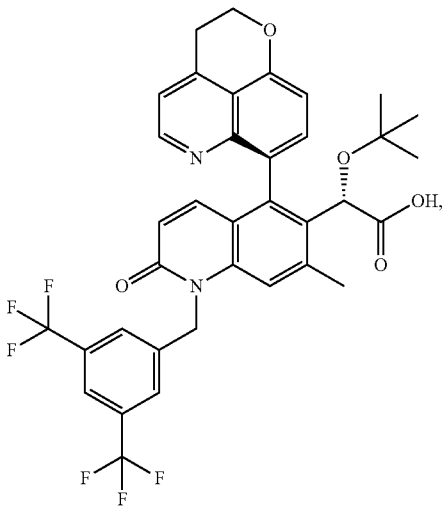
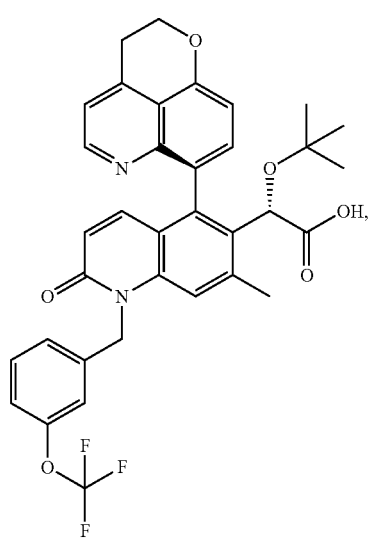
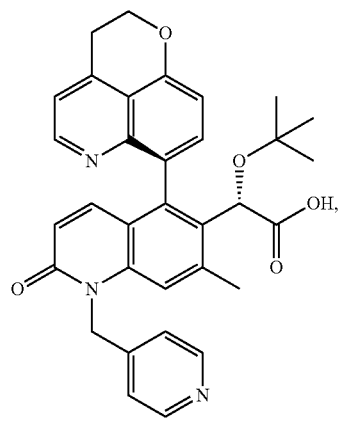
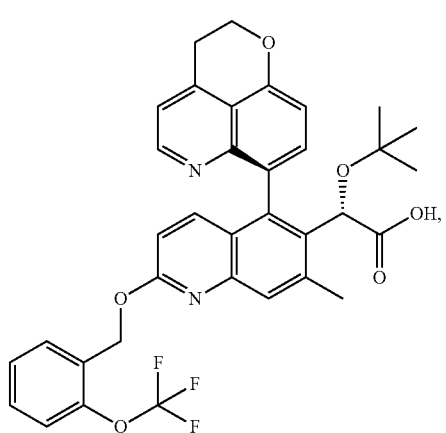
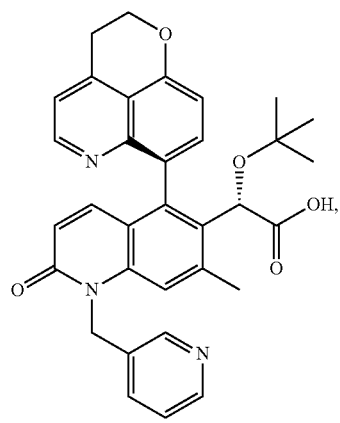

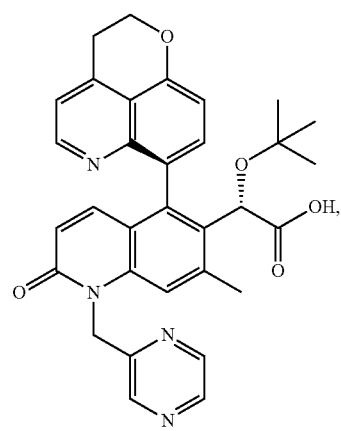
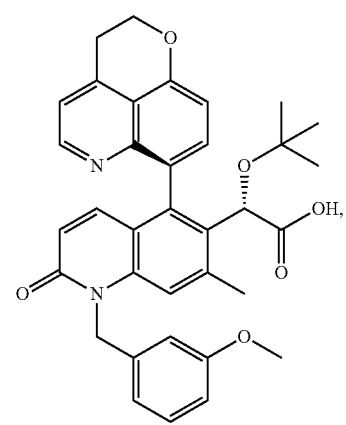
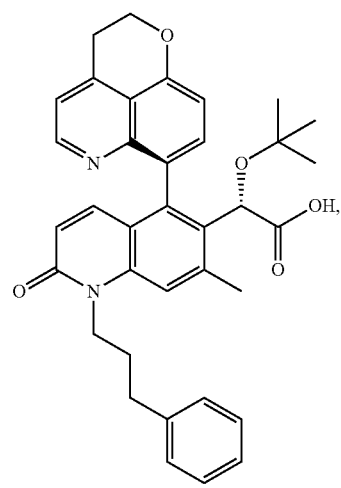
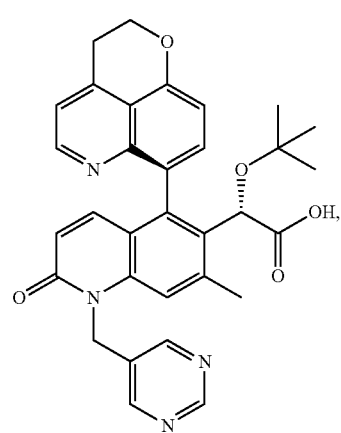
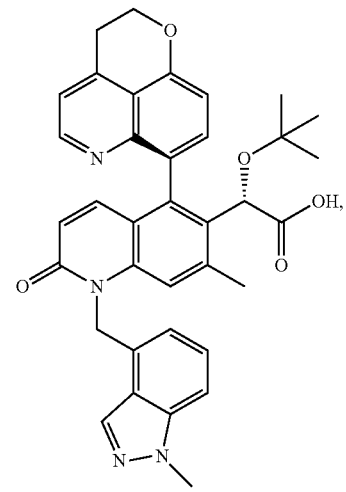

25
-continued
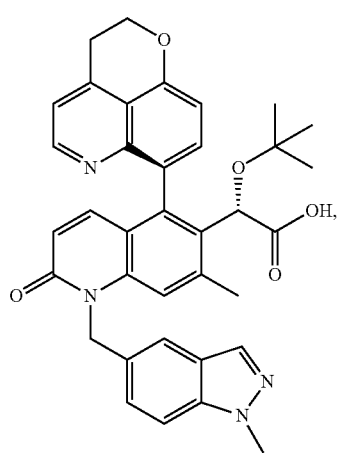
26
-continued
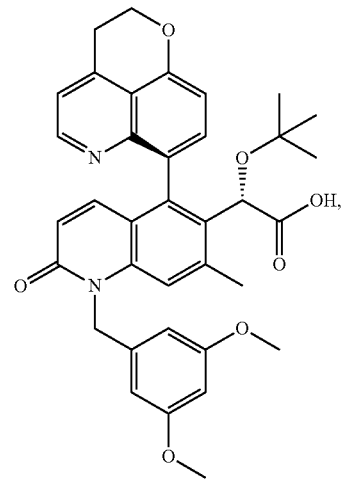
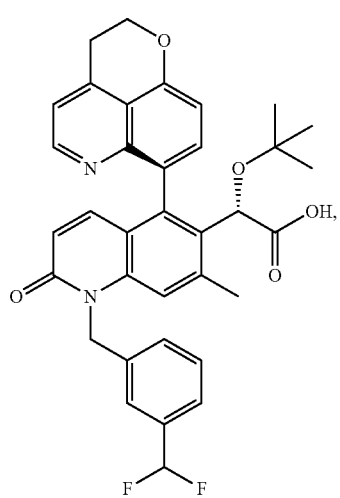
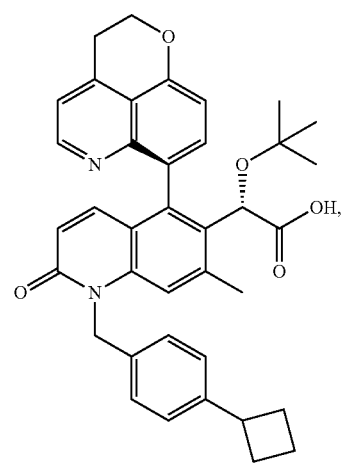
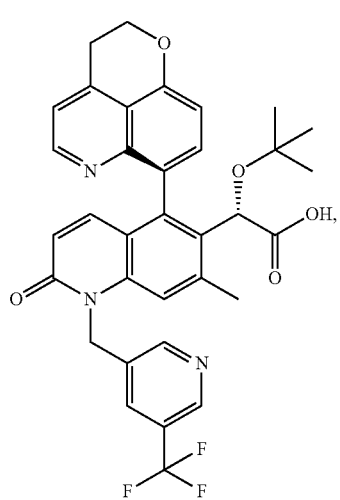
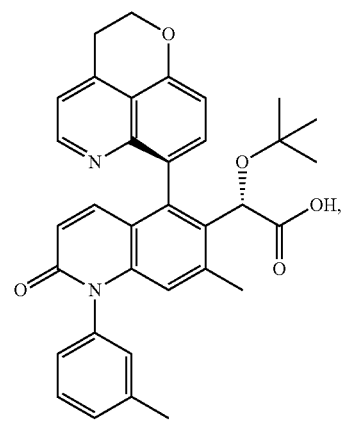

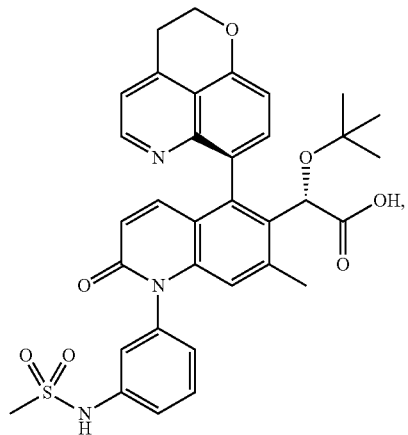
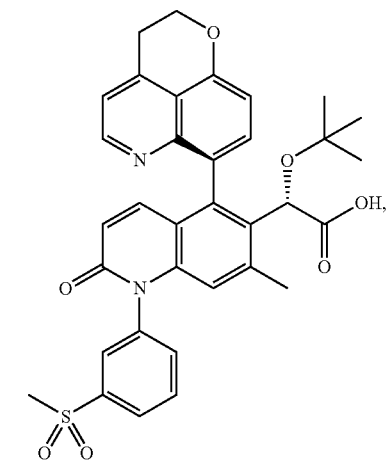
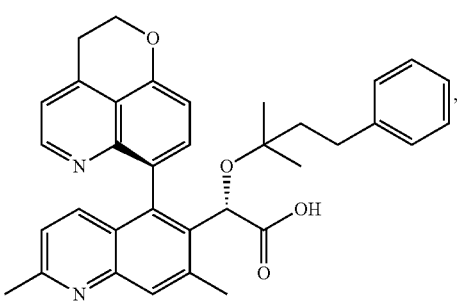
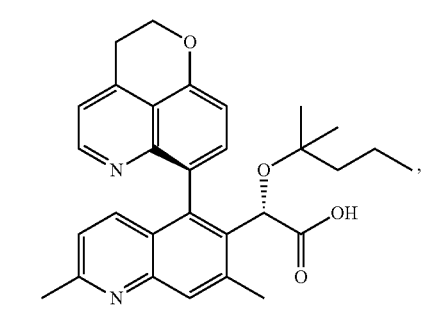
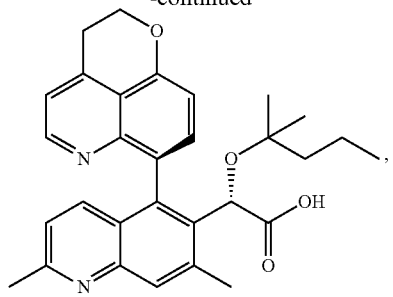
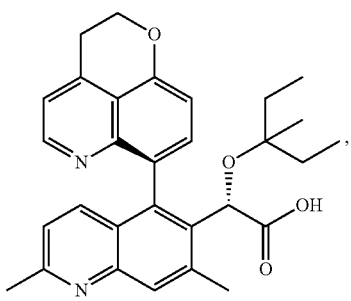
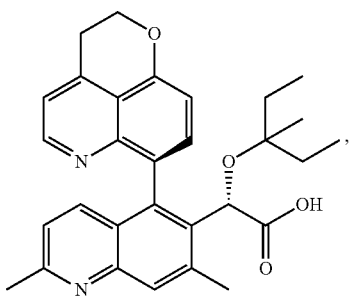
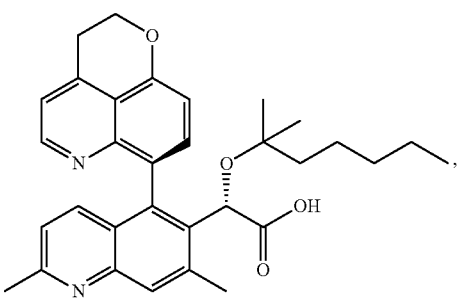
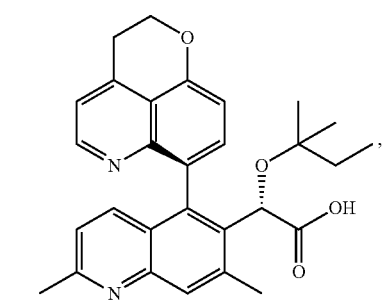

29
-continued
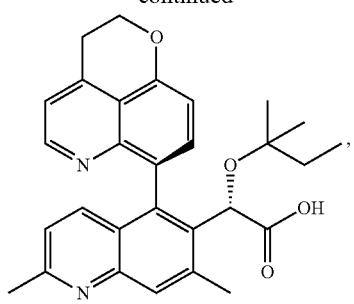
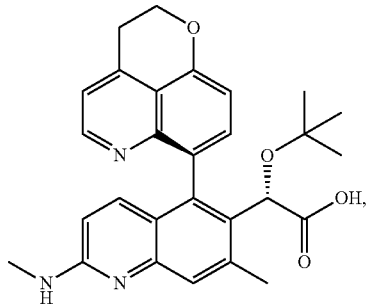
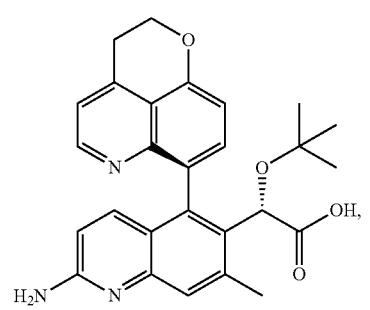
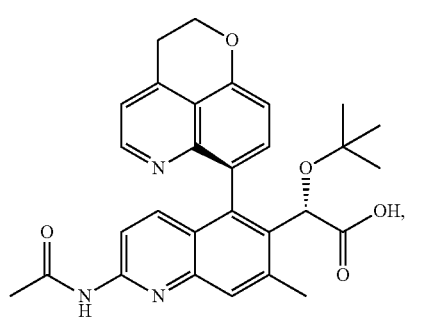
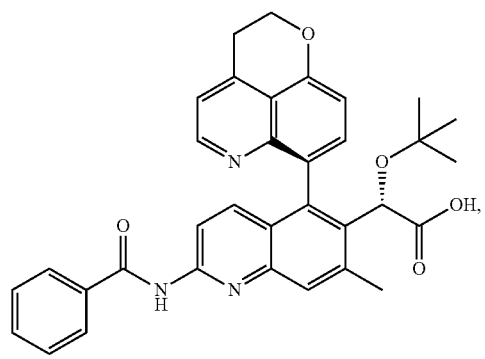
30
-continued
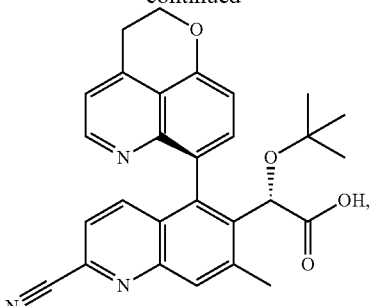
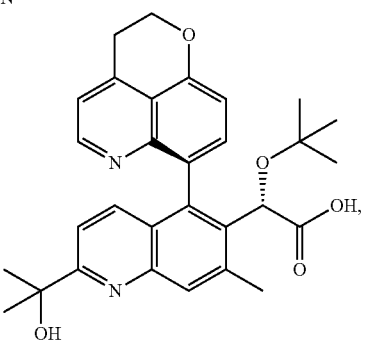
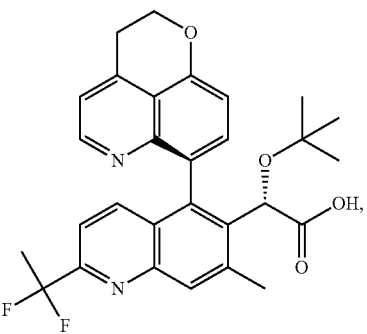
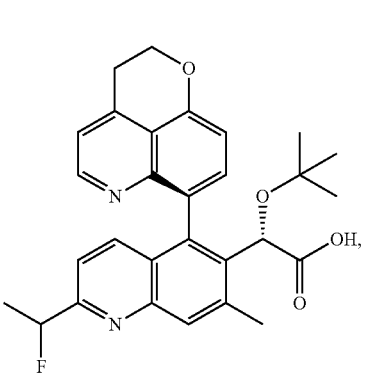
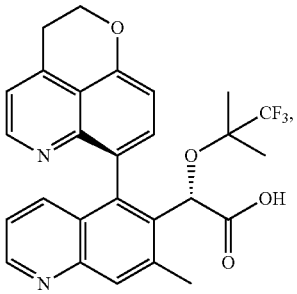

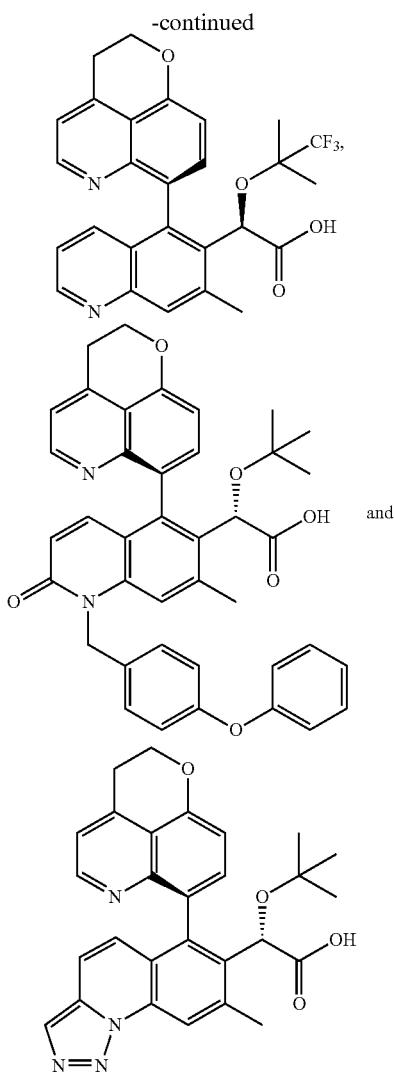

and salts thereof.

Another embodiment provides a compound as described in any one of the Examples herein or a non-salt thereof or a salt thereof or an alternative salt thereof.

Another embodiment provides a pharmaceutical composition comprising a compound disclosed herein, or a pharmaceutically acceptable salt thereof, and a pharmaceutically acceptable carrier.

Another embodiment provides a method for treating (e.g., preventing, mediating or inhibiting) the proliferation of the HIV virus, treating AIDS or delaying the onset of AIDS or ARC symptoms in a mammal (e.g., a human), comprising administering a compound disclosed herein, or a pharmaceutically acceptable salt thereof, to the mammal.

Another embodiment provides a method for treating an HIV infection in a mammal (e.g., a human) comprising administering one or more of the compounds disclosed herein, or a pharmaceutically acceptable salt thereof, to the mammal.

Another embodiment provides a method for treating an HIV infection in a mammal (e.g., a human) comprising administering to the mammal in need thereof a therapeutically effective amount of a compound disclosed herein, or a pharmaceutically acceptable salt thereof, in combination with a therapeutically effective amount of one or more additional therapeutic agents selected from the group consisting HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

Another embodiment provides a compound disclosed herein, or a pharmaceutically acceptable salt thereof for use in medical therapy (e.g., for use in treating (e.g., preventing, mediating or inhibiting) the proliferation of the HIV virus or AIDS or delaying the onset of AIDS or ARC symptoms in a mammal (e.g., a human)).

Another embodiment provides a compound disclosed herein, or a pharmaceutically acceptable salt thereof for use in medical therapy (e.g., for use in treating (e.g., preventing, mediating or inhibiting) an HIV infection in a mammal (e.g., a human)).

Another embodiment provides a compound disclosed herein, or a pharmaceutically acceptable salt thereof for use in the manufacture of a medicament for treating (e.g., preventing, mediating or inhibiting) the proliferation of the HIV virus or AIDS or delaying the onset of AIDS or ARC symptoms in a mammal (e.g., a human).

Another embodiment provides a compound disclosed herein, or a pharmaceutically acceptable salt thereof, for use in the prophylactic or therapeutic treatment (e.g., prevention, mediation or inhibition) of the proliferation of the HIV virus or AIDS or for use in the therapeutic treatment of delaying the onset of AIDS or ARC symptoms.

Another embodiment provides a compound disclosed herein, or a pharmaceutically acceptable salt thereof, for the manufacture of a medicament for treating an HIV infection in a mammal (e.g., a human).

Another embodiment provides a compound disclosed herein, or a pharmaceutically acceptable salt thereof, for use in the prophylactic or therapeutic treatment of an HIV infection.

Another embodiment provides processes and intermediates disclosed herein that are useful for preparing compounds disclosed herein or salts thereof.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way.

Embodiments illustrated under any heading may be combined with embodiments illustrated under any other heading.
Definitions Unless stated otherwise, the following terms and phrases as used herein are intended to have the following meanings:

When trade names are used herein, applicants intend to independently include the tradename product and the active pharmaceutical ingredient(s) of the tradename product.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH ~7).

The term "treatment" or "treating," to the extent it relates to a disease or condition includes preventing the disease or condition from occurring, inhibiting the disease or condition, eliminating the disease or condition, and/or relieving one or more symptoms of the disease or condition.
Stereoisomers Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The compounds disclosed herein may have chiral centers, e.g., chiral carbon atoms. Such compounds thus include racemic mixtures of all stereoisomers, including enantiomers, diastereomers and atropisomers. In addition, the compounds disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.
Tautomers The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.
Salts and Hydrates Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds disclosed herein will typically be pharmaceutically acceptable, i.e. they will be salts derived from a physiologically acceptable acid or base. However, salts of acids or bases which are not pharmaceutically acceptable may also find use, for example, in the preparation or purification of a compound of formula I or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form, and combinations with water as in hydrates.

Isotopes

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

Compounds

In one embodiment, compounds are selected from:

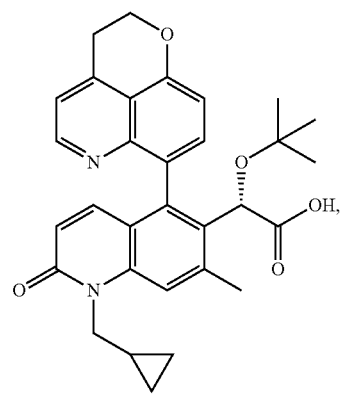

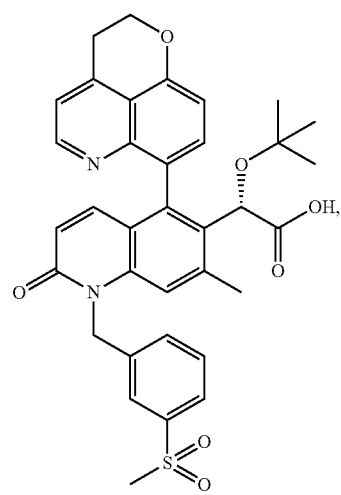

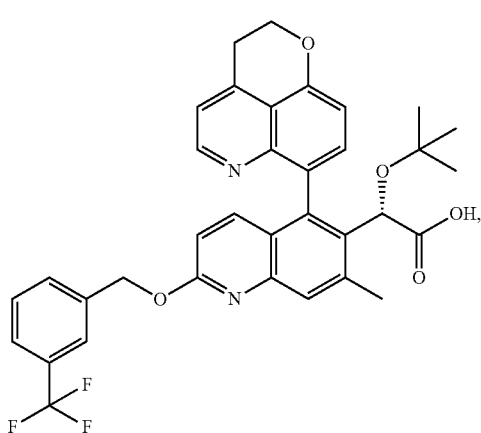

-continued

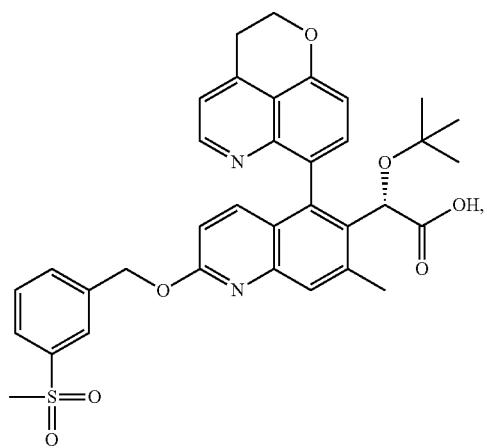

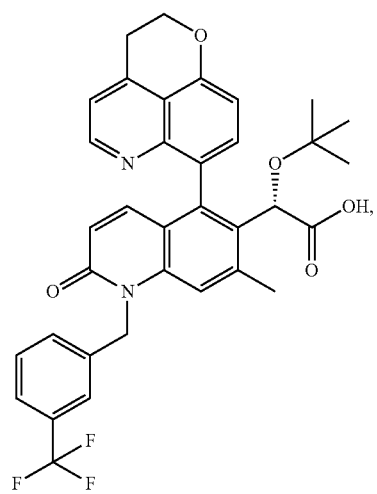

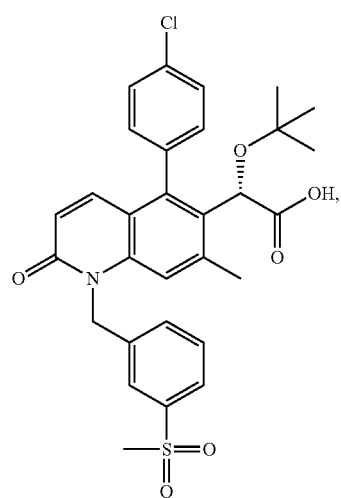

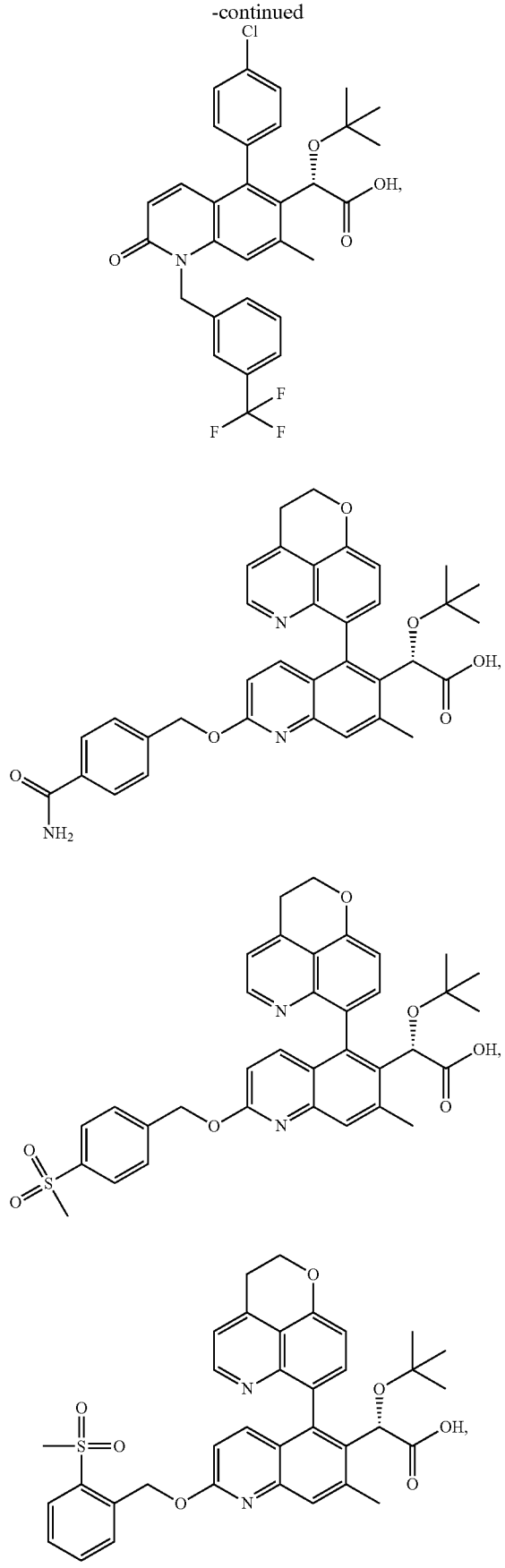

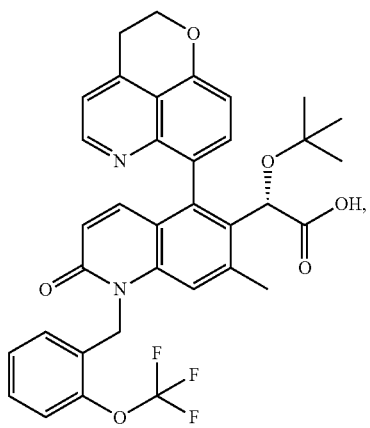
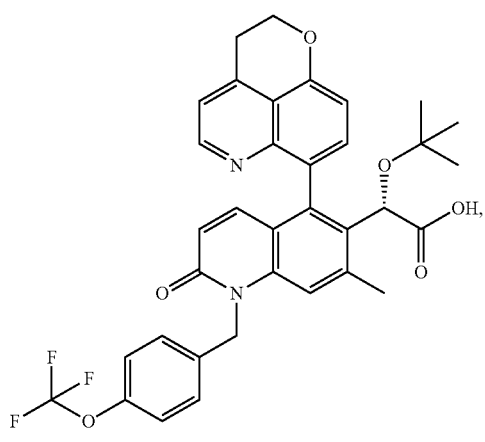
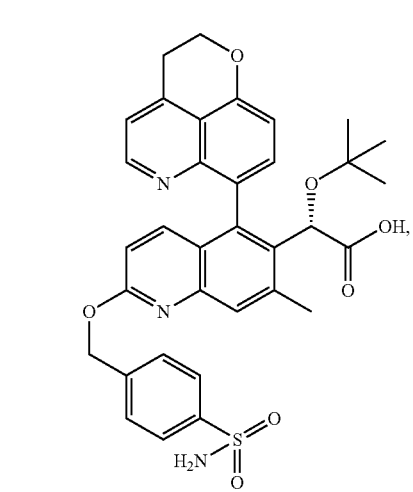
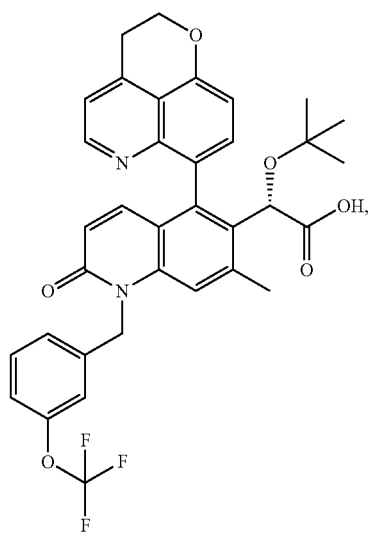
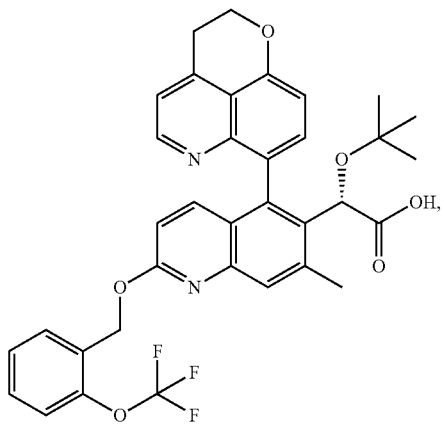
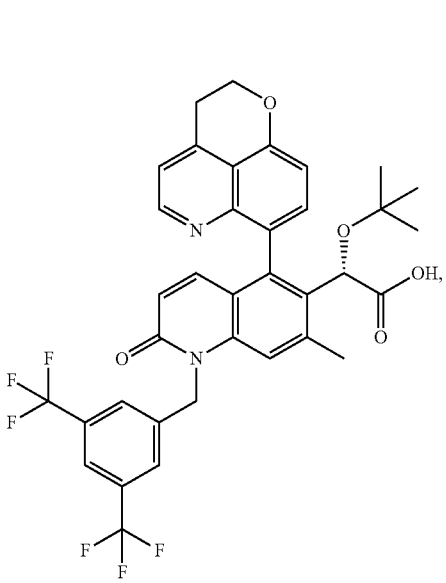

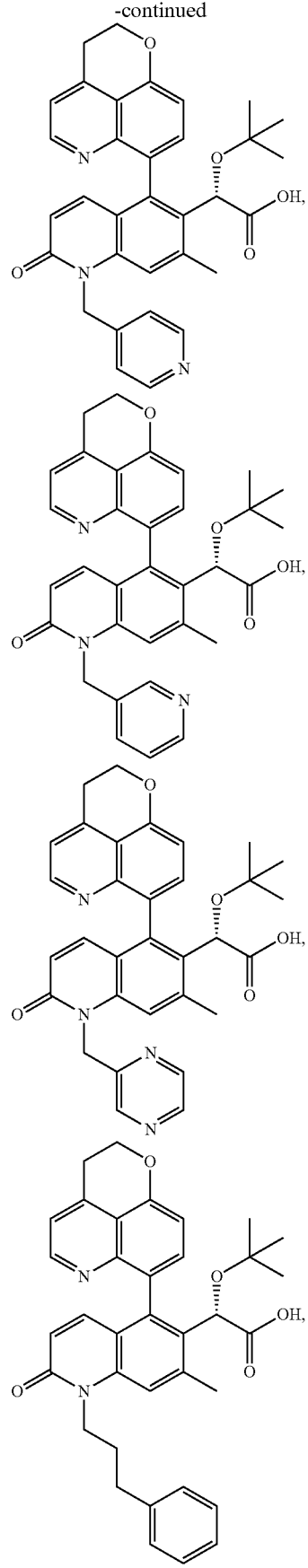
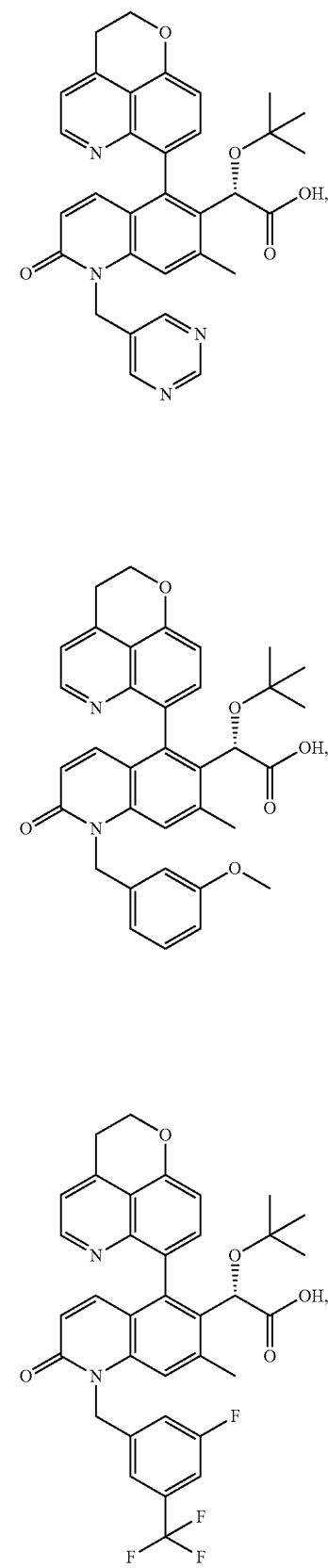

-continued
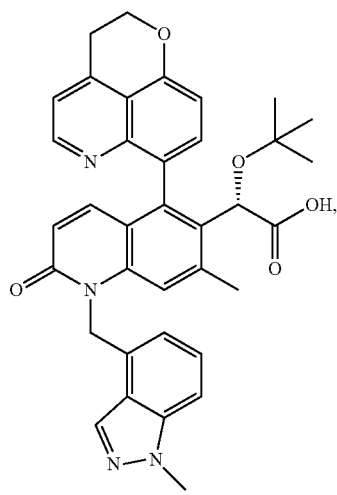
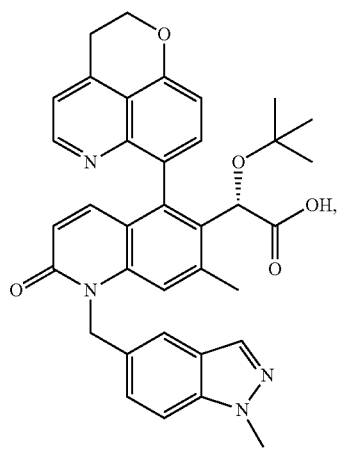
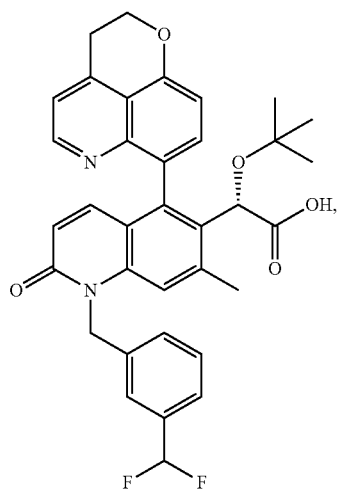
-continued
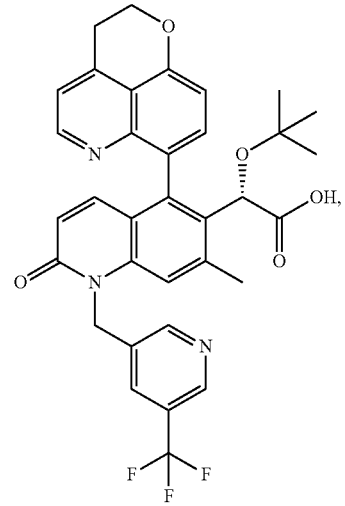
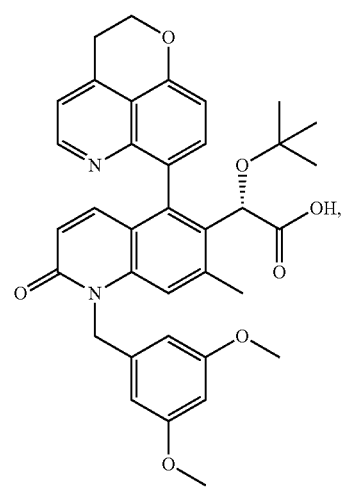
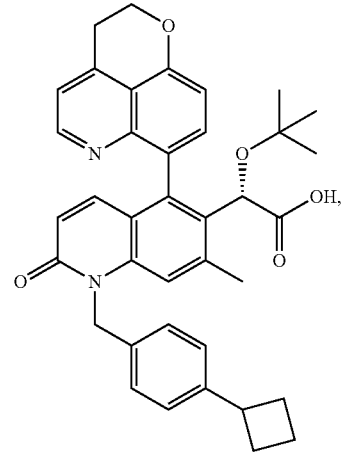

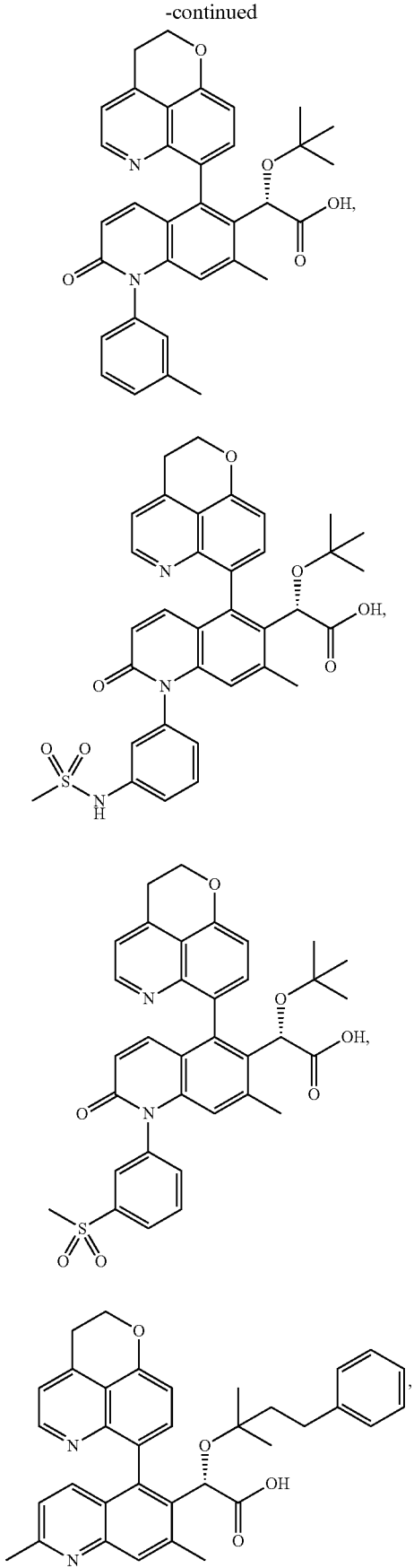

47
-continued
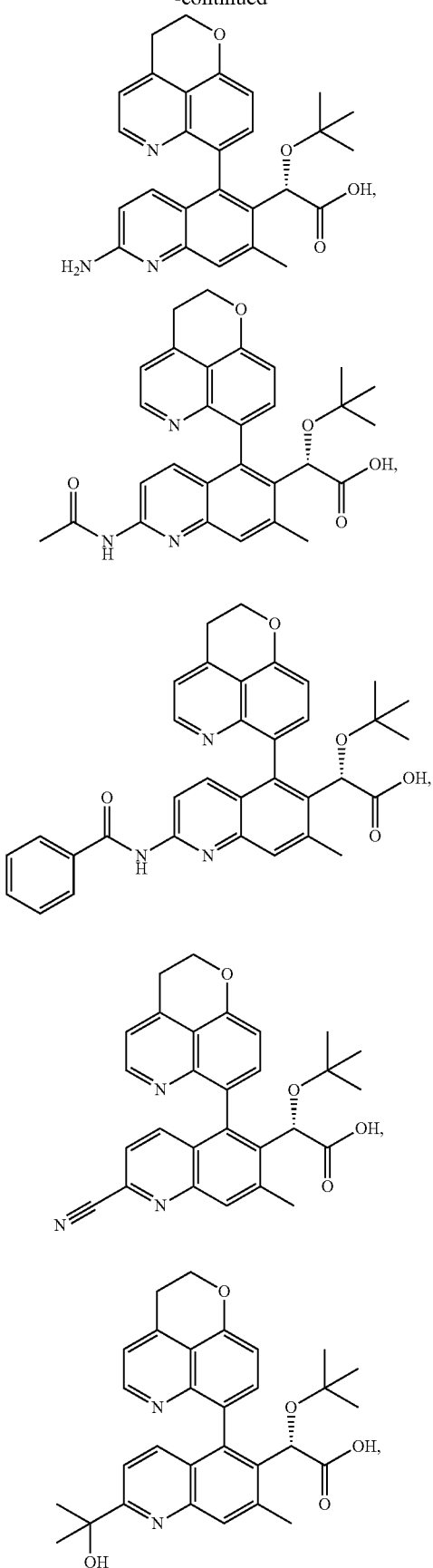
48
-continued
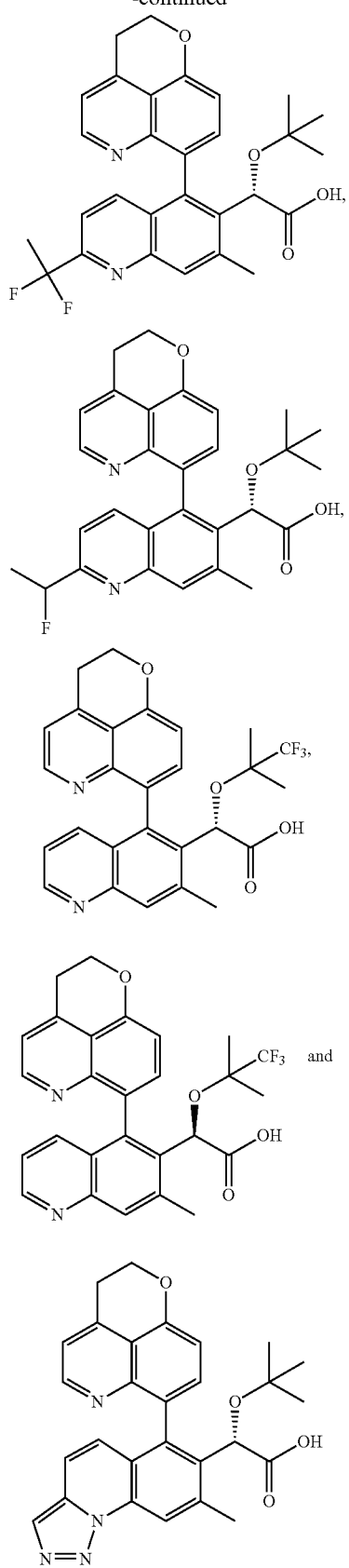
and salts thereof

In one embodiment, compounds are selected from:
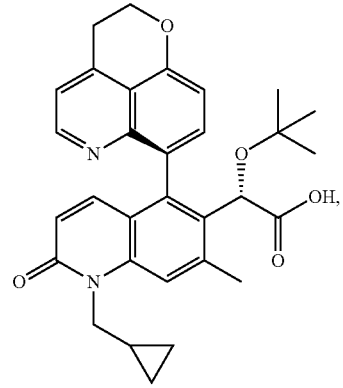
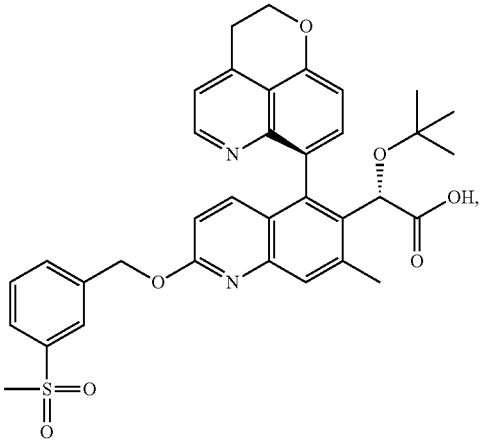
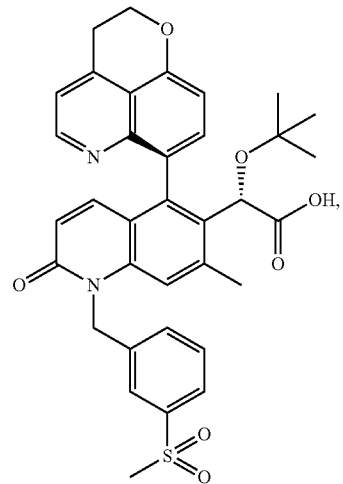
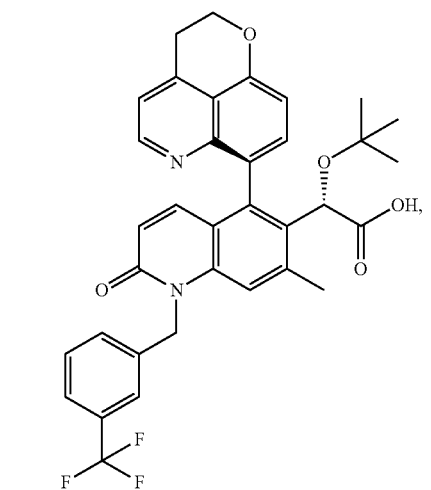
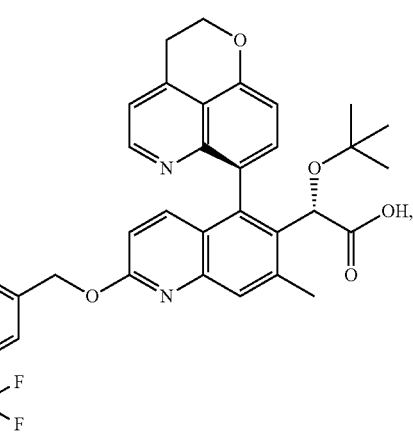
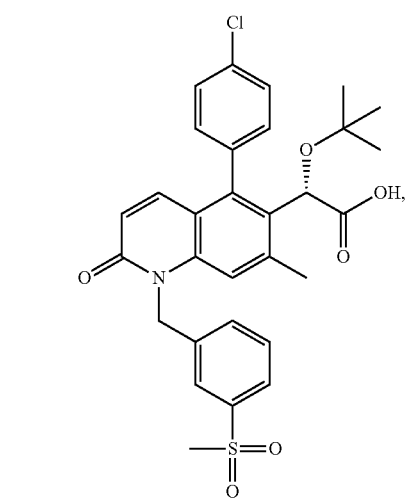

51
-continued
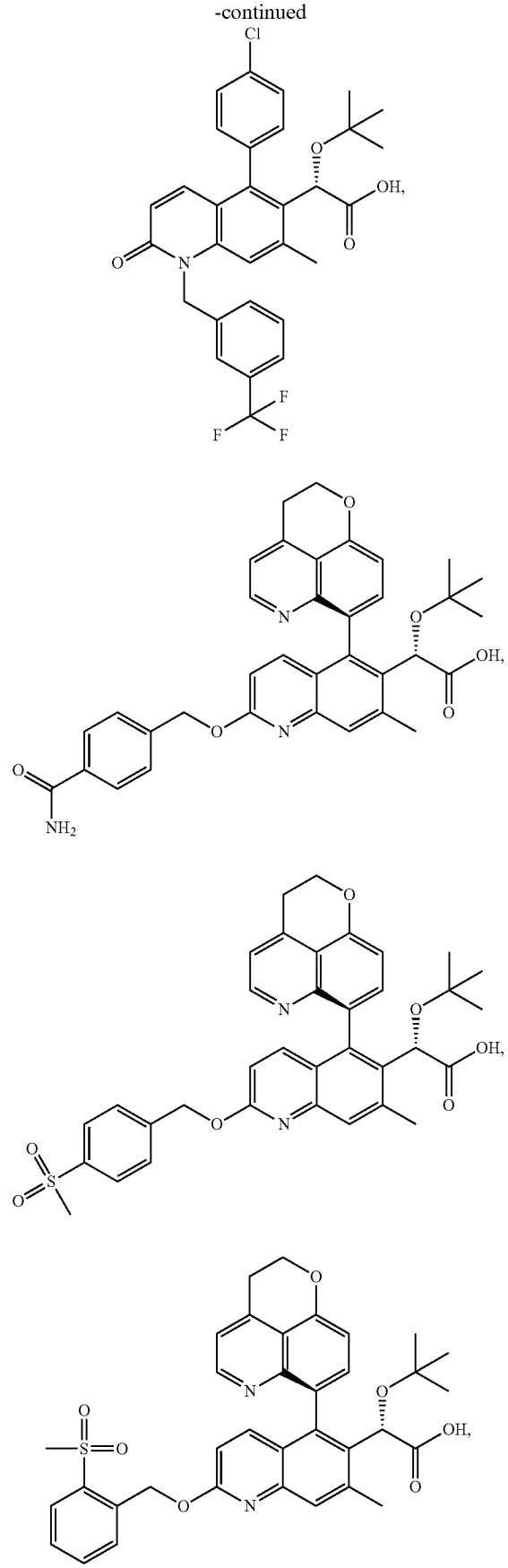
52
-continued
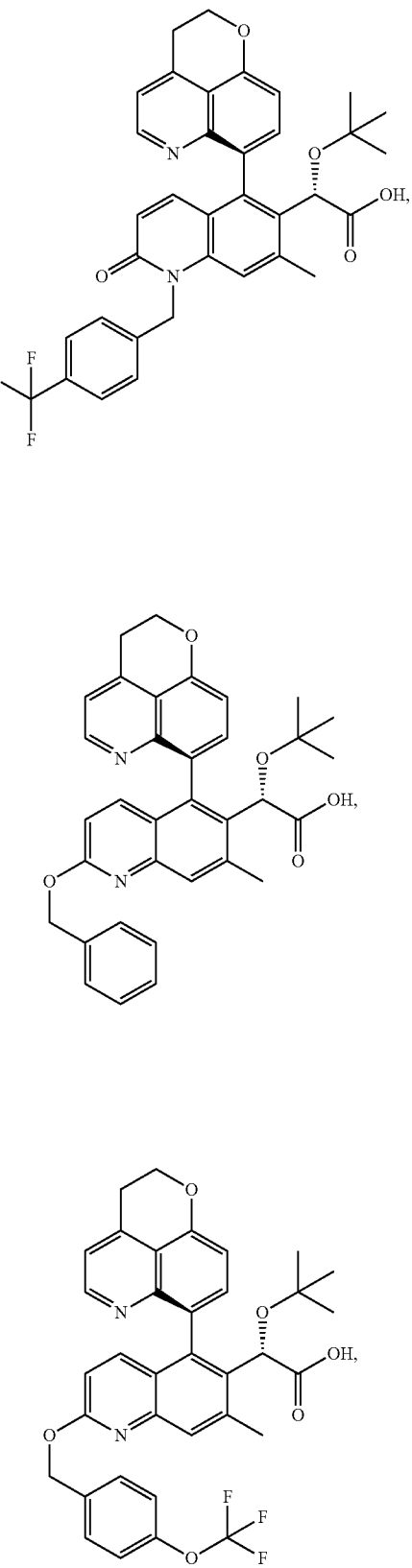

53
-continued
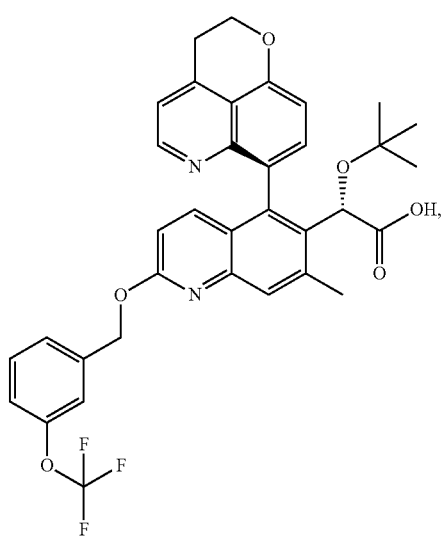
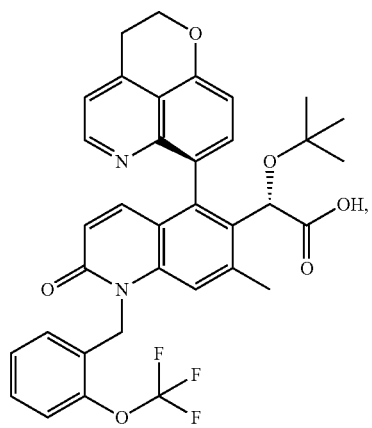
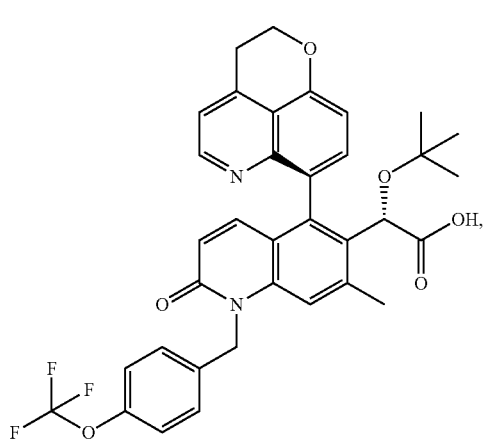
54
-continued
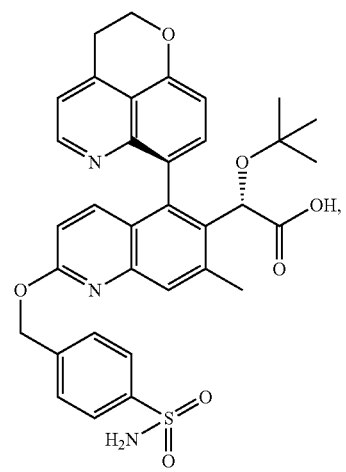
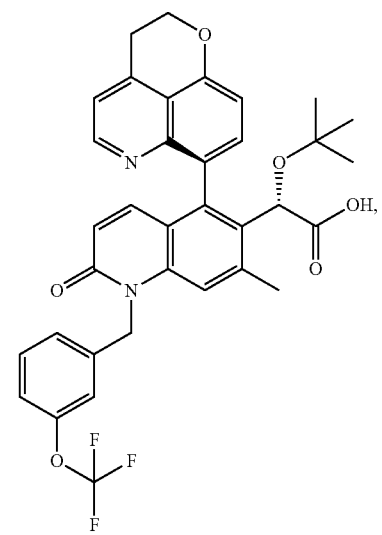
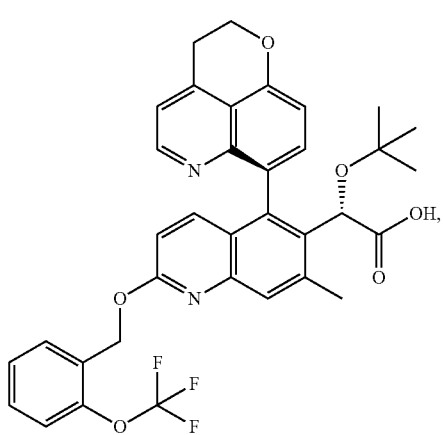

55
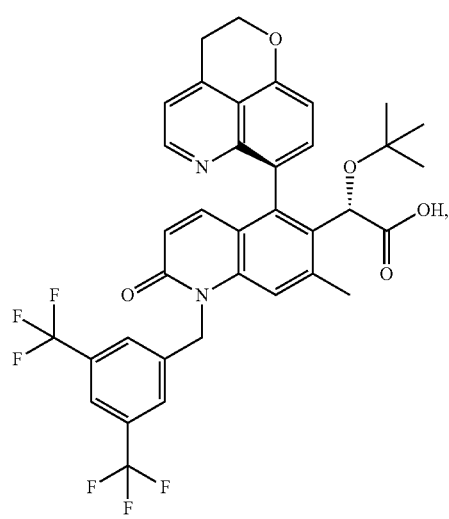
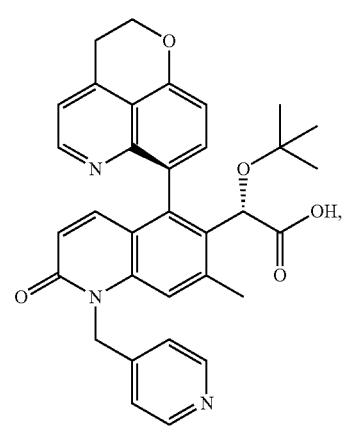
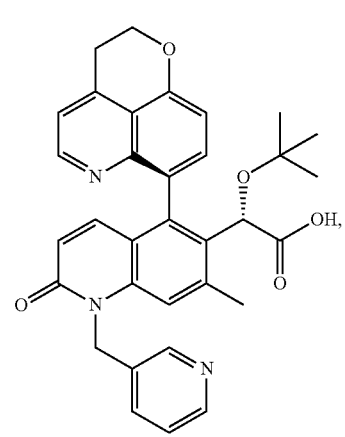
56
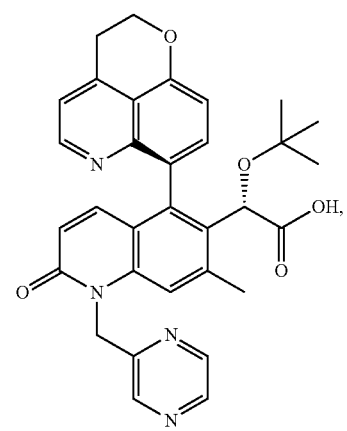
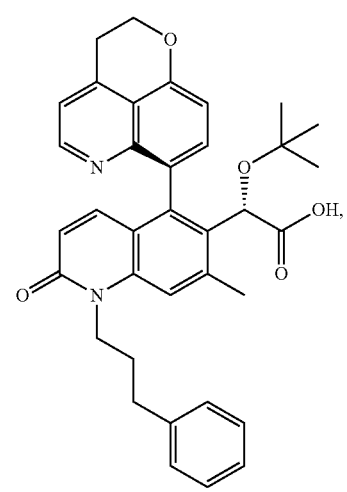
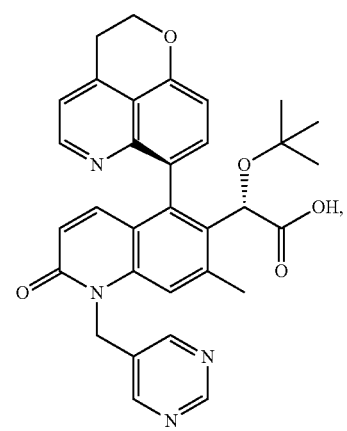

57
-continued
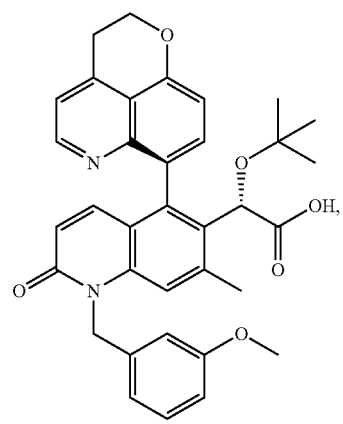
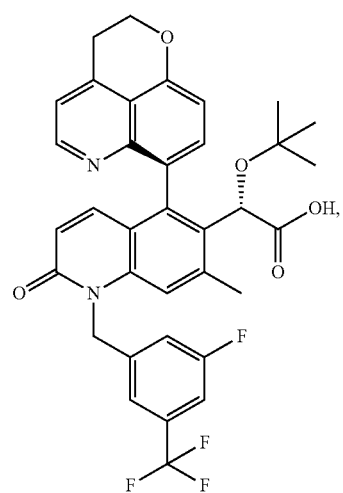
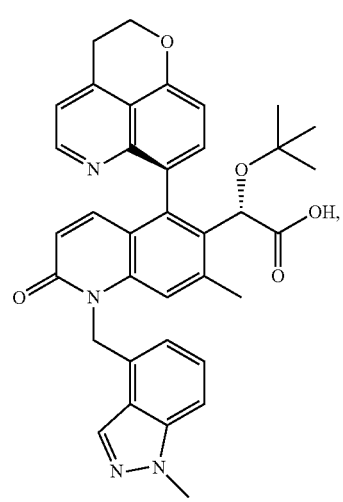
58
-continued
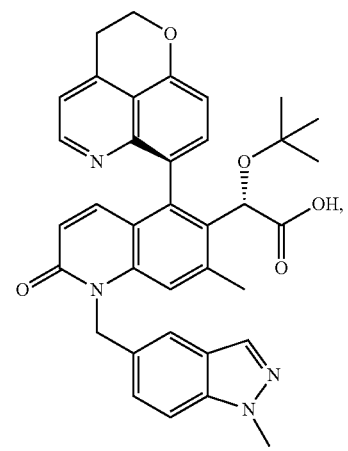
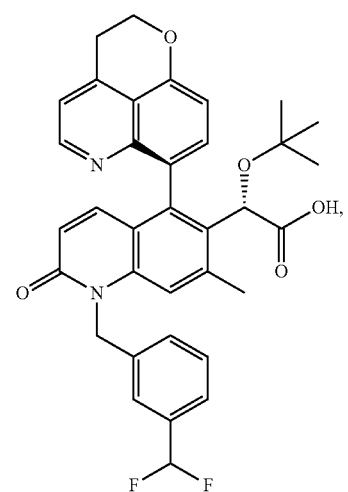
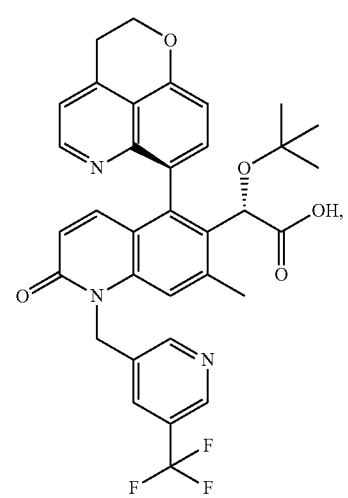

59
-continued
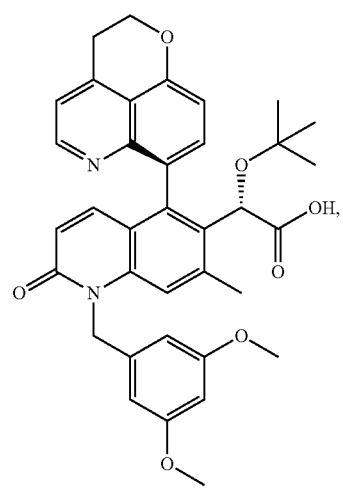
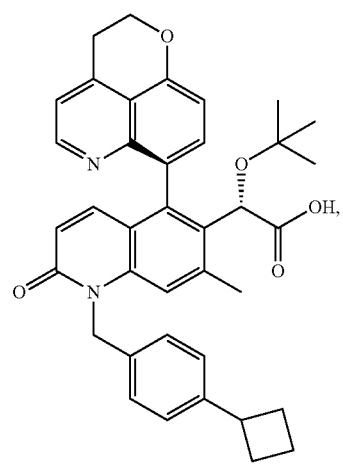
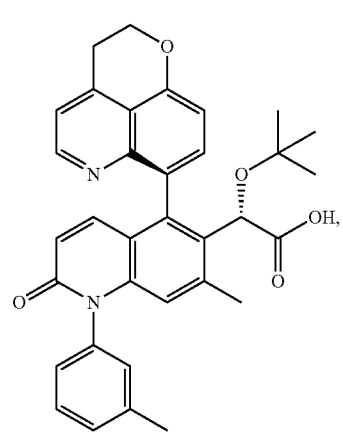
60
-continued
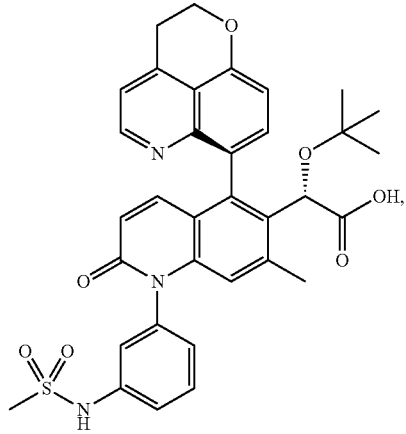
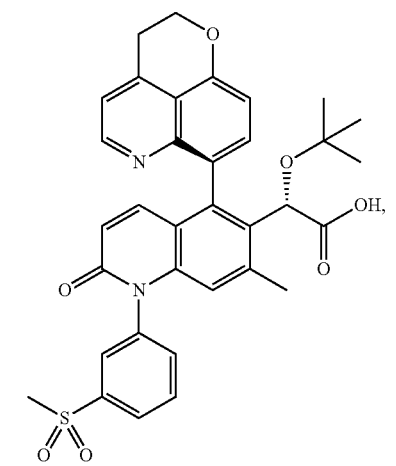
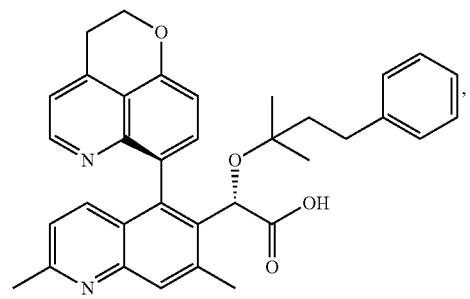
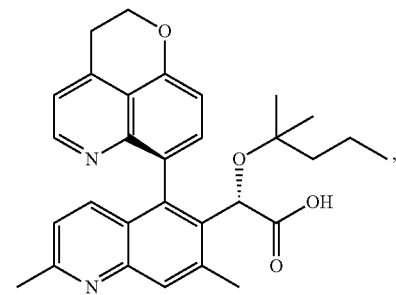

61
-continued
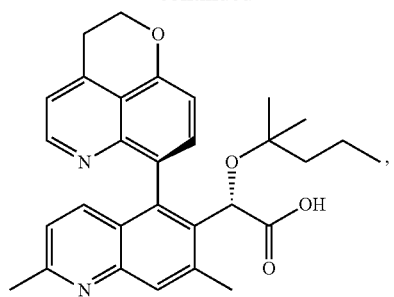
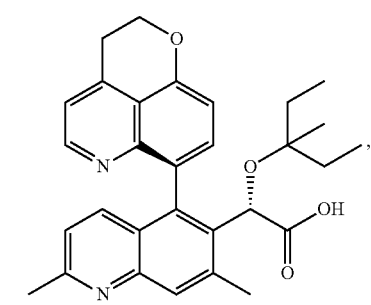
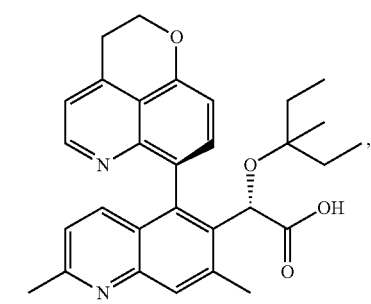
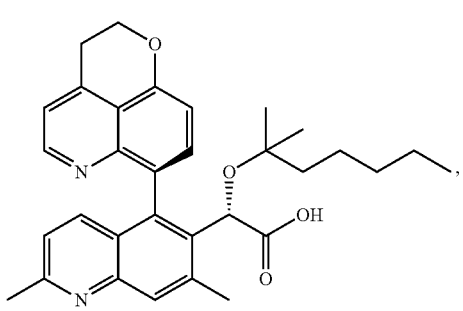
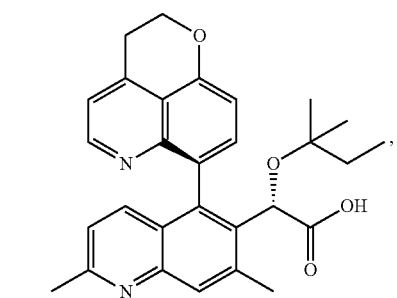
62
-continued
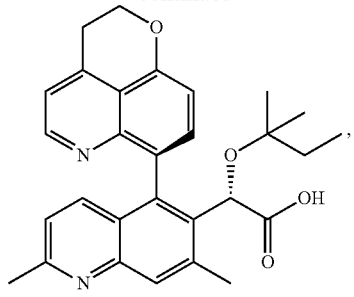
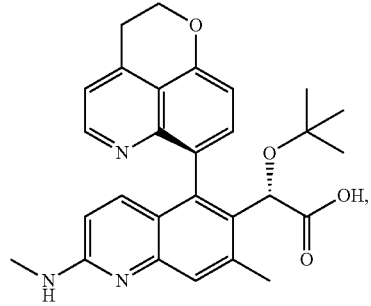
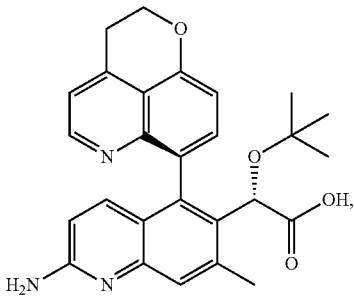
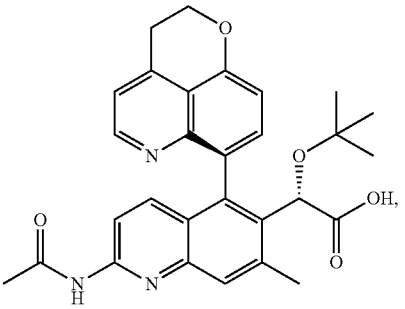
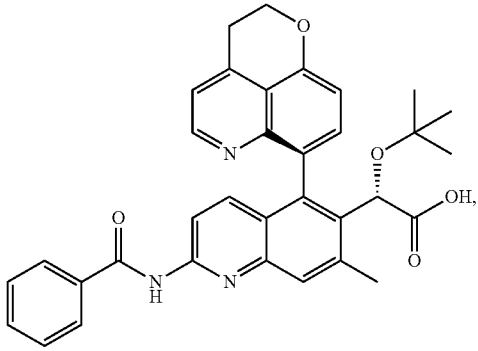

-continued
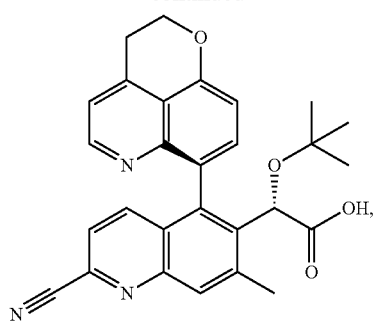
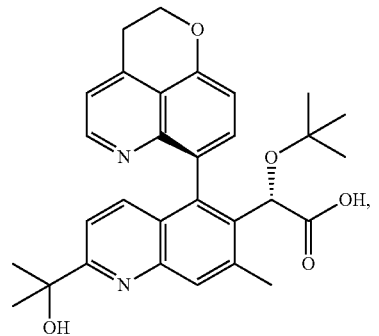
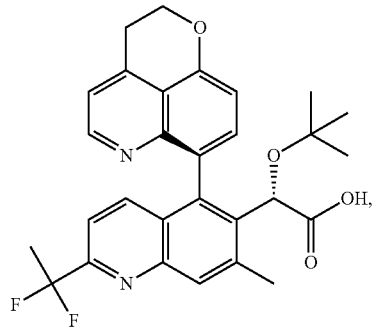
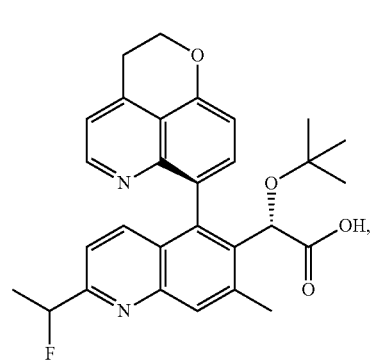
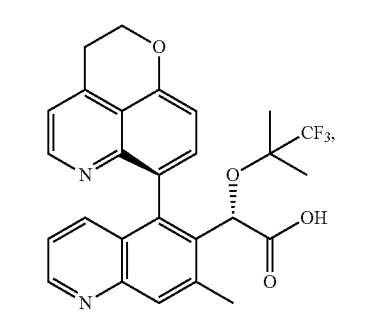
-continued
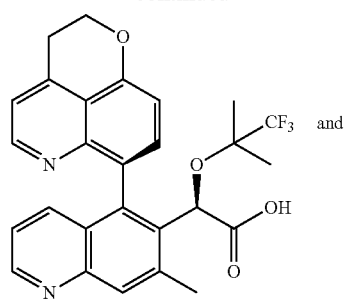
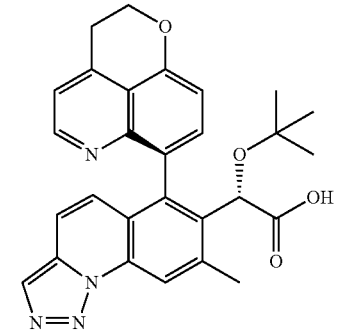
and salts thereof.
In one embodiment, compounds are selected from:
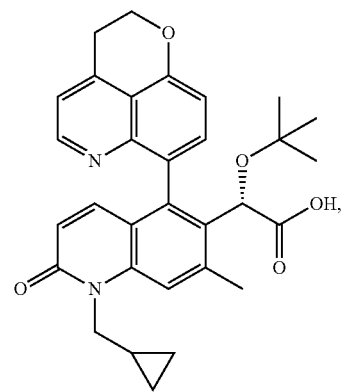
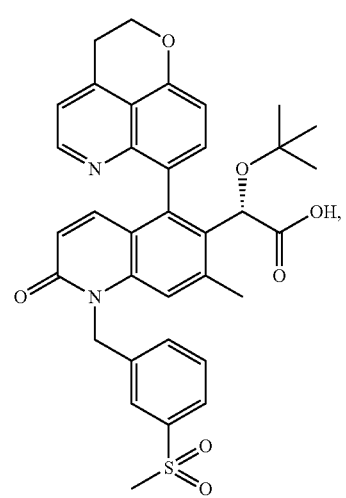

65
-continued
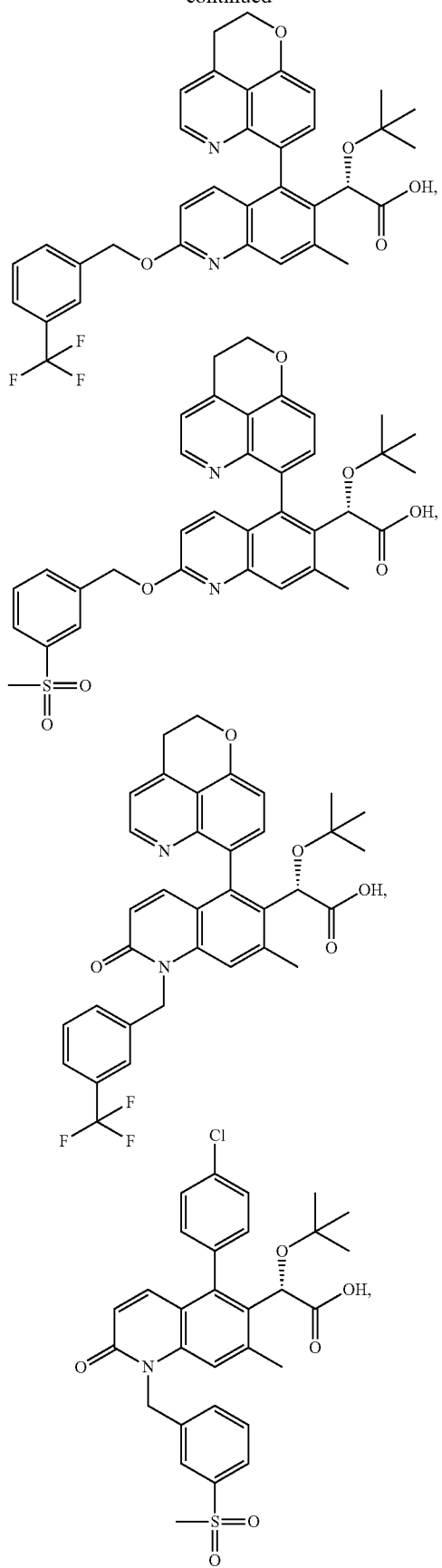
66
-continued
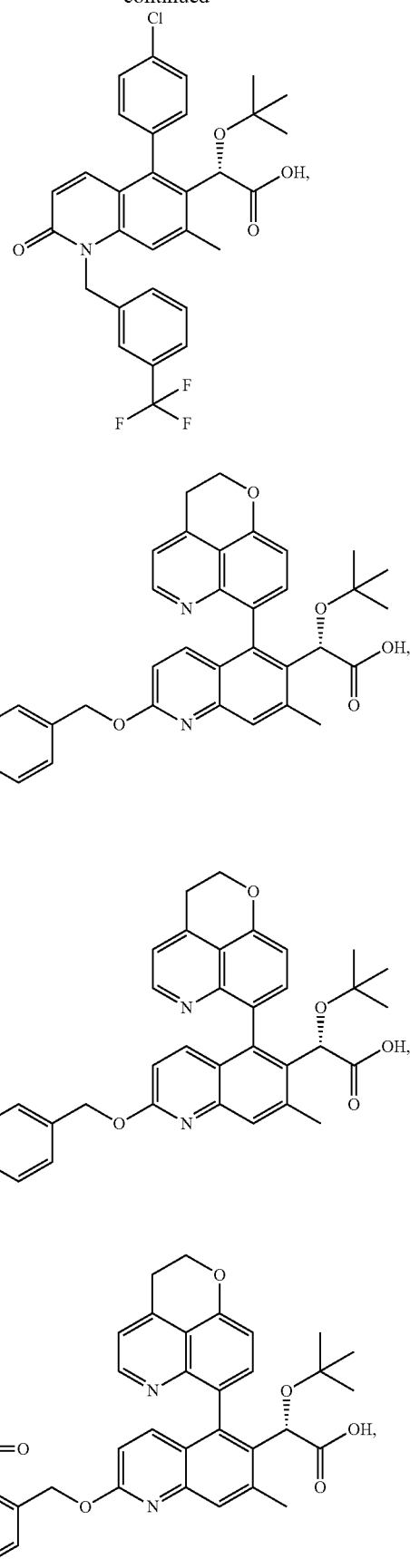

67
-continued
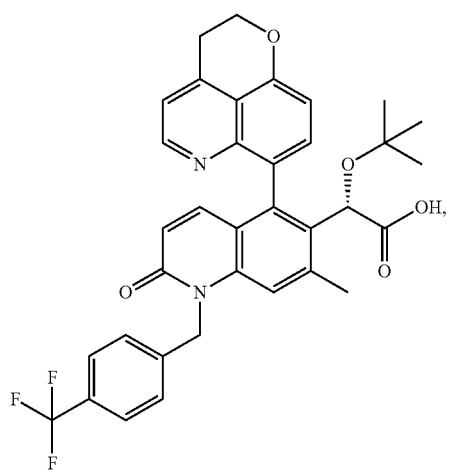
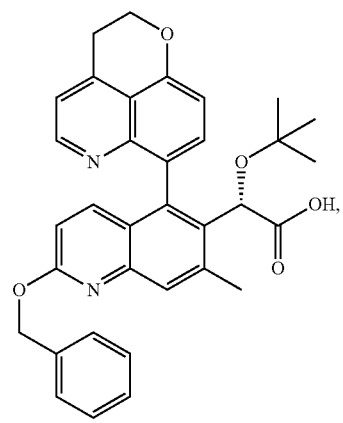
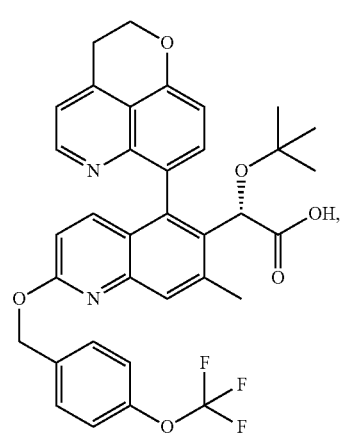
68
-continued
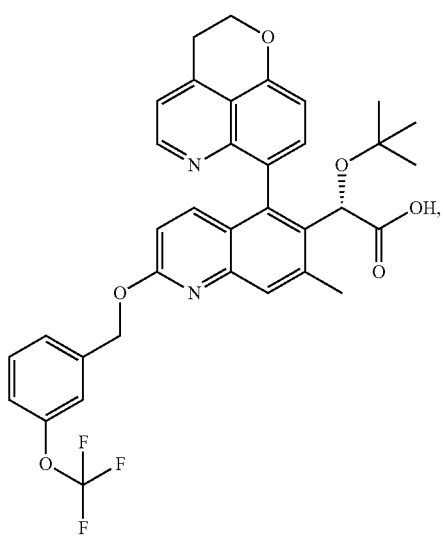
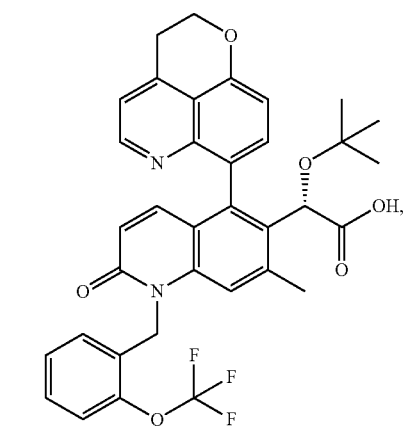
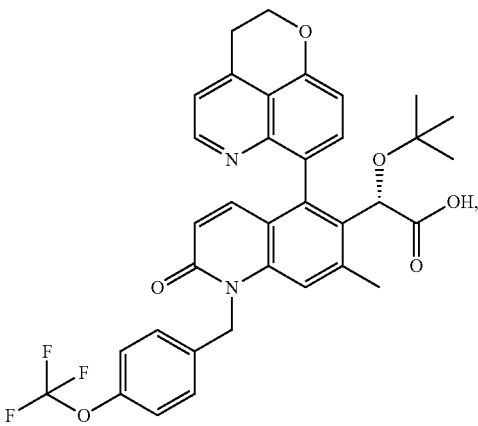

-continued
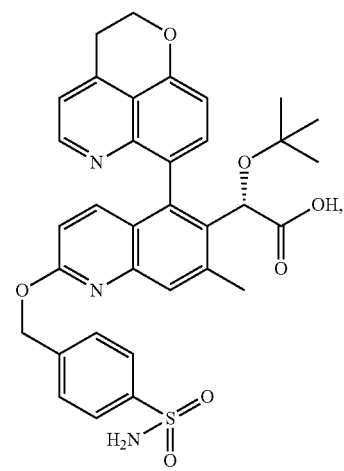
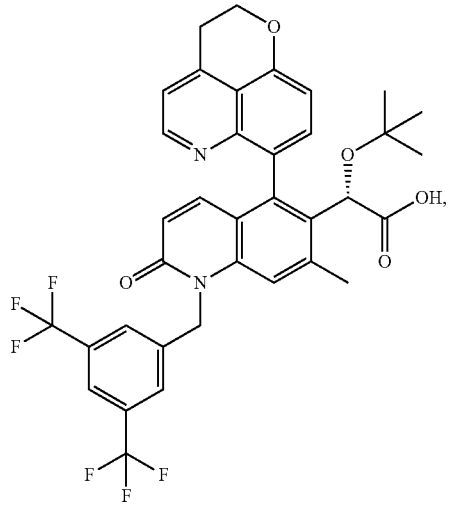
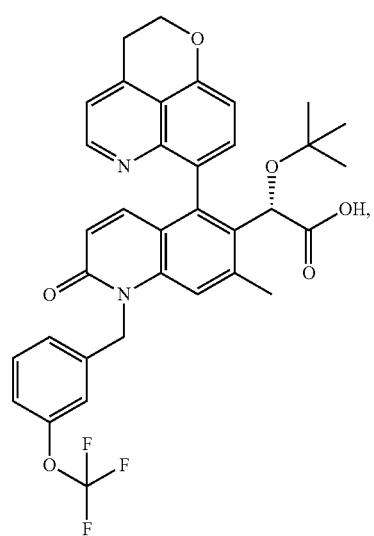
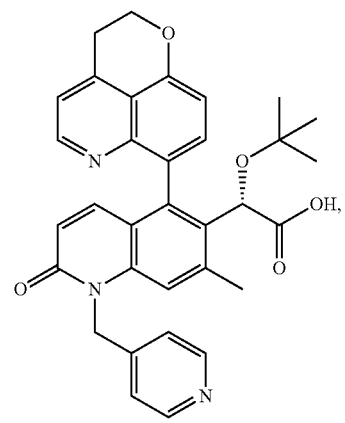
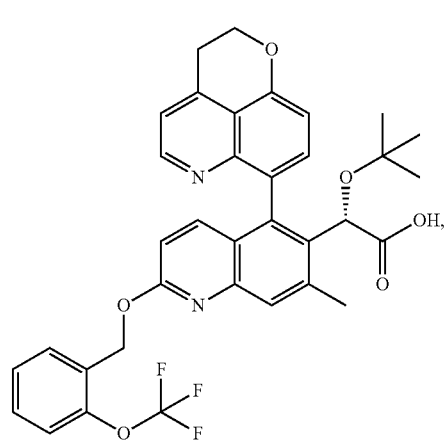
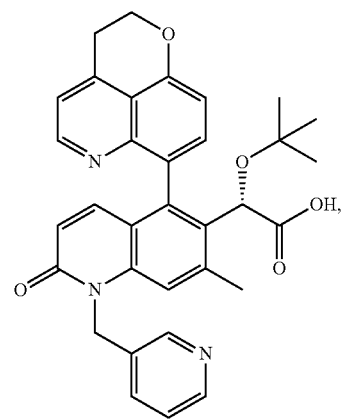

71
-continued
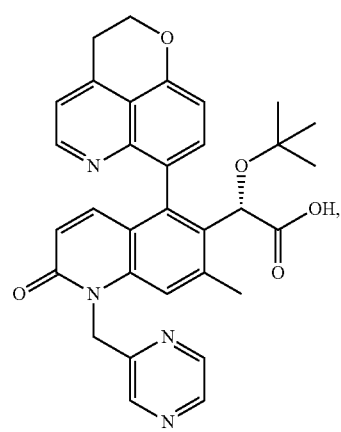
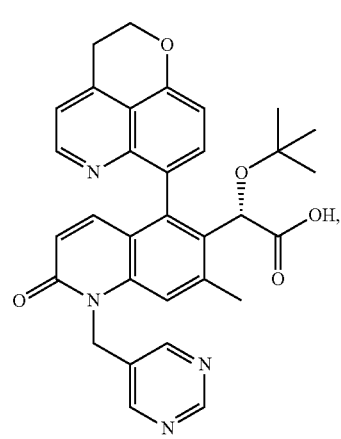
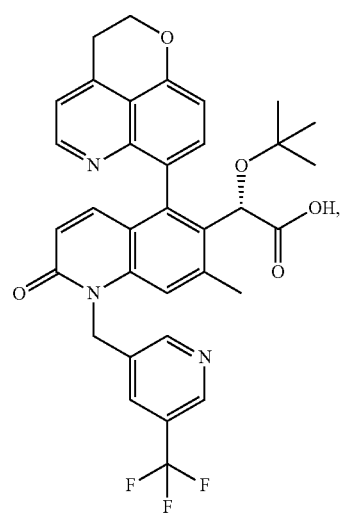
72
-continued
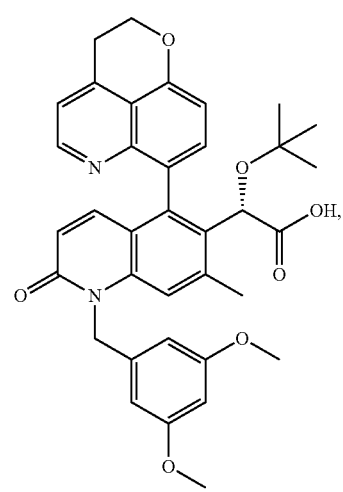
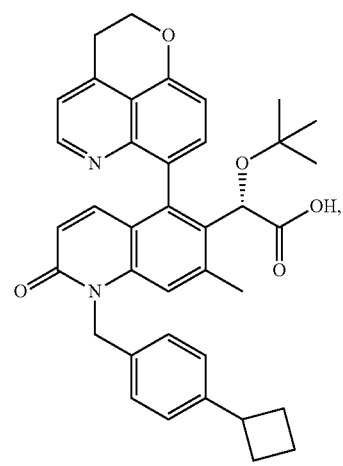
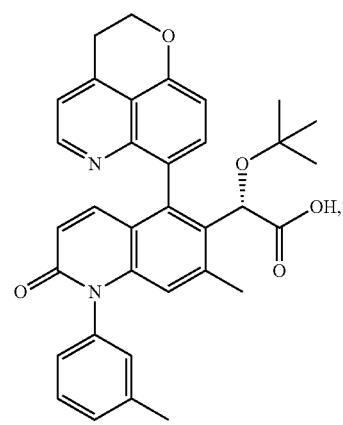

73
-continued
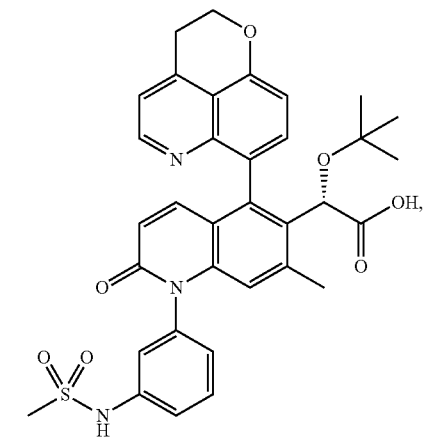
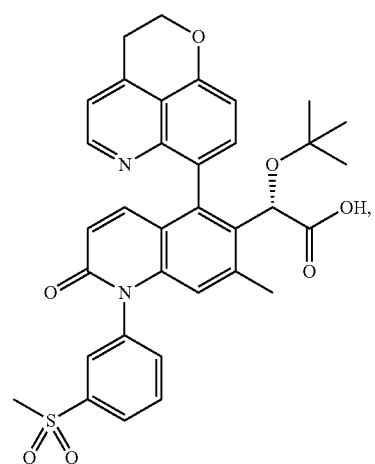
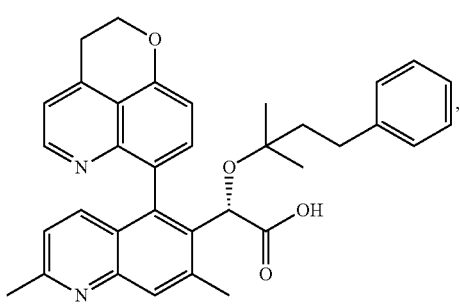
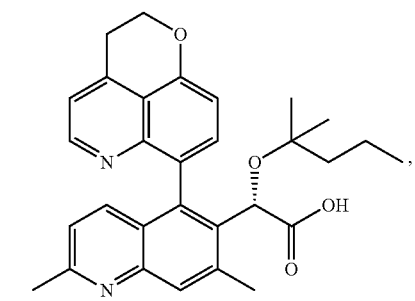
74
-continued
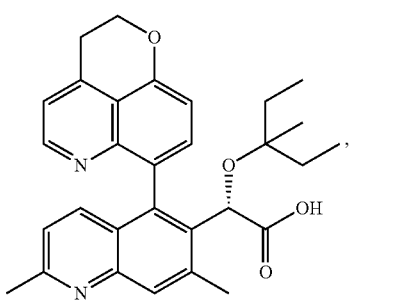
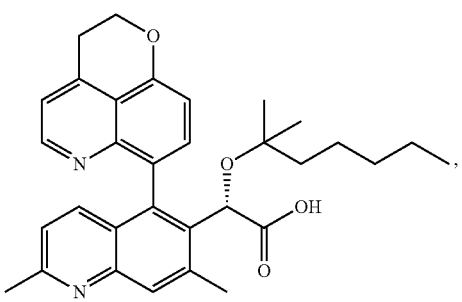
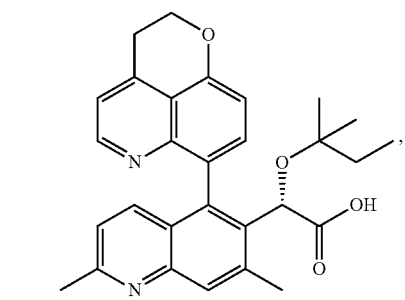
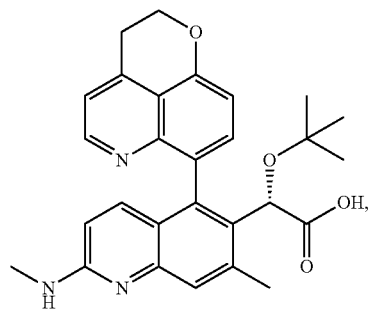
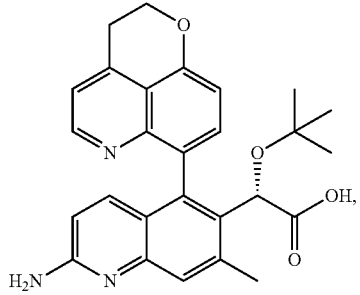

75
-continued
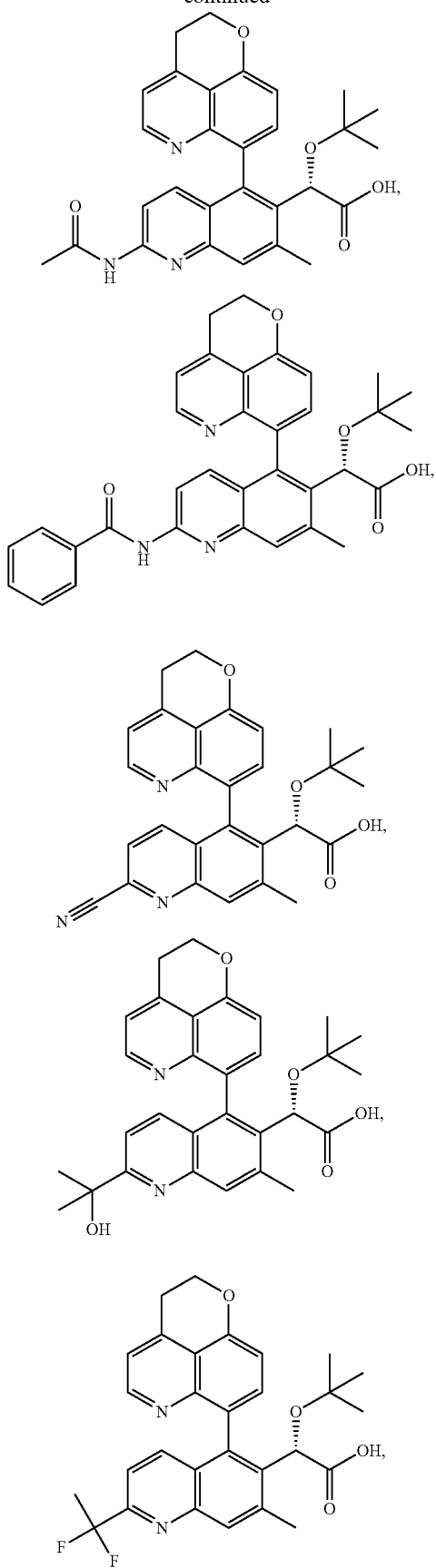
76
-continued
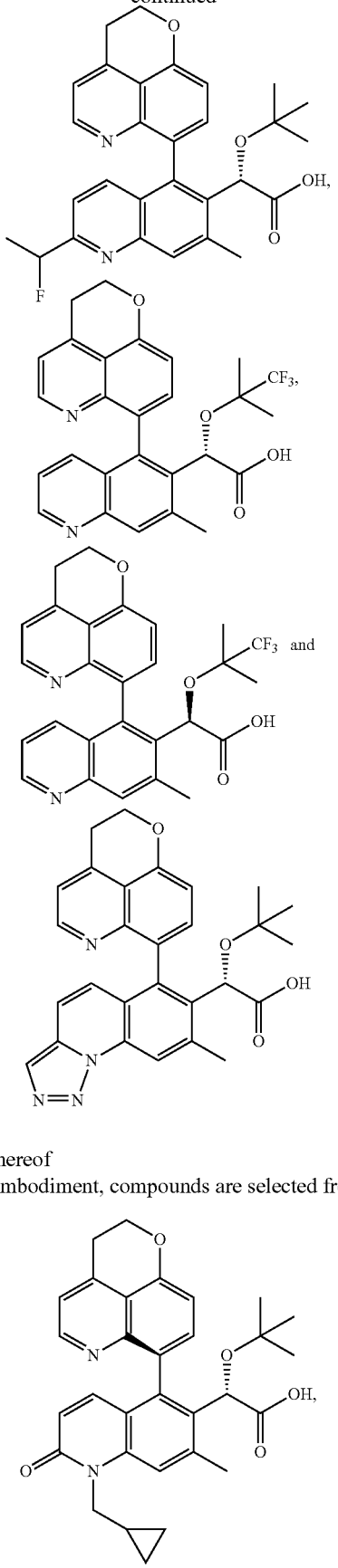
and salts thereof
In one embodiment, compounds are selected from:

77
-continued
78
-continued
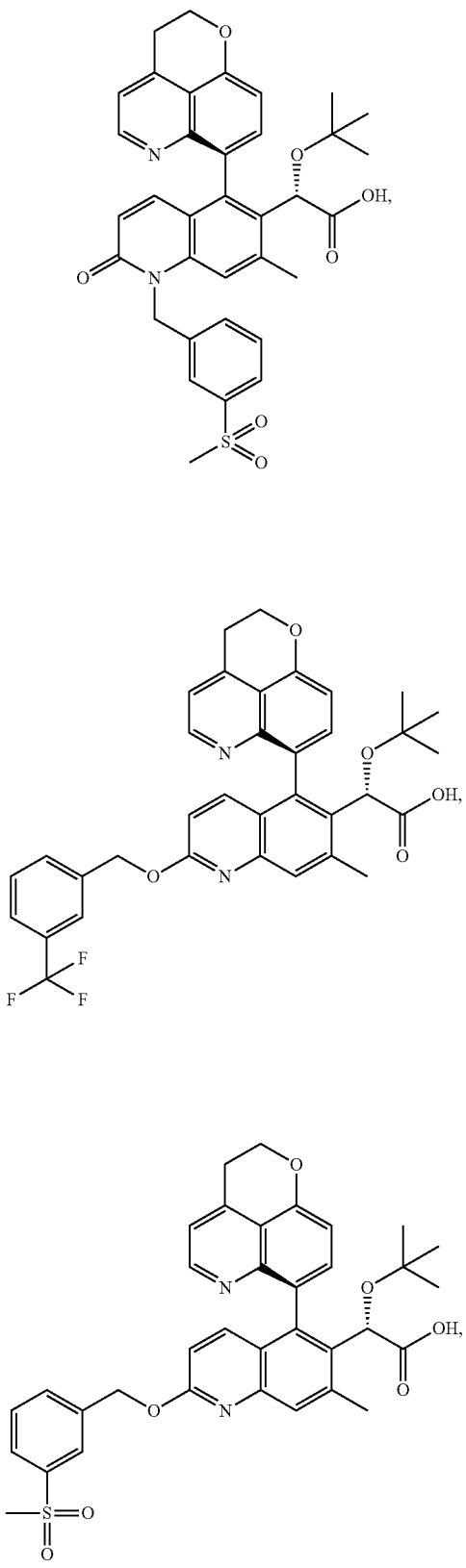
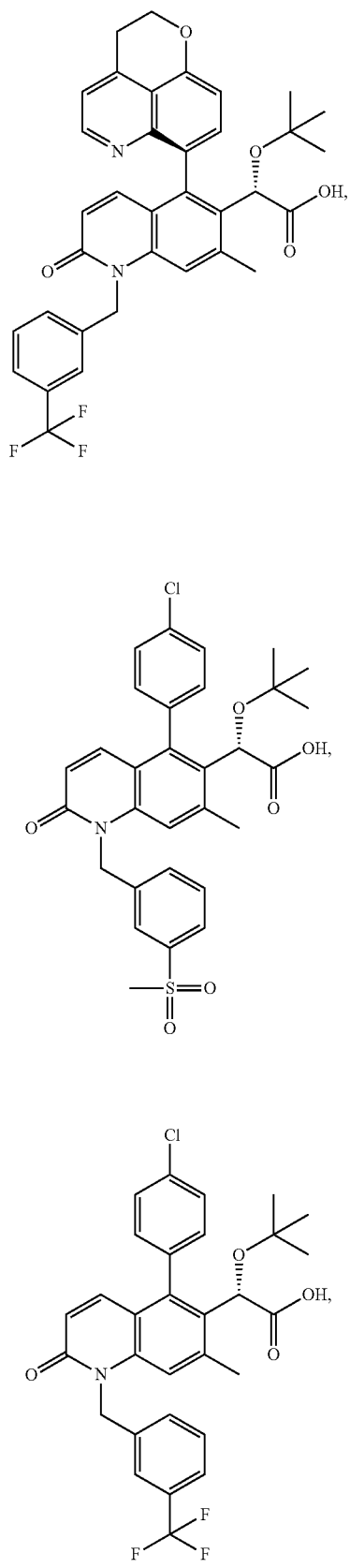

79
-continued
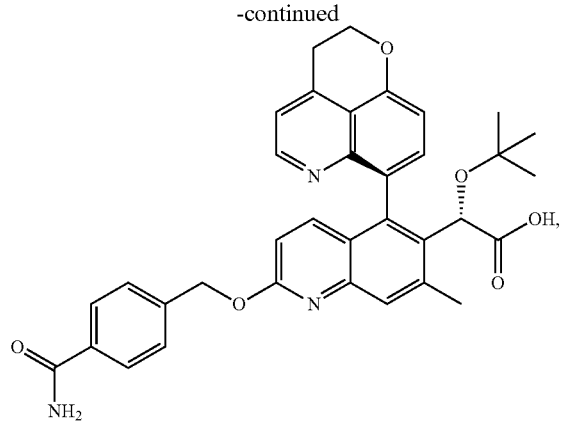
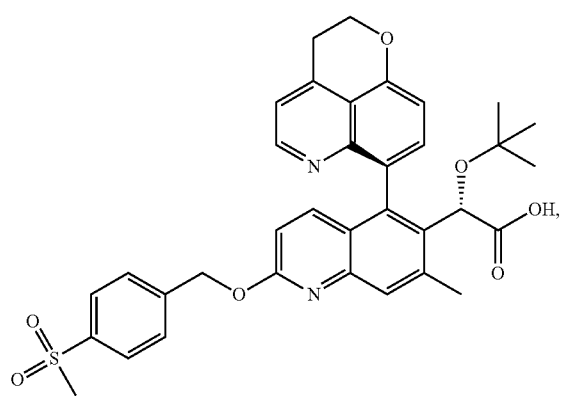
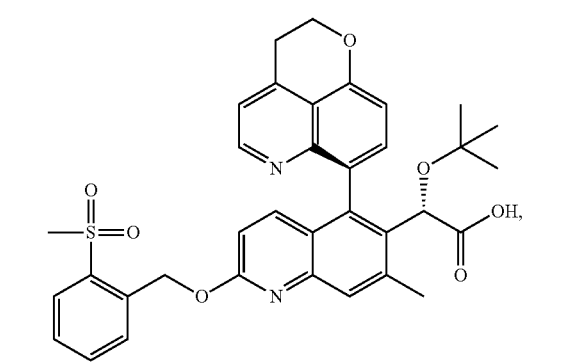
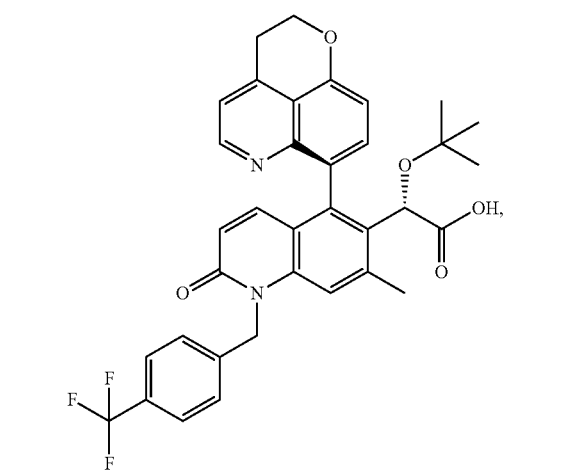
80
-continued
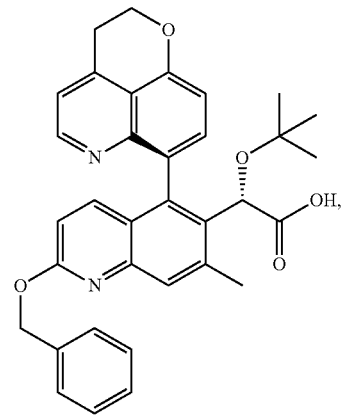
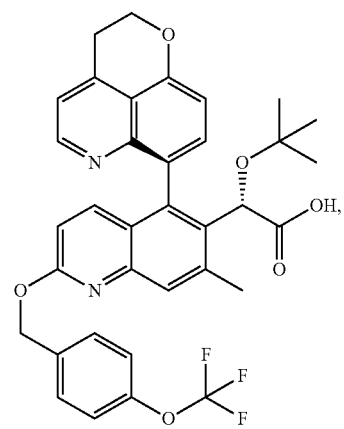
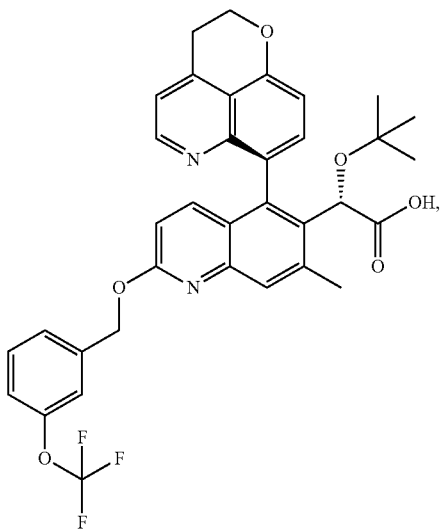

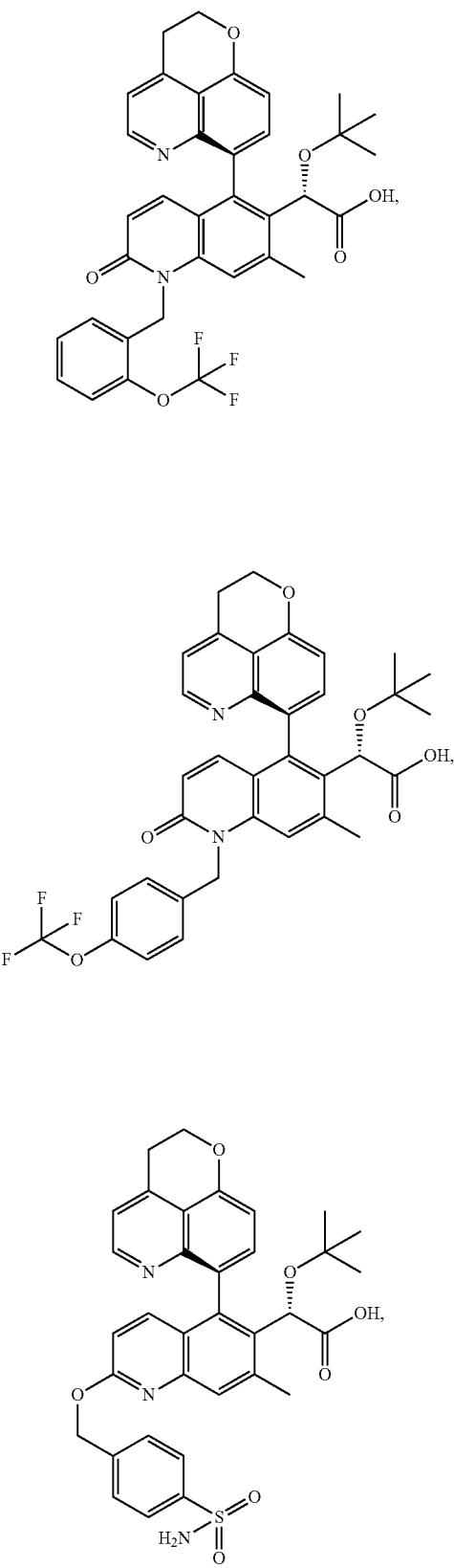
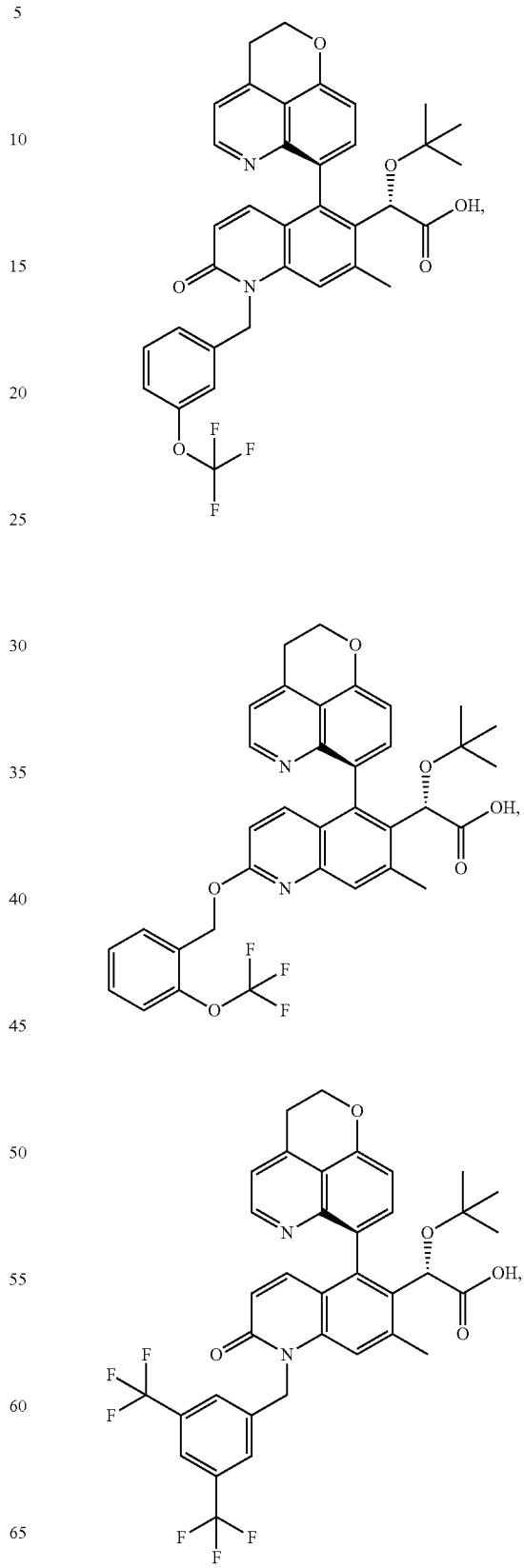

83
-continued
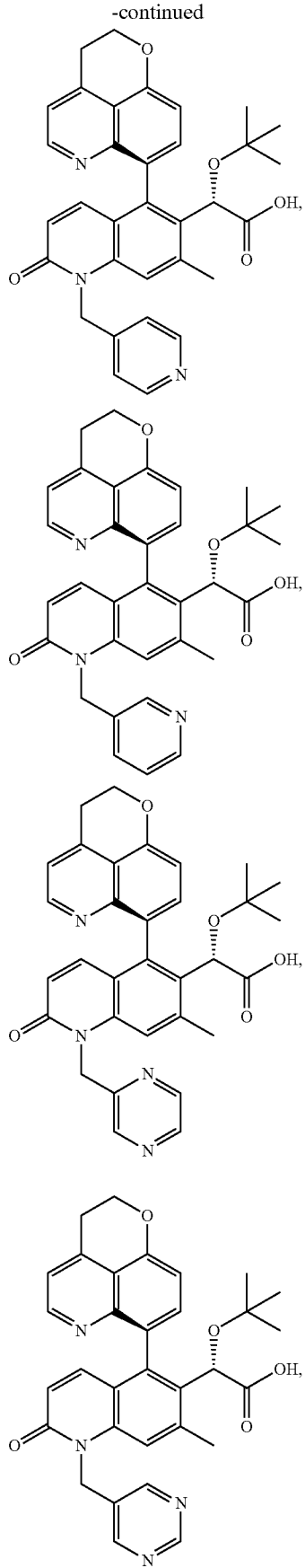
84
-continued
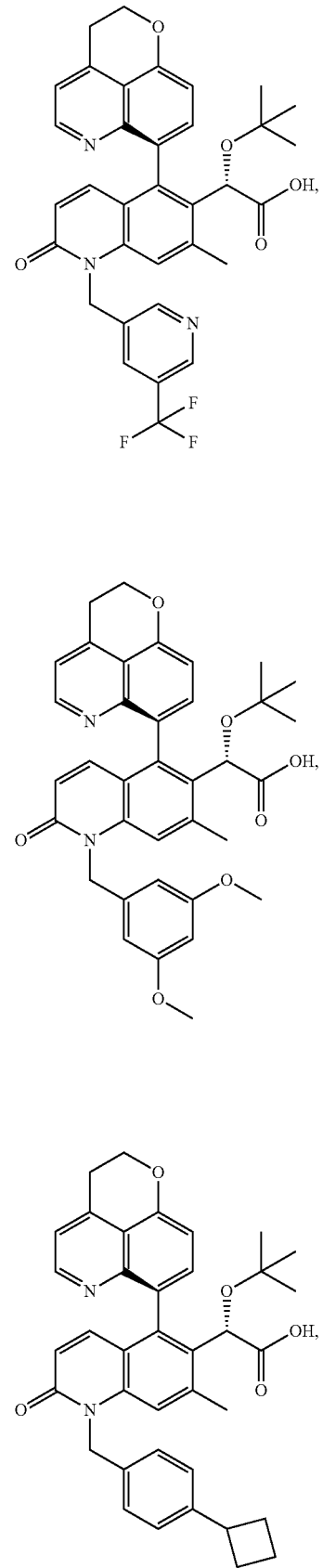

85
-continued
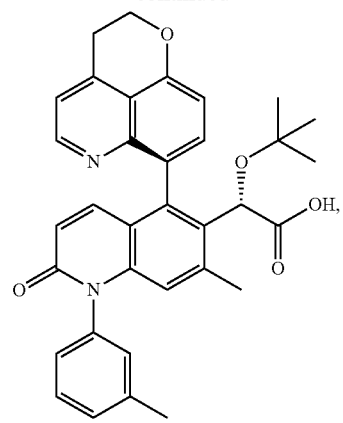
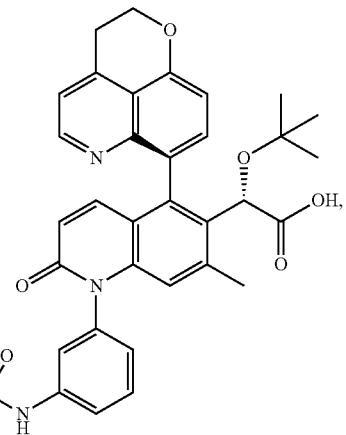
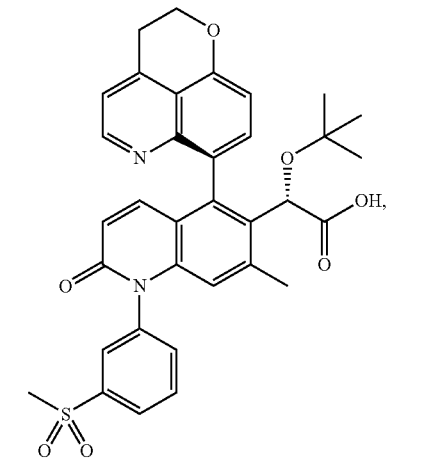
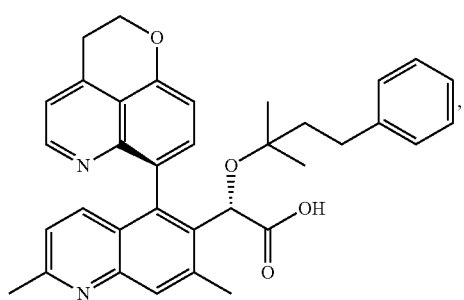
86
-continued
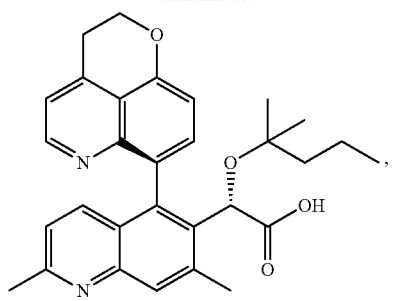
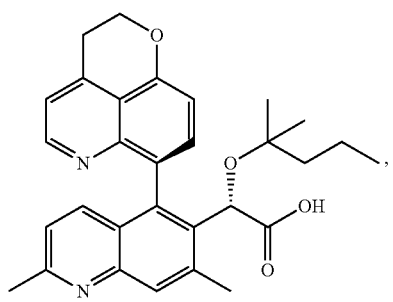
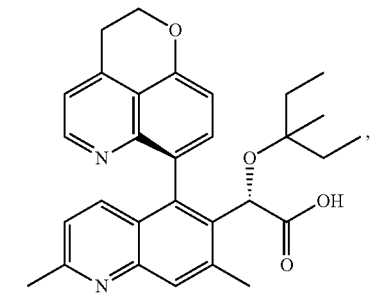
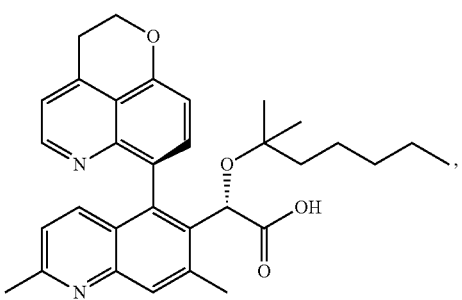

87
-continued
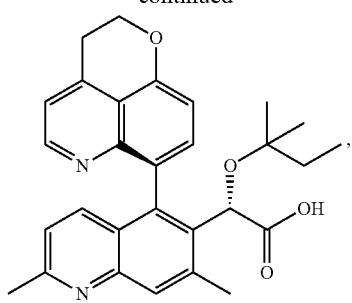
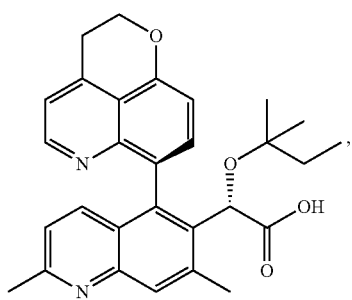
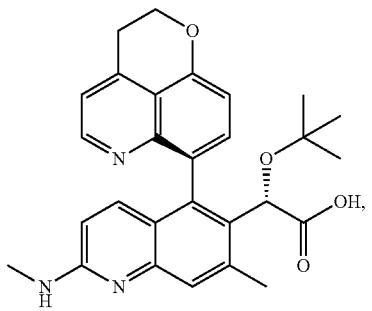
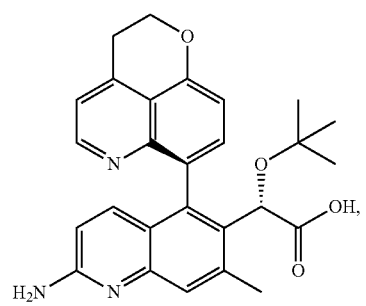
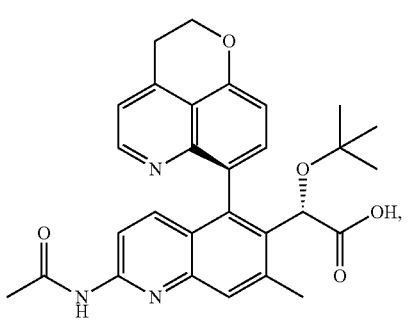
88
-continued
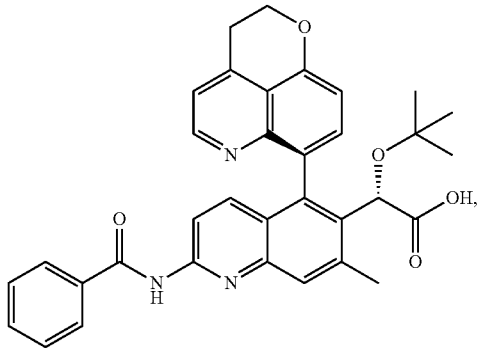
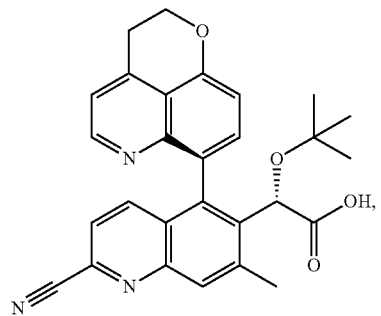
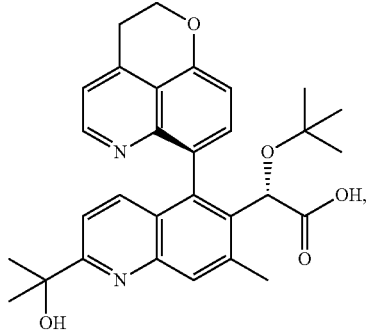
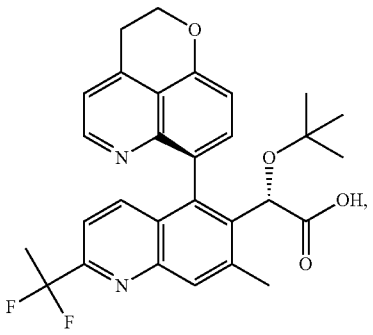
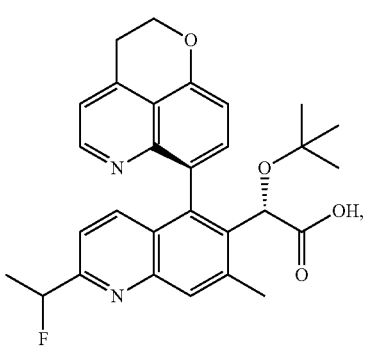

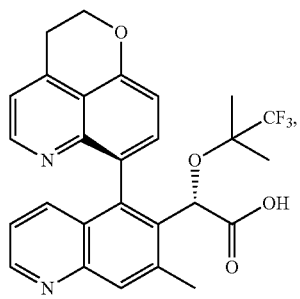
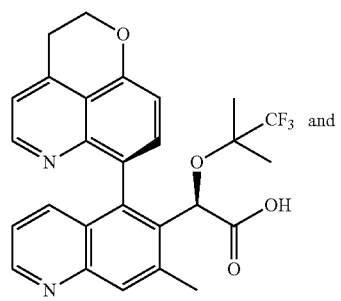 and
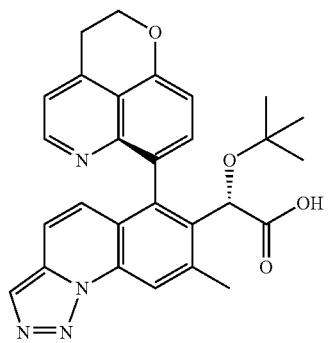
and salts thereof.
In one embodiment, compounds are selected from:
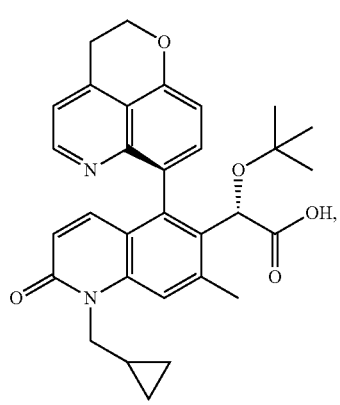
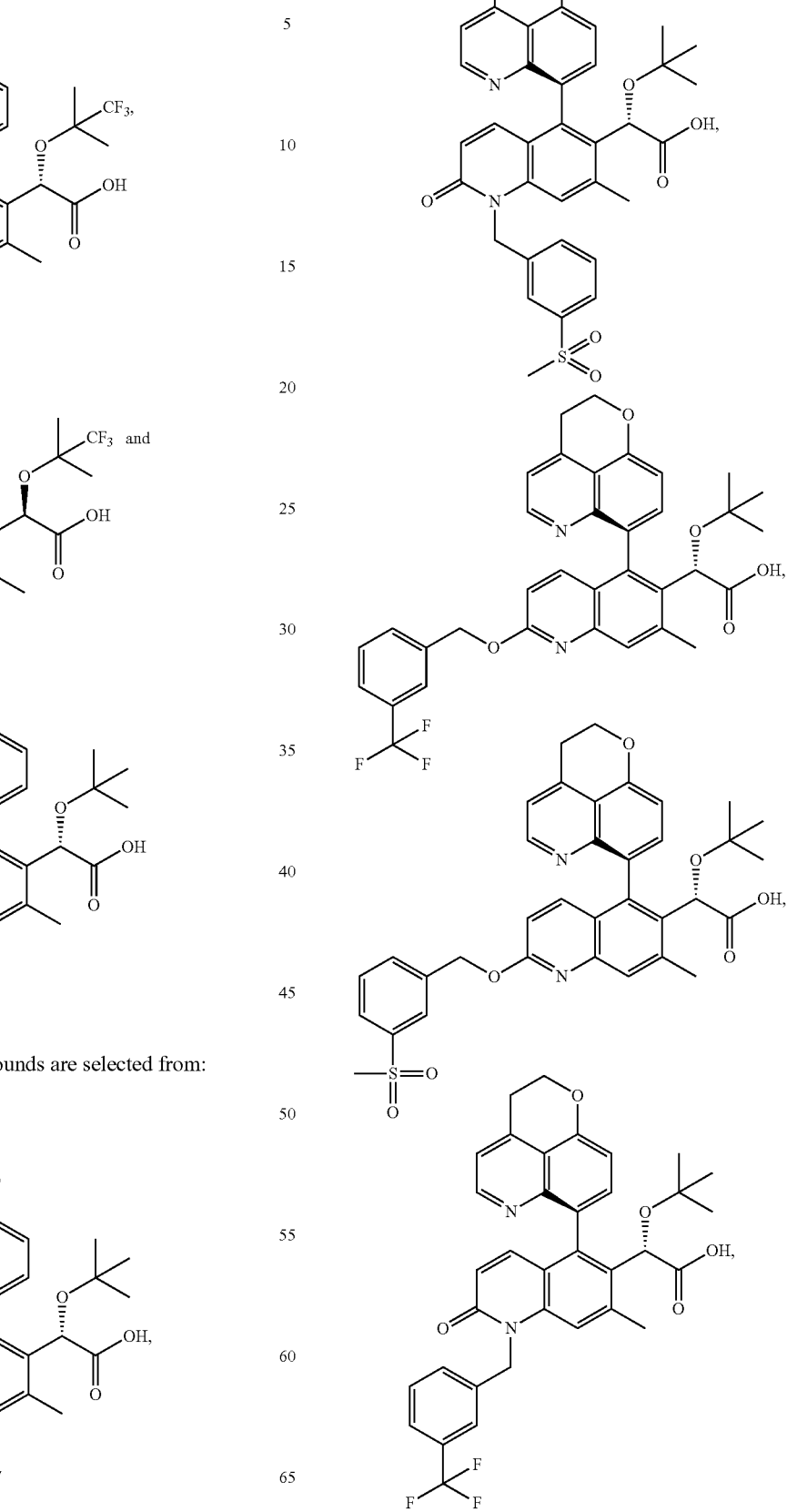

91
-continued
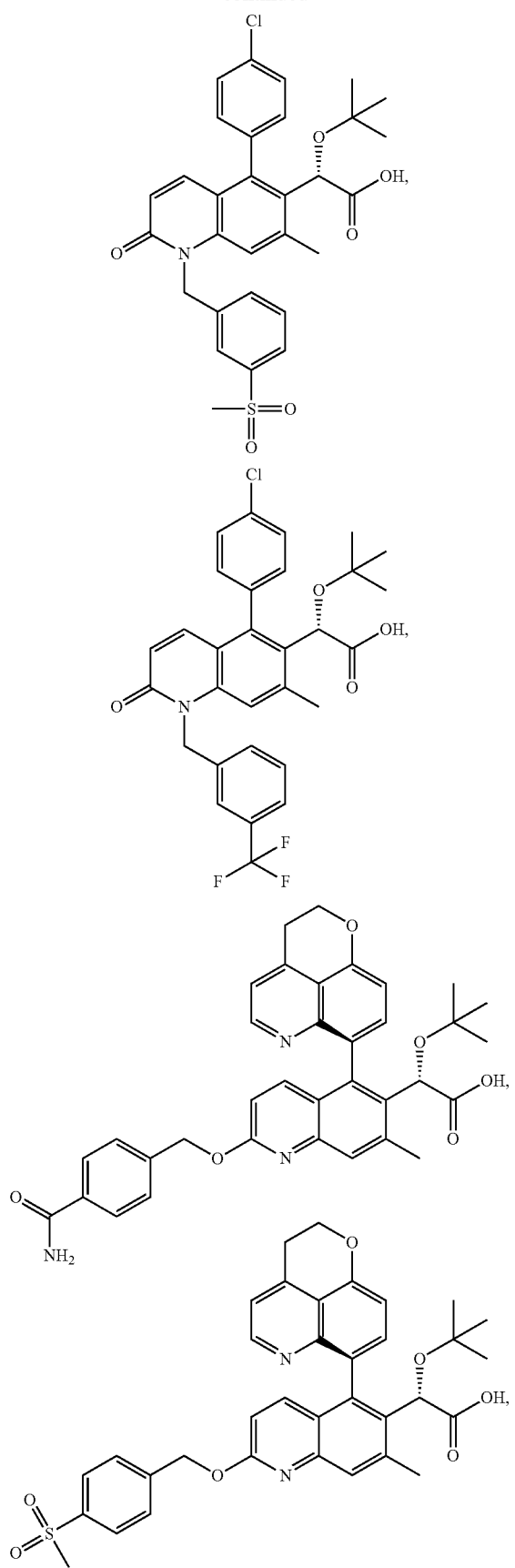
92
-continued
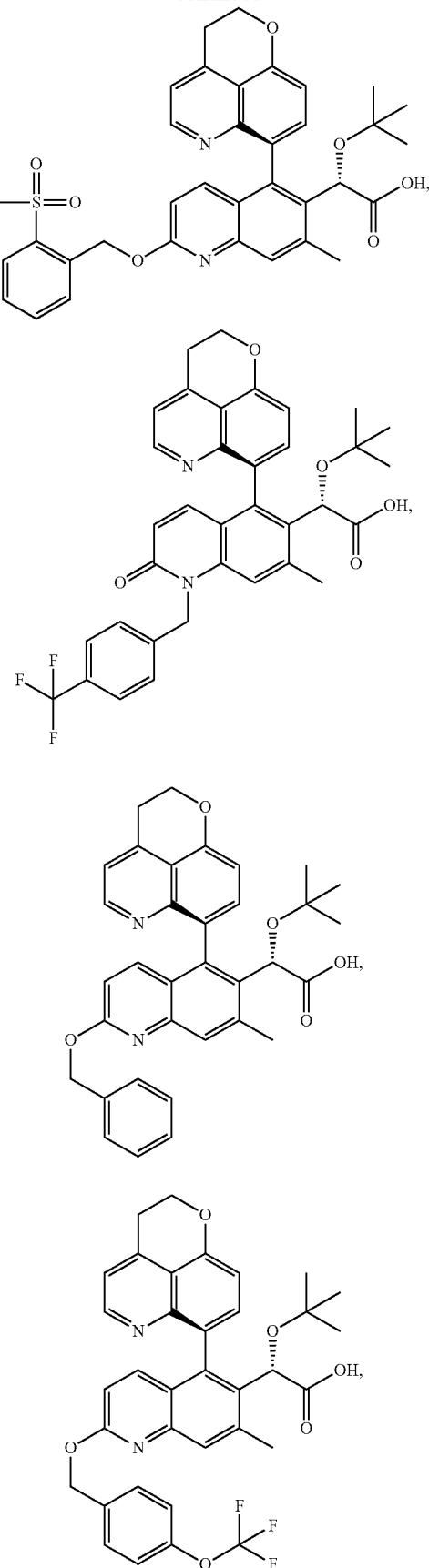

93
-continued
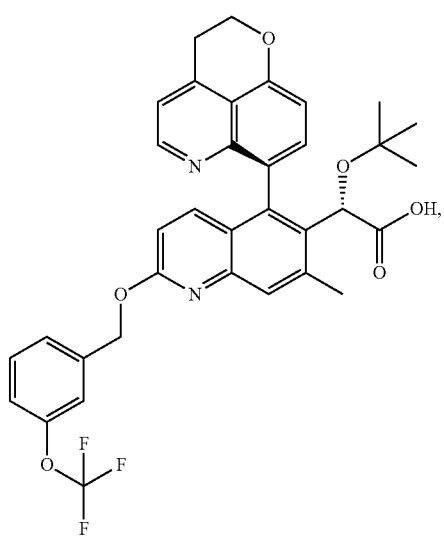
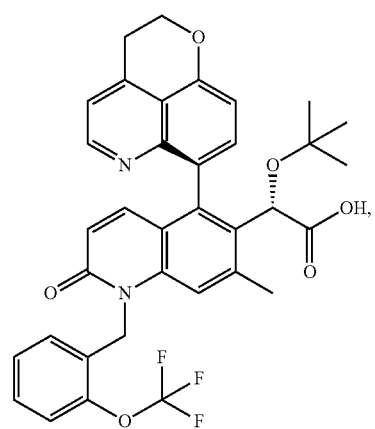
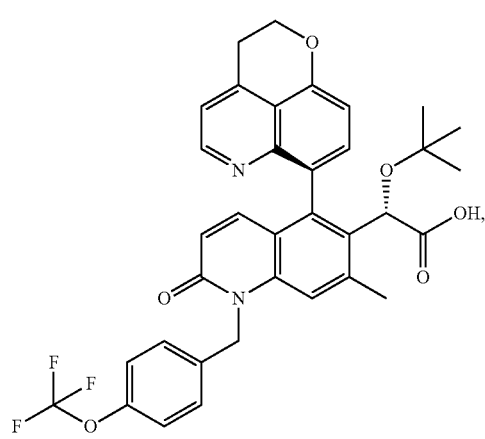
94
-continued
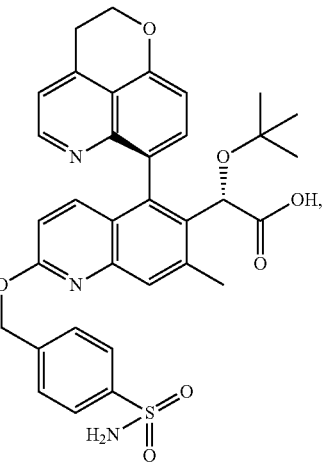
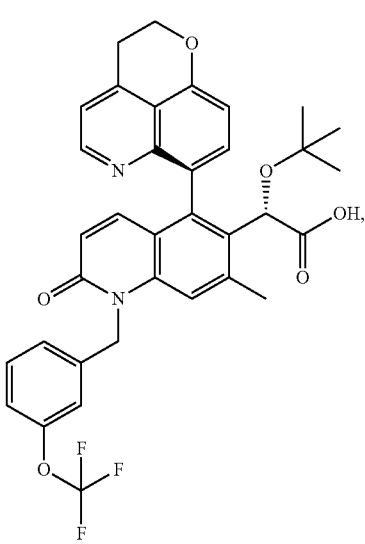
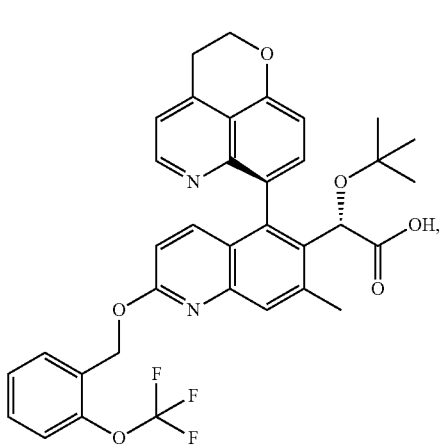

95
-continued
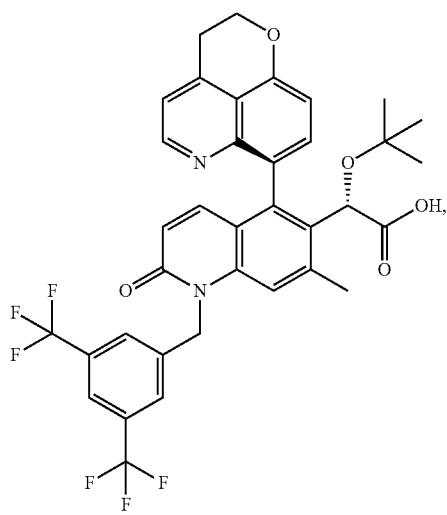
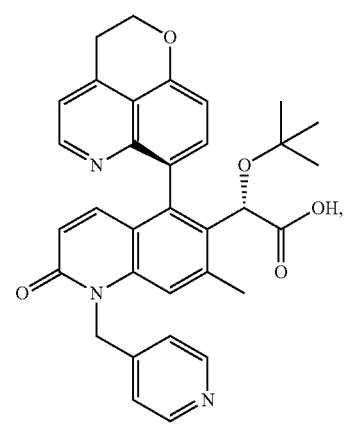
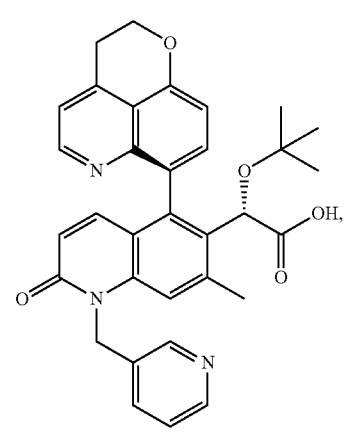
96
-continued
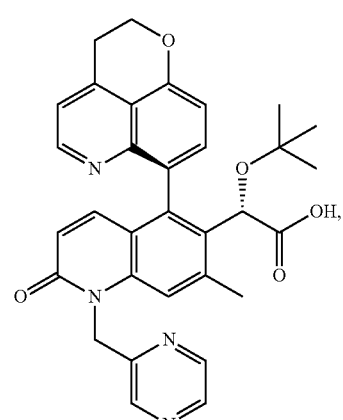
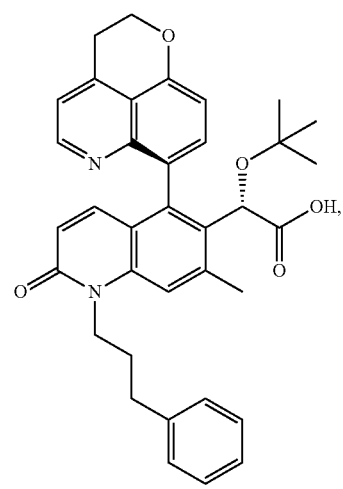
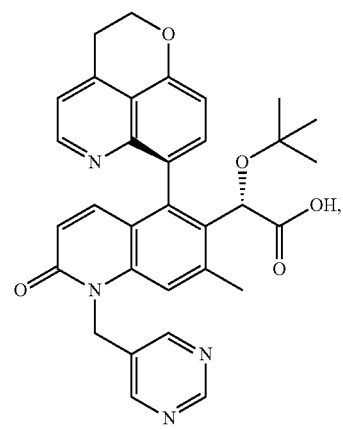

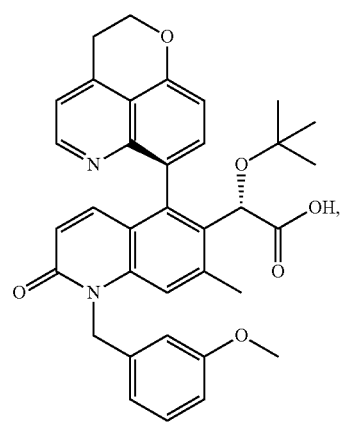
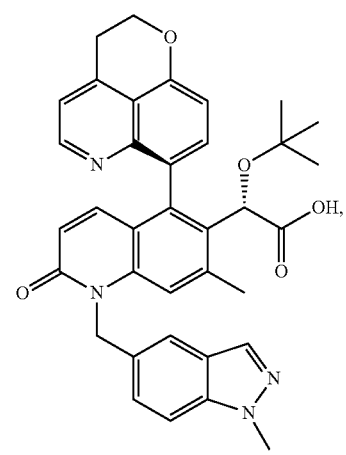
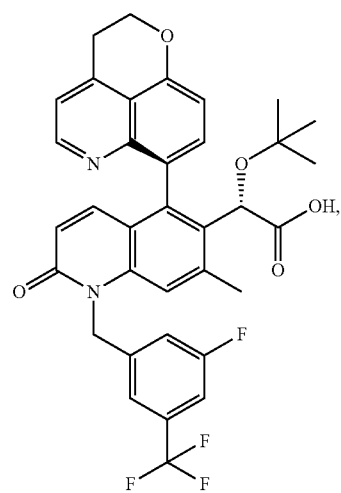
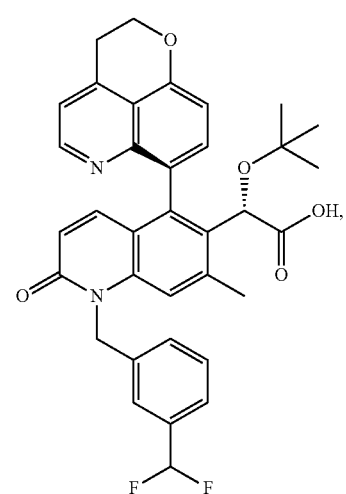
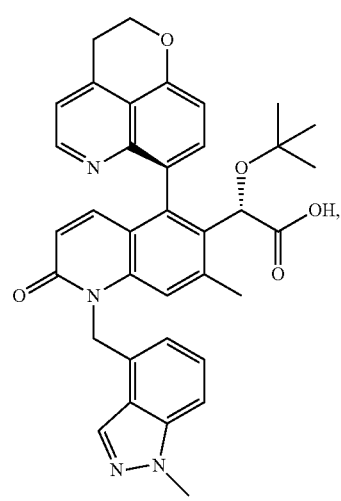
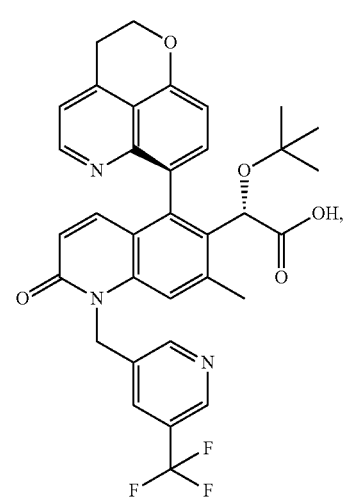

99
-continued
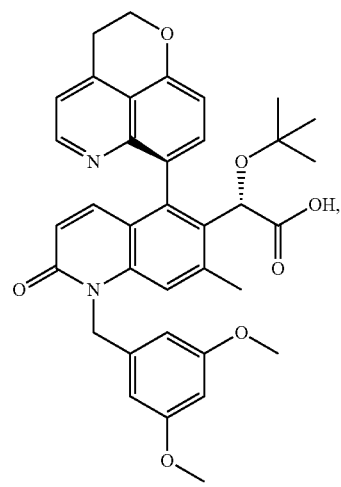
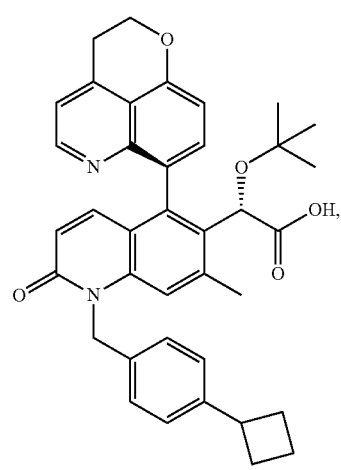
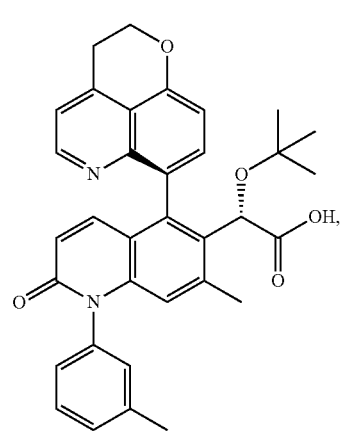
100
-continued
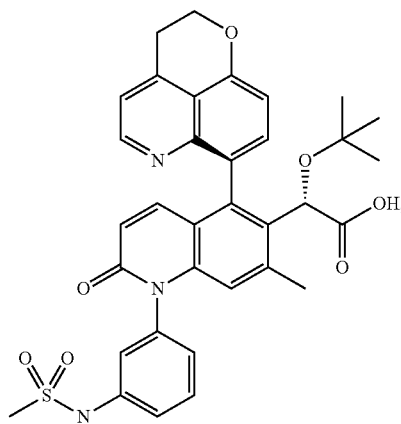
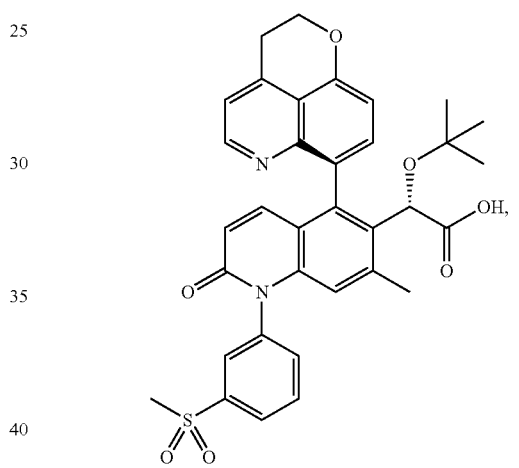
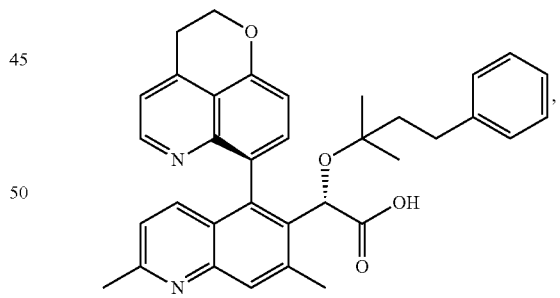
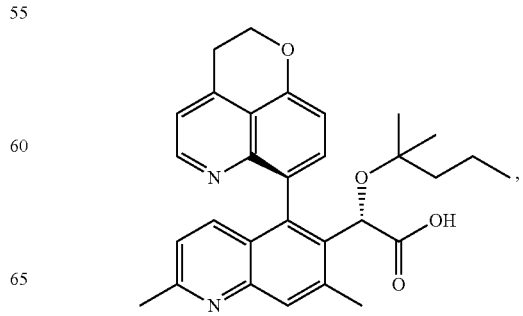

-continued
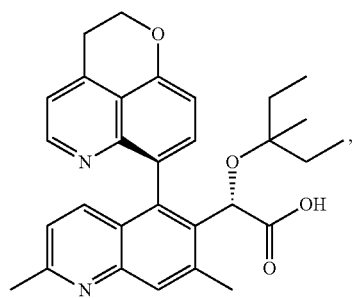
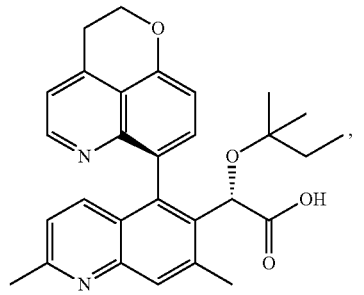
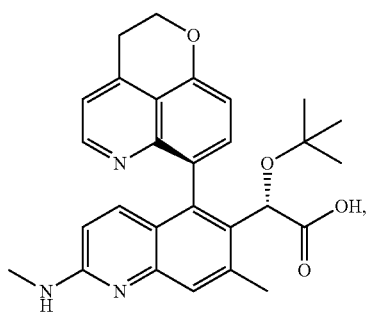
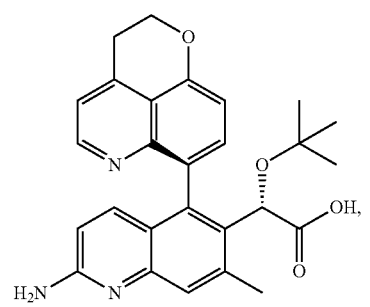
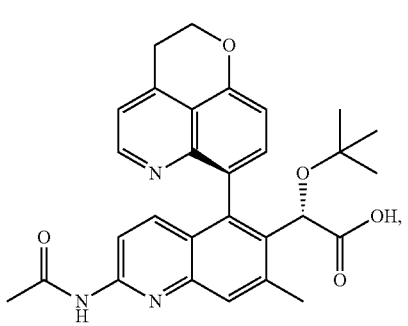
-continued
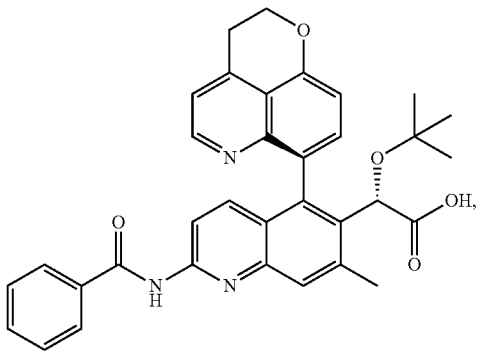
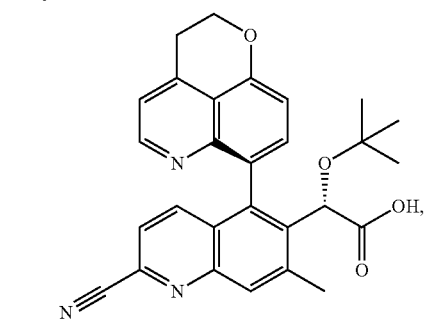
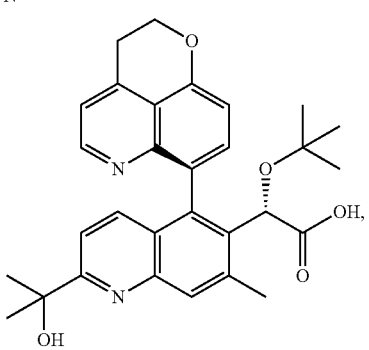
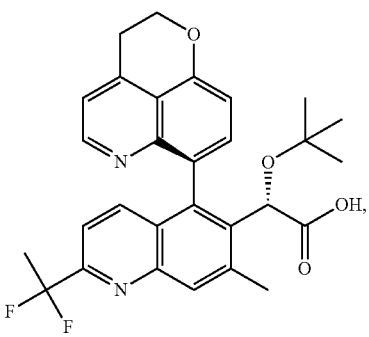
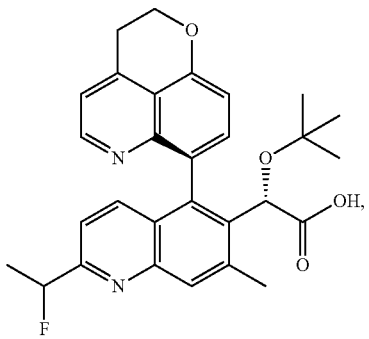

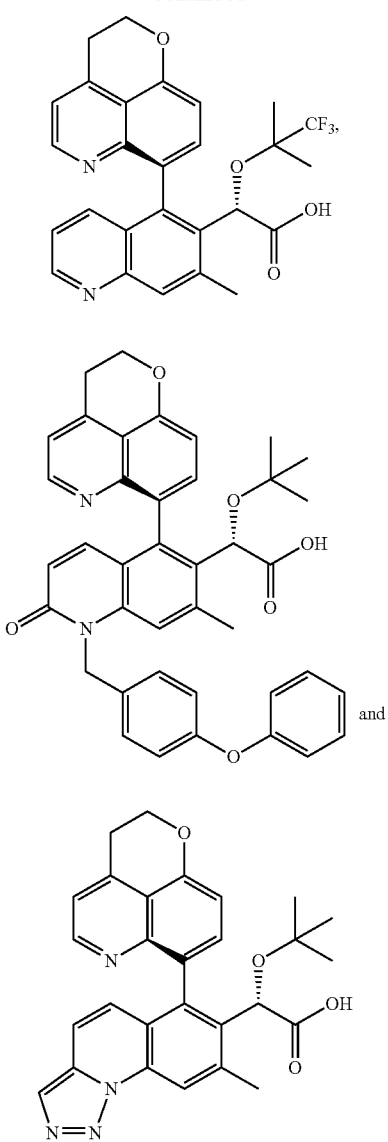
and salts thereof
In one embodiment, compounds are selected from:

105
-continued
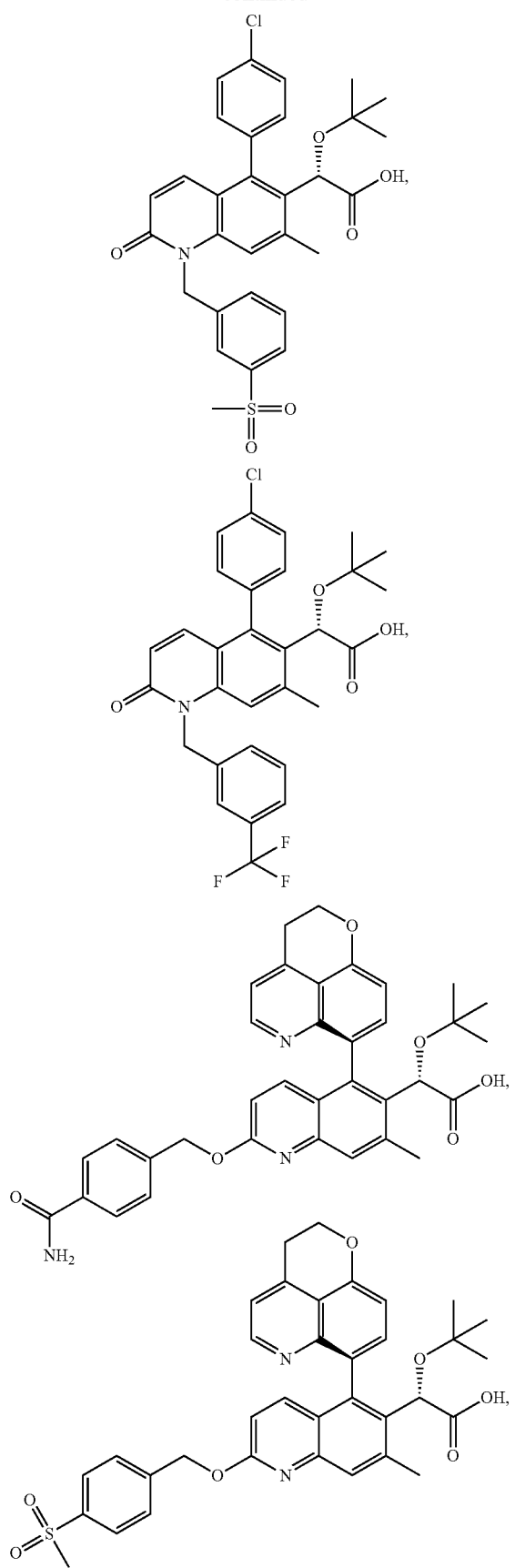
106
-continued
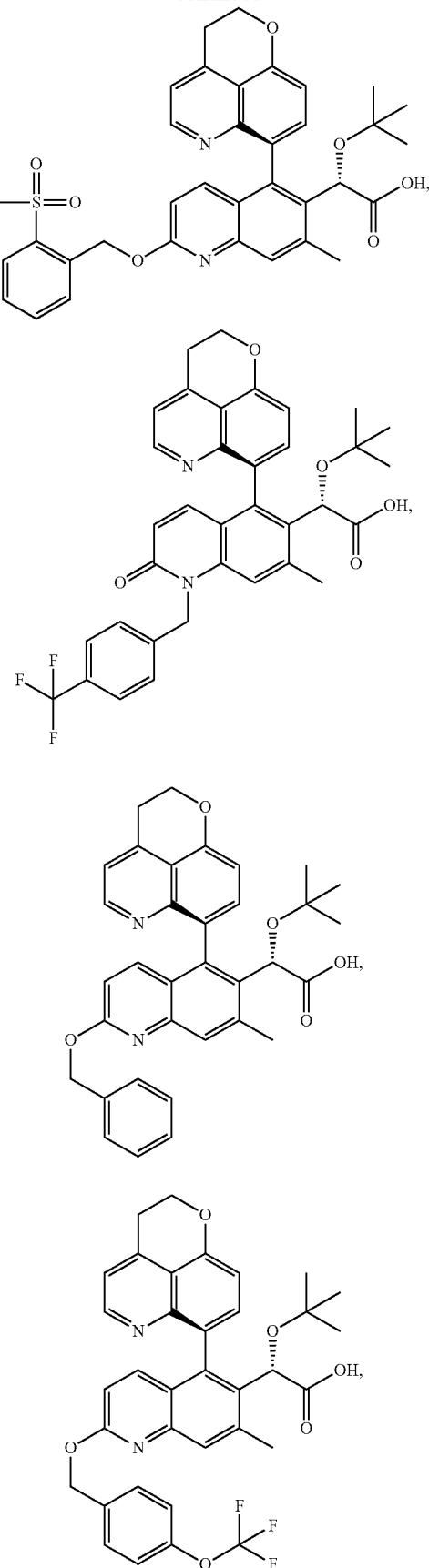

107
-continued
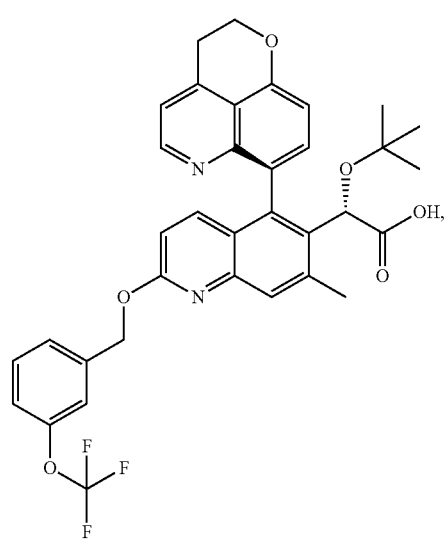
108
-continued
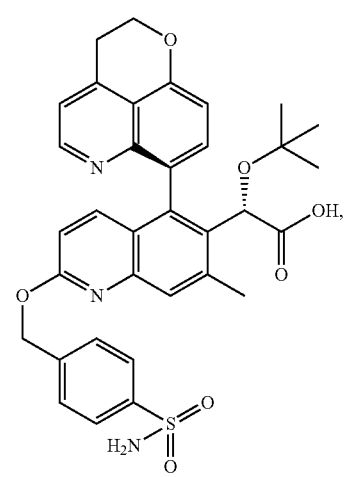
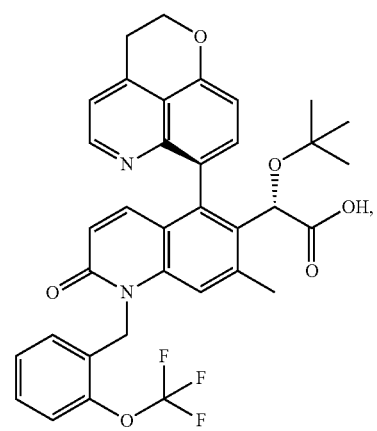
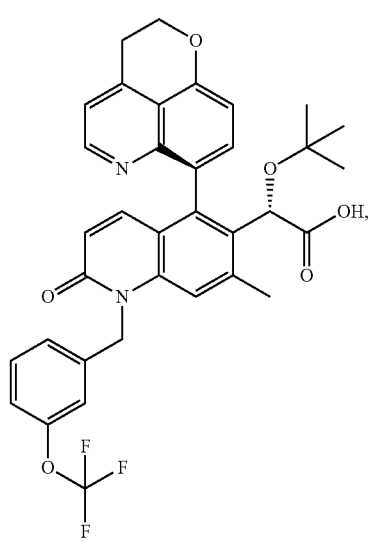
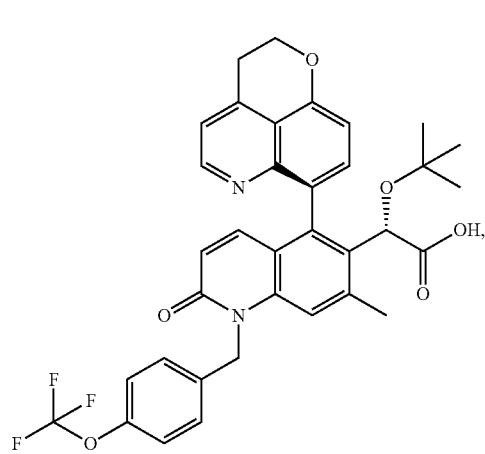
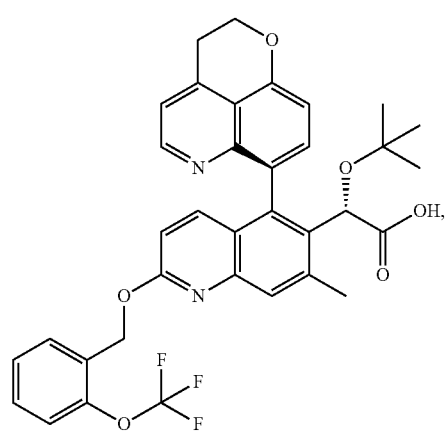

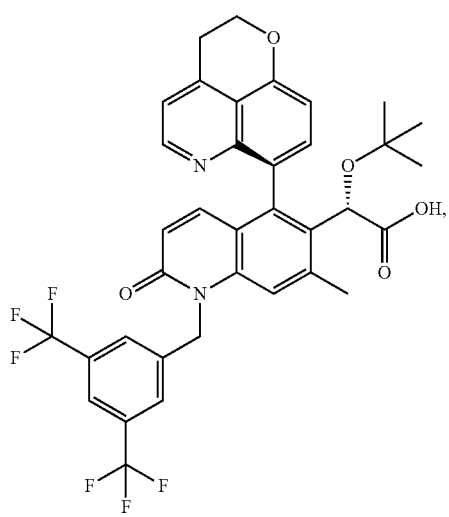
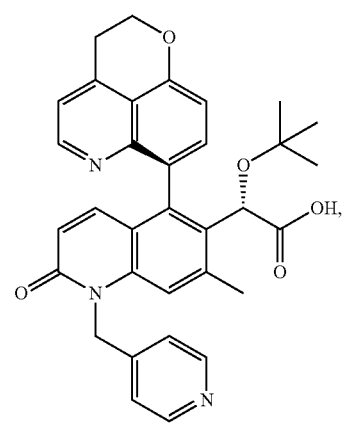
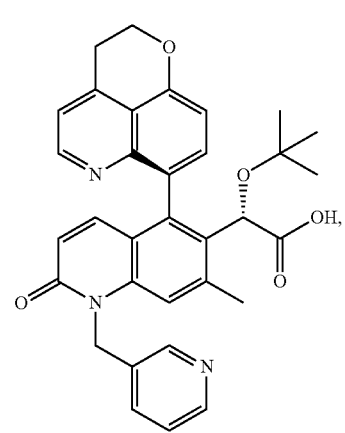
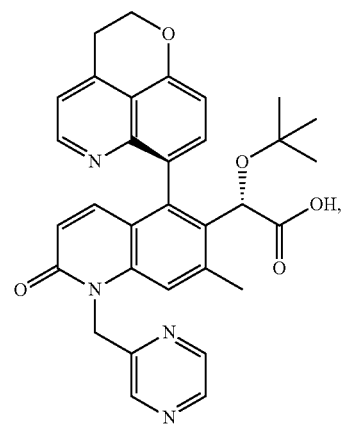
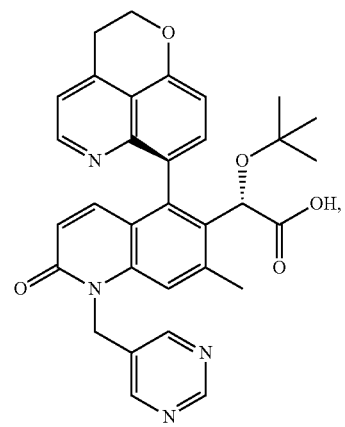
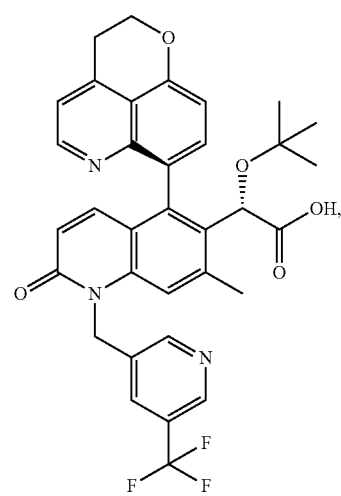

111
-continued
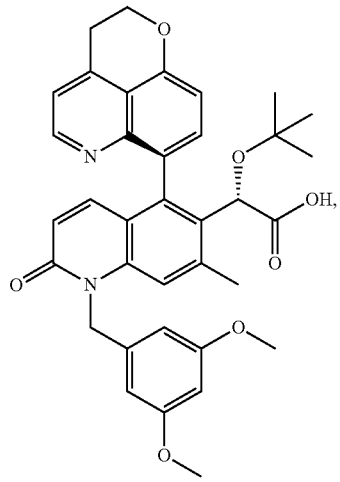
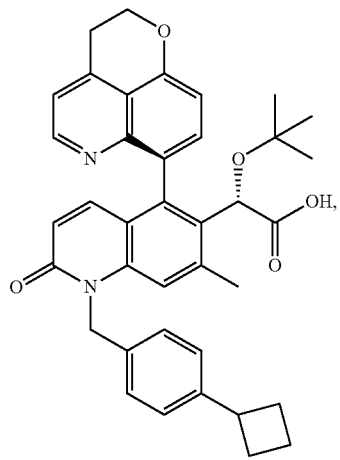
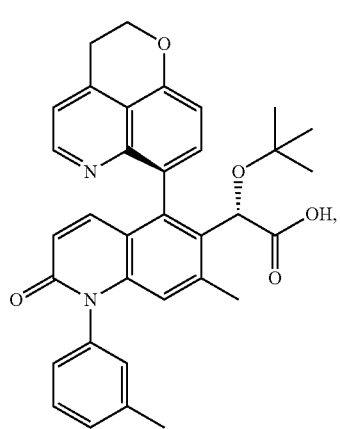
112
-continued
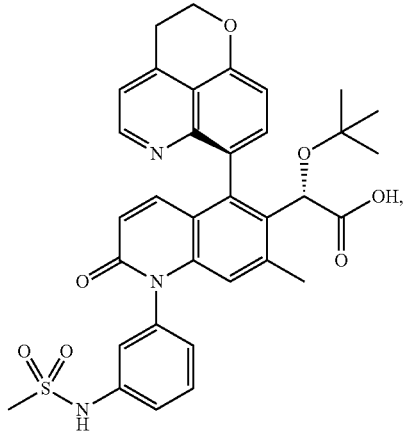
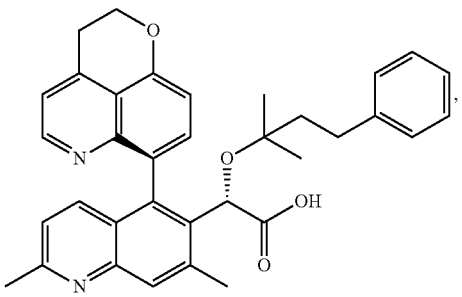
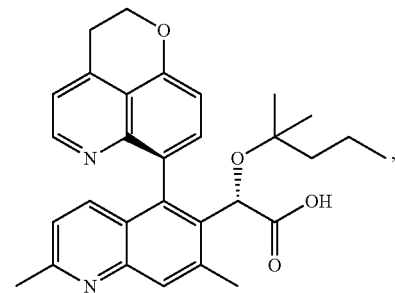

113
-continued
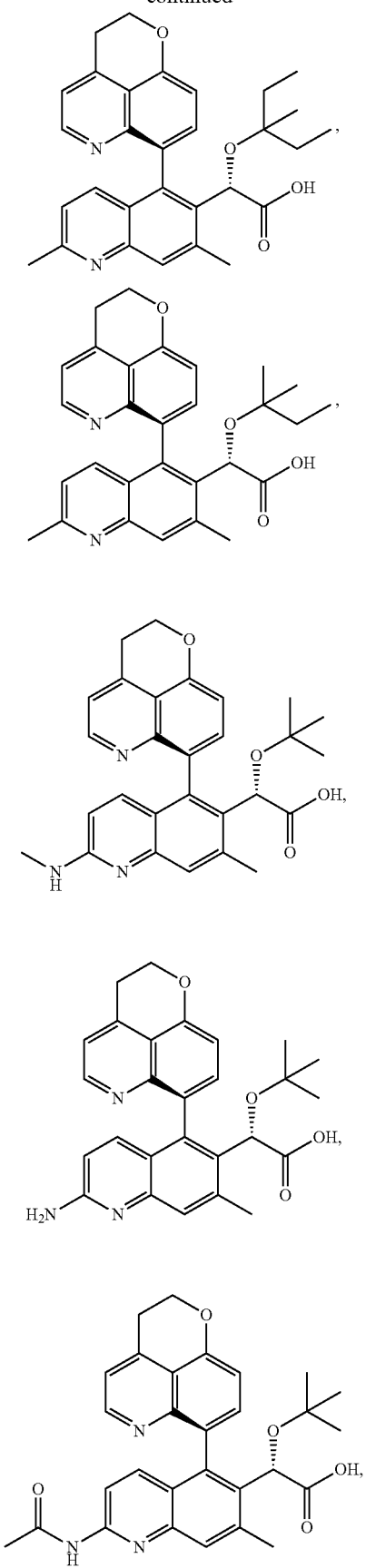
114
-continued
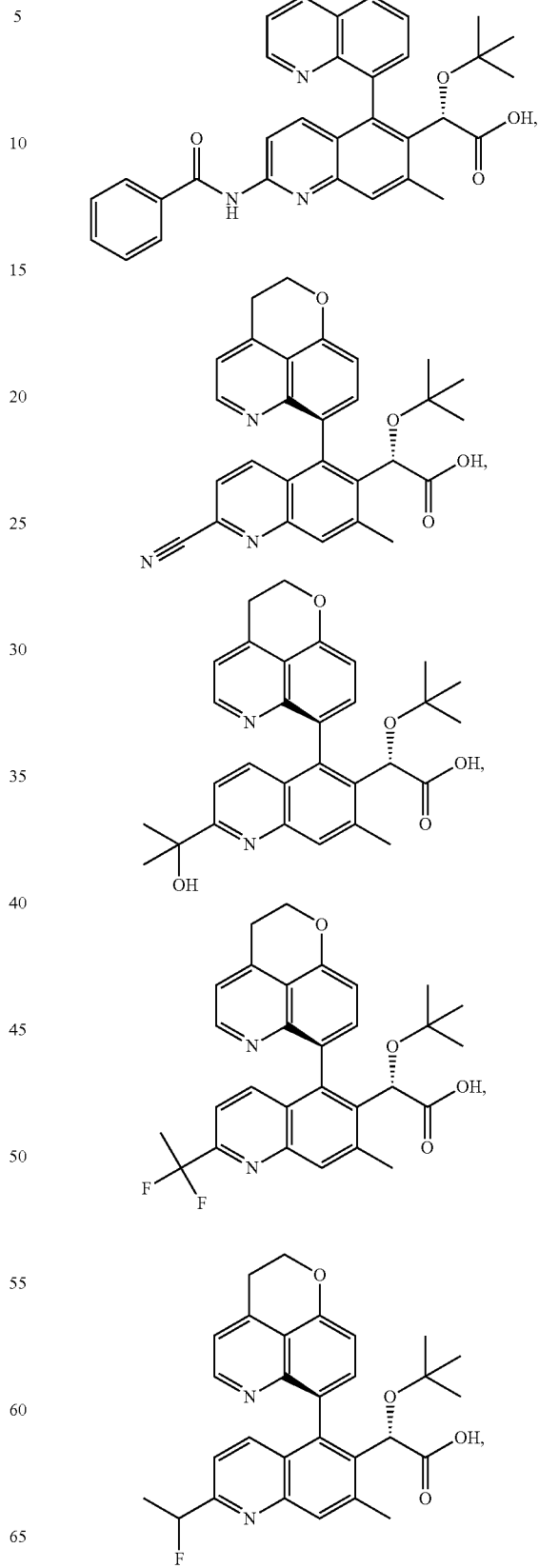

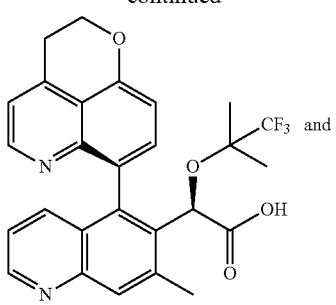
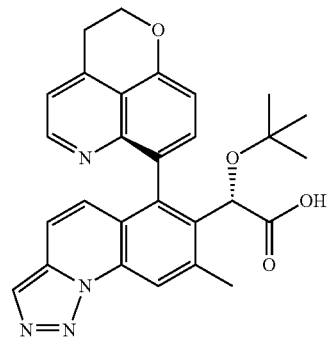
and salts thereof.
In one embodiment, compounds are selected from:
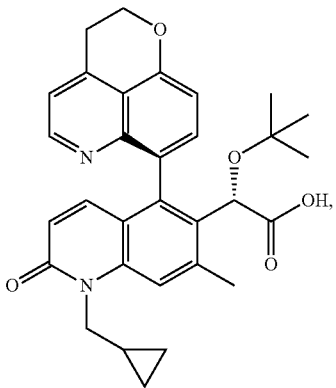
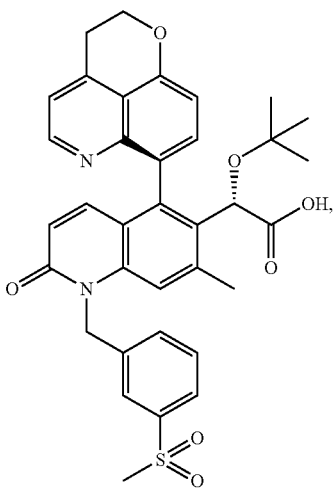
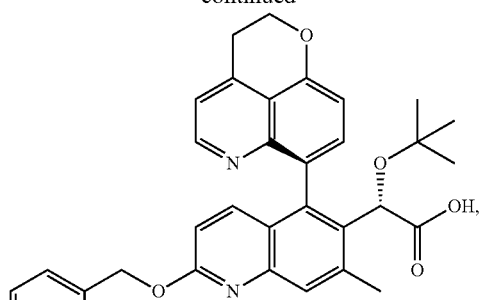
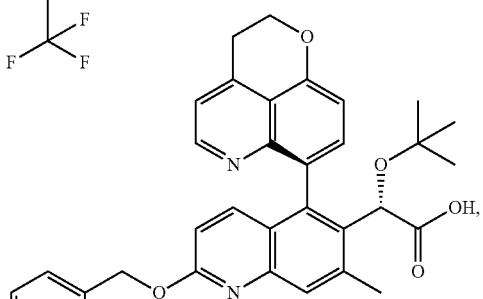
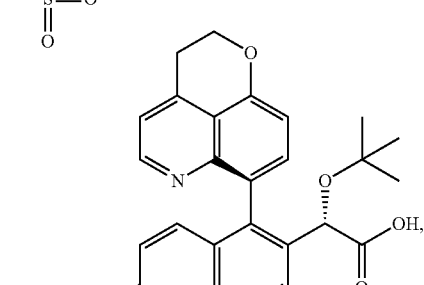
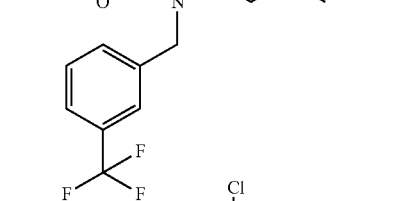
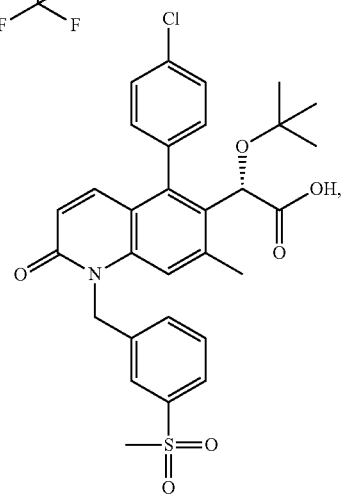

117
-continued
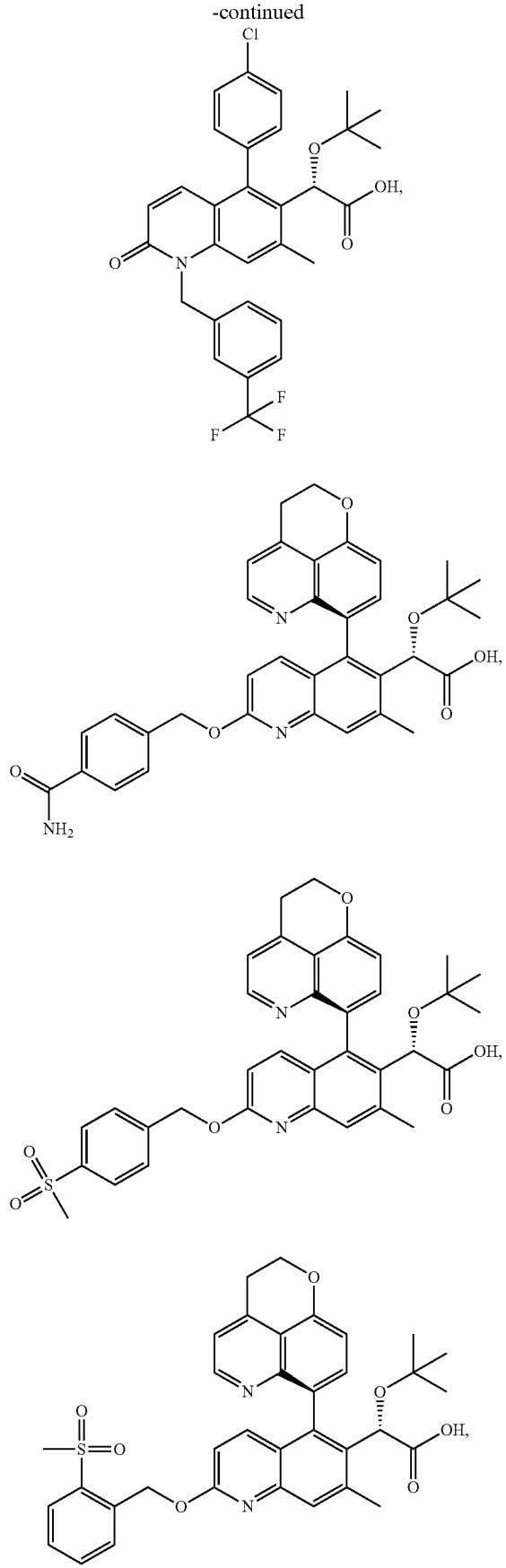
118
-continued
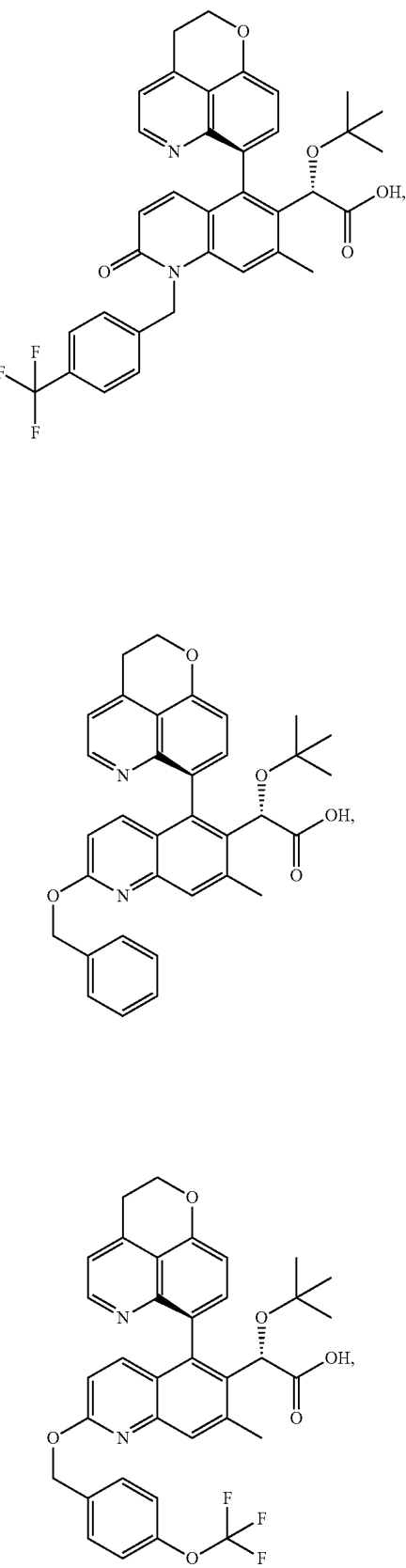

119
-continued
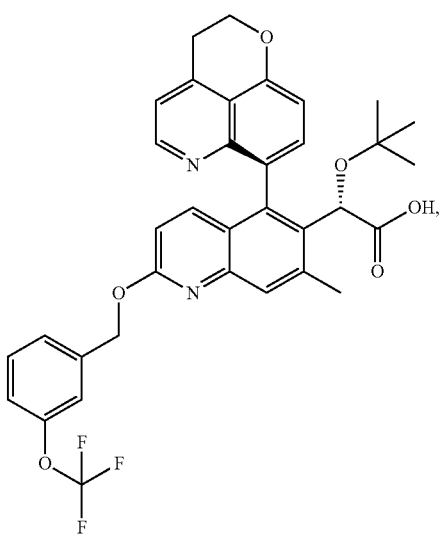
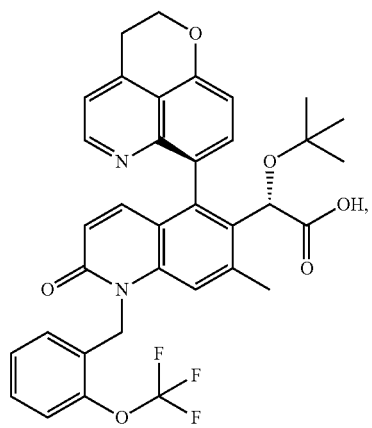
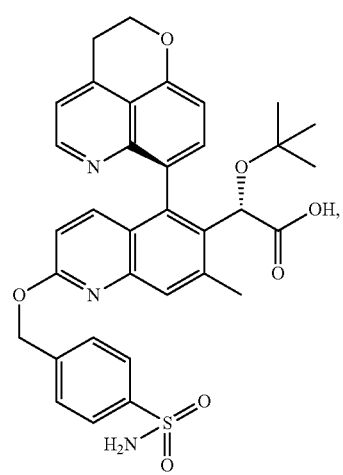
120
-continued
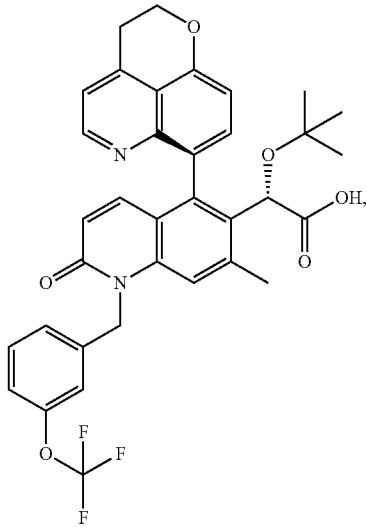
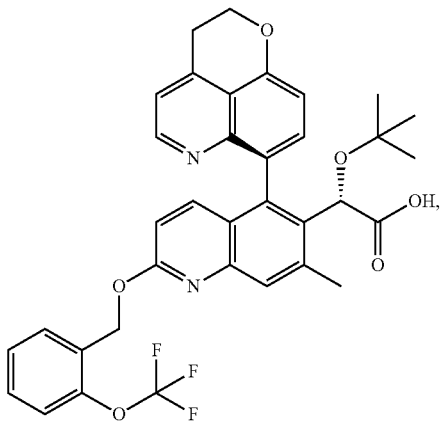
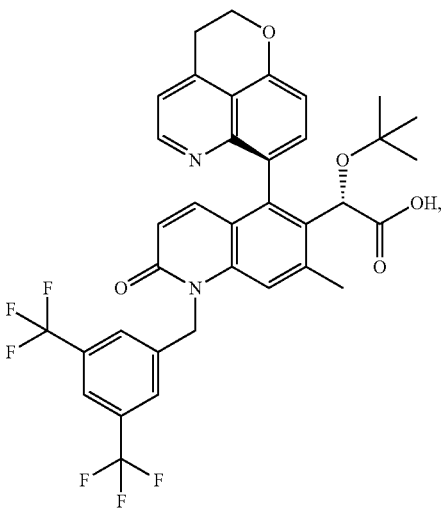

121
-continued
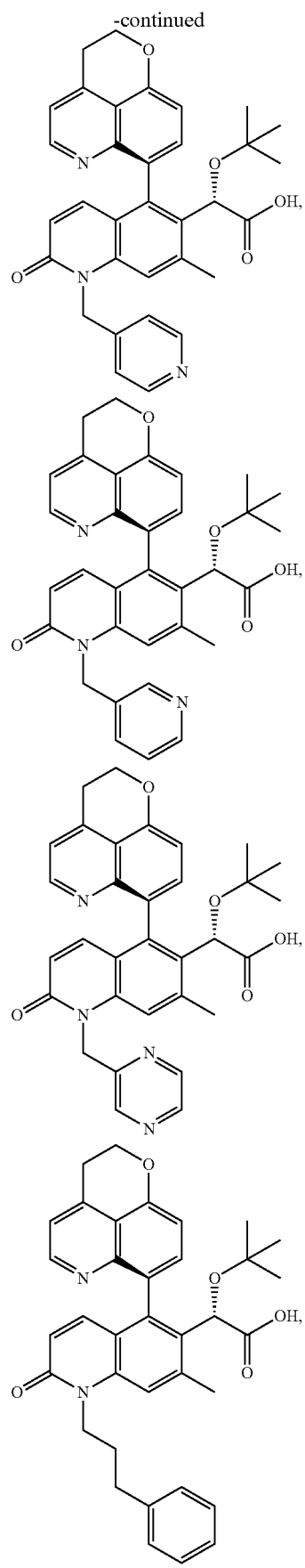
122
-continued
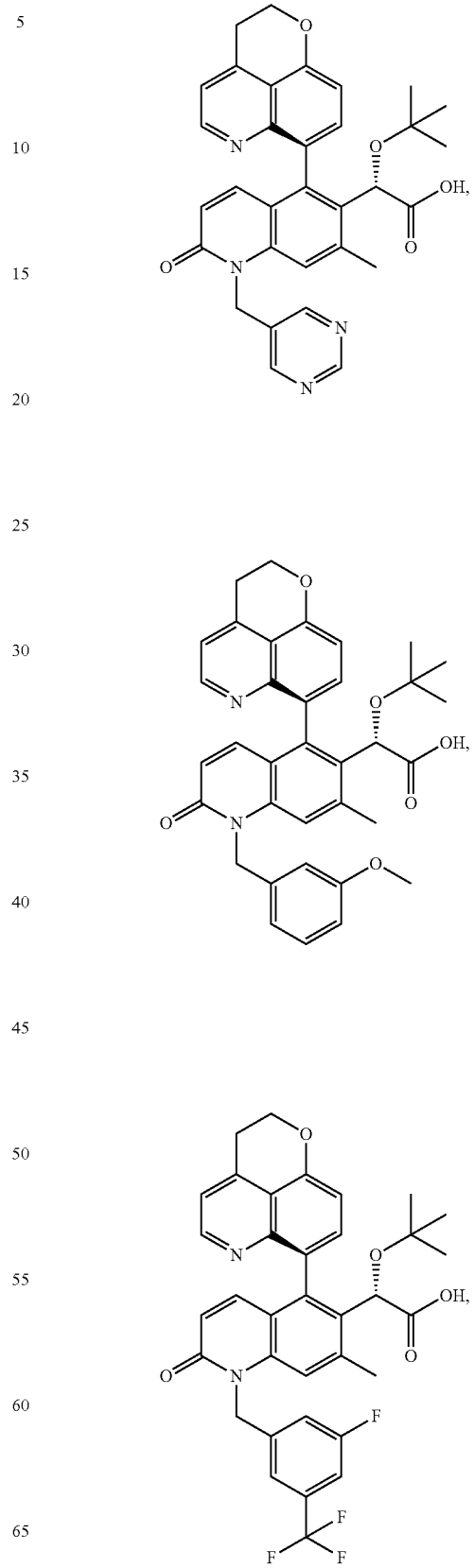

123
-continued
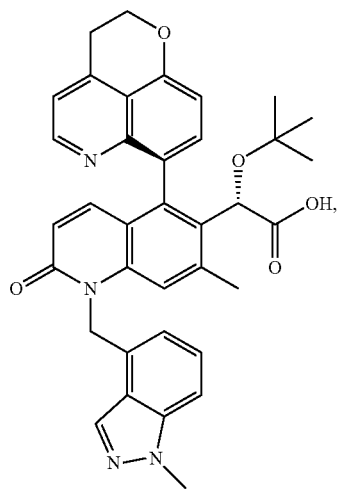
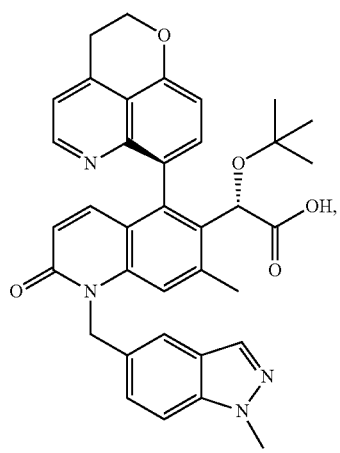
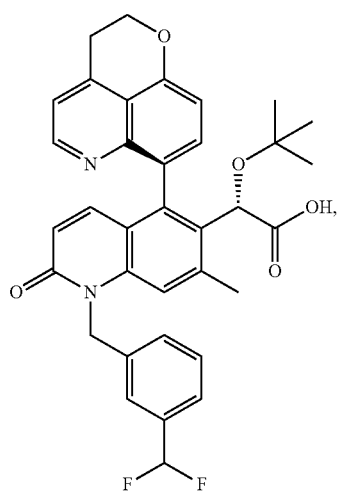
124
-continued
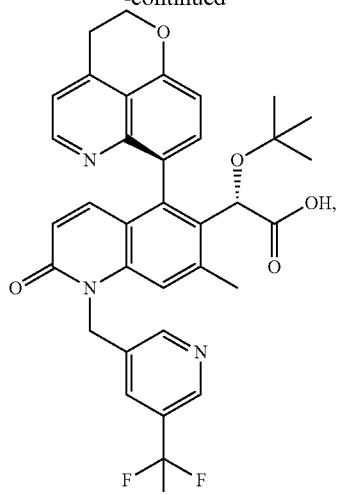
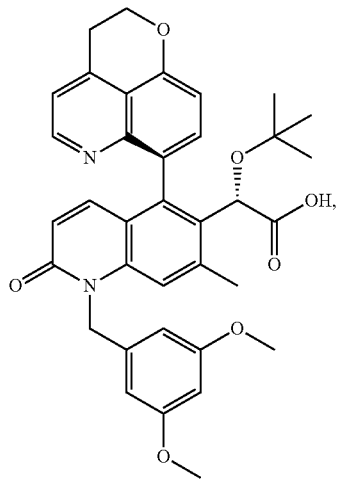
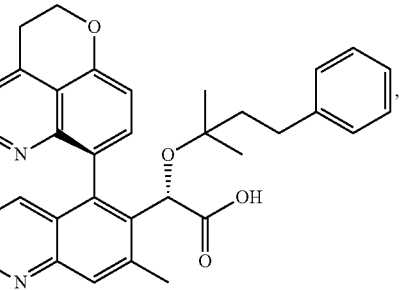
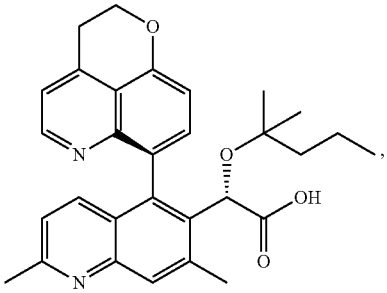

-continued
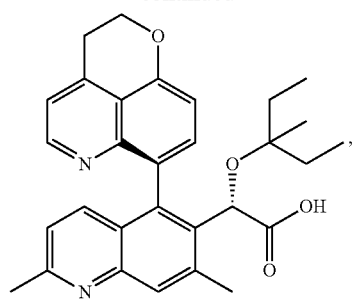
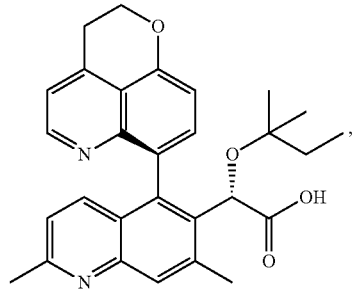
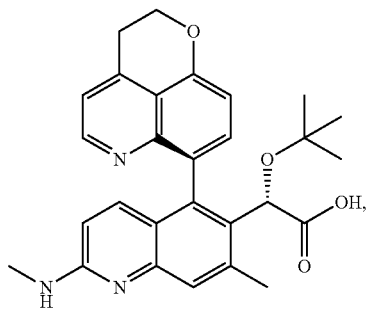
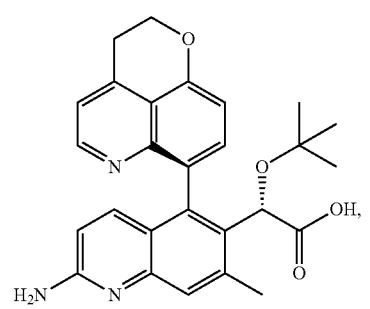
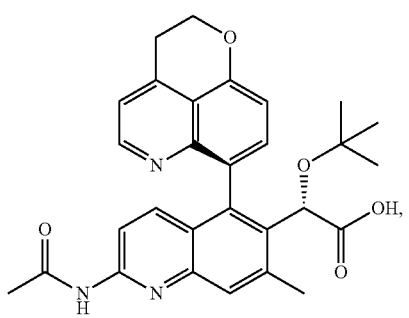
-continued
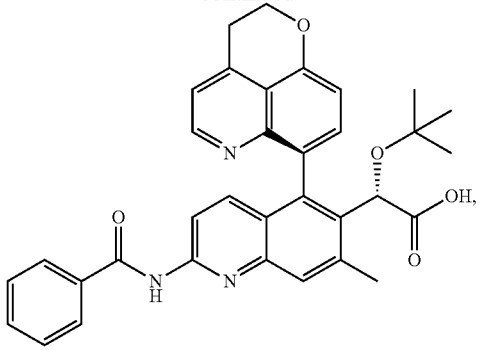
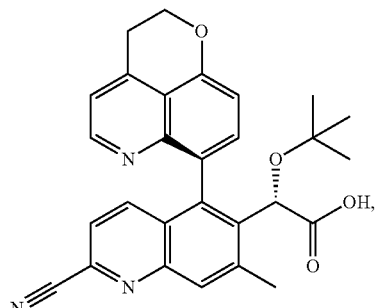
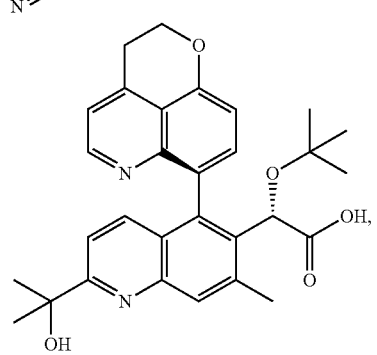
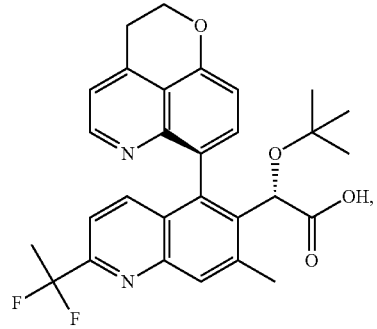
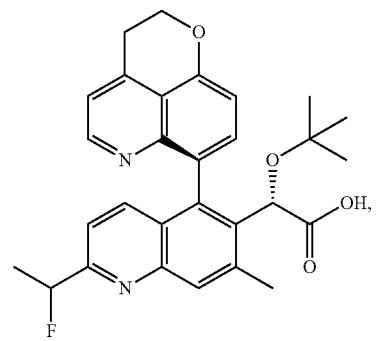

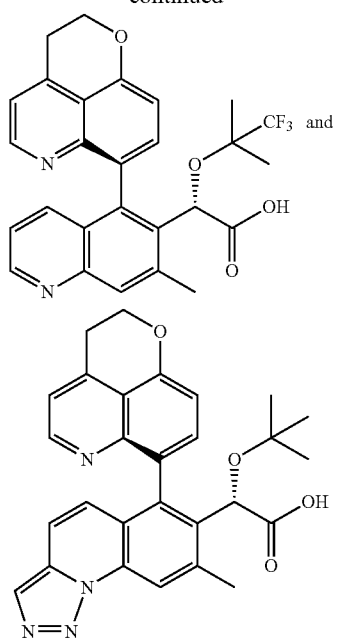
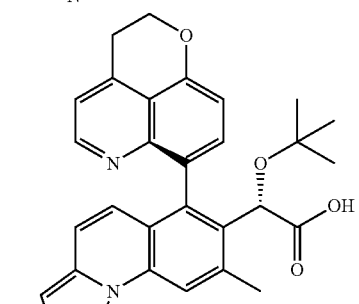
and salts thereof.
In one embodiment, compounds are selected from:
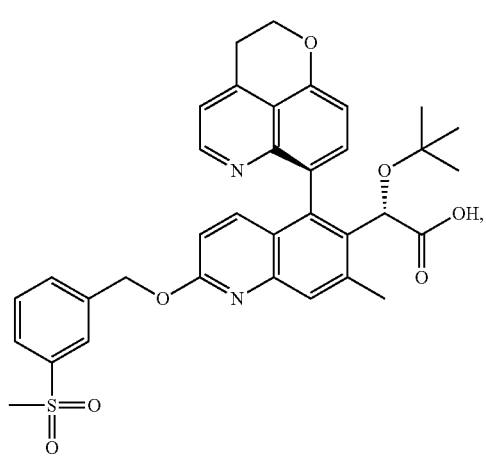
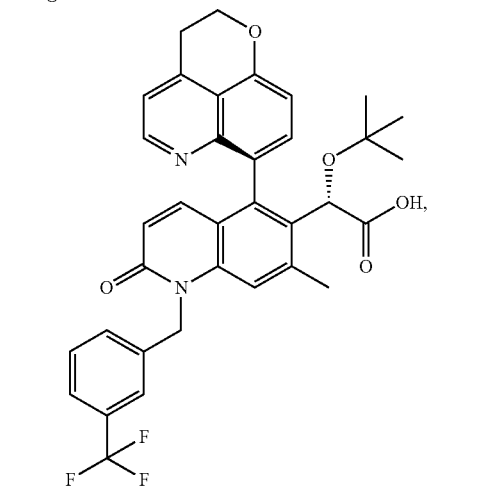
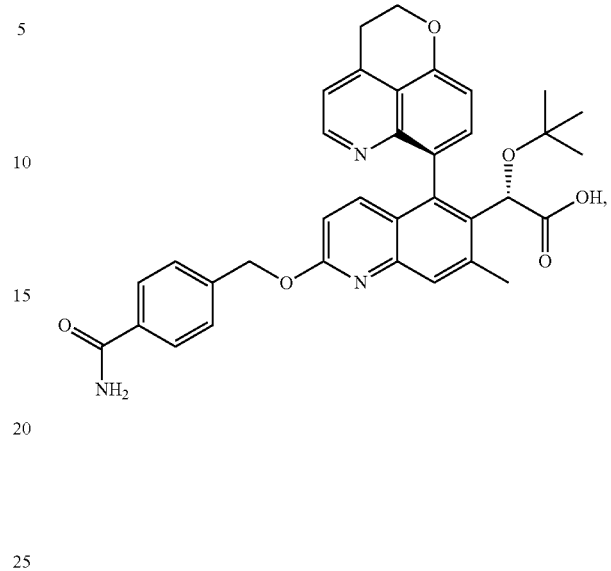
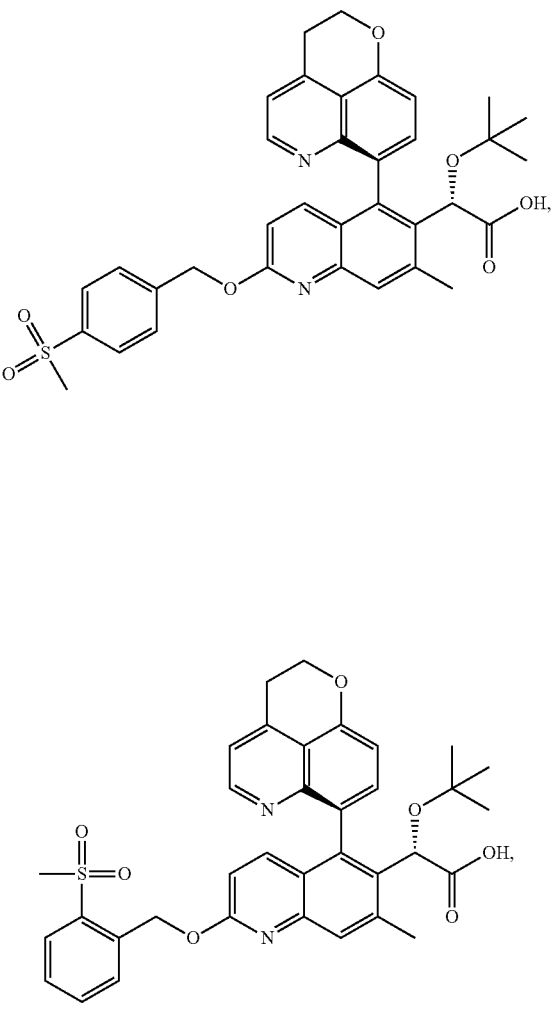

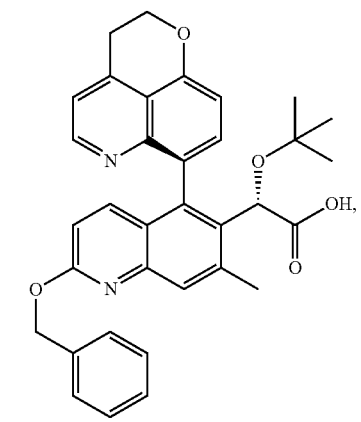
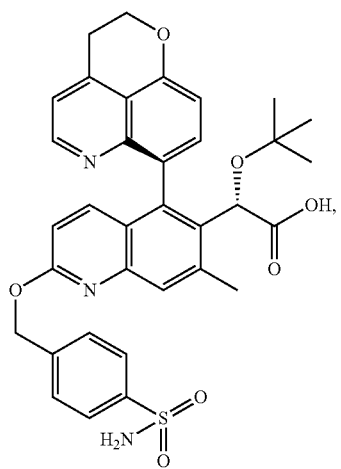
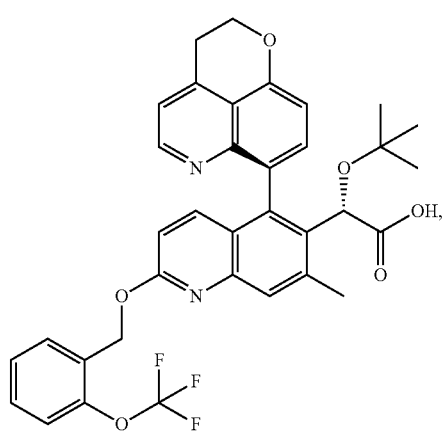
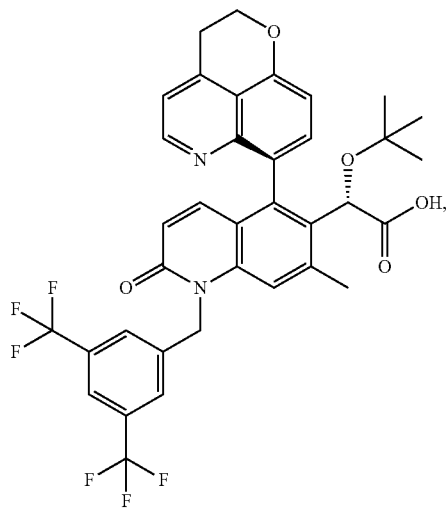
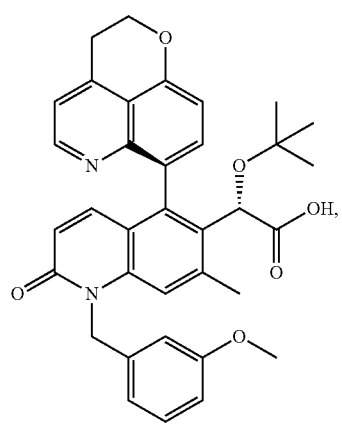
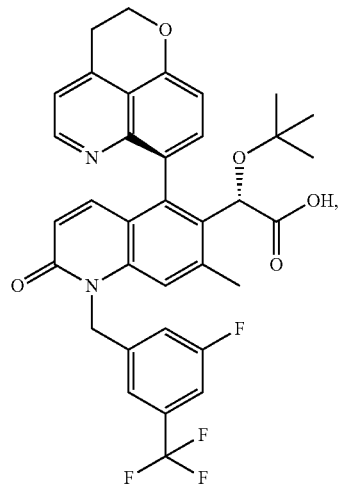

131
-continued
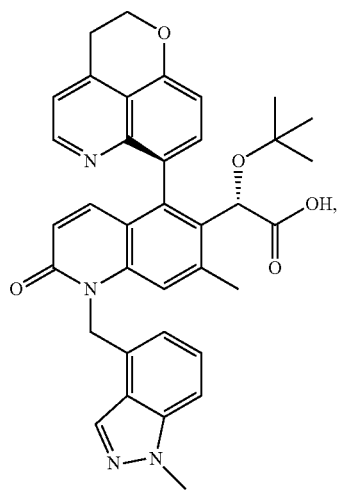
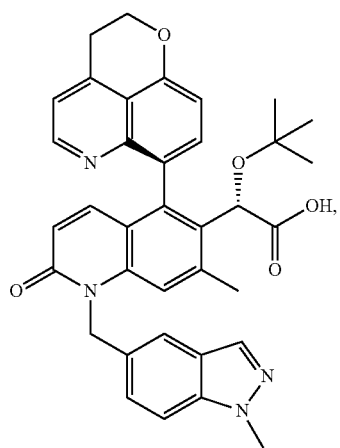
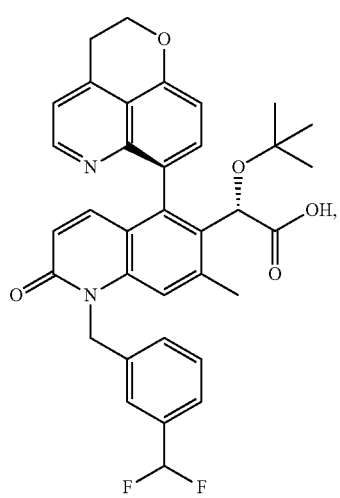
132
-continued
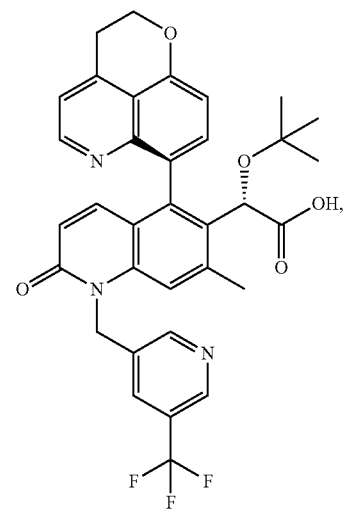
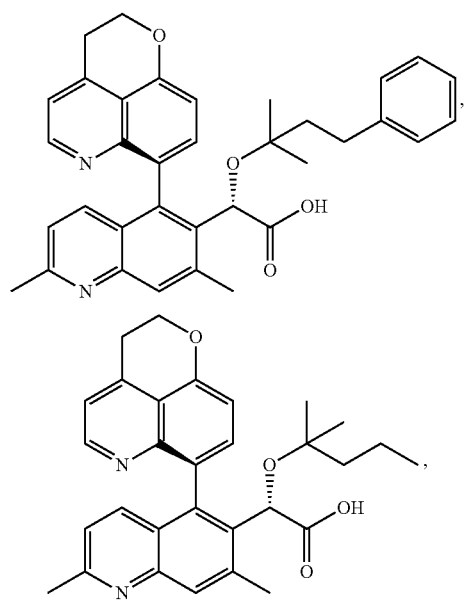
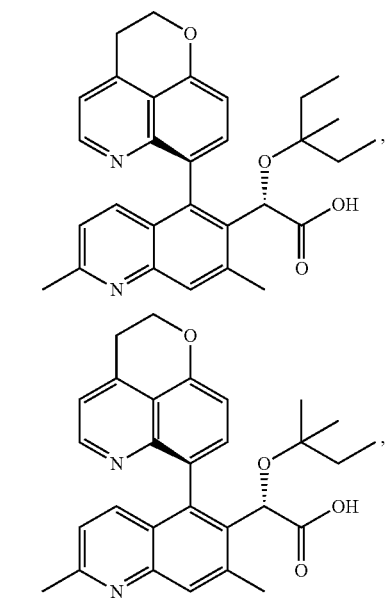

133
-continued
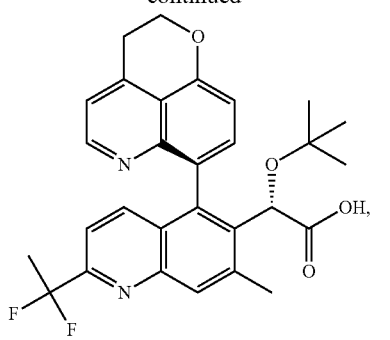
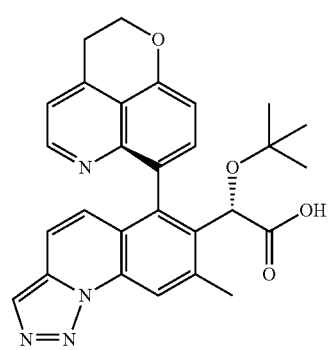
and salts thereof.
In one embodiment, compounds are selected from:
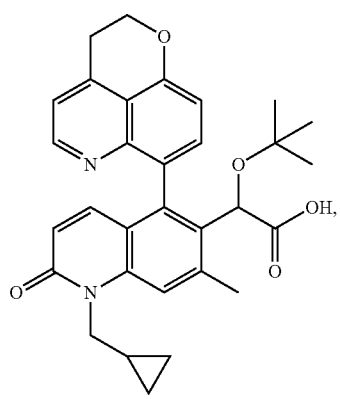
134
-continued
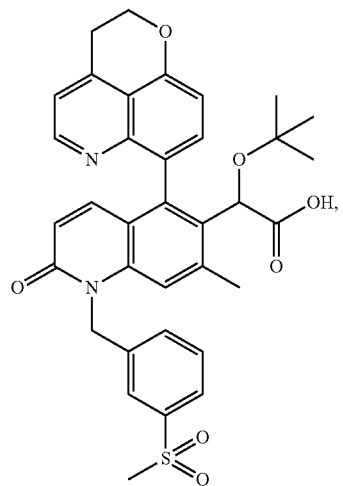
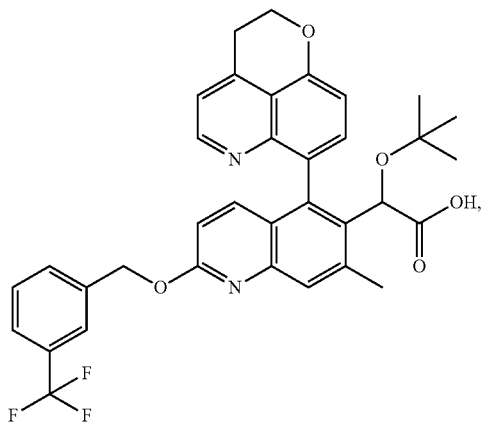
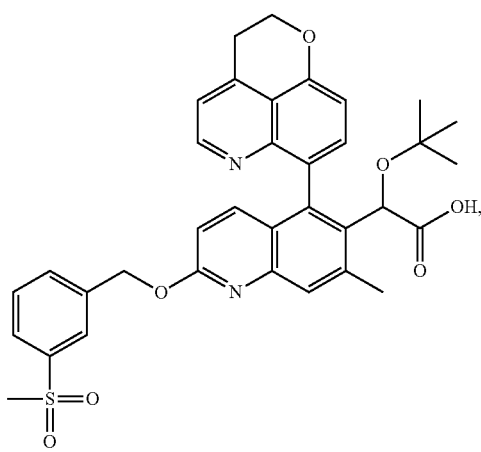

135
-continued
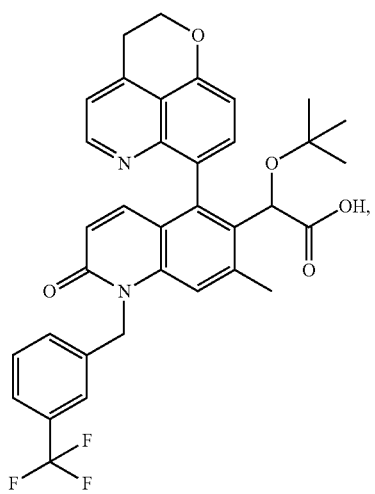
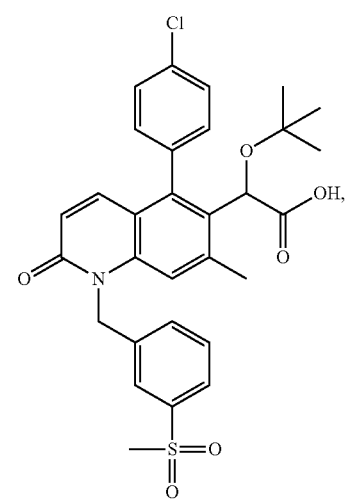
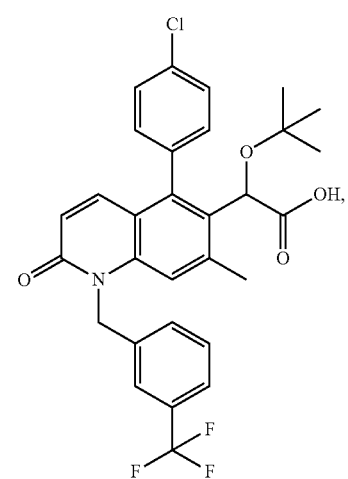
136
-continued
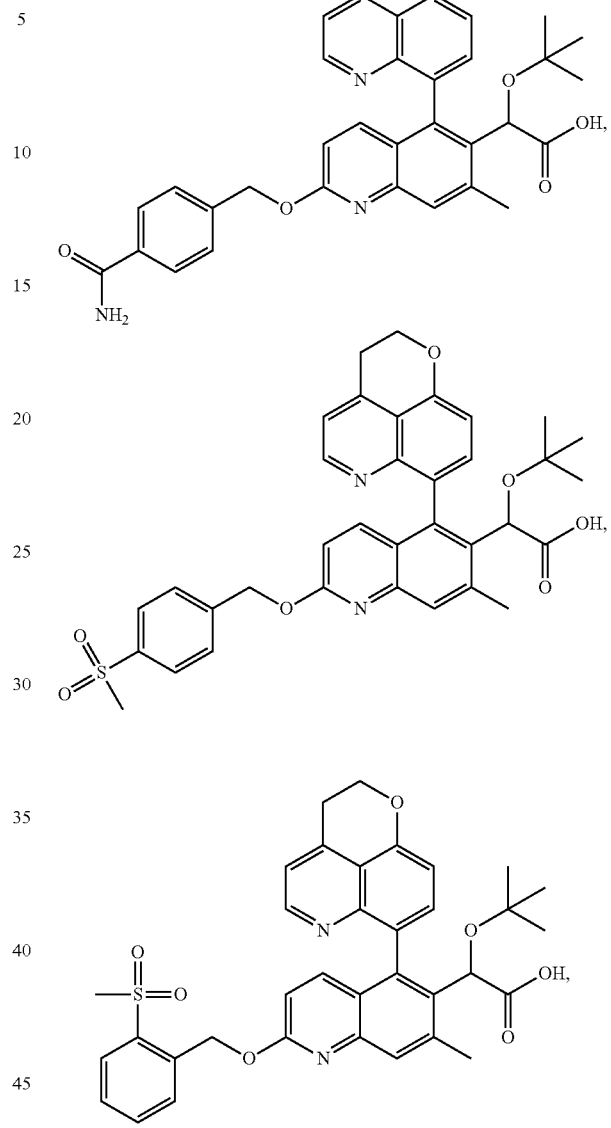
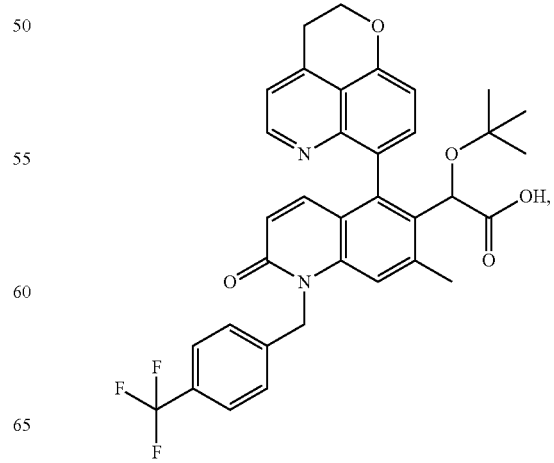

137
-continued
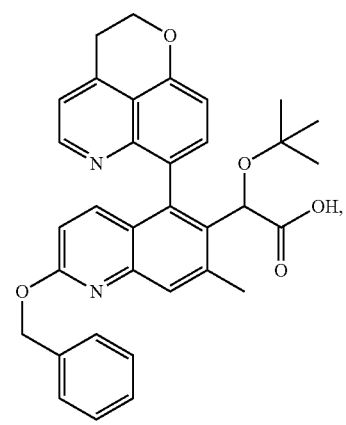
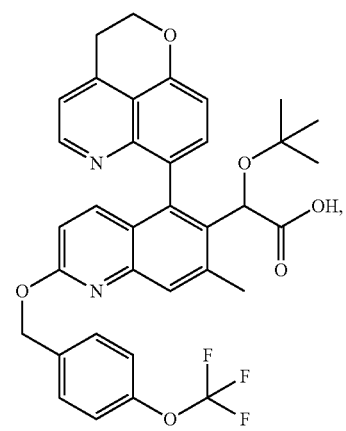
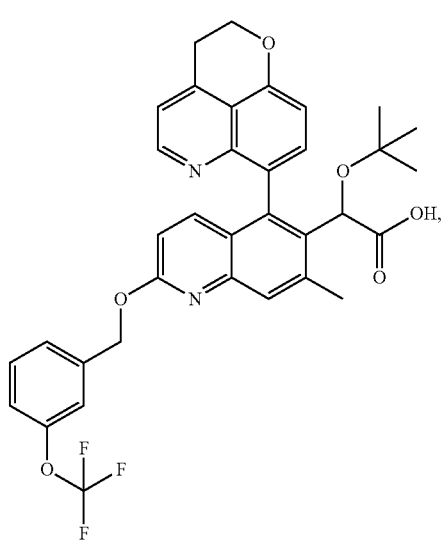
138
-continued
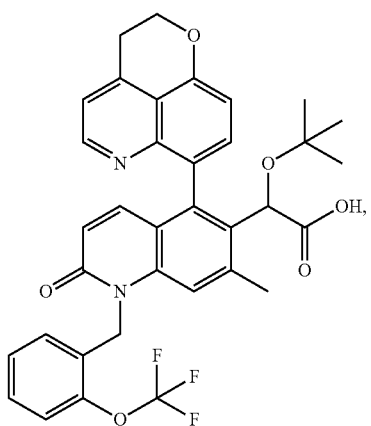
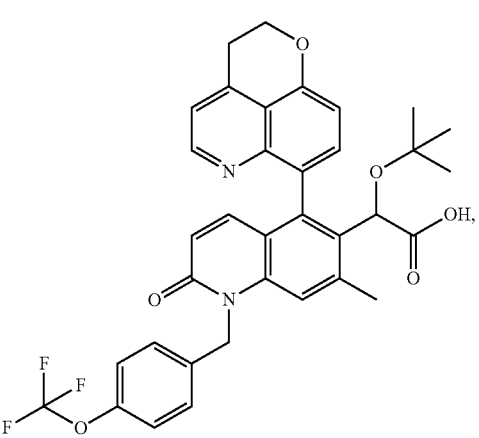
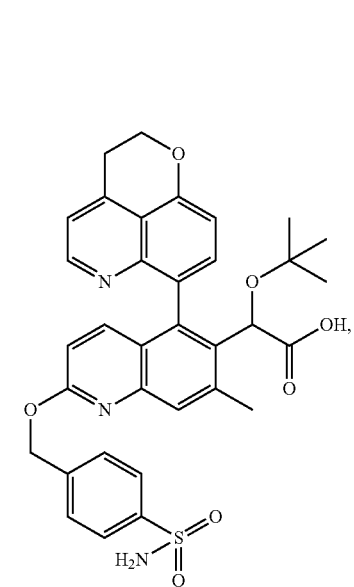

139
-continued
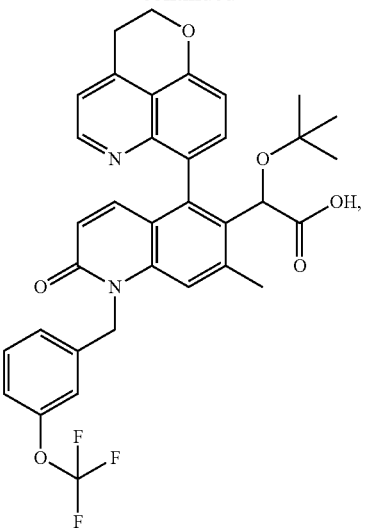
140
-continued
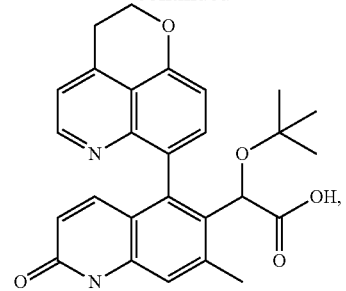
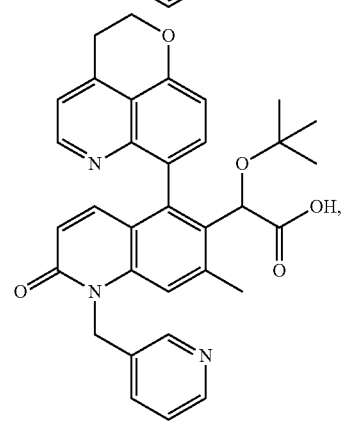
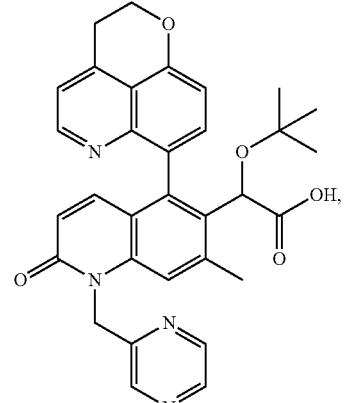
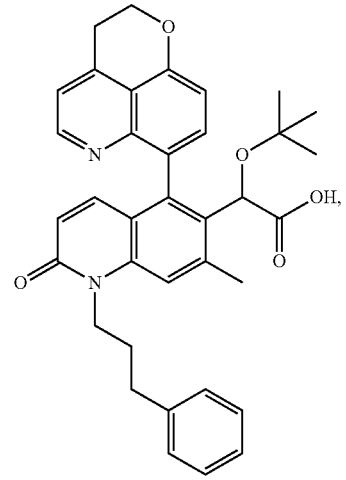

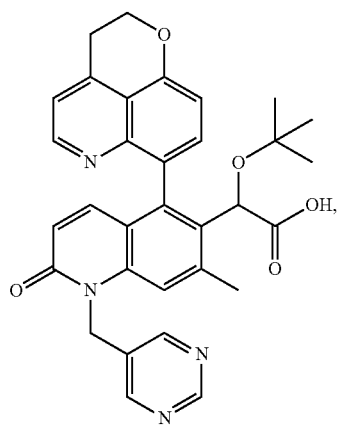
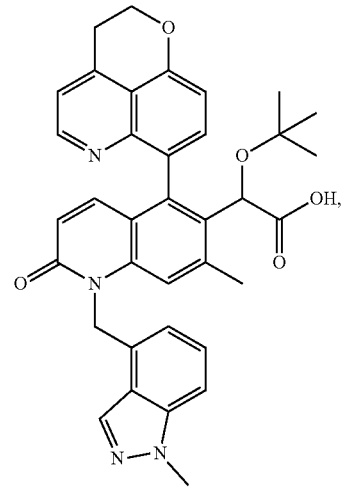
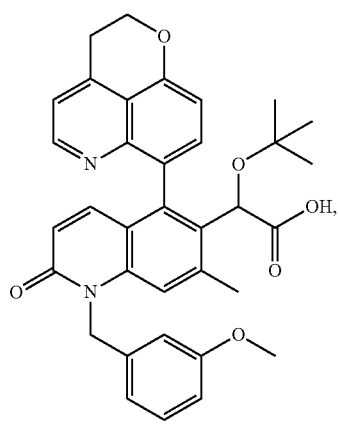
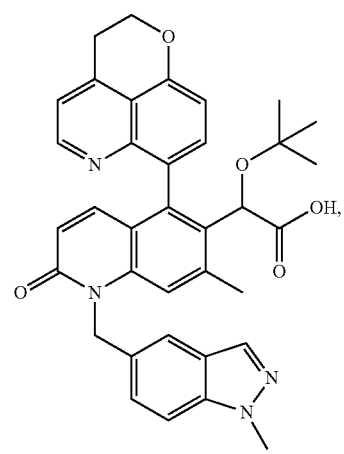
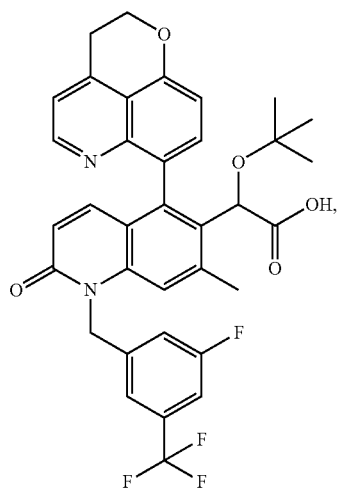
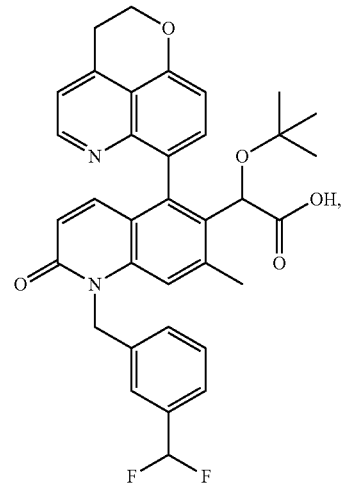

143
-continued
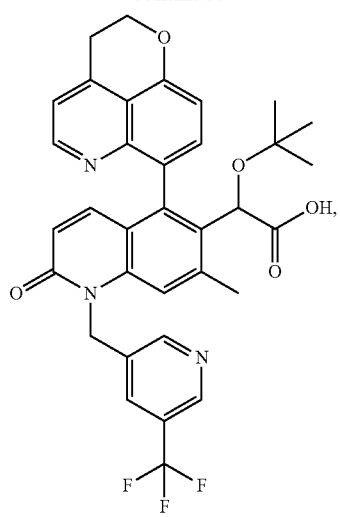
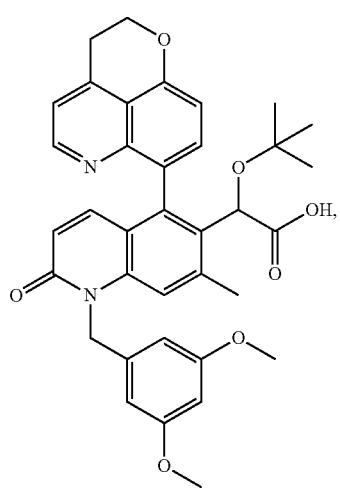
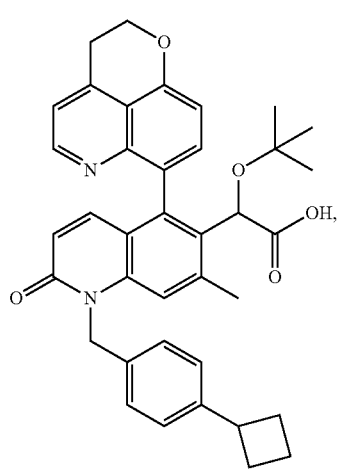
144
-continued
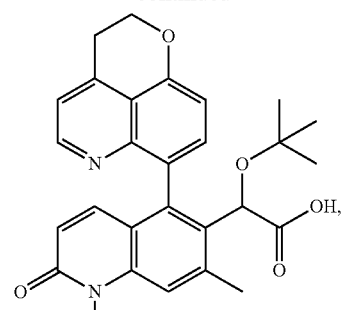
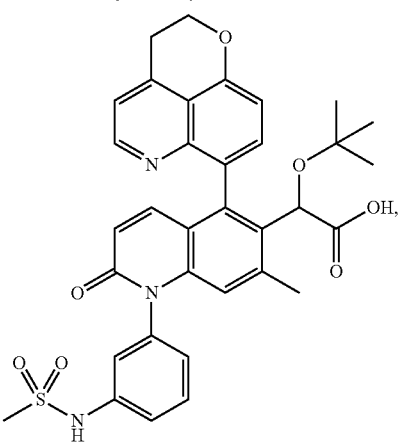
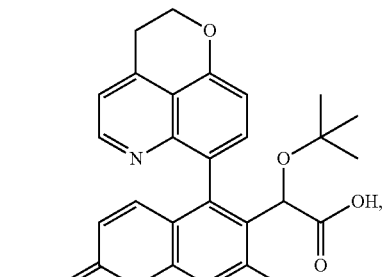
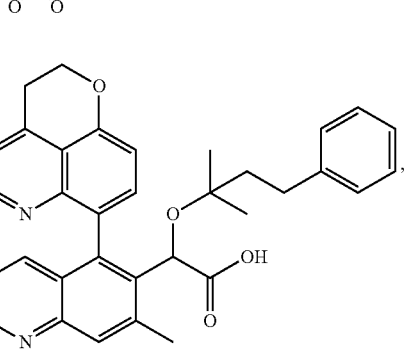

145
-continued
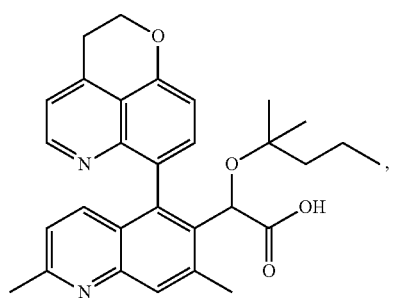,
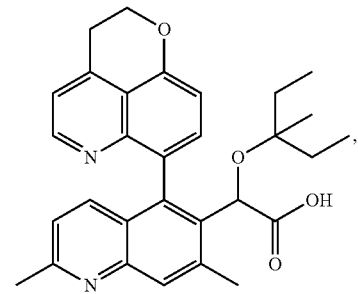,
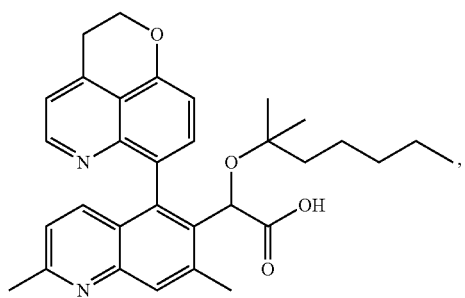,
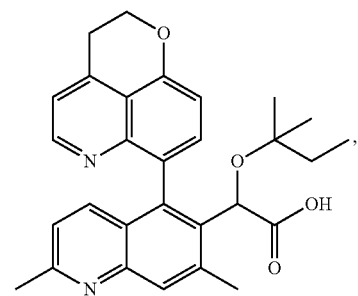,
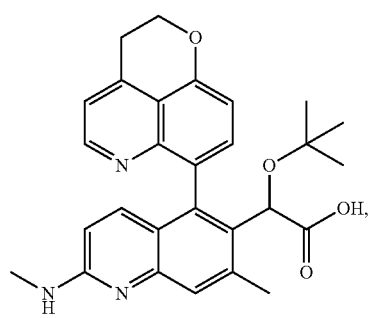,
146
-continued
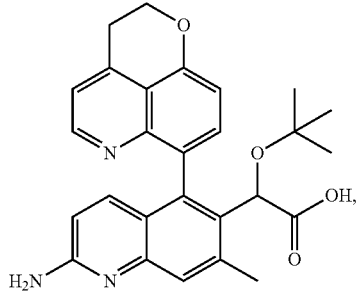,
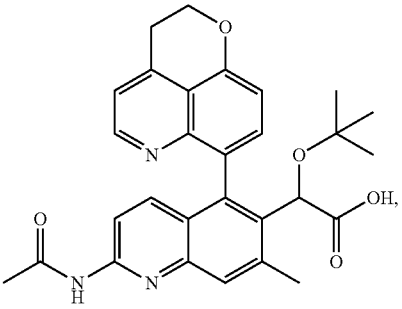,
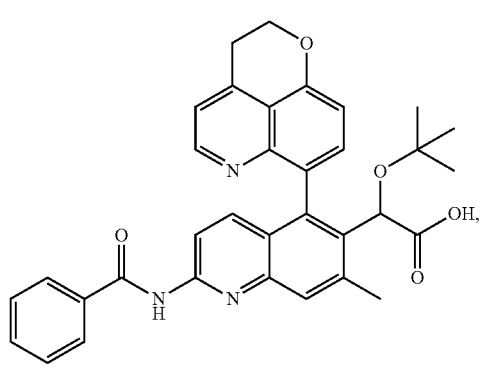,
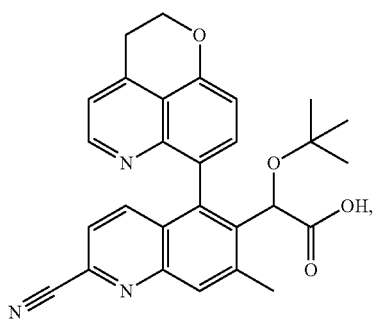,
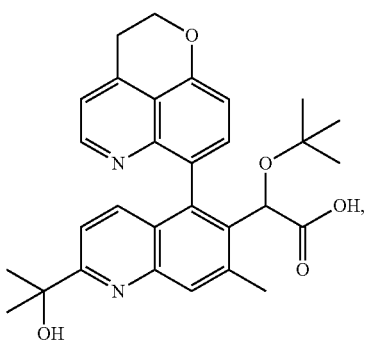, -continued

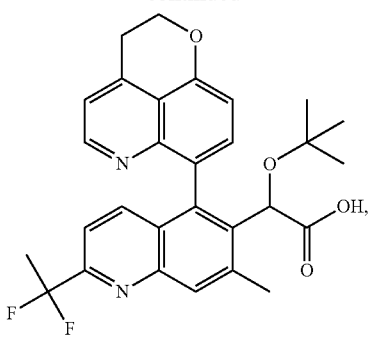

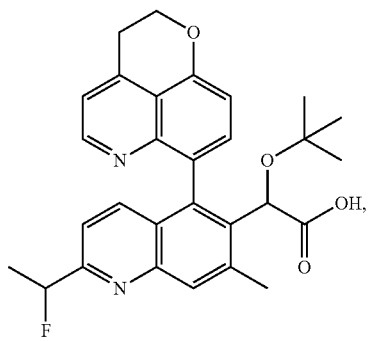

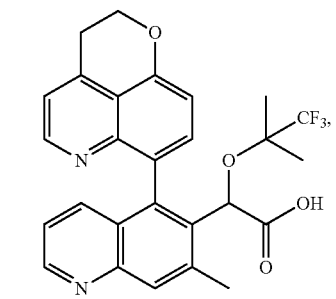

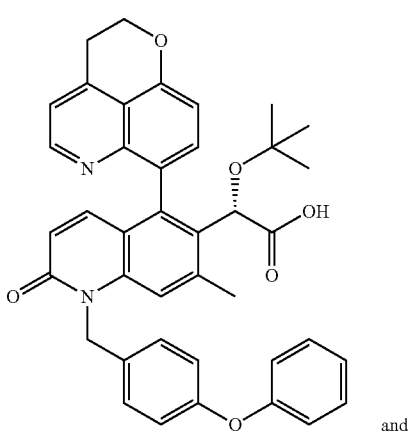

and

-continued

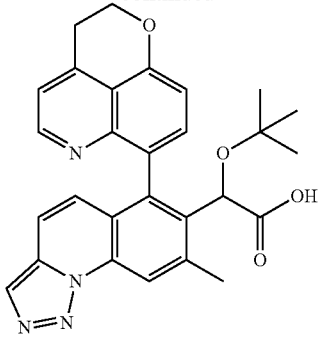

and salts thereof.

Combination Therapy

In one embodiment, the invention provides for a method for treating an HIV infection, comprising administering to a patient in need thereof a therapeutically effective amount of a compound of the invention, or a pharmaceutically acceptable salt, thereof, in combination with a therapeutically effective amount of one or more additional therapeutic agents which are suitable for treating an HIV infection.

In one embodiment, the invention provides pharmaceutical compositions comprising a compound of the present invention, or a pharmaceutically acceptable salt thereof, in combination with at least one additional therapeutic agent, and a pharmaceutically acceptable carrier. For example, the therapeutic agent used in combination with the compound of the present invention can be any anti-HIV agent.

In one embodiment, the invention provides pharmaceutical compositions comprising a compound of the present invention, or a pharmaceutically acceptable salt thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof, and a pharmaceutically acceptable carrier.

In another embodiment, the invention provides pharmaceutical compositions comprising a compound of the present invention, or a pharmaceutically acceptable salt thereof, in combination with at least one additional therapeutic agent selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, RDEA806 and KM023;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide fumarate (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, GS-5696, elvitegravir and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In some embodiments, one or more of the compounds disclosed herein are combined with one or more other active therapeutic agents in a unitary dosage form for simultaneous or sequential administration to a patient. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

In yet another embodiment, the present application provides a method for treating an HIV infection comprising administering to a patient in need thereof a therapeutically effective amount of a compound of the present invention, or a pharmaceutically acceptable salt thereof, in combination with a therapeutically effective amount of one or more additional therapeutic agents such as those disclosed above.

Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units including but not limited to capsules, cachets or tablets each containing a predetermined amount of the active ingredient.

Pharmaceutical formulations according to the present invention comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or *acacia*; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (i.e., inactive ingredient or excipient material). In certain embodiments, the carrier material varies from about 5 to about 95% of the total compositions (weight:weight).

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The antiviral properties of a compound disclosed herein may be determined using Test A described below.

Test A: Antiviral Assays in MT4 Cells

For the antiviral assay utilizing MT-4 cells, 0.4 µL of 189X test concentration of 3-fold serially diluted compound in DMSO was added to 40 µL of cell growth medium (RPMI 1640, 10% FBS, 1% penicillin/Streptomycin, 1% L-Glutamine, 1% HEPES) in each well of 384-well assay plates (10 concentrations) in quadruplicate.

1 mL aliquots of 2×10e6 MT-4 cells are pre-infected for 1 and 3 hrs respectively, @ 37° C. with 25 µL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 µL of 2000 (for MT4) cells is added to each well of the assay plates.

Assay plates were then incubated in a 37° C. incubator. After 5 days of incubation, 25 of 2× concentrated CellTiter-Glo™ Reagent (catalog #G7573, Promega Biosciences, Inc., Madison, Wis.) was added to each well of the assay plate. Cell lysis was carried out by incubating at room temperature for 2-3 min and then chemiluminescence was read using the Envision reader (PerkinElmer).

Compounds of the present invention demonstrate antiviral activity in this assay (Test A) as depicted in the table below.

| Example | Compound Name | Compound Structure | $EC_{50}$ (nM) |
|---|---|---|---|
| 1 | (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid | 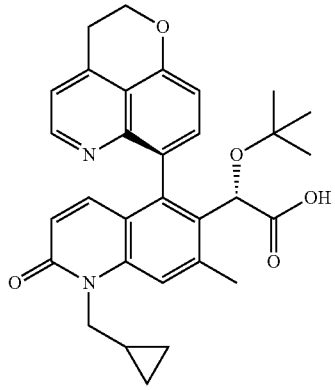 | 409 |

-continued

| Example | Compound Name | Compound Structure | EC$_{50}$ (nM) |
|---|---|---|---|
| 2 | (S)-2-tert-butoxy-2-((R)-5-(2,3-dihydropyrano[4,3,2-de]quinolin-7-yl)-7-methyl-1-(3-(methylsulfonyl)benzyl)-2-oxo-1,2-dihydroquinolin-6-yl)acetic acid | 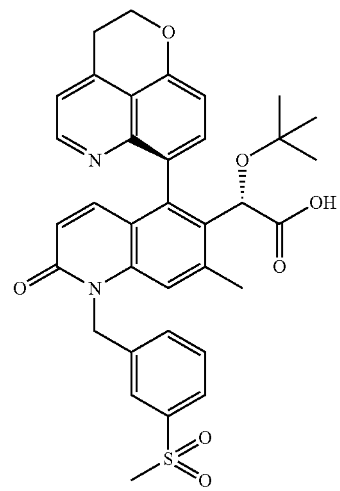 | 460 |
| 3 | (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid | 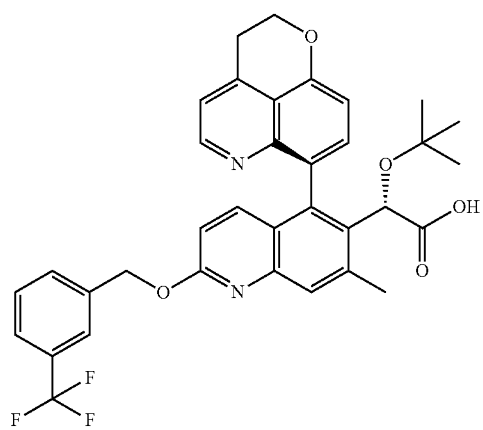 | 123 |
| 4 | (S)-2-tert-butoxy-2-((R)-5-(2,3-dihydropyrano[4,3,2-de]quinolin-7-yl)-7-methyl-2-(3-(methylsulfonyl)benzyloxy)quinolin-6-yl)acetic acid | 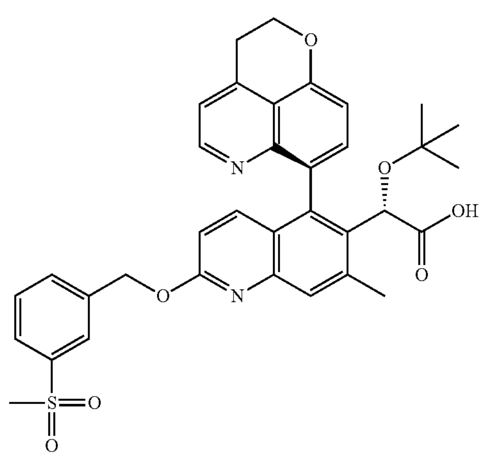 | 13.6 |

| Example | Compound Name | Compound Structure | EC$_{50}$ (nM) |
|---|---|---|---|
| 5 | (S)-2-tert-butoxy-2-((R)-5-(2,3-dihydropyrano[4,3,2-de]quinolin-7-yl)-7-methyl-2-oxo-1-(3-(trifluoromethyl)benzyl)-1,2-dihydroquinolin-6-yl)acetic acid | 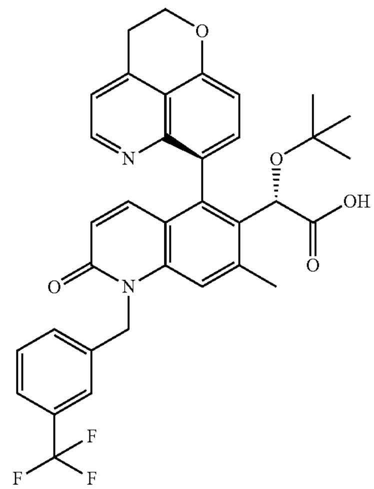 | 30.7 |
| 6 | (S)-2-tert-butoxy-2-(5-(4-chlorophenyl)-7-methyl-1-(3-(methylsulfonyl)benzyl)-2-oxo-1,2-dihydroquinolin-6-yl)acetic acid | 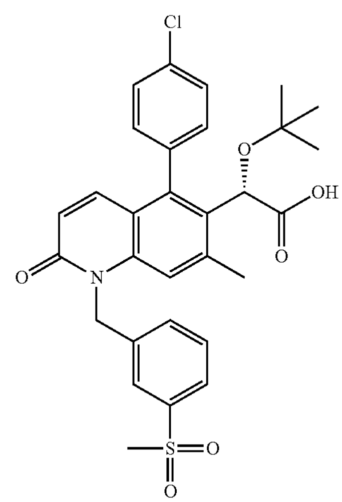 [SMILES: Cc1cc2c(ccc(=O)n2Cc2cccc(S(C)(=O)=O)c2)c(-c2ccc(Cl)cc2)c1[C@H](OC(C)(C)C)C(=O)O] | 290 |
| 7 | (S)-2-tert-butoxy-2-(5-(4-chlorophenyl)-7-methyl-2-oxo-1-(3-(trifluoromethyl)benzyl)-1,2-dihydroquinolin-6-yl)acetic acid | 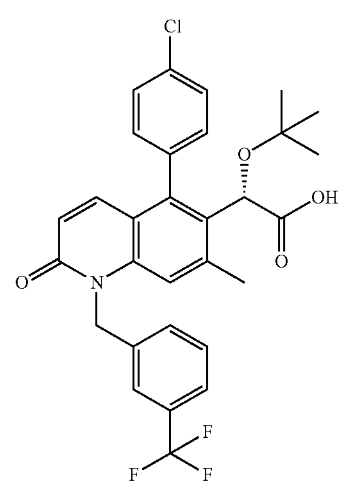 [SMILES: Cc1cc2c(ccc(=O)n2Cc2cccc(C(F)(F)F)c2)c(-c2ccc(Cl)cc2)c1[C@H](OC(C)(C)C)C(=O)O] | 187 |

-continued

| Example | Compound Name | Compound Structure | EC$_{50}$ (nM) |
|---|---|---|---|
| 8 | (S)-2-tert-butoxy-2-(5-(4-chlorophenyl)-7-methyl-2-oxo-1-(3-(trifluoromethyl)benzyl)-1,2-dihydroquinolin-6-yl)acetic acid | 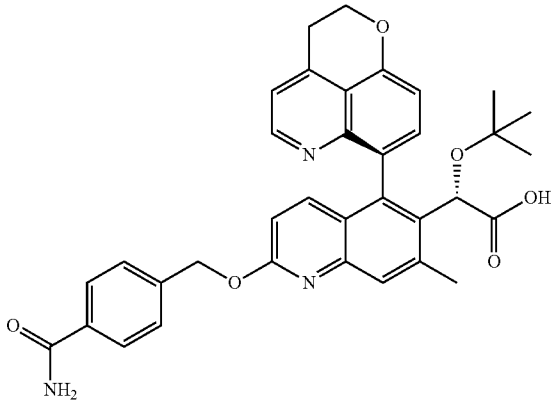 | 36.8 |
| 9 | (S)-2-tert-butoxy-2-((R)-5-(2,3-dihydropyrano[4,3,2-de]quinolin-7-yl)-7-methyl-2-(4-(methylsulfonyl)benzyloxy)quinolin-6-yl)acetic acid | 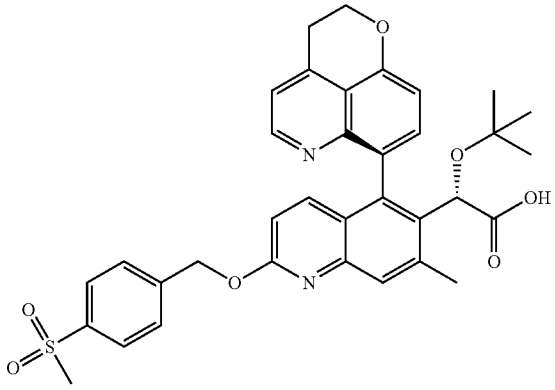 | 21.2 |
| 10 | (S)-2-tert-butoxy-2-((R)-5-(2,3-dihydropyrano[4,3,2-de]quinolin-7-yl)-7-methyl-2-(2-(methylsulfonyl)benzyloxy)quinolin-6-yl)acetic acid | 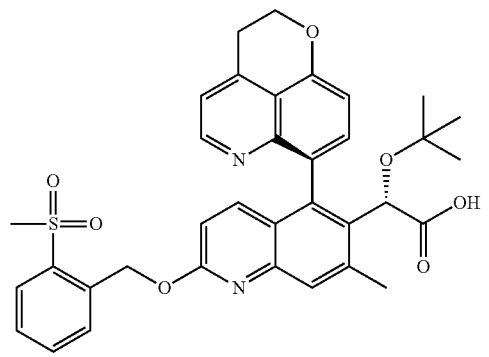 | 8.63 |

| Example | Compound Name | Compound Structure | EC$_{50}$ (nM) |
|---------|---------------|--------------------|----------------|
| 11 | (S)-2-tert-butoxy-2-((R)-5-(2,3-dihydropyrano[4,3,2-de]quinolin-7-yl)-7-methyl-2-oxo-1-(4-(trifluoromethyl)benzyl)-1,2-dihydroquinolin-6-yl)acetic acid | 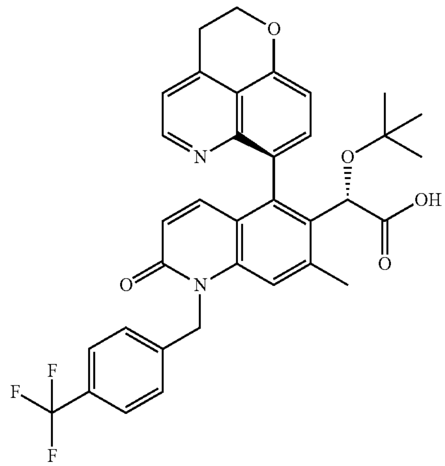 | 983 |
| 12 | (S)-2-((R)-2-(benzyloxy)-5-(2,3-dihydropyrano[4,3,2-de]quinolin-7-yl)-7-methylquinolin-6-yl)-2-tert-butoxyacetic acid | 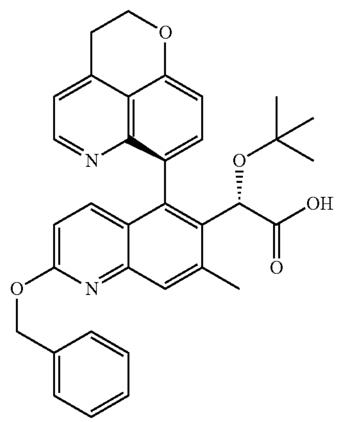 | 50 |
| 13 | (S)-2-tert-butoxy-2-((R)-5-(2,3-dihydropyrano[4,3,2-de]quinolin-7-yl)-7-methyl-2-(4-(trifluoromethoxy)benzyloxy)quinolin-6-yl)acetic acid | 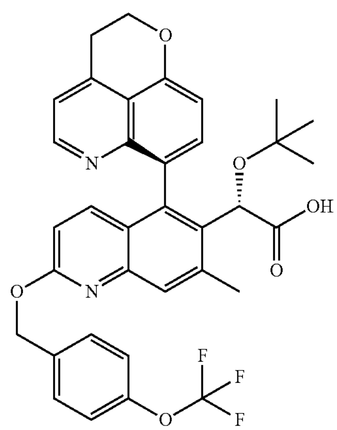 | 285 |

| Example | Compound Name | Compound Structure | EC$_{50}$ (nM) |
|---|---|---|---|
| 14 | (S)-2-tert-butoxy-2-((R)-5-(2,3-dihydropyrano[4,3,2-de]quinolin-7-yl)-7-methyl-2-(3-(trifluoromethoxy)benzyloxy)quinolin-6-yl)acetic acid | 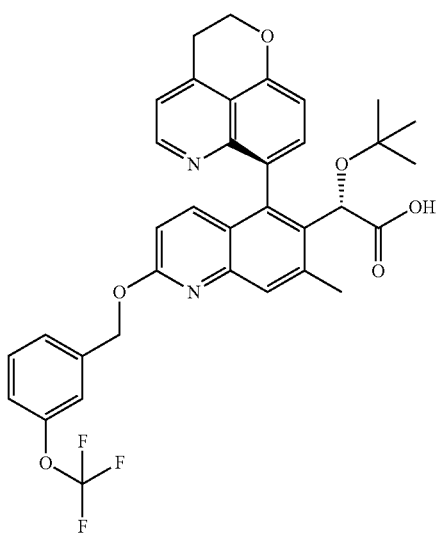 | 217 |
| 15 | (S)-2-tert-butoxy-2-((R)-5-(2,3-dihydropyrano[4,3,2-de]quinolin-7-yl)-7-methyl-2-oxo-1-(2-(trifluoromethoxy)benzyl)-1,2-dihydroquinolin-6-yl)acetic acid | 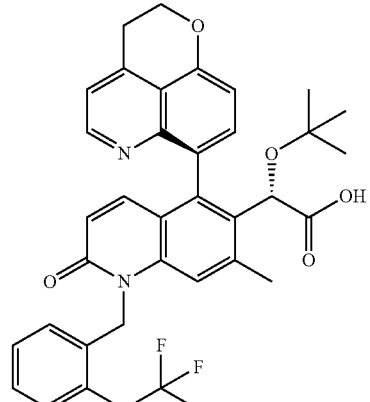 | 359 |
| 16 | (S)-2-tert-butoxy-2-((R)-5-(2,3-dihydropyrano[4,3,2-de]quinolin-7-yl)-7-methyl-2-oxo-1-(4-(trifluoromethoxy)benzyl)-1,2-dihydroquinolin-6-yl)acetic acid | 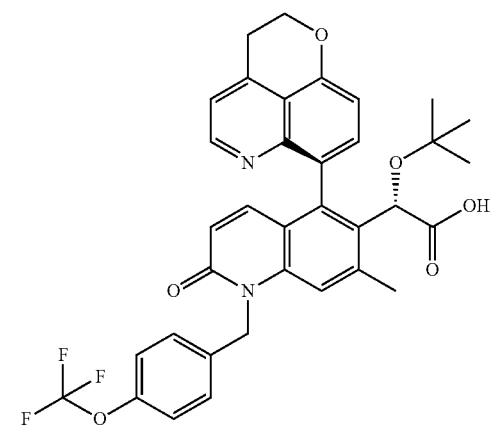 | 1614 |

-continued

| Example | Compound Name | Compound Structure | EC$_{50}$ (nM) |
|---|---|---|---|
| 17 | (S)-2-tert-butoxy-2-((R)-5-(2,3-dihydropyrano[4,3,2-de]quinolin-7-yl)-7-methyl-2-sulfamoylbenzyloxy)quinolin-(4-6-yl)acetic acid | 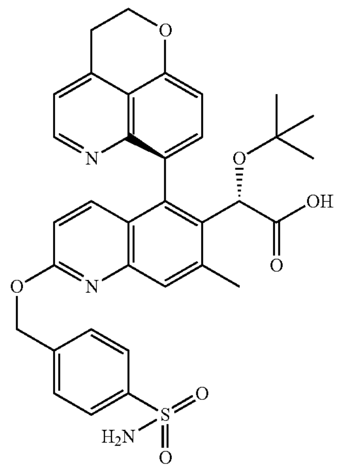 | 84 |
| 18 | (S)-2-tert-butoxy-2-((R)-5-(2,3-dihydropyrano[4,3,2-de]quinolin-7-yl)-7-methyl-2-oxo-1-(3-(trifluoromethoxy)benzyl)-1,2-dihydroquinolin-6-yl)acetic acid | 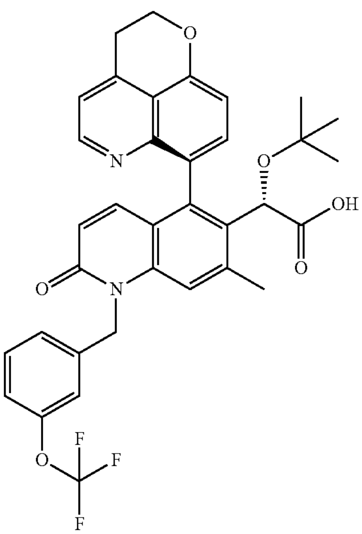 | 185 |
| 19 | (S)-2-tert-butoxy-2-((R)-5-(2,3-dihydropyrano[4,3,2-de]quinolin-7-yl)-7-methyl-2-(2-(trifluoromethoxy)benzyloxy)quinolin-6-yl)acetic acid | 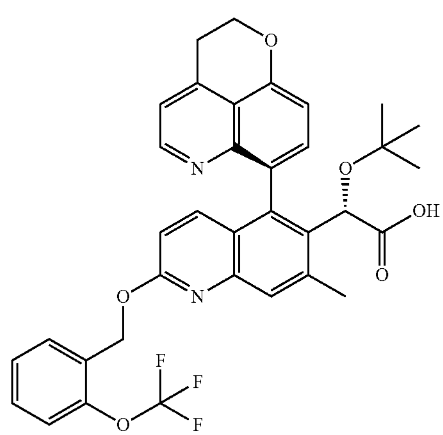 | 70 |

-continued

| Example | Compound Name | Compound Structure | EC$_{50}$ (nM) |
|---------|---------------|--------------------|----------------|
| 20 | (S)-2-((R)-1-(3,5-bis(trifluoromethyl)benzyl)-5-(2,3-dihydropyrano[4,3,2-de]quinolin-7-yl)-7-methyl-2-oxo-1,2-dihydroquinolin-6-yl)-2-tert-butoxyacetic acid | 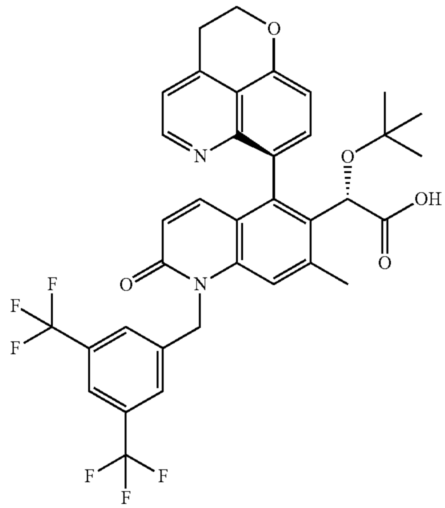 | 90 |
| 21 | (S)-2-tert-butoxy-2-((R)-5-(2,3-dihydropyrano[4,3,2-de]quinolin-7-yl)-7-methyl-2-oxo-1-(pyridin-4-ylmethyl)-1,2-dihydroquinolin-6-yl)acetic acid | 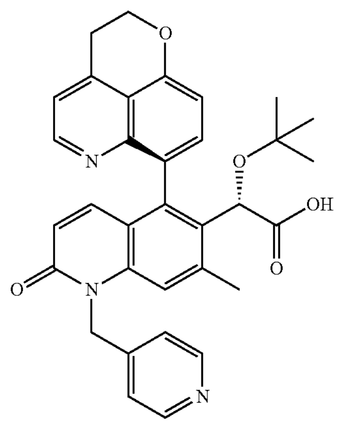 | 755 |
| 22 | (S)-2-tert-butoxy-2-((R)-5-(2,3-dihydropyrano[4,3,2-de]quinolin-7-yl)-7-methyl-2-oxo-1-(pyridin-3-ylmethyl)-1,2-dihydroquinolin-6-yl)acetic acid | 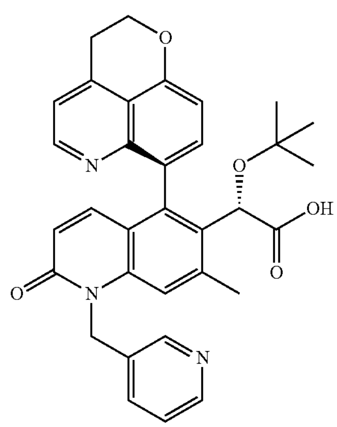 | 318 |

-continued

| Example | Compound Name | Compound Structure | EC$_{50}$ (nM) |
|---|---|---|---|
| 23 | (S)-2-tert-butoxy-2-((R)-5-(2,3-dihydropyrano[4,3,2-de]quinolin-7-yl)-7-methyl-2-oxo-1-(pyrazin-2-ylmethyl)-1,2-dihydroquinolin-6-yl)acetic acid | 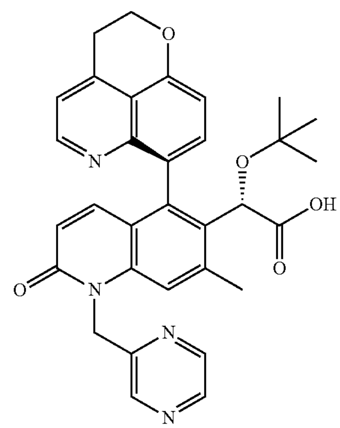 | 383 |
| 24 | (S)-2-tert-butoxy-2-((R)-5-(2,3-dihydropyrano[4,3,2-de]quinolin-7-yl)-7-methyl-2-oxo-1-(3-phenylpropyl)-1,2-dihydroquinolin-6-yl)acetic acid | 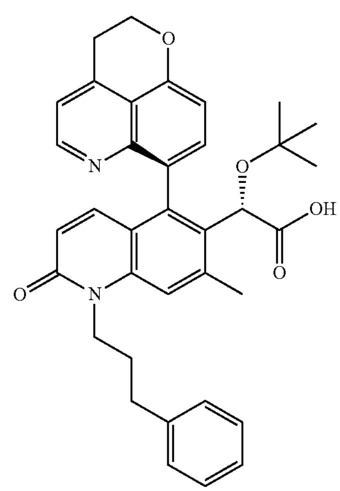 | 687 |
| 25 | (S)-2-tert-butoxy-2-((R)-5-(2,3-dihydropyrano[4,3,2-de]quinolin-7-yl)-7-methyl-2-oxo-1-(pyrimidin-5-ylmethyl)-1,2-dihydroquinolin-6-yl)acetic acid | 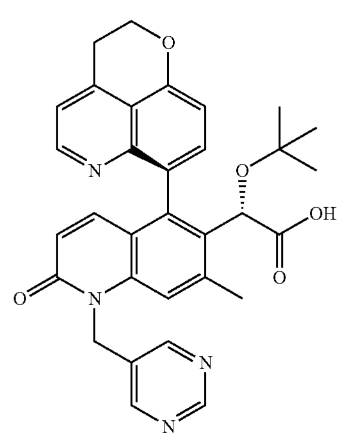 | 472 |

-continued

| Example | Compound Name | Compound Structure | EC$_{50}$ (nM) |
|---|---|---|---|
| 26 | (S)-2-tert-butoxy-2-((R)-5-(2,3-dihydropyrano[4,3,2-de]quinolin-7-yl)-1-(3-methoxybenzyl)-7-methyl-2-oxo-1,2-dihydroquinolin-6-yl)acetic acid | 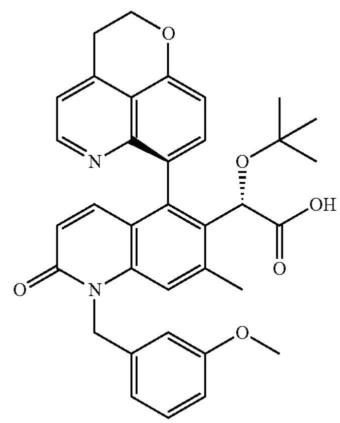 | 99.3 |
| 27 | (S)-2-tert-butoxy-2-((R)-5-(2,3-dihydropyrano[4,3,2-de]quinolin-7-yl)-1-(3-fluoro-5-(trifluoromethyl)benzyl)-7-methyl-2-oxo-1,2-dihydroquinolin-6-yl)acetic acid | 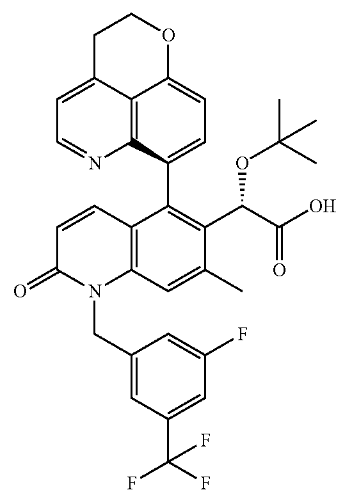 | 53.5 |
| 28 | (S)-2-tert-butoxy-2-((R)-5-(2,3-dihydropyrano[4,3,2-de]quinolin-7-yl)-7-methyl-1-((1-methyl-1H-indazol-4-yl)methyl)-2-oxo-1,2-dihydroquinolin-6-yl)acetic acid | 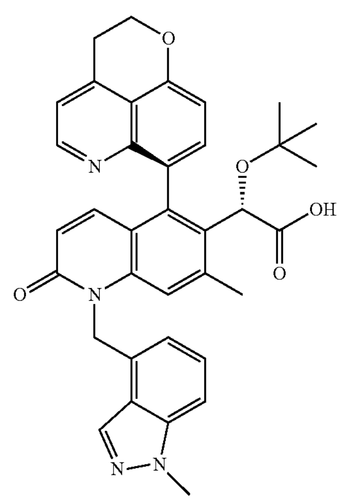 | 45.8 |

-continued

| Example | Compound Name | Compound Structure | EC$_{50}$ (nM) |
|---------|---------------|-------------------|----------------|
| 29 | (S)-2-tert-butoxy-2-((R)-5-(2,3-dihydropyrano[4,3,2-de]quinolin-7-yl)-7-methyl-1-((1-methyl-1H-indazol-5-yl)methyl)-2-oxo-1,2-dihydroquinolin-6-yl)acetic acid | 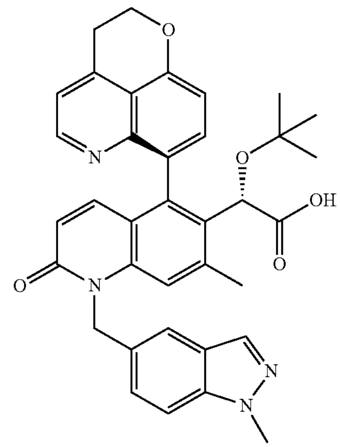 | 85.5 |
| 30 | (S)-2-tert-butoxy-2-((R)-1-(3-(difluoromethyl)benzyl)-5-(2,3-dihydropyrano[4,3,2-de]quinolin-7-yl)-7-methyl-2-oxo-1,2-dihydroquinolin-6-yl)acetic acid | 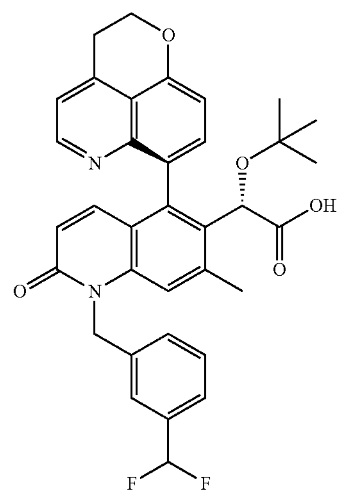 | 34.7 |
| 31 | S)-2-tert-Butoxy-2-((R)-5-(2,3-dihydropyrano[4,3,2-de]quinolin-7-yl)-7-methyl-2-oxo-1-((5-(trifluoromethyl)pyridin-3-yl)methyl)-1,2-dihydroquinolin-6-yl)acetic acid | 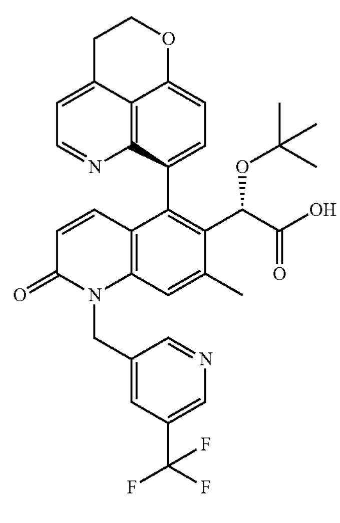 | 68.2 |

| Example | Compound Name | Compound Structure | EC$_{50}$ (nM) |
|---|---|---|---|
| 32 | (S)-2-tert-Butoxy-2-((R)-5-(2,3-dihydropyrano[4,3,2-de]quinolin-7-yl)-7-methyl-2-oxo-1-(4-phenoxybenzyl)-1,2-dihydroquinolin-6-yl)acetic acid | 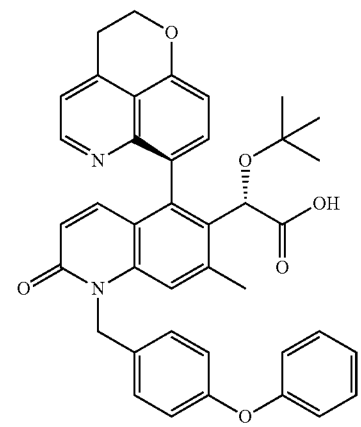 | 3060 |
| 33 | (S)-2-tert-Butoxy-2-((R)-5-(2,3-dihydropyrano[4,3,2-de]quinolin-7-yl)-1-(3,5-dimethoxybenzyl)-7-methyl-2-oxo-1,2-dihydroquinolin-6-yl)acetic acid | 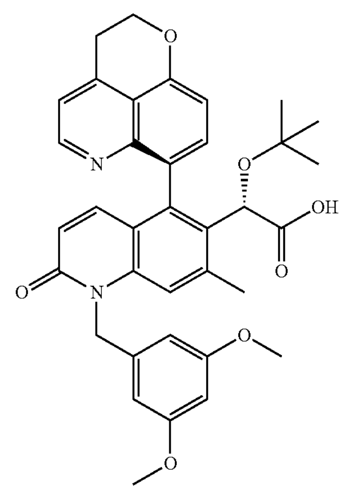 | 133 |
| 34 | (S)-2-tert-butoxy-2-((R)-1-(4-cyclobutylbenzyl)-5-(2,3-dihydropyrano[4,3,2-de]quinolin-7-yl)-7-methyl-2-oxo-1,2-dihydroquinolin-6-yl)acetic acid | 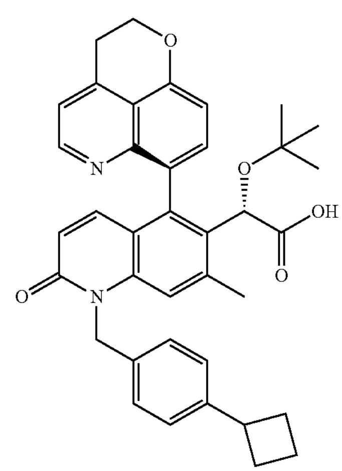 | n.d. |

| Example | Compound Name | Compound Structure | EC$_{50}$ (nM) |
|---|---|---|---|
| 35 | (S)-2-tert-Butoxy-2-((R)-5-(2,3-dihydropyrano[4,3,2-de]quinolin-7-yl)-7-methyl-2-oxo-1-m-tolyl-1,2-dihydroquinolin-6-yl)acetic acid | 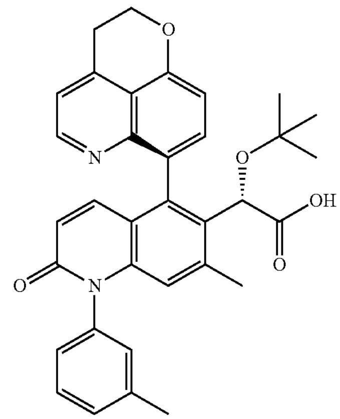 | 1470 |
| 36 | (S)-2-tert-butoxy-2-((R)-5-(2,3-dihydropyrano[4,3,2-de]quinolin-7-yl)-7-methyl-1-(3-(methylsulfonamido)phenyl)-2-oxo-1,2-dihydroquinolin-6-yl)acetic acid | 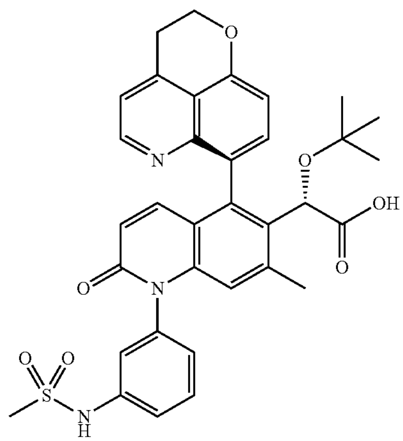 | 37400 |
| 37 | (S)-2-tert-butoxy-2-((R)-5-(2,3-dihydropyrano[4,3,2-de]quinolin-7-yl)-7-methyl-1-(3-(methylsulfonyl)phenyl)-2-oxo-1,2-dihydroquinolin-6-yl)acetic acid | 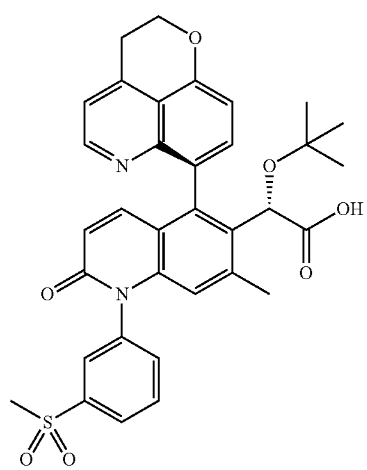 | 8430 |

| Example | Compound Name | Compound Structure | EC$_{50}$ (nM) |
|---|---|---|---|
| 38 | (2S)-2-((R)-5-(2,3-dihydropyrano[4,3,2-de]quinolin-7-yl)-2,7-dimethylquinolin-6-yl)-2-(2-methyl-4-phenylbutan-2-yloxy)acetic acid | 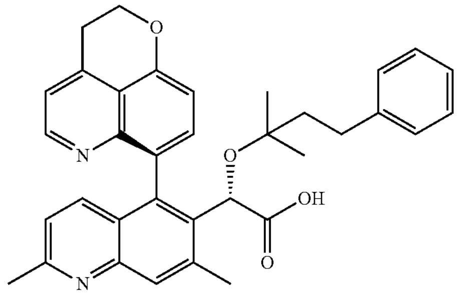 | 38.1 |
| 39 | (2S)-2-((R)-5-(2,3-dihydropyrano[4,3,2-de]quinolin-7-yl)-2,7-dimethylquinolin-6-yl)-2-(2-methylpentan-2-yloxy)acetic acid | 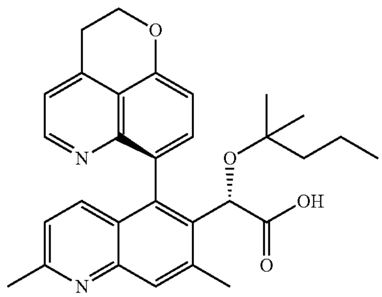 | 12.3 |
| 40 | (2S)-2-((S)-5-(2,3-dihydropyrano[4,3,2-de]quinolin-7-yl)-2,7-dimethylquinolin-6-yl)-2-(2-methylpentan-2-yloxy)acetic acid | 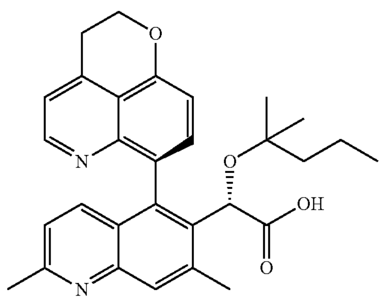 | 2760 |
| 41 | (S)-2-((R)-5-(2,3-dihydropyrano[4,3,2-de]quinolin-7-yl)-2,7-dimethylquinolin-6-yl)-2-(3-methylpentan-3-yloxy)acetic acid | 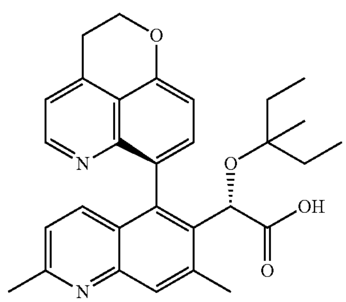 | 39.0 |
| 42 | (S)-2-((S)-5-(2,3-dihydropyrano[4,3,2-de]quinolin-7-yl)-2,7-dimethylquinolin-6-yl)-2-(3-methylpentan-3-yloxy)acetic acid | 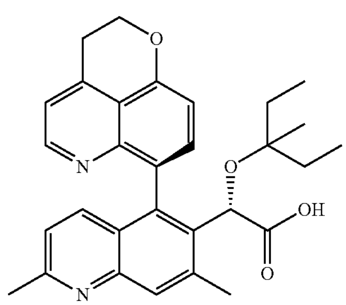 | 5630 |

-continued

| Example | Compound Name | Compound Structure | EC$_{50}$ (nM) |
|---|---|---|---|
| 43 | (S)-2-((S)-5-(2,3-dihydropyrano[4,3,2-de]quinolin-7-yl)-2,7-dimethylquinolin-6-yl)-2-(2-methylheptan-2-yloxy)acetic acid | 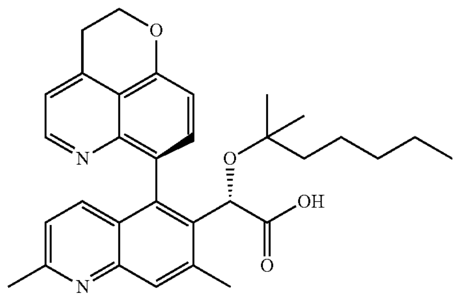 | 39400 |
| 44 | (S)-2-((R)-5-(2,3-dihydropyrano[4,3,2-de]quinolin-7-yl)-2,7-dimethylquinolin-6-yl)-2-(tert-pentyloxy)acetic acid | 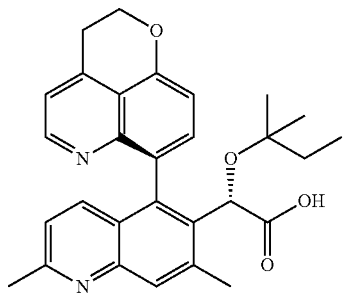 | 11.7 |
| 45 | (S)-2-((S)-5-(2,3-dihydropyrano[4,3,2-de]quinolin-7-yl)-2,7-dimethylquinolin-6-yl)-2-(tert-pentyloxy)acetic acid | 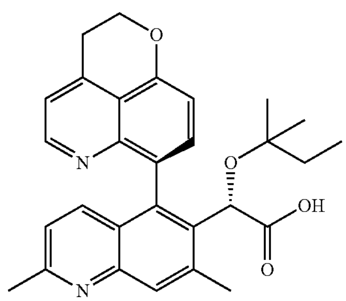 | 13200 |
| 46 | (S)-2-tert-butoxy-2-((R)-5-(2,3-dihydropyrano[4,3,2-de]quinolin-7-yl)-7-methyl-2-(methylamino)quinolin-6-yl)acetic acid. | 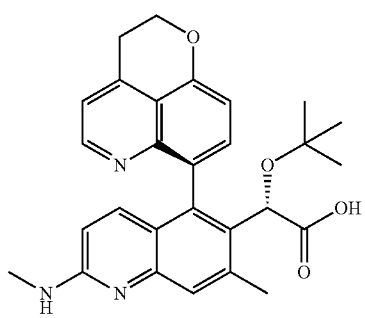 | 265 |
| 47 | (S)-2-((R)-2-amino-5-(2,3-dihydropyrano[4,3,2-de]quinolin-7-yl)-7-methylquinolin-6-yl)-2-tert-butoxyacetic acid | 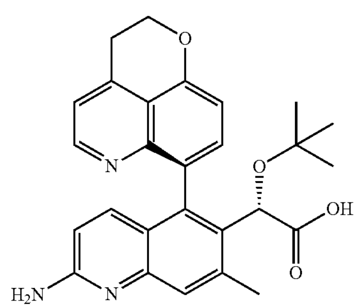 | 292 |

-continued

| Example | Compound Name | Compound Structure | EC₅₀ (nM) |
|---|---|---|---|
| 48 | (S)-2-((R)-2-acetamido-5-(2,3-dihydropyrano[4,3,2-de]quinolin-7-yl)-7-methylquinolin-6-yl)-2-tert-butoxyacetic acid | 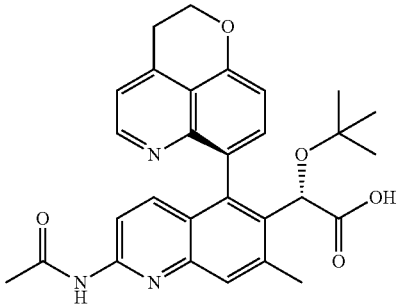 | 361 |
| 49 | (S)-2-((R)-2-benzamido-5-(2,3-dihydropyrano[4,3,2-de]quinolin-7-yl)-7-methylquinolin-6-yl)-2-tert-butoxyacetic acid | 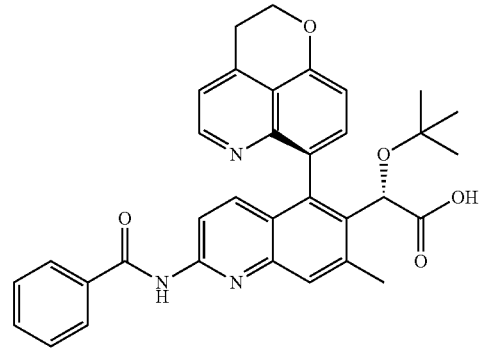 | 134 |
| 50 | (S)-2-tert-butoxy-2-((R)-2-cyano-5-(2,3-dihydropyrano[4,3,2-de]quinolin-7-yl)-7-methylquinolin-6-yl)acetic acid | 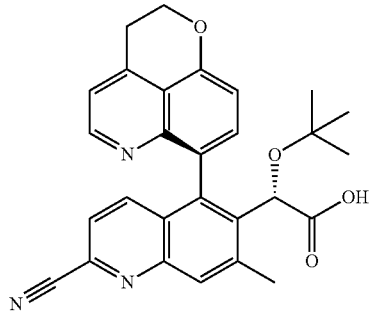 | 166 |
| 51 | (S)-2-tert-butoxy-2-((R)-5-(2,3-dihydropyrano[4,3,2-de]quinolin-7-yl)-2-(2-hydroxypropan-2-yl)-7-methylquinolin-6-yl)acetic acid | 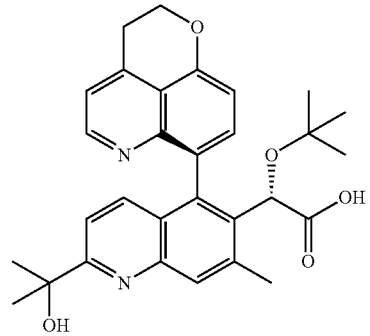 | 186 |

| Example | Compound Name | Compound Structure | EC$_{50}$ (nM) |
|---|---|---|---|
| 52 | (S)-2-tert-butoxy-2-((R)-2-(1,1-difluoroethyl)-5-(2,3-dihydropyrano[4,3,2-de]quinolin-7-yl)-7-methylquinolin-6-yl)acetic acid | 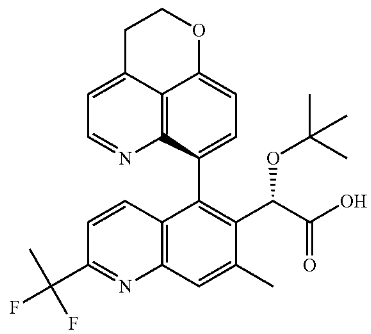 | 65.1 |
| 53 | (2S)-2-tert-butoxy-2-((5R)-5-(2,3-dihydropyrano[4,3,2-de]quinolin-7-yl)-2-(1-fluoroethyl)-7-methylquinolin-6-yl)acetic acid | 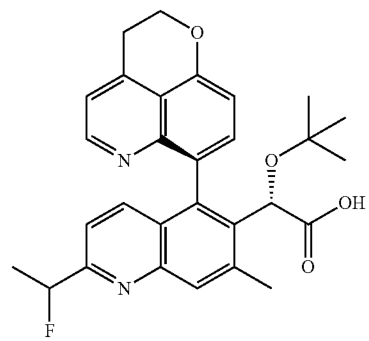 | 22.1 |
| 54 | Mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)acetic acid and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)acetic acid | | 220 |
| 55 | (S)-2-tert-butoxy-2-((R)-6-(2,3-dihydropyrano[4,3,2-de]quinolin-7-yl)-8-methyl-[1,2,3]triazolo[1,5-a]quinolin-7-yl)acetic acid | | 78.4 | n.d. not determined

In certain embodiments, the compounds demonstrate an EC50 of <50 In certain embodiments, the compounds demonstrate an EC50 of <30 µM. In certain embodiments, the compounds demonstrate an EC50 of <10 µM. In certain embodiments, the compounds demonstrate an EC50 of <1 µM. In certain embodiments, the compounds demonstrate an EC50 of <0.5 µM. In certain embodiments, the compounds demonstrate an EC50 of <0.2 µM. In certain embodiments, the compounds demonstrate an EC50 of <0.1 µM. It is to be understood that the compounds disclosed herein can be grouped according to the EC50 activities described above.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

EXAMPLE 1

(S)-2-tert-Butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid

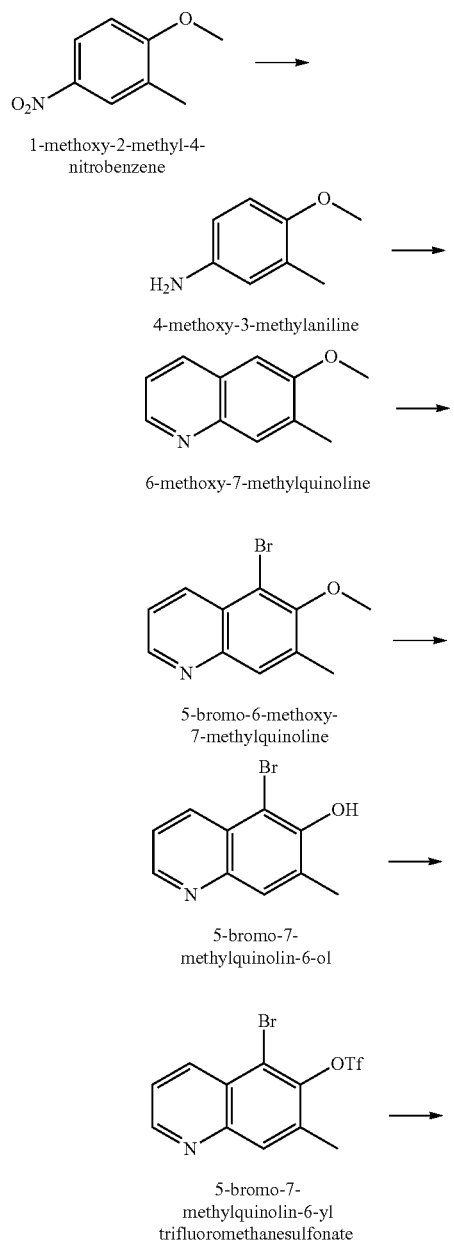

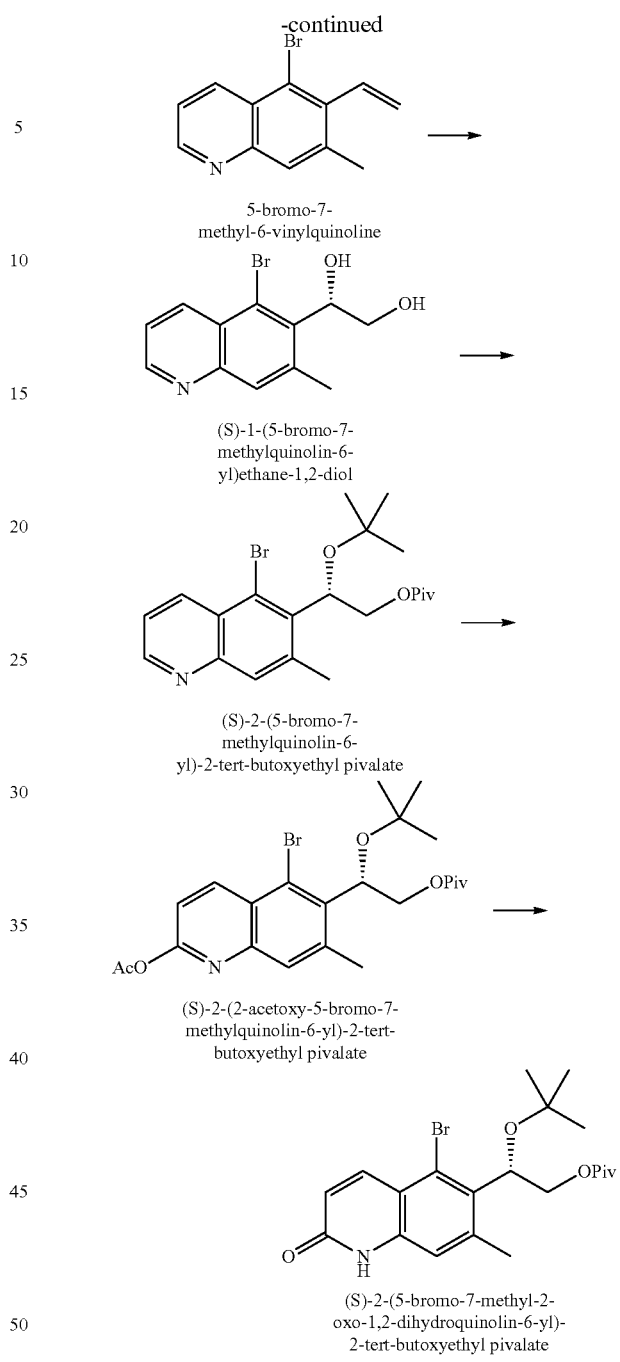

Preparation of 4-methoxy-3-methylaniline: To the solution of 1-methoxy-2-methyl-4-nitrobenzene (10 g, 60 mmol) in EtOH and EtOAc (250 mL, 3:2) was added 10% Pd/C (2 g). The mixture was stirred for 24 h under one atmosphere of hydrogen. Celite was added and the mixture was stirred for 10 min. The mixture was filtered through a pad of Celite. Concentration under reduced pressure gave 4-methoxy-3-methylaniline. LCMS-ESI⁺ (m/z): 138.2 (M+H)⁺.

Preparation of 6-methoxy-7-methylquinoline: To 4-methoxy-3-methylaniline (6.7 g) was added concentrated $H_2SO_4$ (12.4 mL), followed by glycerin (21.1 g), m-nitrobenzenesulfonic acid (6.53 g), $H_3BO_3$ (3.4 g) and $FeSO_4.7H_2O$ (3.2 g). The mixture was stirred at 140° C. for 1 h. The reaction was cooled to 25° C., quenched with ice-water and neutralized with 30% KOH. The mixture was extracted with DCM (2×), and the combined extracts dried with Na$_2$SO$_4$ and concentrated in vacuo. The crude product was purified by column chromatography (EtOAc) to give 6-methoxy-7-methylquinoline LCMS-ESI$^+$ (m/z): 174.1 (M+H)$^+$.

Preparation of 5-bromo-6-methoxy-7-methylquinoline: To the solution of 6-methoxy-7-methylquinoline (4.28 g, 24.6 mmol) in 50 mL of concentrated H$_2$SO$_4$ was added N-bromosuccinimide (4.41 g, 14.6 mmol) at 15° C., and the reaction was stirred at 15° C. for 3.5 hours. The reaction mixture was poured into ice-water (600 mL). The aqueous mixture was adjusted with a 50% KOH solution to pH ~10, and then extracted with DCM (3×). The combined extract was dried with sodium sulfate. Concentration under reduced pressure gave 5-bromo-6-methoxy-7-methylquinoline. LCMS-ESI$^+$ (m/z): 252.1, 254.1 (M+H)$^+$.

Preparation of 5-bromo-7-methylquinolin-6-ol: To the solution of 5-bromo-6-methoxy-7-methylquinoline (6.5 g, 25.8 mmol) in DCM (150 mL) was added boron tribromide slowly (77.3 mL, 1.0 M in DCM, 77.3 mmol). The mixture was stirred for 3 hours and cooled to 0° C. Methanol (40 mL) was added slowly and the mixture was stirred for 20 minutes. The solvents were removed under reduced pressure. The solid was dissolved in methanol (100 mL) and was treated with 1.0 N sodium hydroxide solution (50 mL) (pH ~12). The mixture was stirred for 12 hours and acetic acid was added to adjust pH to between 4-5. The mixture was filtered and washed with water. The gray solid was dried under reduced pressure to give 5-bromo-7-methylquinolin-6-ol. LCMS-ESI$^+$ (m/z): 238.2, 240.1 (M+H)$^+$, 236.1, 238.0 (M−H).

Preparation of 5-bromo-7-methylquinolin-6-yltrifluoromethanesulfonate: To the solution of 5-bromo-7-methylquinolin-6-ol (238 mg, 1.0 mmol) in dichloromethane (10 mL) and pyridine (2 mL) was added Tf$_2$O (0.34 mL, 2.0 mmol) at −30° C. The mixture was stirred and warmed to 0° C. over a period of 2 hours. The reaction was quenched with slow addition of NaHCO$_3$ solution. The mixture was extracted with ethyl acetate. The organic layer was washed with brine, dried over sodium sulfate and concentrated to give 5-bromo-7-methylquinolin-6-yl trifluoromethanesulfonate. LCMS-ESI$^+$ (m/z): 369.9, 371.9 (M+H)$^+$.

Preparation of 5-bromo-7-methyl-6-vinylquinoline: A mixture of 5-bromo-7-methylquinolin-6-yltrifluoromethanesulfonate (230 mg, 0.62 mmol), tributyl(vinyl)stannane (200 μL, 0.68 mmol), lithium chloride (78 mg, 1.86 mmol) and PdCl$_2$(PPh$_3$)$_2$ (43 mg) in DMF (10 mL) was heated at 80° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The residue was purified by flash chromatography (hexanes/EtOAc) to provide 5-bromo-7-methyl-6-vinylquinoline. LCMS-ESI$^+$ (m/z): 248.2, 250.2 (M+H)$^+$.

Preparation of (S)-1-(5-bromo-7-methylquinolin-6-yl) ethane-1,2-diol: AD-mix-α (Aldrich, 0.7 g) was added to a mixed solvent of t-butanol and water (2.5 mL/2.5 mL) and stirred at 25° C. for 5 min, cooled to 0° C. The mixture was transferred to another flask containing 5-bromo-7-methyl-6-vinylquinoline (120 mg) and stirred at 0° C. for 48 hours. The mixture was diluted with ethyl acetate, washed with NaHCO$_3$ solution, water and brine, dried over Na$_2$SO$_4$, filtered and concentrated in vacuo. The residue was purified by flash column chromatography (EtOAc) to provide (S)-1-(5-bromo-7-methylquinolin-6-yl)ethane-1,2-diol. LCMS-ESI$^+$ (m/z): 282.1, 284.1 (M+H)$^+$.

Preparation of (S)-2-(5-bromo-7-methylquinolin-6-yl)-2-tert-butoxyethyl pivalate: To a stirred solution of (S)-1-(5-bromo-7-methylquinolin-6-yl)ethane-1,2-diol (118 mg, 0.42 mmol) in dichloromethane (5 mL) and pyridine (1 mL) was added trimethylacetyl chloride (100 μL, 0.84 mmol) at 0° C. The mixture was stirred at room temperature for 12 hours, quenched with slow addition of NaHCO$_3$ solution. The mixture was extracted with ethyl acetate. The organic layer was washed with brine, dried over Na$_2$SO$_4$. Concentration gave a residue (124 mg). To the solution of above residue (124 mg, 0.34 mmol) in t-butylacetate (3 mL) was added 70% perchloric acid (67 μL, 1.1 mmol) at 25° C. The mixture was stirred at 25° C. for 2 hours, quenched with slow addition of NaHCO$_3$ solution. The mixture was extracted with ethyl acetate. The organic layer was washed with brine, dried and concentrated in vacuo. The residue was purified by flash chromatography (hexanes/EtOAc) to provide (S)-2-(5-bromo-7-methylquinolin-6-yl)-2-tert-butoxyethyl pivalate. LCMS-ESI$^+$ (m/z): 422.1, 424.2 (M+H)$^+$.

Preparation of (S)-2-(2-acetoxy-5-bromo-7-methylquinolin-6-yl)-2-tert-butoxyethyl pivalate: To the solution of (S)-2-(5-bromo-7-methylquinolin-6-yl)-2-tert-butoxyethyl pivalate (130 mg, 0.31 mmol) in DCM (2 mL) was added 3-chloroperoxybenzoic acid (70%, 95 mg, 0.39 mmol). The mixture was stirred for 12 hours. The mixture was diluted with EtOAc, washed with saturated sodium bicarbonate solution, water and brine, and dried over sodium sulfate. Concentration under reduced pressure gave the intermediate N-oxide (147 mg). LCMS-ESI$^+$ (m/z): 438.2, 440.2 (M+H)$^+$. To the above intermediate was added acetic anhydride (5 mL). The mixture was heated at 140° C. for 10 hours. The excess reagents were removed under reduced pressure. The mixture was diluted with EtOAc, washed with saturated sodium bicarbonate solution, water and brine, and dried over sodium sulfate. Concentration gave (S)-2-(2-acetoxy-5-bromo-7-methylquinolin-6-yl)-2-tert-butoxyethyl pivalate. LCMS-ESI$^+$ (m/z): 480.0, 482.0 (M+H)$^+$.

Preparation of (S)-2-(5-bromo-7-methyl-2-oxo-1,2-dihydroquinolin-6-yl)-2-tert-butoxyethyl pivalate: To the solution of (S)-2-(2-acetoxy-5-bromo-7-methylquinolin-6-yl)-2-tert-butoxyethyl pivalate (130 mg) in ethanol (7.5 mL) was added aqueous methylamine solution (0.5 mL, 50%). The mixture was heated at 78° C. for 80 min. Concentration and purification gave (S)-2-(5-bromo-7-methyl-2-oxo-1,2-dihydroquinolin-6-yl)-2-tert-butoxyethyl pivalate. LCMS-ESI$^+$ (m/z): 438.2, 440.2 (M+H)$^+$.

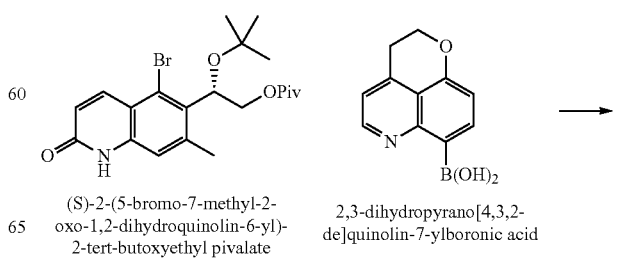

(S)-2-(5-bromo-7-methyl-2-oxo-1,2-dihydroquinolin-6-yl)-2-tert-butoxyethyl pivalate 2,3-dihydropyrano[4,3,2-de]quinolin-7-ylboronic acid

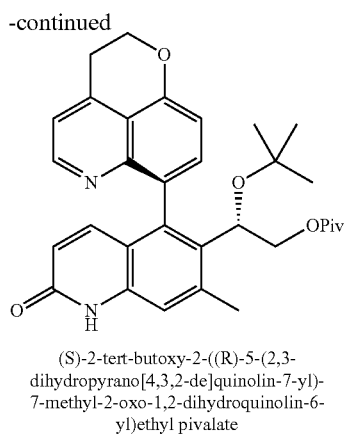

(S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate Preparation of (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate: To a solution of (S)-2-(5-bromo-7-methyl-2-oxo-1,2-dihydroquinolin-6-yl)-2-tert-butoxyethyl pivalate (4.76 g, 10.9 mmol) and 2,3-dihydropyrano[4,3,2-de]quinolin-7-ylboronic acid (3.28 g, 13.07 mmol) (prepared by the method of WO2009/062289) in DME was added Pd(PPh$_3$)$_4$ (1.26 g, 1.09 mmol) and 2M K$_2$CO$_3$ (21.8 mL). The reaction was degassed for 15 minutes with argon and then heated to 90° C. overnight. The crude reaction mixture was absorbed onto silica and purified by flash column chromatography (silica gel, ethyl acetate/hexanes, methanol/ethyl acetate) to give the desired compound. LCMS-ESI$^+$ (m/z): [M+H]$^+$ calc'd for C$_{32}$H$_{36}$N2O$_5$: 529.26; found: 529.63.

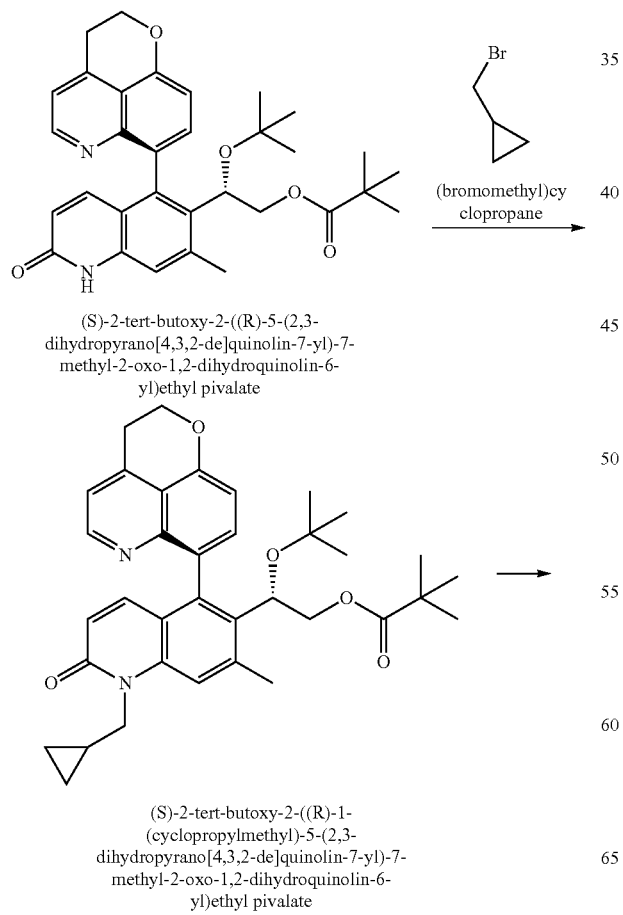

(S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate (bromomethyl)cyclopropane (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)ethyl pivalate

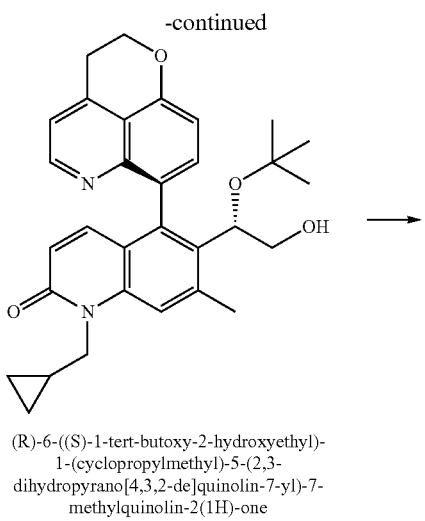

(R)-6-((S)-1-tert-butoxy-2-hydroxyethyl)-1-(cyclopropylmethyl)-5-(2,3-dihydropyrano[4,3,2-de]quinolin-7-yl)-7-methylquinolin-2(1H)-one (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid Preparation of (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)ethyl pivalate: To a solution of (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate (100 mg, 0.189 mmol) in THF at –78° C. was added 1M KOtBu in THF (0.22 mL, 0.227) and the reaction was stirred 15 minutes. (Bromomethyl)cyclopropane (0.227 mL, 0.227 mmol) was then added and the reaction was stirred at room temperature until no more coversion was observed. The reaction mixture was quenched with water and absorbed onto silica and purified by flash column chromatography (silica gel, ethyl acetate/hexanes, methanol/ethyl acetate) to give the desired compound. LCMS-ESI$^+$ (m/z): [M+H]$^+$ calc'd for C$_{36}$H$_{42}$N$_2$O$_5$: 583.31; found: 583.54.

Preparation of (R)-6-((S)-1-tert-butoxy-2-hydroxyethyl)-1-(cyclopropylmethyl)-5-(2,3-dihydropyrano[4,3,2-de]quinolin-7-yl)-7-methylquinolin-2(1H)-one: To a solution of (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)ethyl pivalate (29.2 mg, 0.05 mmol) in THF/methanol (5/1) was added 1M sodium hydroxide (2 mL) and the reaction was heated to 45° C. overnight. The reaction was diluted with water, extracted with ethyl acetate (2×), washed with brine, dried over sodium sulfate and concentrated. The residue was then co-evaporated two times with acetonitrile to give the desired compound. LCMS-ESI⁺ (m/z): [M+H]⁺ calc'd for $C_{31}H_{34}N_2O_4$: 499.25; found: 499.93.

Preparation of (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid: To a solution of (R)-6-((S)-1-tert-butoxy-2-hydroxyethyl)-1-(cyclopropylmethyl)-5-(2,3-dihydropyrano[4,3,2-de]quinolin-7-yl)-7-methylquinolin-2(1H)-one (26.4 mg, 0.05 mmol) in wet acetonitrile at 0° C. was added $CrO_3/H_5IO_6$ (1.2% $CrO_3$–0.4M, 0.794 mL, 0.318 mmol) and the reaction was stirred approximately 3 hours. The crude reaction was diluted with water, filtered and purified by reverse phase HPLC (Gemini, 10-50% ACN/$H_2O$+0.1% TFA) and the desired product was lyophilized to give the TFA salt. LCMS-ESI⁺ (m/z): [M+H]⁺ calc'd for $C_{31}H_{32}N_2O_5$: 513.23; found: 513.39. ¹H NMR (400 MHz, $CD_3CN$) δ 8.67 (d, J=5.0 Hz, 1H), 7.66-7.59 (m, 2H), 7.52 (d, J=5.0 Hz, 1H), 7.24 (d, J=8.0 Hz, 1H), 6.81 (d, J=9.8 Hz, 1H), 6.27 (d, J=9.8 Hz, 1H), 5.05 (s, 1H), 4.68-4.50 (m, 2H), 4.25 (d, J=6.9 Hz, 2H), 3.46 (t, J=5.8 Hz, 2H), 2.67 (s, 3H), 1.35 (dt, J=13.1, 6.6 Hz, 1H), 0.88 (s, 9H), 0.52 (d, J=6.5 Hz, 4H).

EXAMPLE 2

(S)-2-tert-Butoxy-2-((R)-5-(2,3-dihydropyrano[4,3,2-de]quinolin-7-yl)-7-methyl-1-(3-(methylsulfonyl)benzyl)-2-oxo-1,2-dihydroquinolin-6-yl)acetic acid

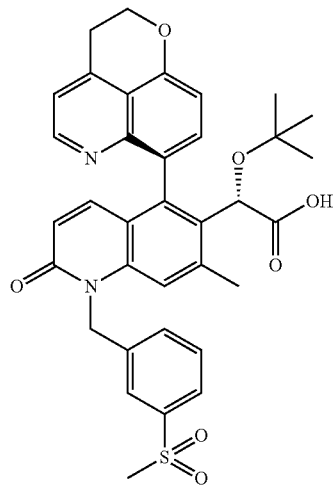

(S)-2-tert-butoxy-2-((R)-5-(2,3-dihydropyrano[4,3,2-de]quinolin-7-yl)-7-methyl-1-(3-(methylsulfonyl)benzyl)-2-oxo-1,2-dihydroquinolin-6-yl)acetic acid (S)-2-tert-Butoxy-2-((R)-5-(2,3-dihydropyrano[4,3,2-de]quinolin-7-yl)-7-methyl-1-(3-(methylsulfonyl)benzyl)-2-oxo-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl) acetic acid using 1-(bromomethyl)-3-(methylsulfonyl)benzene instead of (bromomethyl)cyclopropane. LCMS-ESI⁺ (m/z): [M+H]⁺ calc'd for $C_{35}H_{34}N_2O_7S$: 627.21; found: 627.59 ¹H NMR (400 MHz, $CD_3CN$) δ 8.66 (d, J=5.1 Hz, 1H), 7.93 (s, 1H), 7.85 (d, J=7.5 Hz, 1H), 7.68-7.52 (m, 3H), 7.37 (s, 1H), 7.27 (d, J=8.0 Hz, 1H), 6.92 (d, J=9.9 Hz, 1H), 6.41 (d, J=9.9 Hz, 1H), 5.65 (q, J=15.9 Hz, 2H), 5.02 (s, 1H), 4.60 (tt, J=11.4, 5.7 Hz, 2H), 3.48 (t, J=5.8 Hz, 2H), 3.06 (s, 3H), 2.53 (s, 2H), 0.85 (s, 7H).

EXAMPLE 3

(S)-2-tert-Butoxy-2-((R)-5-(2,3-dihydropyrano[4,3,2-de]quinolin-7-yl)-7-methyl-2-(3-(trifluoromethyl)benzyloxy)quinolin-6-yl)acetic acid

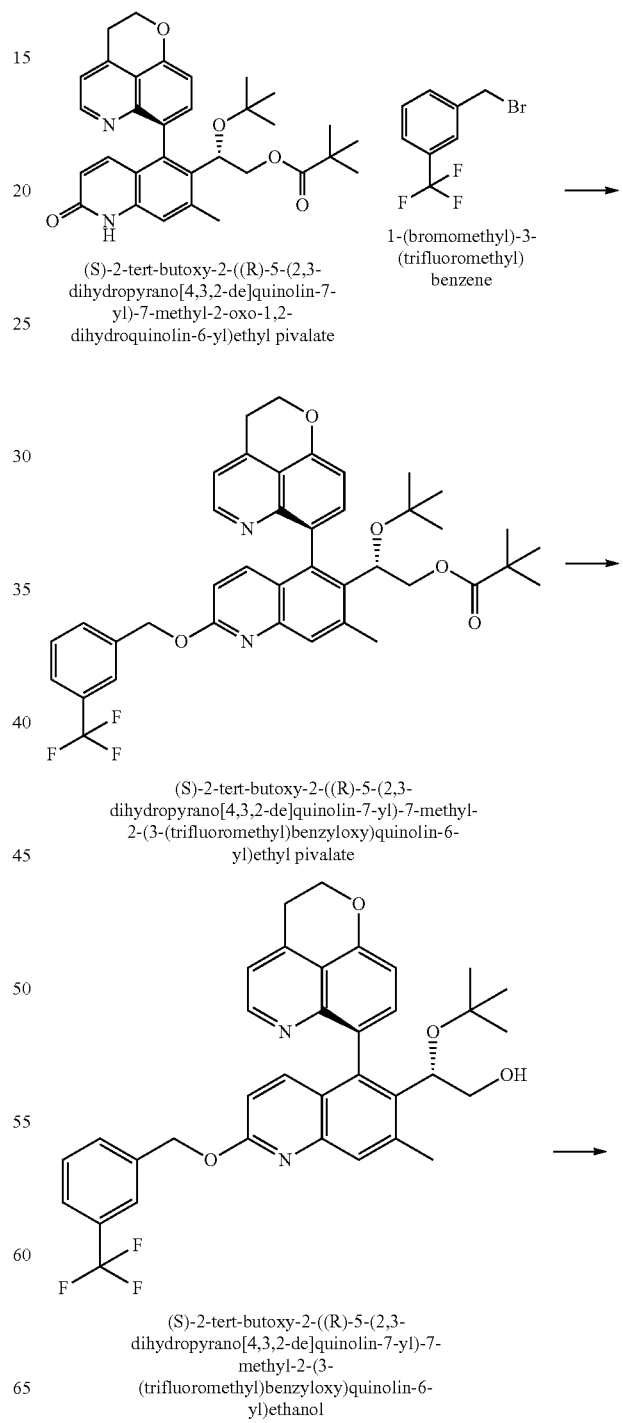

193

-continued

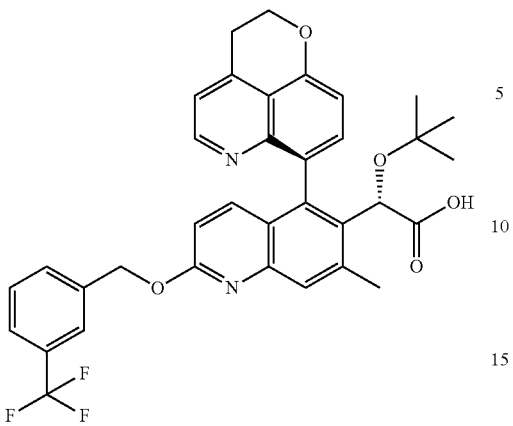

(S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid Preparation of (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)ethyl pivalate: To a solution of (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate (100 mg, 0.189 mmol) in benzene/dichloroethane (1:1) and silver carbonate (156 mg, 0.567 mmol) was added 1-(bromomethyl)-3-(trifluoromethyl)benzene (90 mg, 0.378 mmol) and the reaction was sealed and heated 45° C. overnight. The crude reaction mixture was absorbed onto silica and purified by flash column chromatography (silica gel, ethyl acetate/hexanes) to give the desired compound. LCMS-ESI$^+$ (m/z): [M+H]$^+$ calc'd for $C_{40}H_{41}F_3N_2O_5$: 687.30; found: 687.54.

Preparation of (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)ethanol: To a solution of (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)ethyl pivalate in THF/methanol (5:1) was added 1M sodium hydroxide (3 mL) and the reaction was heated to 45° C. overnight. The reaction was diluted with water, extracted with ethyl acetate (2×), washed with brine, dried over sodium sulfate and concentrated. The residue was then co-evaporated two times with acetonitrile to give the desired compound. LCMS-ESI$^+$ (m/z): [M+H]$^+$ calc'd for $C_{35}H_{33}F_3N_2O_4$: 603.24; found: 603.39.

Preparation of (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid: To a solution of (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)ethanol (88.7 mg, 0.147 mmol) in wet acetonitrile at 0° C. was added $CrO_3/H_5IO_6$ (1.2% $CrO_3$–0.4M, 2.2 mL, 0.88 mmol) and the reaction was stirred approximately 3 hours. The crude reaction was diluted with water, filtered and purified by reverse phase HPLC (Gemini, 10-75% ACN/$H_2O$+0.1% TFA) and the desired product was lyophilized to give the TFA salt. LCMS-ESI$^+$ (m/z): [M+H]$^+$ calc'd for $C_{35}H_{31}F_3N_2O_5$: 617.22; found: 617.53. $^1$H NMR (400 MHz, $CD_3CN$) δ 8.59 (d, J=5.1 Hz, 1H), 7.86 (s, 1H), 7.80 (d, J=5.6 Hz, 2H), 7.75-7.63 (m, 2H), 7.59 (d, J=7.7 Hz, 1H), 7.52 (d, J=5.0 Hz, 1H), 7.28 (d, J=8.0 Hz, 1H), 7.17 (d, J=9.0 Hz, 1H), 6.75 (d, J=9.1 Hz, 1H), 5.60 (s, 2H), 5.14 (s, 1H), 4.71-4.50 (m, 2H), 3.47 (t, J=5.9 Hz, 2H), 2.68 (s, 3H), 0.91 (s, J=17.3 Hz, 9H). $^{19}$F NMR (376 MHz, $CD_3CN$) δ −63.62 (s).

194

EXAMPLE 4

(S)-2-tert-Butoxy-2-((R)-5-(2,3-dihydropyrano[4,3,2-de]quinolin-7-yl)-7-methyl-2-(3-(methylsulfonyl)benzyloxy)quinolin-6-yl)acetic acid

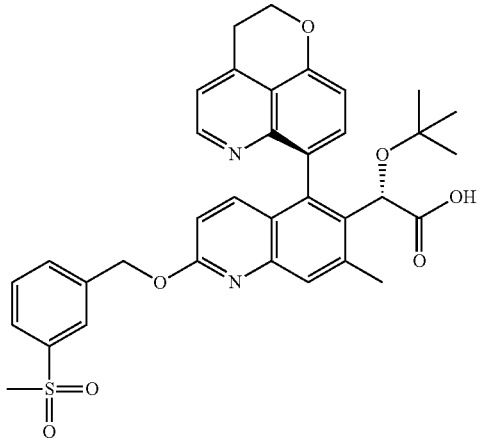

(S)-2-tert-butoxy-2-((R)-5-(2,3-dihydropyrano[4,3,2-de]quinolin-7-yl)-7-methyl-2-(3-methylsulfonyl)benzyloxy)quinolin-6-yl)acetic acid (S)-2-tert-Butoxy-2-((R)-5-(2,3-dihydropyrano[4,3,2-de]quinolin-7-yl)-7-methyl-2-(3 (methylsulfonyl)benzyloxy)quinolin-6-yl)acetic acid was prepared in a similar manner as used to prepare (S)-2-tert-butoxy-2-((R)-5-(2,3-dihydropyrano[4,3,2-de]quinolin-7-yl)-7-methyl-2-(3 (trifluoromethyl)benzyloxy)quinolin-6-yl)acetic acid using 1-(bromomethyl)-3-(methylsulfonyl)benzene instead of 1-(bromomethyl)-3-(trifluoromethyl)benzene. LCMS-ESI$^+$ (m/z): [M+H]$^+$ calc'd for $C_{35}H_{34}N_2O_7S$: 627.21; found: 627.62. $^1$H NMR (400 MHz, $CD_3CN$) δ 8.57 (d, J=5.4 Hz, 1H), 8.10 (s, 1H), 7.91-7.81 (m, 3H), 7.81-7.72 (m, 1H), 7.65 (d, J=7.8 Hz, 1H), 7.62-7.58 (m, 1H), 7.34 (dd, J=8.1, 2.9 Hz, 1H), 7.19 (d, J=9.1 Hz, 1H), 6.79 (d, J=9.1 Hz, 1H), 5.73-5.57 (m, 2H), 5.14 (s, 1H), 4.73-4.54 (m, 2H), 3.52 (t, J=5.1 Hz, 2H), 3.06 (s, 3H), 2.70 (s, 3H), 0.92 (s, 9H).

EXAMPLE 5

(S)-2-tert-Butoxy-2-((R)-5-(2,3-dihydropyrano[4,3,2-de]quinolin-7-yl)-7-methyl-2-oxo-1-(3-(trifluoromethyl)benzyl)-1,2-dihydroquinolin-6-yl)acetic acid

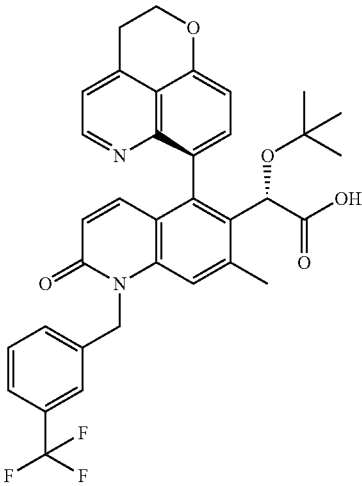

(S)-2-tert-butoxy-2-((R)-5-(2,3-dihydropyrano[4,3,2-de]quinolin-7-yl)-7-methyl-2-oxo-1-(3-(trifluoromethyl)benzyl)-1,2-dihydroquinolin-6-yl) acetic acid (S)-2-tert-Butoxy-2-((R)-5-(2,3-dihydropyrano[4,3,2-de]quinolin-7-yl)-7-methyl-2-oxo-1-(3-(trifluoromethyl)benzyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl) acetic acid using 1-(bromomethyl)-3-(trifluoromethyl)benzene instead of (bromomethyl)cyclopropane. LCMS-ESI⁺ (m/z): [M+H]⁺ calc'd for $C_{35}H_{31}F_3N_2O_5$: 617.22; found: 617.47. ¹H NMR (400 MHz, CD₃CN) δ 8.65 (d, J=5.1 Hz, 1H), 7.64 (dd, J=14.1, 6.3 Hz, 3H), 7.58-7.50 (m, 3H), 7.36 (s, 1H), 7.27 (d, J=8.0 Hz, 1H), 6.92 (d, J=9.8 Hz, 1H), 6.41 (d, J=9.9 Hz, 1H), 5.63 (q, J=16.5 Hz, 2H), 5.02 (s, 1H), 4.70-4.52 (m, 2H), 3.48 (t, J=5.9 Hz, 2H), 2.53 (s, 3H), 0.85 (s, 9H).

EXAMPLE 6

(S)-2-tert-Butoxy-2-(5-(4-chlorophenyl)-7-methyl-1-(3 (methylsulfonyl)benzyl)-2-oxo-1,2-dihydroquinolin-6-yl)acetic acid

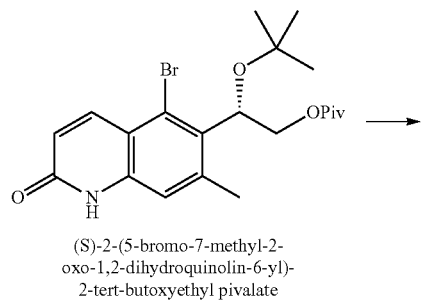

(S)-2-(5-bromo-7-methyl-2-oxo-1,2-dihydroquinolin-6-yl)-2-tert-butoxyethyl pivalate

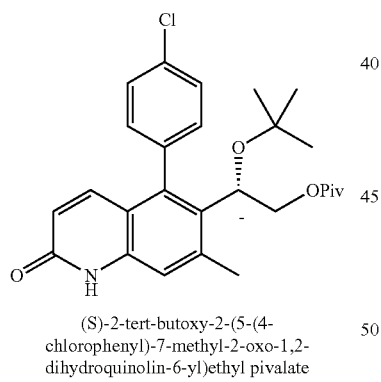

(S)-2-tert-butoxy-2-(5-(4-chlorophenyl)-7-methyl-2-oxo-1,2-dihydroquinolin-6-yl)ethyl pivalate Preparation of (S)-2-tert-butoxy-2-(5-(4-chlorophenyl)-7-methyl-2-oxo-1,2-dihydroquinolin-6-yl)ethyl pivalate: The mixture of (S)-2-(5-bromo-7-methyl-2-oxo-1,2-dihydroquinolin-6-yl)-2-tert-butoxyethyl pivalate (34 mg, 0.078 mmol), Pd(PPh₃)₄ (9 mg), 4-chlorophenylboronic acid (16 mg, 0.1 mmol), aqueous K₂CO₃ solution (0.15 mL, 2 M, 0.3 mmol) in 1,2-dimethoxyethane (2 mL) was heated at 100° C. for 90 minutes. The residue was diluted with ethyl acetate (100 mL), washed with NaHCO₃ solution, water and brine, dried over Na₂SO₄. Concentration and purification gave (S)-2-tert-butoxy-2-(5-(4-chlorophenyl)-7-methyl-2-oxo-1,2-dihydroquinolin-6-yl)ethyl pivalate. LCMS-ESI⁺ (m/z): 470.3 (M+H)⁺.

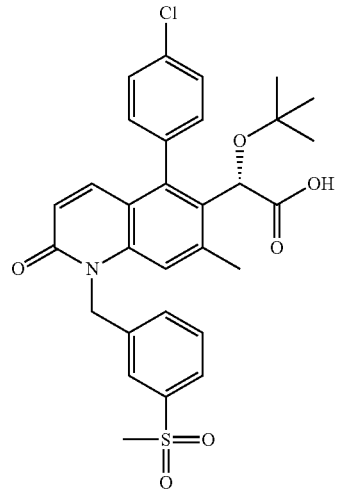

(S)-2-tert-butoxy-2-(5-(4-chlorophenyl)-7-methyl-1-(3-(methylsulfonyl)benzyl)-2-oxo-1,2-dihydroquinolin-6-yl)acetic acid (S)-2-tert-Butoxy-2-(5-(4-chlorophenyl)-7-methyl-1-(3-(methylsulfonyl)benzyl)-2-oxo-1,2-dihydroquinolin-6-yl) acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-3-(methylsulfonyl)benzene instead of (bromomethyl)cyclopropane, and (S)-2-tert-butoxy-2-(5-(4-chlorophenyl)-7-methyl-2-oxo-1,2-dihydroquinolin-6-yl)ethyl pivalate instead of (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate. LCMS-ESI⁺ (m/z): [M+H]⁺ calc'd for $C_{30}H_{30}ClNO_6S$: 568.15; found: 568.84. ¹H NMR (400 MHz, CD₃CN) δ 7.88 (s, 1H), 7.83 (d, J=7.7 Hz, 1H), 7.63-7.46 (m, 5H), 7.34-7.25 (m, 2H), 7.23 (s, 1H), 6.52 (d, J=9.9 Hz, 1H), 5.63 (q, J=16.3 Hz, 2H), 5.04 (s, 1H), 3.04 (s, 3H), 2.42 (s, 3H), 0.94 (s, 9H).

EXAMPLE 7

(S)-2-tert-Butoxy-2-(5-(4-chlorophenyl)-7-methyl-2-oxo-1-(3-(trifluoromethyl)benzyl)-1,2-dihydroquinolin-6-yl)acetic acid

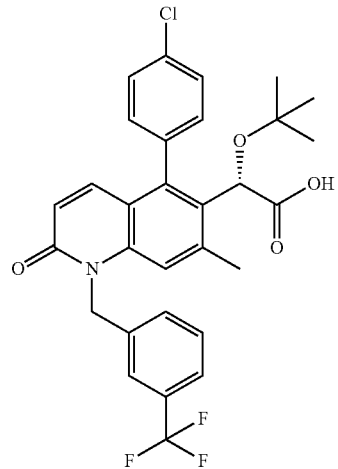

(S)-2-tert-butoxy-2-(5-(4-chlorophenyl)-7-methyl-2-oxo-1-(3-(trifluoromethyl)benzyl)-1,2-dihydroquinolin-6-yl)acetic acid (S)-2-tert-Butoxy-2-(5-(4-chlorophenyl)-7-methyl-2-oxo-1-(3-(trifluoromethyl)benzyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-3-(trifluoromethyl)benzene instead of (bromomethyl)cyclopropane, and (S)-2-tert-butoxy-2-(5-(4-chlorophenyl)-7-methyl-2-oxo-1,2-dihydroquinolin-6-yl)ethyl pivalate instead of (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate. LCMS-ESI$^+$ (m/z): [M+H]$^+$ calc'd for $C_{30}H_{27}ClF_3NO_4$: 558.16; found: 558.90. $^1$H NMR (400 MHz, CD$_3$CN) δ 7.65-7.59 (m, 2H), 7.57-7.52 (m, 2H), 7.49 (t, J=5.2 Hz, 2H), 7.32-7.25 (m, 2H), 7.22 (s, 1H), 6.51 (d, J=9.9 Hz, 1H), 5.66-5.53 (m, 2H), 5.04 (s, 1H), 2.42 (s, 3H), 0.94 (s, 9H). $^{19}$F NMR (376 MHz, CD$_3$CN) δ −63.66 (s).

EXAMPLE 8

(S)-2-tert-Butoxy-2-(5-(4-chlorophenyl)-7-methyl-2-oxo-1-(3-(trifluoromethyl)benzyl)-1,2-dihydroquinolin-6-yl)acetic acid

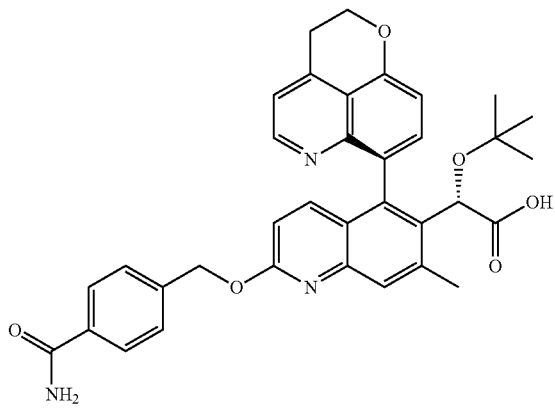

(S)-2-tert-butoxy-2-((R)-2-(4-carbamoylbenzyloxy)-5-(2,3-dihydropyrano[4,3,2-de]quinolin-7-yl)-7-methylquinolin-6-yl)acetic acid (S)-2-tert-Butoxy-2-((R)-2-(4-carbamoylbenzyloxy)-5-(2,3-dihydropyrano[4,3,2-de]quinolin-7-yl)-7-methylquinolin-6-yl)acetic acid was prepared in a similar manner as used to prepare (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid using 4-(bromomethyl)benzamide instead of 1-(bromomethyl)-3-(trifluoromethyl)benzene. If necessary, reaction temperature was increased to 70° C. and one additional equivalent of 4-(bromomethyl)benzamide and base were added. LCMS-ESI$^+$ (m/z): [M+H]$^+$ calc'd for $C_{35}H_{33}N_3O_6$: 592.24; found: 592.58. $^1$H NMR (400 MHz, CD$_3$CN) δ 8.60 (d, J=4.8 Hz, 1H), 7.82 (d, J=8.4 Hz, 2H), 7.74 (s, 1H), 7.59 (t, J=8.8 Hz, 3H), 7.43 (d, J=4.3 Hz, 1H), 7.21 (d, J=8.0 Hz, 1H), 7.15 (d, J=9.6 Hz, 1H), 6.73 (d, J=9.1 Hz, 2H), 5.59 (s, 2H), 5.14 (s, 1H), 4.67-4.52 (m, 2H), 3.43 (t, J=4.6 Hz, 2H), 2.66 (s, 4H), 0.90 (s, 9H).

EXAMPLE 9

(S)-2-tert-Butoxy-2-((R)-5-(2,3-dihydropyrano[4,3,2-de]quinolin-7-yl)-7-methyl-2-(4-(methylsulfonyl)benzyloxy)quinolin-6-yl)acetic acid

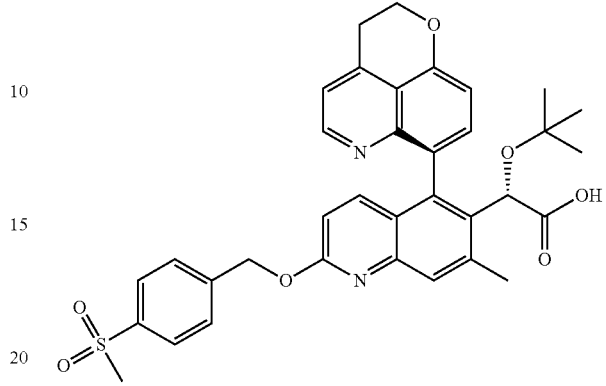

(S)-2-tert-butoxy-2-((R)-5-(2,3-dihydropyrano[4,3,2-de]quinolin-7-yl)-7-methyl-2-(4-(methylsulfonyl)benzyloxy)quinolin-6-yl)acetic acid (S)-2-tert-butoxy-2-((R)-5-(2,3-dihydropyrano[4,3,2-de]quinolin-7-yl)-7-methyl-2-(4-(methylsulfonyl)benzyloxy)quinolin-6-yl)acetic acid was prepared in a similar manner as used to prepare (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid using 1-(bromomethyl)-4-(methylsulfonyl)benzene instead of 1-(bromomethyl)-3-(trifluoromethyl)benzene. If necessary, reaction temperature was increased to 70° C. and one additional equivalent of 1-(bromomethyl)-4-(methylsulfonyl)benzene and base were added. LCMS-ESI$^+$ (m/z): [M+H]$^+$ calc'd for $C_{35}H_{34}N_2O_7S$: 627.21; found: 627.62. $^1$H NMR (400 MHz, CD$_3$CN) δ 8.59 (d, J=5.0 Hz, 1H), 7.92 (d, J=8.4 Hz, 2H), 7.80-7.72 (m, 3H), 7.68 (d, J=8.3 Hz, 1H), 7.51 (d, J=4.8 Hz, 1H), 7.28 (d, J=8.1 Hz, 1H), 7.18 (d, J=9.1 Hz, 1H), 6.77 (d, J=9.1 Hz, 1H), 5.70-5.59 (m, 2H), 5.14 (s, 1H), 4.70-4.47 (m, 2H), 3.47 (t, J=5.8 Hz, 2H), 3.05 (s, 3H), 2.67 (s, 3H), 0.91 (s, 9H).

EXAMPLE 10

(S)-2-tert-Butoxy-2-((R)-5-(2,3-dihydropyrano[4,3,2-de]quinolin-7-yl)-7-methyl-2-(2-(methylsulfonyl)benzyloxy)quinolin-6-yl)acetic acid

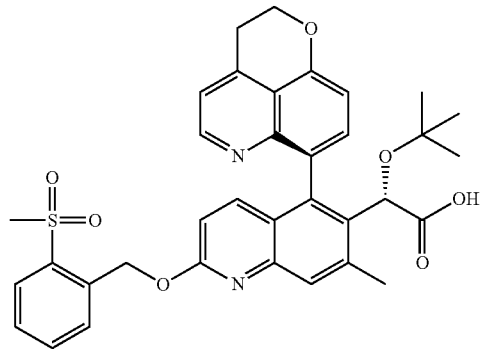

(S)-2-tert-butoxy-2-((R)-5-(2,3-dihydropyrano[4,3,2-de]quinolin-7-yl)-7-methyl-2-(2-(methylsulfonyl)benzyloxy)quinolin-6-yl)acetic acid (S)-2-tert-Butoxy-2-((R)-5-(2,3-dihydropyrano[4,3,2-de]quinolin-7-yl)-7-methyl-2-(2-(methylsulfonyl)benzyloxy)quinolin-6-yl)acetic acid was prepared in a similar manner as used to prepare (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid using 1-(bromomethyl)-2-(methylsulfonyl)benzene instead of 1-(bromomethyl)-3-(trifluoromethyl)benzene. If necessary, reaction temperature was increased to 50° C. and one additional equivalent of 1-(bromomethyl)-4-(methylsulfonyl)benzene and base were added and the first reaction was heated to 50° C. with one additional equivalent of 1-(bromomethyl)-2-(methylsulfonyl)benzene and base added and heated three days. LCMS-ESI⁺ (m/z): [M+H]⁺ calc'd for $C_{35}H_{34}N_2O_7S$: 627.21; found: 627.64. ¹H NMR (400 MHz, CD₃CN) δ 8.58 (d, J=5.3 Hz, 1H), 8.05 (d, J=7.9 Hz, 1H), 7.82-7.72 (m, 3H), 7.68 (td, J=7.5, 1.2 Hz, 1H), 7.62-7.53 (m, 2H), 7.33 (d, J=8.1 Hz, 1H), 7.21 (d, J=9.2 Hz, 1H), 6.82 (d, J=9.1 Hz, 1H), 5.93 (q, J=13.8 Hz, 2H), 5.13 (s, 1H), 4.76-4.52 (m, 2H), 3.52 (t, J=5.9 Hz, 2H), 3.33 (d, J=2.7 Hz, 3H), 2.67 (s, 3H), 0.91 (s, 9H).

EXAMPLE 11

(S)-2-tert-Butoxy-2-((R)-5-(2,3-dihydropyrano[4,3,2-de]quinolin-7-yl)-7-methyl-2-oxo-1-(4-(trifluoromethyl)benzyl)-1,2-dihydroquinolin-6-yl)acetic acid

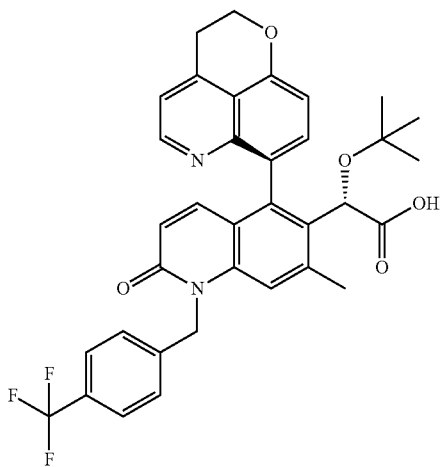

(S)-2-tert-butoxy-2-((R)-5-(2,3-dihydropyrano[4,3,2-de]quinolin-7-yl)-7-methyl-2-oxo-1-(4-(trifluoromethyl)benzyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(4-(trifluoromethyl)benzyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-4-(trifluoromethyl)benzene instead of (bromomethyl)cyclopropane and the first reaction was stirred overnight. LCMS-ESI⁺ (m/z): [M+H]⁺ calc'd for $C_{35}H_{31}F_3N_2O_5$: 617.22; found: 617.48. ¹H NMR (400 MHz, CD₃CN) δ 8.68 (d, J=5.2 Hz, 1H), 7.71-7.62 (m, 3H), 7.60-7.53 (m, 1H), 7.46 (d, J=8.1 Hz, 2H), 7.33 (s, 1H), 7.28 (d, J=8.1 Hz, 1H), 6.92 (d, J=9.9 Hz, 1H), 6.40 (d, J=9.9 Hz, 1H), 5.63 (q, J=16.7 Hz, 2H), 5.02 (s, 1H), 4.68-4.54 (m, 2H), 3.49 (t, J=5.9 Hz, 2H), 2.53 (s, 3H), 0.85 (s, 9H).

EXAMPLE 12

(S)-2-((R)-2-(Benzyloxy)-5-(2,3-dihydropyrano[4,3,2-de]quinolin-7-yl)-7-methylquinolin-6-yl)-2-tert-butoxyacetic acid

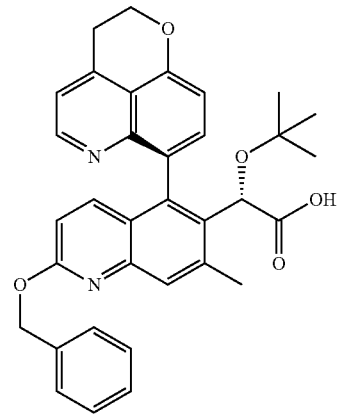

(S)-2-((R)-2-(benzyloxy)-5-(2,3-dihydropyrano[4,3,2-de]quinolin-7-yl)-7-methylquinolin-6-yl)-2-tert-butoxyacetic acid (S)-2-((R)-2-(Benzyloxy)-5-(2,3-dihydropyrano[4,3,2-de]quinolin-7-yl)-7-methylquinolin-6-yl)-2-tert-butoxyacetic acid was prepared in a similar manner as used to prepare (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid using (bromomethyl)benzene instead of 1-(bromomethyl)-3-(trifluoromethyl)benzene. LCMS-ESI⁺ (m/z): [M+H]⁺ calc'd for $C_{34}H_{32}N_2O_5$: 549.28; found: 549.39. ¹H NMR (400 MHz, CD₃CN) δ 8.58 (d, J=5.2 Hz, 1H), 7.82 (s, 1H), 7.73 (d, J=7.9 Hz, 1H), 7.56 (d, J=5.3 Hz, 1H), 7.52 (d, J=7.0 Hz, 2H), 7.39 (t, J=7.3 Hz, 2H), 7.35-7.28 (m, 2H), 7.16 (d, J=9.1 Hz, 1H), 6.73 (d, J=9.1 Hz, 1H), 5.59-5.48 (m, 2H), 5.14 (s, 1H), 4.71-4.54 (m, 2H), 3.50 (t, J=5.8 Hz, 2H), 2.69 (s, 3H), 0.92 (s, 9H).

EXAMPLE 13

(S)-2-tert-Butoxy-2-((R)-5-(2,3-dihydropyrano[4,3,2-de]quinolin-7-yl)-7-methyl-2-(4-(trifluoromethoxy)benzyloxy)quinolin-6-yl)acetic acid

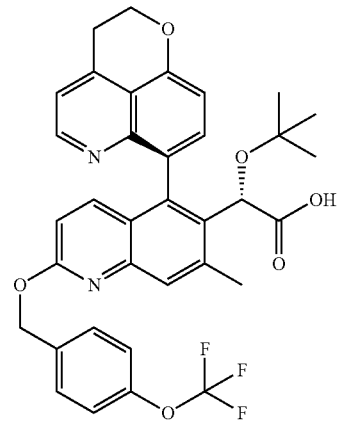

(S)-2-tert-butoxy-2-((R)-5-(2,3-dihydropyrano[4,3,2-de]quinolin-7-yl)-methyl-2-(4-(trifluoro-methoxy)benzyloxy)quinolin-6-yl)acetic acid (S)-2-tert-Butoxy-2-((R)-5-(2,3-dihydropyrano[4,3,2-de]quinolin-7-yl)-7-methyl-2-(4-(trifluoromethoxy)benzyloxy)quinolin-6-yl)acetic acid was prepared in a similar method as used to prepare (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid using 1-(bromomethyl)-4-(trifluoromethoxy)benzene instead of 1-(bromomethyl)-3-(trifluoromethyl)benzene. LCMS-ESI⁺ (m/z): [M+H]⁺ calc'd for $C_{35}H_{31}F_3N_2O_6$: 633.21; found: 633.38. ¹H NMR (400 MHz, CD₃CN) δ 8.60 (d, J=4.9 Hz, 1H), 7.77 (s, 1H), 7.66-7.56 (m, 3H), 7.46 (d, J=4.7 Hz, 1H), 7.30 (d, J=8.0 Hz, 2H), 7.23 (d, J=8.0 Hz, 1H), 7.15 (d, J=9.1 Hz, 1H), 6.71 (d, J=9.1 Hz, 1H), 5.56 (d, J=7.3 Hz, 2H), 5.14 (s, 1H), 4.68-4.50 (m, 2H), 3.44 (t, J=5.8 Hz, 2H), 2.67 (s, 3H), 0.90 (s, 9H).

EXAMPLE 14

(S)-2-tert-Butoxy-2-((R)-5-(2,3-dihydropyrano[4,3,2-de]quinolin-7-yl)-7-methyl-2-(3-(trifluoromethoxy)benzyloxy)quinolin-6-yl)acetic acid

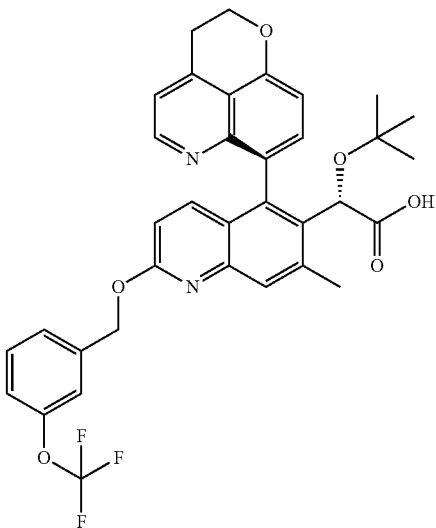

(S)-2-tert-butoxy-2-((R)-5-(2,3-dihydropyrano[4,3,2-de]quinolin-7-yl)-7-methyl-2-(3-(trifluoromethoxy)benzyloxy)quinolin-6-yl)acetic acid (S)-2-tert-Butoxy-2-((R)-5-(2,3-dihydropyrano[4,3,2-de]quinolin-7-yl)-7-methyl-2-(3-(trifluoromethoxy)benzyloxy)quinolin-6-yl)acetic acid was prepared in a similar manner as used to prepare (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid using 1-(bromomethyl)-3-(trifluoromethoxy)benzene instead of 1-(bromomethyl)-3-(trifluoromethyl)benzene. LCMS-ESI⁺ (m/z): [M+H]⁺ calc'd for $C_{35}H_{31}F_3N_2O_6$: 633.21; found: 633.46. ¹H NMR (400 MHz, CD₃CN) δ 8.60 (d, J=5.0 Hz, 1H), 7.77 (s, 1H), 7.66 (d, J=8.1 Hz, 1H), 7.55-7.43 (m, 4H), 7.26 (d, J=8.0 Hz, 2H), 7.16 (d, J=9.1 Hz, 1H), 6.74 (d, J=9.1 Hz, 1H), 5.56 (s, 2H), 5.14 (s, 1H), 4.70-4.52 (m, 2H), 3.46 (t, J=5.9 Hz, 2H), 2.67 (s, 3H), 0.90 (s, 9H). ¹⁹F NMR (376 MHz, CD₃CN) δ −59.05 (s).

EXAMPLE 15

(S)-2-tert-Butoxy-2-((R)-5-(2,3-dihydropyrano[4,3,2-de]quinolin-7-yl)-7-methyl-2-oxo-1-(2-(trifluoromethoxy)benzyl)-1,2-dihydroquinolin-6-yl)acetic acid

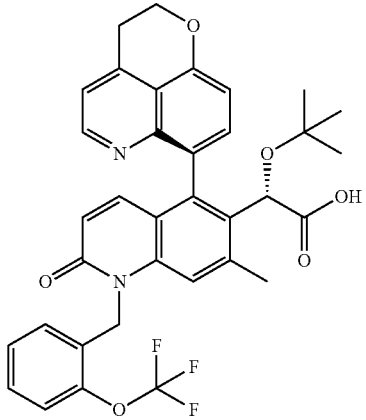

(S)-2-tert-butoxy-2-((R)-5-(2,3-dihydropyrano[4,3,2-de]quinolin-7-yl)-7-methyl-2-oxo-1-(2-(trifluoromethoxy)benzyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(2-(trifluoromethoxy)benzyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-2-(trifluoromethoxy)benzene instead of (bromomethyl)cyclopropane. LCMS-ESI⁺ (m/z): [M+H]⁺ calc'd for $C_{35}H_{31}F_3N_2O_6$: 633.21; found: 633.41. ¹H NMR (400 MHz, CD₃CN) δ 8.68 (d, J=5.0 Hz, 1H), 7.64 (d, J=8.0 Hz, 1H), 7.53 (d, J=5.0 Hz, 1H), 7.48-7.39 (m, 2H), 7.32-7.23 (m, 2H), 7.19 (s, 1H), 6.93 (d, J=9.7 Hz, 2H), 6.39 (d, J=9.9 Hz, 1H), 5.61 (q, J=17.0 Hz, 2H), 5.02 (s, 1H), 4.66-4.53 (m, 2H), 3.47 (t, J=5.8 Hz, 2H), 2.50 (s, 3H), 0.85 (s, 9H). ¹⁹F NMR (376 MHz, CD₃CN) δ −58.36 (d, J=1.0 Hz).

EXAMPLE 16

(S)-2-tert-Butoxy-2-((R)-5-(2,3-dihydropyrano[4,3,2-de]quinolin-7-yl)-7-methyl-2-oxo-1-(4-(trifluoromethoxy)benzyl)-1,2-dihydroquinolin-6-yl)acetic acid

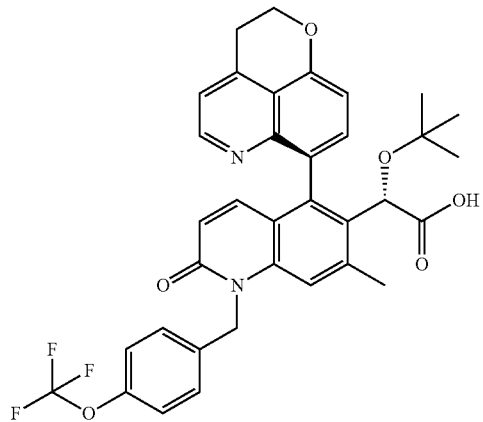

(S)-2-tert-butoxy-2-((R)-5-(2,3-dihydropyrano[4,3,2-de]quinolin-7-yl)-7-methyl-2-oxo-1-(4-(trifluoromethoxy)benzyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(4-(trifluoromethoxy)benzyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-4-(trifluoromethoxy)benzene instead of (bromomethyl)cyclopropane. LCMS-ESI+ (m/z): [M+H]+ calc'd for $C_{35}H_{31}F_3N_2O_6$: 633.21; found: 633.27. $^1$H NMR (400 MHz, CD$_3$CN) δ 8.66 (dd, J=4.9, 2.7 Hz, 1H), 7.60 (d, J=8.3 Hz, 1H), 7.54-7.45 (m, 1H), 7.39 (d, J=8.7 Hz, 2H), 7.34 (s, 1H), 7.28 (d, J=8.2 Hz, 2H), 7.23 (d, J=8.0 Hz, 1H), 6.90 (d, J=9.9 Hz, 1H), 6.38 (d, J=9.9 Hz, 1H), 5.57 (q, J=16.3 Hz, 2H), 5.02 (s, 1H), 4.68-4.51 (m, 2H), 3.45 (t, J=5.6 Hz, 2H), 2.52 (s, 3H), 0.85 (s, 9H). $^{19}$F NMR (376 MHz, CD$_3$CN) δ −59.17 (s).

EXAMPLE 17

(S)-2-tert-Butoxy-2-((R)-5-(2,3-dihydropyrano[4,3,2-de]quinolin-7-yl)-7-methyl-2-(4-sulfamoylbenzyloxy)quinolin-6-yl)acetic acid

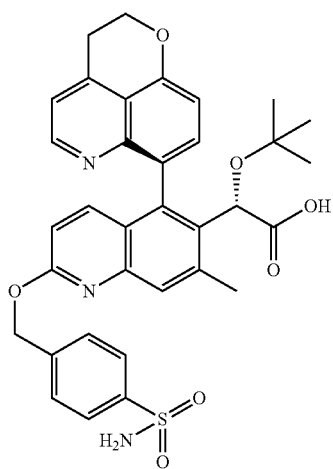

(S)-2-tert-butoxy-2-((R)-5-(2,3-dihydropyrano[4,3,2-de]quinolin-7-yl)-7-methyl-2-(4-sulfamoylbenzyloxy)quinolin-6-yl)acetic acid (S)-2-tert-Butoxy-2-((R)-5-(2,3-dihydropyrano[4,3,2-de]quinolin-7-yl)-7-methyl-2-(4-sulfamoylbenzyloxy)quinolin-6-yl)acetic acid was prepared in a similar manner as used to prepare (S)-2-tert-butoxy-2-((R)-5-(2,3-dihydropyrano[4,3,2-de]quinolin-7-yl)-7-methyl-2-(3-(trifluoromethyl)benzyloxy)quinolin-6-yl)acetic acid using 4-(bromomethyl)benzenesulfonamide instead of 1-(bromomethyl)-3-(trifluoromethyl)benzene. LCMS-ESI+ (m/z): [M+H]+ calc'd for $C_{34}H_{33}N_3O_7S$: 628.20; found: 628.57. $^1$H NMR (400 MHz, CD$_3$CN) δ 8.58 (d, J=5.4 Hz, 1H), 7.87 (d, J=8.4 Hz, 2H), 7.82 (s, 1H), 7.76 (d, J=8.2 Hz, 1H), 7.70 (d, J=8.5 Hz, 2H), 7.61 (d, J=5.4 Hz, 1H), 7.34 (d, J=8.1 Hz, 1H), 7.19 (d, J=9.1 Hz, 1H), 6.79 (d, J=9.1 Hz, 1H), 5.71-5.60 (m, J=8.4 Hz, 2H), 5.14 (s, 1H), 4.63 (dd, J=11.1, 5.7 Hz, 2H), 3.52 (t, J=5.9 Hz, 2H), 2.69 (s, 3H), 0.92 (s, 9H).

EXAMPLE 18

(S)-2-tert-Butoxy-2-((R)-5-(2,3-dihydropyrano[4,3,2-de]quinolin-7-yl)-7-methyl-2-oxo-1-(3-(trifluoromethoxy)benzyl)-1,2-dihydroquinolin-6-yl)acetic acid

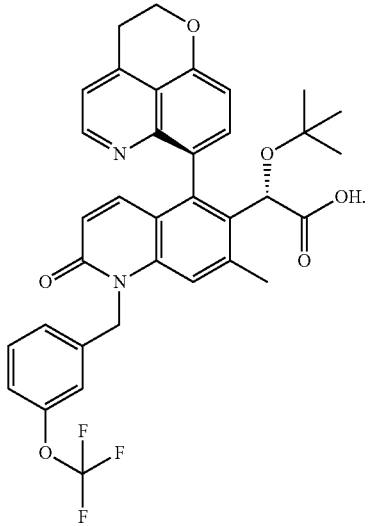

(S)-2-tert-butoxy-2-((R)-5-(2,3-dihydropyrano[4,3,2-de]quinolin-7-yl)-7-methyl-2-oxo-1-(3-(trifluoromethoxy)benzyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(3-(trifluoromethoxy)benzyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-3-(trifluoromethoxy)benzene instead of (bromomethyl)cyclopropane. LCMS-ESI+ (m/z): [M+H]+ calc'd for $C_{35}H_{31}F_3N_2O_6$: 633.21; found: 633.43. $^1$H NMR (400 MHz, CD$_3$CN) δ 8.65 (d, J=5.0 Hz, 1H), 7.60 (d, J=8.0 Hz, 1H), 7.50 (d, J=4.8 Hz, 1H), 7.45 (t, J=8.2 Hz, 1H), 7.34 (s, 1H), 7.30-7.20 (m, 4H), 6.90 (d, J=9.8 Hz, 1H), 6.39 (d, J=9.9 Hz, 1H), 5.58 (q, J=16.0 Hz, 2H), 5.02 (s, 1H), 4.68-4.50 (m, 2H), 3.45 (t, J=5.8 Hz, 2H), 2.52 (s, 3H), 0.85 (s, 9H). $^{19}$F NMR (376 MHz, CD$_3$CN) δ −59.04 (s).

EXAMPLE 19

(S)-2-tert-Butoxy-2-((R)-5-(2,3-dihydropyrano[4,3,2-de]quinolin-7-yl)-7-methyl-2-(2-(trifluoromethoxy)benzyloxy)quinolin-6-yl)acetic acid

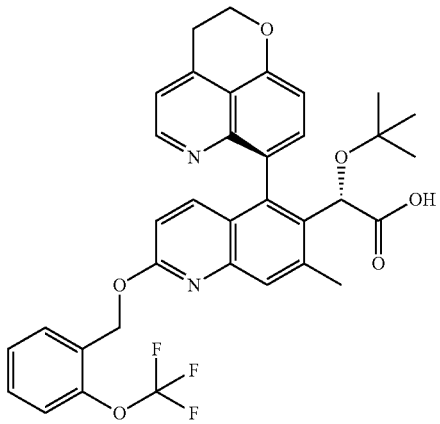

(S)-2-tert-butoxy-2-((R)-5-(2,3-dihydropyrano[4,3,2-de]quinolin-7-yl)-7-methyl-2-(2-(trifluoromethoxy)benzyloxy)quinolin-6-yl)acetic acid (S)-2-tert-Butoxy-2-((R)-5-(2,3-dihydropyrano[4,3,2-de]quinolin-7-yl)-7-methyl-2-(2-(trifluoromethoxy)benzyloxy)quinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-2-(trifluoromethoxy)benzene instead of (bromomethyl)cyclopropane. LCMS-ESI$^+$ (m/z): [M+H]$^+$ calc'd for $C_{35}H_{31}F_3N_2O_6$: 633.21; found: 633.44. $^1$H NMR (400 MHz, CD$_3$CN) δ 8.60 (d, J=5.0 Hz, 1H), 7.77 (s, 1H), 7.67 (t, J=7.2 Hz, 2H), 7.49 (d, J=5.0 Hz, 1H), 7.47-7.41 (m, 1H), 7.40-7.33 (m, 2H), 7.26 (d, J=8.0 Hz, 1H), 7.16 (d, J=9.1 Hz, 1H), 6.71 (d, J=9.1 Hz, 1H), 5.70-5.51 (m, 2H), 5.14 (s, 1H), 4.70-4.53 (m, 2H), 3.46 (t, J=5.8 Hz, 2H), 2.67 (s, 3H), 0.90 (s, 9H). $^{19}$F NMR (376 MHz, CD$_3$CN) δ−58.28 (s).

EXAMPLE 20

(S)-2-((R)-1-(3,5-Bis(trifluoromethyl)benzyl)-5-(2,3-dihydropyrano[4,3,2-de]quinolin-7-yl)-7-methyl-2-oxo-1,2-dihydroquinolin-6-yl)-2-tert-butoxyacetic acid

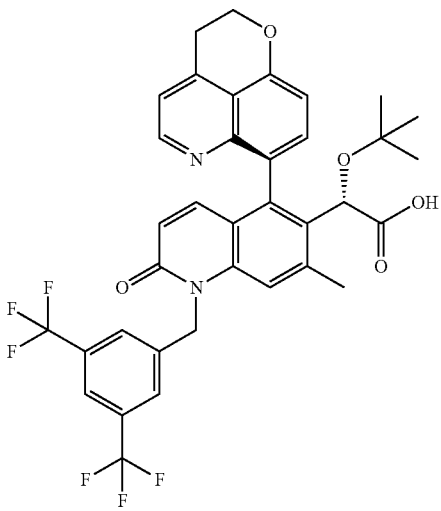

(S)-2-((R)-1-(3,5-bis(trifluoromethyl)benzyl)-5-(2,3-dihydropyrano[4,3,2-de]quinolin-7-yl)-7-methyl-2-oxo-1,2-dihdyroquinolin-6-yl)-2-tert-butoxyacetic acid (S)-2-((R)-1-(3,5-Bis(trifluoromethyl)benzyl)-5-(2,3-dihydropyrano[4,3,2-de]quinolin-7-yl)-7-methyl-2-oxo-1,2-dihydroquinolin-6-yl)-2-tert-butoxyacetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-3,5-bis(trifluoromethyl)benzene instead of (bromomethyl)cyclopropane. LCMS-ESI$^+$ (m/z): [M+H]$^+$ calc'd for $C_{36}H_{30}F_6N_2O_5$: 685.21; found: 685.21. $^1$H NMR (400 MHz, CD$_3$CN) δ 8.65 (d, J=4.9 Hz, 1H), 7.95 (s, 1H), 7.88 (s, 2H), 7.59 (d, J=7.8 Hz, 1H), 7.48 (d, J=4.8 Hz, 1H), 7.32 (s, 1H), 7.23 (d, J=8.0 Hz, 1H), 6.92 (d, J=10.0 Hz, 1H), 6.40 (d, J=9.9 Hz, 1H), 5.66 (dd, J=51.3, 16.5 Hz, 2H), 5.02 (s, 1H), 4.67-4.52 (m, 2H), 3.44 (t, J=5.9 Hz, 2H), 2.53 (s, 3H), 0.85 (s, 9H). $^{19}$F NMR (376 MHz, CD$_3$CN) δ −63.87 (s).

EXAMPLE 21

(S)-2-tert-Butoxy-2-((R)-5-(2,3-dihydropyrano[4,3,2-de]quinolin-7-yl)-7-methyl-2-oxo-1-(pyridin-4-ylmethyl)-1,2-dihydroquinolin-6-yl)acetic acid

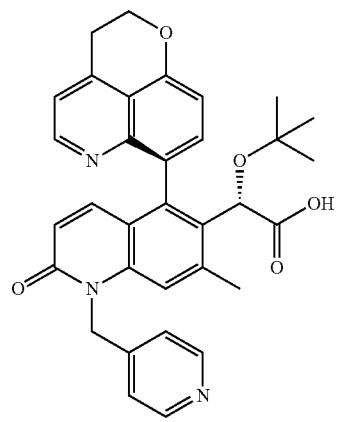

(S)-2-tert-butoxy-2-((R)-5-(2,3-dihydropyrano[4,3,2-de]quinolin-7-yl)-7-methyl-2-oxo-1-(pyridin-4-ylmethyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(pyridin-4-ylmethyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 4-(bromomethyl)pyridine instead of (bromomethyl)cyclopropane. LCMS-ESI$^+$ (m/z): [M+H]$^+$ calc'd for $C_{33}H_{31}N_3O_5$: 550.23; found: 550.24. $^1$H NMR (400 MHz, CD$_3$CN) δ 8.73-8.66 (m, 3H), 7.72 (d, J=6.3 Hz, 2H), 7.59 (d, J=8.0 Hz, 1H), 7.50 (d, J=4.8 Hz, 1H), 7.24 (d, J=8.0 Hz, 1H), 7.18 (s, 1H), 6.96 (d, J=9.9 Hz, 1H), 6.40 (d, J=9.9 Hz, 1H), 5.74 (dd, J=38.4, 18.0 Hz, 2H), 5.04 (s, 1H), 4.66-4.52 (m, 2H), 3.45 (t, J=5.8 Hz, 2H), 2.52 (s, 3H), 0.84 (s, 9H).

EXAMPLE 22

(S)-2-tert-Butoxy-2-((R)-5-(2,3-dihydropyrano[4,3,2-de]quinolin-7-yl)-7-methyl-2-oxo-1-(pyridin-3-ylmethyl)-1,2-dihydroquinolin-6-yl)acetic acid

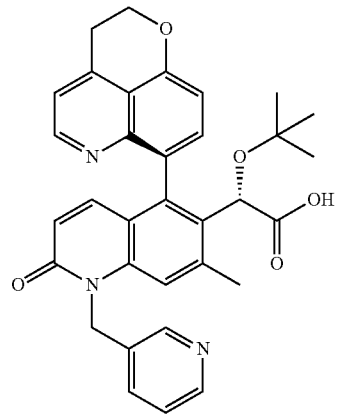

(S)-2-tert-butoxy-2-((R)-5-(2,3-dihydropyrano[4,3,2-de]quinolin-7-yl)-7-methyl-2-oxo-1-(pyridin-3-ylmethyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(pyridin-3-ylmethyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 3-(bromomethyl)pyridine instead of (bromomethyl)cyclopropane. LCMS-ESI$^+$ (m/z): [M+H]$^+$ calc'd for $C_{33}H_{31}N_3O_5$: 550.23; found: 550.27. $^1$H NMR (400 MHz, CD$_3$CN) δ 8.70 (s, 1H), 8.66 (d, J=4.9 Hz, 1H), 8.63 (s, 1H), 8.16-8.08 (m, 1H), 7.77-7.67 (m, 1H), 7.59 (d, J=8.3 Hz, 1H), 7.49 (s, 1H), 7.34 (s, 1H), 7.23 (d, J=7.8 Hz, 1H), 6.93 (d, J=9.7 Hz, 1H), 6.39 (d, J=9.8 Hz, 1H), 5.66 (q, J=16.7 Hz, 2H), 5.03 (s, 1H), 4.66-4.55 (m, 2H), 3.45 (t, J=5.4 Hz, 2H), 2.59-2.52 (m, 3H), 0.85 (s, 9H).

EXAMPLE 23

(S)-2-tert-Butoxy-2-((R)-5-(2,3-dihydropyrano[4,3,2-de]quinolin-7-yl)-7-methyl-2-oxo-1-(pyrazin-2-ylmethyl)-1,2-dihydroquinolin-6-yl)acetic acid

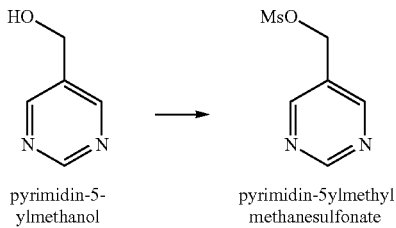 [SMILES: OCc1cncnc1 ; CS(=O)(=O)OCc1cncnc1]

pyrimidin-5-ylmethanol → pyrimidin-5ylmethyl methanesulfonate

Preparation of pyrimidin-5-ylmethyl methanesulfonate: To a solution of pyrimidin-5-ylmethanol (200 mg, 1.82 mmol) and triethylamine (0.558 mL, 4.00 mmol) in dichloromethane was added methansulfonic anhydride (348 mg, 1.20 mmol) and the reaction was stirred at room temperature for 15 minutes. The product was diluted with water, extracted with dichloromethane (2x), washed with brine, dried over sodium sulfate and concentrated to give the desired product. LCMS-ESI$^+$ (m/z): [M+H]$^+$ calc'd for $C_6H_8N_2O_3S$: 189.03; found: 189.00.

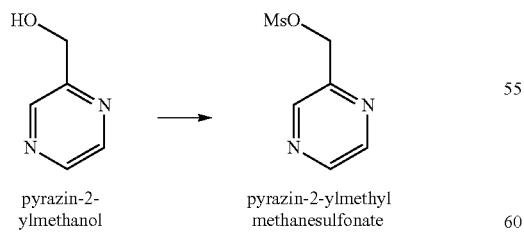

pyrazin-2-ylmethanol → pyrazin-2-ylmethyl methanesulfonate

Pyrazin-2-ylmethyl methanesulfonate was prepared in a similar manner as used to prepare pyrimidin-5-ylmethyl methanesulfonate using pyrazin-2-ylmethanol instead of pyrimidin-5-ylmethanol. LCMS-ESI$^+$ (m/z): [M+H]$^+$ calc'd for $C_6H_8N_2O_3S$: 189.03; found: 189.01.

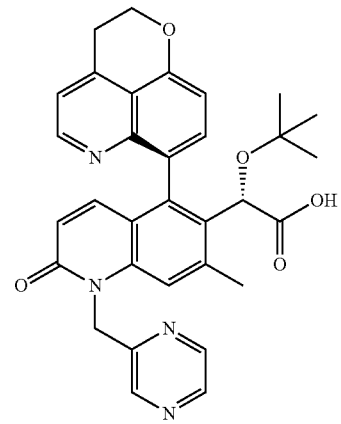

(S)-2-tert-butoxy-2-((R)-5-(2,3-dihydropyrano[4,3,2-de]quinolin-7-yl)-7-methyl-2-oxo-1-(pyrazin-2-ylmethyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(pyrazin-2-ylmethyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using pyrazin-2-ylmethyl methanesulfonate instead of (bromomethyl)cyclopropane. LCMS-ESI$^+$ (m/z): [M+H]$^+$ calc'd for $C_{32}H_{30}N_4O_5$: 551.22; found: 551.26. $^1$H NMR (400 MHz, CD$_3$CN) δ 8.66 (d, J=4.9 Hz, 1H), 8.61 (s, 1H), 8.50 (s, 2H), 7.61 (d, J=8.0 Hz, 1H), 7.50 (d, J=4.5 Hz, 1H), 7.44 (s, 1H), 7.24 (d, J=8.0 Hz, 1H), 6.90 (d, J=9.9 Hz, 1H), 6.36 (d, J=10.0 Hz, 1H), 5.69 (s, 2H), 5.03 (s, 1H), 4.59 (dd, J=9.7, 6.1 Hz, 2H), 3.45 (t, J=6.0 Hz, 2H), 2.53 (s, 3H), 0.85 (s, 9H).

EXAMPLE 24

(S)-2-tert-Butoxy-2-((R)-5-(2,3-dihydropyrano[4,3,2-de]quinolin-7-yl)-7-methyl-2-oxo-1-(3-phenylpropyl)-1,2-dihydroquinolin-6-yl)acetic acid

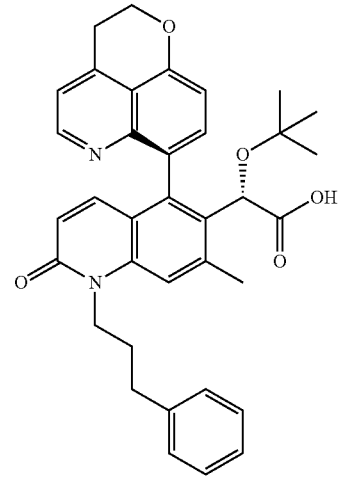

(S)-2-tert-butoxy-2-((R)-5-(2,3-dihydropyrano[4,3,2-de]quinolin-7-yl)-7-methyl-2-oxo-1-(3-phenylpropyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(3-phenylpropyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using (3-bromopropyl)benzene instead of (bromomethyl)cyclopropane. LCMS-ESI⁺ (m/z): [M+H]⁺ calc'd for $C_{36}H_{36}N_2O_5$: 577.26; found: 577.34. ¹H NMR (400 MHz, CD₃CN) δ 8.65 (d, J=5.0 Hz, 1H), 7.57 (d, J=8.0 Hz, 1H), 7.49 (d, J=4.9 Hz, 1H), 7.38-7.30 (m, 4H), 7.26-7.20 (m, 3H), 6.78 (d, J=9.8 Hz, 1H), 6.23 (d, J=9.8 Hz, 1H), 5.03 (s, J=21.2 Hz, 1H), 4.67-4.50 (m, 2H), 4.26 (dd, J=13.0, 7.3 Hz, 2H), 3.44 (t, J=5.8 Hz, 2H), 2.81 (t, J=7.4 Hz, 2H), 2.57 (s, 3H), 2.09-1.98 (m, 2H), 0.86 (s, 9H).

EXAMPLE 25

(S)-2-tert-butoxy-2-((R)-5-(2,3-dihydropyrano[4,3,2-de]quinolin-7-yl)-7-methyl-2-oxo-1-(pyrimidin-5-ylmethyl)-1,2-dihydroquinolin-6-yl)acetic acid

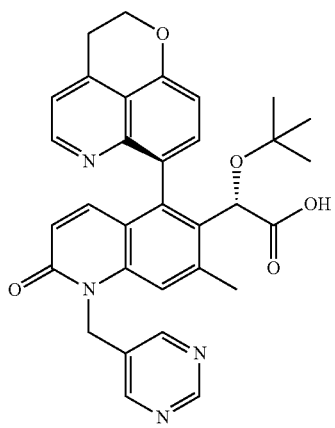

(S)-2-tert-butoxy-2-((R)-5-(2,3-dihydropyrano[4,3,2-de]quinolin-7-yl)-7-methyl-2-oxo-1-(pyrimidin-5-ylmethyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(pyrimidin-5-ylmethyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using pyrimidin-5-ylmethyl methanesulfonate instead of (bromomethyl)cyclopropane. LCMS-ESI⁺ (m/z): [M+H]⁺ calc'd for $C_{32}H_{30}N_4O_5$: 551.22; found: 551.27. ¹H NMR (400 MHz, CD₃CN) δ 8.66 (d, J=5.2 Hz, 1H), 8.61 (s, 1H), 8.51 (s, 2H), 7.67 (d, J=8.0 Hz, 1H), 7.58 (d, J=5.3 Hz, 1H), 7.47 (s, 1H), 7.29 (d, J=8.1 Hz, 1H), 6.91 (d, J=9.9 Hz, 1H), 6.38 (d, J=9.9 Hz, 1H), 5.69 (d, J=2.4 Hz, 2H), 5.03 (s, 1H), 4.68-4.53 (m, 2H), 3.50 (t, J=6.0 Hz, 2H), 2.55 (s, 3H), 0.86 (s, 9H).

EXAMPLE 26

(S)-2-tert-butoxy-2-((R)-5-(2,3-dihydropyrano[4,3,2-de]quinolin-7-yl)-1-(3-methoxybenzyl)-7-methyl-2-oxo-1,2-dihydroquinolin-6-yl)acetic acid

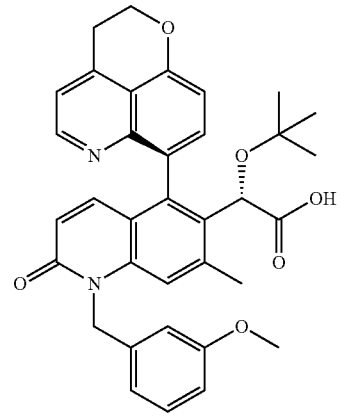

(S)-2-tert-butoxy-2-((R)-5-(2,3-dihydropyrano[4,3,2-de]quinolin-7-yl)-1-(3-methoxybenzyl)-7-methyl-2-oxo-1,2-dihydroquinolin-6-yl)acetic acid (S)-2-tert-Butoxy-2-((R)-5-(2,3-dihydropyrano[4,3,2-de]quinolin-7-yl)-1-(3-methoxybenzyl)-7-methyl-2-oxo-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-3-methoxybenzene instead of (bromomethyl)cyclopropane. LCMS-ESI⁺ (m/z): [M+H]⁺ calc'd for $C_{35}H_{34}N_2O_6$: 579.24; found: 579.23. ¹H NMR (400 MHz, CD₃CN) δ 8.65 (d, J=5.1 Hz, 1H), 7.66 (d, J=8.1 Hz, 1H), 7.56 (d, J=4.6 Hz, 1H), 7.39 (s, 1H), 7.31-7.23 (m, 2H), 6.90 (d, J=9.9 Hz, 1H), 6.88-6.80 (m, 3H), 6.39 (d, J=9.9 Hz, 1H), 5.53 (bs, 2H), 5.01 (s, 1H), 4.69-4.52 (m, 2H), 3.77 (s, 3H), 3.49 (t, J=5.7 Hz, 2H), 2.53 (s, 3H), 0.86 (s, 9H).

EXAMPLE 27

(S)-2-tert-Butoxy-2-((R)-5-(2,3-dihydropyrano[4,3,2-de]quinolin-7-yl)-1-(3-fluoro-5-(trifluoromethyl)benzyl)-7-methyl-2-oxo-1,2-dihydroquinolin-6-yl)acetic acid

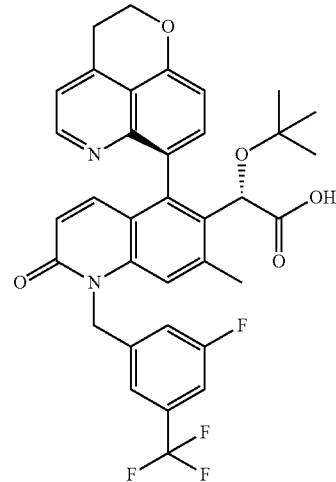

(S)-2-tert-butoxy-2-((R)-5-(2,3-dihydropyrano[4,3,2-de]quinolin-7-yl)-1-(3-fluoro-5-(trifluoromethyl)benzyl)-7-methyl-2-oxo-1,2-dihydroquinolin-6-yl)acetic acid

211

(S)-2-tert-Butoxy-2-((R)-5-(2,3-dihydropyrano[4,3,2-de]quinolin-7-yl)-1-(3-methoxybenzyl)-7-methyl-2-oxo-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-3-fluoro-5-(trifluoromethyl)benzene instead of (bromomethyl)cyclopropane. LCMS-ESI$^+$ (m/z): [M+H]$^+$ calc'd for $C_{35}H_{30}F_4N_2O_5$: 635.21; found: 635.20. $^1$H NMR (400 MHz, CD$_3$CN) δ 8.66 (d, J=5.1 Hz, 1H), 7.64 (d, J=8.1 Hz, 1H), 7.54 (d, J=5.1 Hz, 1H), 7.51 (s, 1H), 7.40 (d, J=9.0 Hz, 1H), 7.32 (s, 1H), 7.29-7.22 (m, 2H), 6.92 (d, J=9.9 Hz, 1H), 6.40 (d, J=9.9 Hz, 1H), 5.61 (dd, J=40.0, 16.5 Hz, 2H), 5.03 (s, 1H), 4.67-4.53 (m, 2H), 3.48 (t, J=5.9 Hz, 2H), 2.54 (s, 3H), 0.86 (s, 9H).

EXAMPLE 28

(S)-2-tert-Butoxy-2-((R)-5-(2,3-dihydropyrano[4,3,2-de]quinolin-7-yl)-7-methyl-1-((1-methyl-1H-indazol-4-yl)methyl)-2-oxo-1,2-dihydroquinolin-6-yl)acetic acid

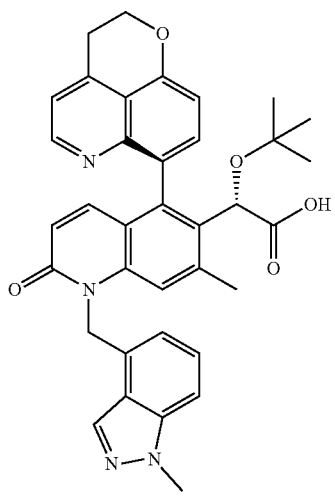

(S)-2-tert-butoxy-2-((R)-5-(2,3-dihydropyrano[4,3,2-de]quinolin-7-yl)-7-methyl-1-((1-methyl-1H-indazol-4-yl)methyl)-2-oxo-1,2-dihydroquinolin-6-yl)acetic acid (S)-2-tert-Butoxy-2-((R)-5-(2,3-dihydropyrano[4,3,2-de]quinolin-7-yl)-7-methyl-1-((1-methyl-1H-indazol-4-yl)methyl)-2-oxo-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 4-(bromomethyl)-1-methyl-1H-indazole instead of (bromomethyl)cyclopropane. LCMS-ESI$^+$ (m/z): [M+H]$^+$ calc'd for $C_{36}H_{34}N_4O_5$: 603.25; found: 603.29. $^1$H NMR (400 MHz, CD$_3$CN) δ 8.66 (d, J=5.1 Hz, 1H), 8.11 (s, 1H), 7.64 (d, J=8.2 Hz, 1H), 7.53 (bs, 1H), 7.46 (d, J=8.4 Hz, 1H), 7.37-7.29 (m, 2H), 7.27 (d, J=8.1 Hz, 1H), 6.93 (d, J=9.9 Hz, 1H), 6.80 (d, J=7.0 Hz, 1H), 6.43 (d, J=9.9 Hz, 1H), 5.87 (dd, J=32.7, 16.6 Hz, 3H), 5.00 (s, 1H), 4.60 (tt, J=11.4, 5.7 Hz, 3H), 4.06 (s, 3H), 3.48 (t, J=5.8 Hz, 2H), 2.42 (s, 3H), 0.83 (s, 9H).

212

EXAMPLE 29

(S)-2-tert-Butoxy-2-((R)-5-(2,3-dihydropyrano[4,3,2-de]quinolin-7-yl)-7-methyl-1-((1-methyl-1H-indazol-5-yl)methyl)-2-oxo-1,2-dihydroquinolin-6-yl)acetic acid

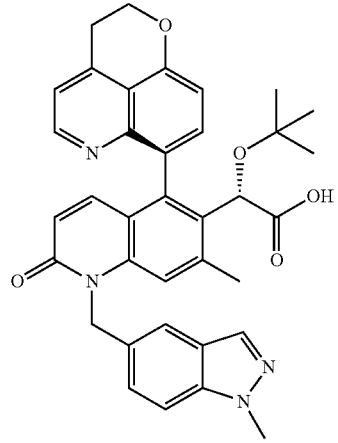

(S)-2-tert-butoxy-2-((R)-5-(2,3-dihydropyrano[4,3,2-de]quinolin-7-yl)-7-methyl-1-((1-methyl-1H-indazole-5-yl)methyl)-2-oxo-1,2-dihydroquinolin-6-yl)acetic acid (S)-2-tert-Butoxy-2-((R)-5-(2,3-dihydropyrano[4,3,2-de]quinolin-7-yl)-7-methyl-1-((1-methyl-1H-indazol-5-yl)methyl)-2-oxo-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 5-(bromomethyl)-1-methyl-1H-indazole instead of (bromomethyl)cyclopropane. LCMS-ESI$^+$ (m/z): [M+H]$^+$ calc'd for $C_{36}H_{34}N_4O_5$: 603.25; found: 603.37. $^1$H NMR (400 MHz, CD$_3$CN) δ 8.66 (d, J=5.1 Hz, 1H), 8.11 (s, 1H), 7.64 (d, J=8.2 Hz, 1H), 7.53 (bs, 1H), 7.46 (d, J=8.4 Hz, 1H), 7.37-7.29 (m, 2H), 7.27 (d, J=8.1 Hz, 1H), 6.93 (d, J=9.9 Hz, 1H), 6.80 (d, J=7.0 Hz, 1H), 6.43 (d, J=9.9 Hz, 1H), 5.87 (dd, J=32.7, 16.6 Hz, 2H), 5.00 (s, 1H), 4.60 (tt, J=11.4, 5.7 Hz, 2H), 4.06 (s, 3H), 3.48 (t, J=5.8 Hz, 2H), 2.42 (s, 3H), 0.83 (s, 9H).

EXAMPLE 30

(S)-2-tert-Butoxy-2-((R)-1-(3-(difluoromethyl)benzyl)-5-(2,3-dihydropyrano[4,3,2-de]quinolin-7-yl)-7-methyl-2-oxo-1,2-dihydroquinolin-6-yl)acetic acid

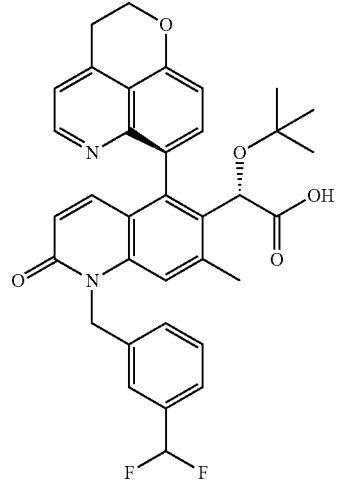

(S)-2-tert-butoxy-2-((R)-1-(3-(difluoromethyl)benzyl)-5-(2,3-dihydropyrano[4,3,2-de]quinolin-7-yl)-7-methyl-2-oxo-1,2-dihydroquinolin-6-yl)acetic acid (S)-2-tert-Butoxy-2-((R)-1-(3-(difluoromethyl)benzyl)-5-(2,3-dihydropyrano[4,3,2-de]quinolin-7-yl)-7-methyl-2-oxo-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-3-(difluoromethyl)benzene instead of (bromomethyl)cyclopropane. LCMS-ESI+ (m/z): [M+H]+ calc'd for $C_{35}H_{32}F_2N_2O_5$: 599.23; found: 599.21. $^1$H NMR (400 MHz, $CD_3CN$) δ 8.65 (d, J=5.1 Hz, 1H), 7.63 (d, J=8.0 Hz, 1H), 7.56-7.42 (m, 5H), 7.37 (s, 1H), 7.26 (d, J=8.0 Hz, 1H), 6.91 (d, J=9.8 Hz, 1H), 6.77 (t, J=56.2 Hz, 1H), 6.40 (d, J=9.9 Hz, 1H), 5.60 (q, J=16.1 Hz, 2H), 5.02 (s, 1H), 4.59 (tt, J=11.2, 5.6 Hz, 2H), 3.47 (t, J=5.8 Hz, 2H), 2.52 (s, 3H), 0.85 (s, 9H).

EXAMPLE 31

(S)-2-tert-Butoxy-2-((R)-5-(2,3-dihydropyrano[4,3,2-de]quinolin-7-yl)-7-methyl-2-oxo-1-((5-(trifluoromethyl)pyridin-3-yl)methyl)-1,2-dihydroquinolin-6-yl)acetic acid

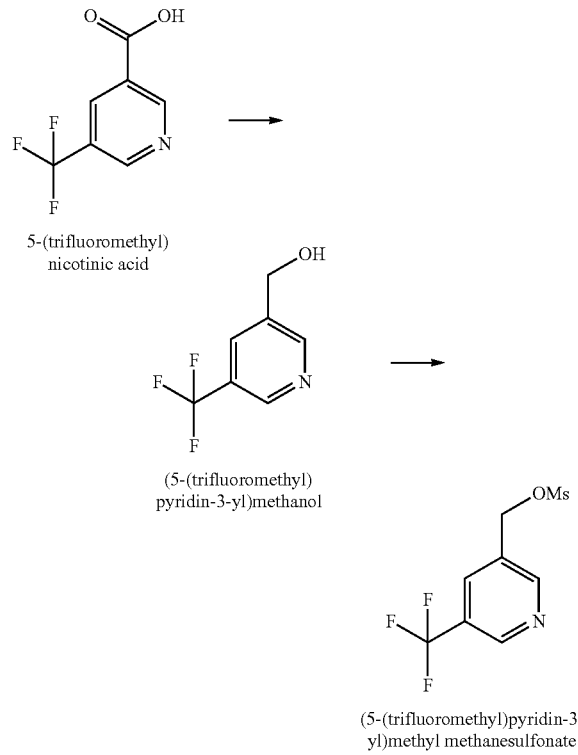

5-(trifluoromethyl)nicotinic acid (5-(trifluoromethyl)pyridin-3-yl)methanol (5-(trifluoromethyl)pyridin-3-yl)methyl methanesulfonate Preparation of (5-(trifluoromethyl)pyridin-3-yl)methanol: To a solution of 5-(trifluoromethyl)nicotinic acid (1.0 g, 5.23 mmol) and triethylamine (0.802 mL, 5.75 mmol) in benzene was added ethyl chloroformate (0.548 mL, 5.75 mmol) and the reaction was stirred 1 hour at room temperature. The reaction was filtered to remove salts and concentrated to dryness. The residue was taken up in tetrahydrofuran and cooled to −78° C. Lithium aluminum hydride (2M in THF, 2.88 mL, 5.75 mmol) was added dropwise and aged 0.5 hour. Reaction was quenched with water and stirred with 0.5N NaOH for 1 hour. The product was extracted with ethyl acetate (2×), washed brine, dried over sodium sulfate and concentrated to give the desired product. LCMS-ESI+ (m/z): [M+H]+ calc'd for $C_7H_6F_3NO$: 178.04; found: 178.06.

(5-(Trifluoromethyl)pyridin-3-yl)methyl methanesulfonate was prepared in a similar manner as used to prepare pyrimidin-5-ylmethyl methanesulfonate using (5-(trifluoromethyl)pyridin-3-yl)methanol instead of pyrimidin-5-ylmethanol. LCMS-ESI+ (m/z): [M+H]+ calc'd for $C_8H_8F_3NO_3S$: 256.02; found: 256.06.

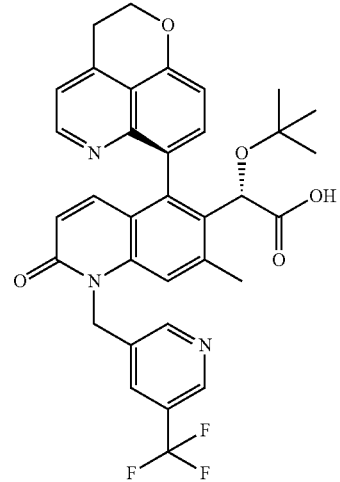

(S)-2-tert-butoxy-2-((R)-5-(2,3-dihydropyrano[4,3,2-de]quinolin-7-yl)-7-methyl-2-oxo-1-((5-(trifluoromethyl)pyridin-3-yl)methyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-((5-(trifluoromethyl)pyridin-3-yl)methyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using (5-(trifluoromethyl)pyridin-3-yl)methyl methanesulfonate instead of (bromomethyl)cyclopropane. LCMS-ESI+ (m/z): [M+H]+ calc'd for $C_{34}H_{30}F_3N_3O_5$: 618.21; found: 618.22. $^1$H NMR (400 MHz, $CD_3CN$) δ 8.85 (s, 1H), 8.74 (s, 1H), 8.67 (d, J=5.2 Hz, 1H), 8.00 (s, 1H), 7.68 (d, J=8.1 Hz, 1H), 7.64-7.56 (m, 1H), 7.39 (s, 1H), 7.31 (dd, J=8.1, 3.0 Hz, 1H), 6.93 (d, J=9.8 Hz, 1H), 6.41 (d, J=9.9 Hz, 1H), 5.65 (d, J=6.5 Hz, 2H), 5.03 (s, 1H), 4.62 (dd, J=10.4, 5.6 Hz, 2H), 3.57-3.47 (m, 2H), 2.56 (s, 3H), 0.86 (s, 914). $^{19}$F NMR (376 MHz, $CD_3CN$) δ −77.17 (s).

EXAMPLE 32

(S)-2-tert-Butoxy-2-((R)-5-(2,3-dihydropyrano[4,3,2-de]quinolin-7-yl)-7-methyl-2-oxo-1-(4-phenoxybenzyl)-1,2-dihydroquinolin-6-yl)acetic acid

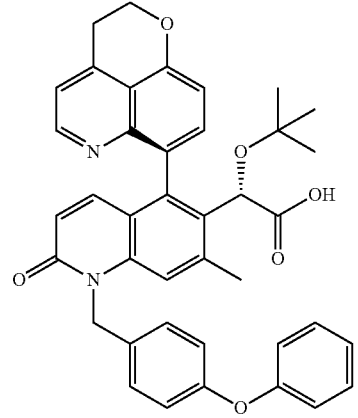

(S)-2-tert-butoxy-2-((R)-5-(2,3-dihydropyrano[4,3,2-de]quinolin-7-yl)-7-methyl-2-oxo-1-(4-phenoxybenzyl)-1,2-dihydroquinolin-6-yl)acetic acid (S)-2-tert-Butoxy-2-((R)-5-(2,3-dihydropyrano[4,3,2-de]quinolin-7-yl)-7-methyl-2-oxo-1-(4-phenoxybenzyl)-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-4-phenoxybenzene instead of (bromomethyl)cyclopropane. LCMS-ESI$^+$ (m/z): [M+H]$^+$ calc'd for $C_{40}H_{36}N_2O_6$: 641.26; found: 641.26. $^1$H NMR (400 MHz, CD$_3$CN) δ 8.65 (d, J=5.3 Hz, 1H), 7.67 (d, J=8.8 Hz, 1H), 7.63-7.56 (m, 1H), 7.44 (s, 1H), 7.41-7.35 (m, 2H), 7.31 (d, J=8.6 Hz, 3H), 7.15 (t, J=7.4 Hz, 1H), 6.99 (t, J=8.8 Hz, 4H), 6.90 (d, J=9.8 Hz, 1H), 6.40 (d, J=9.9 Hz, 1H), 5.54 (bs, 2H), 5.03 (s, 1H), 4.70-4.52 (m, 2H), 3.50 (t, J=5.6 Hz, 2H), 2.56 (s, 3H), 0.86 (s, 9H).

EXAMPLE 33

(S)-2-tert-Butoxy-2-((R)-5-(2,3-dihydropyrano[4,3,2-de]quinolin-7-yl)-1-(3,5-dimethoxybenzyl)-7-methyl-2-oxo-1,2-dihydroquinolin-6-yl)acetic acid

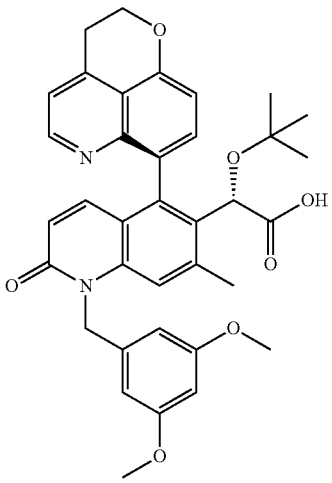

(S)-2-tert-butoxy-2-((R)-5-(2,3-dihydropyrano[4,3,2-de]quinolin-7-yl)-1-(3,5-dimethoxybenzyl)-7-methyl-2-oxo-1,2-dihydroquinolin-6-yl)acetic acid (S)-2-tert-Butoxy-2-((R)-5-(2,3-dihydropyrano[4,3,2-de]quinolin-7-yl)-1-(3,5-dimethoxybenzyl)-7-methyl-2-oxo-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 1-(bromomethyl)-3,5-dimethoxybenzene instead of (bromomethyl)cyclopropane. LCMS-ESI$^+$ (m/z): [M+H]$^+$ calc'd for $C_{36}H_{36}N_2O_7$: 609.25; found: 609.31. $^1$H NMR (400 MHz, CD$_3$CN) δ 8.65 (d, J=5.1 Hz, 1H), 7.65 (d, J=8.1 Hz, 1H), 7.54 (d, J=5.1 Hz, 1H), 7.38 (s, 1H), 7.26 (d, J=8.0 Hz, 1H), 6.89 (d, J=9.7 Hz, 1H), 6.45-6.34 (m, 4H), 5.48 (bs, 2H), 5.01 (s, 1H), 4.66-4.53 (m, 2H), 3.75 (s, 6H), 3.48 (t, J=5.7 Hz, 2H), 2.53 (s, 3H), 0.86 (s, J=11.2 Hz, 9H).

EXAMPLE 34

(S)-2-tert-Butoxy-2-((R)-1-(4-cyclobutylbenzyl)-5-(2,3-dihydropyrano[4,3,2-de]quinolin-7-yl)-7-methyl-2-oxo-1,2-dihydroquinolin-6-yl)acetic acid

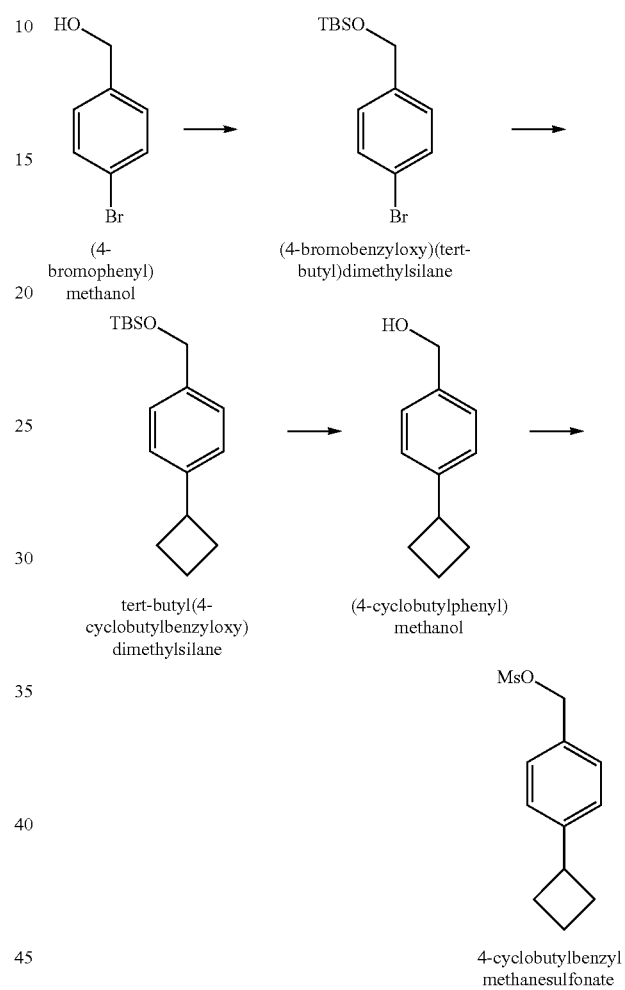

Preparation of (4-bromobenzyloxy)(tert-butyl)dimethylsilane: To a solution of (4-bromophenyl)methanol (3.0 g, 16.04 mmol) and imidazole (1.42 g, 20.85 mmol) in dichloromethane was added tert-butyl dimethylsilyl chloride (3.14 g, 20.85 mmol) and the mixture was stirred at room temperature overnight. The reaction was diluted with water, extracted with ethyl acetate (2×) and concentrated. The residue was absorbed onto silica and purified by flash column chromatography (silica gel, ethyl acetate/hexanes) to give the desired product. $^1$H NMR (400 MHz, CDCl$_3$) δ 7.45 (d, J=8.4 Hz, 2H), 7.20 (d, J=8.3 Hz, 2H), 4.68 (s, 2H), 0.94 (s, 9H), 0.09 (s, 6H).

Preparation of tert-butyl(4-cyclobutylbenzyloxy)dimethylsilane: To a solution of (4-bromobenzyloxy)(tert-butyl)dimethylsilane (500 mg, 1.66 mmol) and potassium cyclobutytrifluoroborate (296 mg, 1.83 mmol), Pd(OAc)$_2$ (111 mg, 0.166 mmol), and cesium carbonate (1.62 g, 4.98 mmol) in toluene:water (10:1, 0.25M) was added di(1-adamantyl)-n- butylphosphine (60 mg, 0.166 mmol) and the reaction was degassed with argon for 10 minutes. The reaction was heated to 100° C. overnight, then cooled to room temperature and dry loaded onto silica gel. It was then purified by flash column chromatography (silica gel, ethyl acetate/hexanes) followed by reverse phase HPLC (Gemini, 20-100% ACN/H$_2$O+0.1% TFA) to give a yellow oil (86 mg) that is a mix of desired product and loss of TBS group. The crude reaction was combined with another run of the same reaction and used directly by dissolving the oil in dichloromethane and then adding trifluoroacetic acid (0.400 mL) and stirring at room temperature for 0.5 hour. The reaction was then concentrated to give the desired product. $^1$H NMR (400 MHz, CDCl$_3$) δ 7.36-7.28 (m, 2H), 7.23 (d, J=8.2 Hz, 2H), 4.69 (s, J=12.0 Hz, 1H), 4.04 (s, 1H), 3.65-3.47 (m, 1H), 2.46-2.28 (m, 2H), 2.24-2.10 (m, 2H), 2.08-1.92 (m, 1H), 1.92-1.78 (m, 1H).

4-Cyclobutylbenzyl methanesulfonate was prepared in a similar manner as used to prepare pyrimidin-5-ylmethyl methanesulfonate using (4-cyclobutylphenyl)methanol instead of pyrimidin-5-ylmethanol. The product was used directly in the next reaction without characterization.

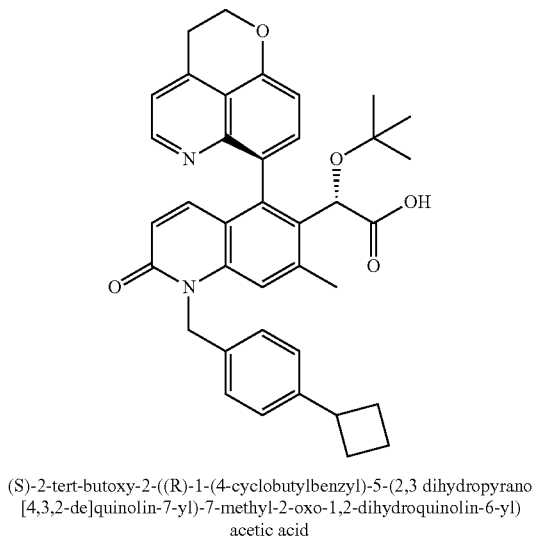

(S)-2-tert-butoxy-2-((R)-1-(4-cyclobutylbenzyl)-5-(2,3 dihydropyrano[4,3,2-de]quinolin-7-yl)-7-methyl-2-oxo-1,2-dihydroquinolin-6-yl)acetic acid ((S)-2-tert-Butoxy-2-((R)-1-(4-cyclobutylbenzyl)-5-(2,3-dihydropyrano[4,3,2-de]quinolin-7-yl)-7-methyl-2-oxo-1,2-dihydroquinolin-6-yl)acetic acid was prepared in a similar manner as used to prepare (S)-2-tert-butoxy-2-((R)-1-(cyclopropylmethyl)-5-(2,3-dihydropyrano[4,3,2-de]quinolin-7-yl)-7-methyl-2-oxo-1,2-dihydroquinolin-6-yl)acetic acid using 4-cyclobutylbenzyl methanesulfonate instead of (bromomethyl)cyclopropane. LCMS-ESI$^+$ (m/z): [M+H]$^+$ calc'd for C$_{38}$H$_{38}$N$_2$O$_5$: 603.28; found: 603.31. $^1$H NMR (400 MHz, CD$_3$CN) δ 8.65 (d, J=4.9 Hz, 1H), 7.59 (d, J=8.0 Hz, 1H), 7.48 (d, J=4.7 Hz, 1H), 7.37 (s, 1H), 7.22 (d, J=4.7 Hz, 5H), 6.87 (d, J=9.8 Hz, 1H), 6.37 (d, J=9.9 Hz, 1H), 5.52 (bs, 2H), 5.00 (s, 1H), 4.66-4.50 (m, 2H), 3.63-3.48 (m, 1H), 3.44 (t, J=5.8 Hz, 2H), 2.51 (s, 3H), 2.36-2.27 (m, 2H), 2.19-1.97 (m, 3H), 1.89-1.74 (m, 1H), 0.84 (s, 9H).

EXAMPLE 35

(S)-2-tert-Butoxy-2-((R)-5-(2,3-dihydropyrano[4,3,2-de]quinolin-7-yl)-7-methyl-2-oxo-1-m-tolyl-1,2-dihydroquinolin-6-yl)acetic acid

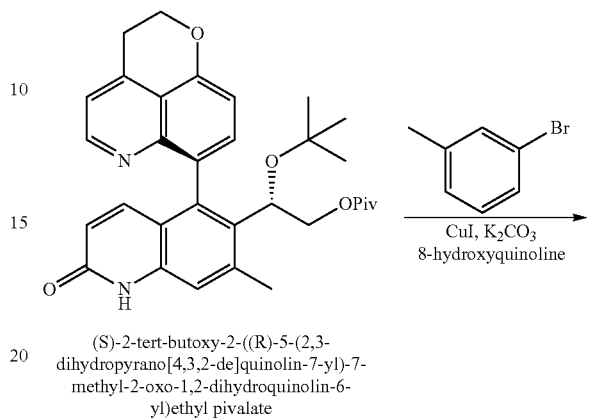

(S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate

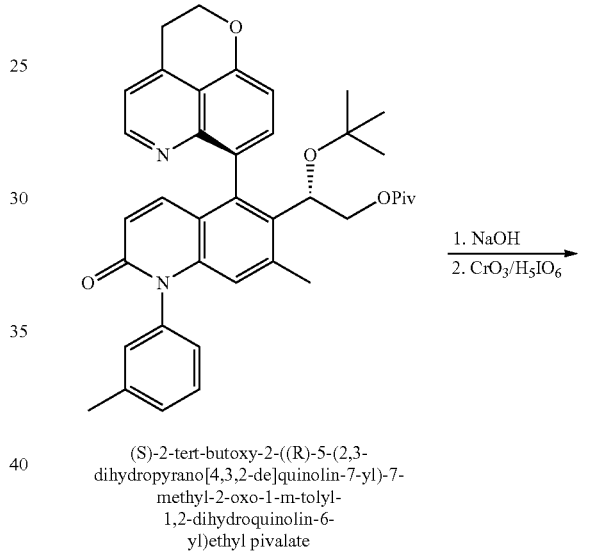

(S)-2-tert-butoxy-2-((R)-5-(2,3-dihydropyrano[4,3,2-de]quinolin-7-yl)-7-methyl-2-oxo-1-m-tolyl-1,2-dihydroquinolin-6-yl)ethyl pivalate

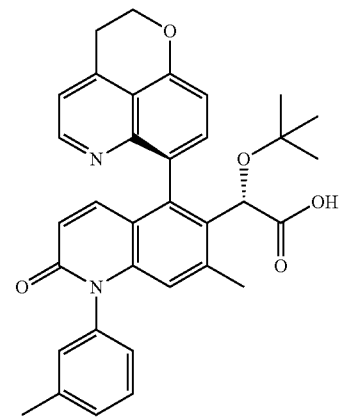

(S)-2-tert-butoxy-2-((R)-5-(2,3-dihydropyrano[4,3,2-de]quinolin-7-yl)-7-methyl-2-oxo-1-m-tolyl-1,2-dihydroquinolin-6-yl)acetic acid Preparation of (S)-2-tert-butoxy-2-((R)-5-(2,3-dihydropyrano[4,3,2-de]quinolin-7-yl)-7-methyl-2-oxo-1-m-tolyl-1,2-dihydroquinolin-6-yl)ethyl pivalate: To a solution of (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate (75 mg, 0.14 mmol) in DMSO (1 mL) was added 1-bromo-3-methylbenzene (48 mg, 0.28 mmol), copper iodide (5 mg, 0.03 mmol), 9-hydroxyquinoline (4 mg, 0.03 mmol), and potassium carbonate (58 mg, 0.42 mmol). The reaction mixture was stirred at 125° C. for 22 h. The reaction was diluted with H$_2$O and EtOAc. The layers were separated, and the organic layer was concentrated in vacuo. The crude product was purified by column chromatography (EtOAc/hexanes) to give the desired product. LCMS-ESI$^+$ (m/z): [M+H]$^+$ calc'd for C$_{39}$H$_{42}$N$_2$O$_5$: 619.3; Found: 619.0.

Preparation of (S)-2-tert-butoxy-2-((R)-5-(2,3-dihydropyrano[4,3,2-de]quinolin-7-yl)-7-methyl-2-oxo-1-m-tolyl-1,2-dihydroquinolin-6-yl)acetic acid: To a solution of (S)-2-tert-butoxy-2-((R)-5-(2,3-dihydropyrano[4,3,2-de]quinolin-7-yl)-7-methyl-2-oxo-1-m-tolyl-1,2-dihydroquinolin-6-yl)ethyl pivalate (33 mg) in THF/MeOH (1:1, 2 mL) was added 2 M NaOH solution (100 μL). The reaction mixture was stirred at 40° C. for 1 day. The reaction was diluted with H$_2$O and EtOAc. The layers were separated, and the organic layer was concentrated in vacuo. The crude product was used without further purification.

A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. To a solution of the above crude product in MeCN (2 mL) was added the above stock solution (200 μL). After 2 h, the mixture was filtered and purified by reverse phase HPLC (MeCN w/0.1% TFA/H$_2$O) to give the TFA salt. $^1$H-NMR: 400 MHz, (CD$_3$OD) δ: 8.83 (m, 1H), 7.87 (m, 2H), 7.59 (t, J=7 Hz, 1H), 7.47 (d, J=8 Hz, 2H), 7.18 (m, 3H), 6.78 (s, 1H), 6.52 (m, 1H), 5.08 (s, 1H), 4.73 (m, 2H), 3.69 (m, 2H), 2.50 (s, 3H), 2.03 (s, 3H), 0.90 (s, 9H). LCMS-ESI$^+$ (m/z): [M+H]$^+$ calc'd for C$_{34}$H$_{32}$N$_2$O$_5$: 549.2; Found: 549.1.

EXAMPLE 36

(S)-2-tert-Butoxy-2-((R)-5-(2,3-dihydropyrano[4,3,2-de]quinolin-7-yl)-7-methyl-1-(3-(methylsulfonamido)phenyl)-2-oxo-1,2-dihydroquinolin-6-yl)acetic acid

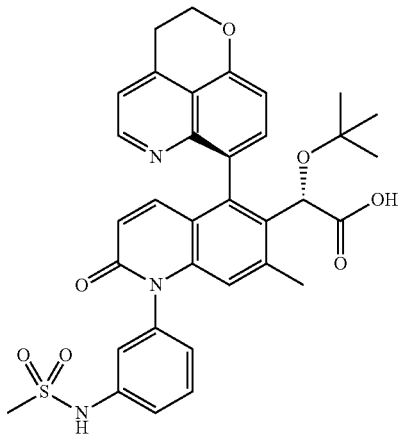

(S)-2-tert-butoxy-2-((R)-5-(2,3-dihydropyrano[4,3,2-de]quinolin-7-yl)-7-methyl-1-(3-(methylsulfonamido)phenyl)-2-oxo-1,2-dihydroquinolin-6-yl)acetic acid (S)-2-tert-Butoxy-2-((R)-5-(2,3-dihydropyrano[4,3,2-de]quinolin-7-yl)-7-methyl-1-(3-(methylsulfonamido)phenyl)-2-oxo-1,2-dihydroquinolin-6-yl)acetic acid was prepared by the method of Example 35 using (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate and using N-(3-bromophenyl)methanesulfonamide. $^1$H-NMR: 400 MHz, (CD$_3$OD) δ: 8.84 (m, 1H), 7.90 (m, 2H), 7.68 (t, J=7 Hz, 1H), 7.47 (m, 2H), 7.15 (m, 3H), 6.82 (s, 1H), 6.53 (m, 1H), 5.11 (s, 1H), 4.73 (m, 2H), 3.69 (m, 2H), 3.08 (s, 3H), 2.03 (s, 3H), 0.90 (s, 9H). LCMS-ESI$^+$ (m/z): [M+H]$^+$ calc'd for C$_{34}$H$_{33}$N$_3$O$_7$S: 628.2; found: 628.1.

EXAMPLE 37

(S)-2-tert-Butoxy-2-((R)-5-(2,3-dihydropyrano[4,3,2-de]quinolin-7-yl)-7-methyl-1-(3-(methylsulfonyl)phenyl)-2-oxo-1,2-dihydroquinolin-6-yl)acetic acid

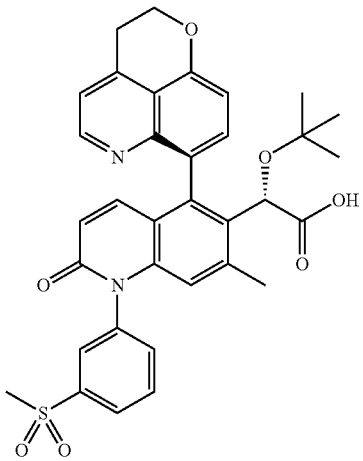

(S)-2-tert-butoxy-2-((R)-5-(2,3-dihydropyrano[4,3,2-de]quinolin-7-yl)-7-methyl-1-(3-(methylsulfonyl)phenyl)-2-oxo-1,2-dihydroquinolin-6-yl)acetic acid (S)-2-tert-Butoxy-2-((R)-5-(2,3-dihydropyrano[4,3,2-de]quinolin-7-yl)-7-methyl-1-(3-(methylsulfonyl)phenyl)-2-oxo-1,2-dihydroquinolin-6-yl)acetic acid was prepared by the method of Example 35 using (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate and using 1-bromo-3-(methylsulfonyl)benzene. $^1$H-NMR: 400 MHz, (CD$_3$OD) δ: 8.85 (m, 1H), 8.24 (d, J=8 Hz, 1H), 7.80-8.03 (m, 5H), 7.28 (d, J=8 Hz, 1H), 7.23 (d, J=8 Hz, 1H), 6.74 (s, 1H), 6.54 (d, J=8 Hz, 1H), 5.10 (s, 1H), 4.74 (m, 2H), 3.70 (m, 2H), 3.26 (s, 3H), 2.56 (s, 3H), 0.91 (s, 9H). LCMS-ESI$^+$ (m/z): [M+H]$^+$ calc'd for C$_{34}$H$_{32}$N$_2$O$_7$S: 613.2; found: 613.1.

EXAMPLE 38

(2S)-2-((R)-5-(2,3-Dihydropyrano[4,3,2-de]quinolin-7-yl)-2,7-dimethylquinolin-6-yl)-2-(2-methyl-4-phenylbutan-2-yloxy)acetic acid

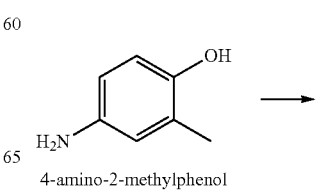

4-amino-2-methylphenol

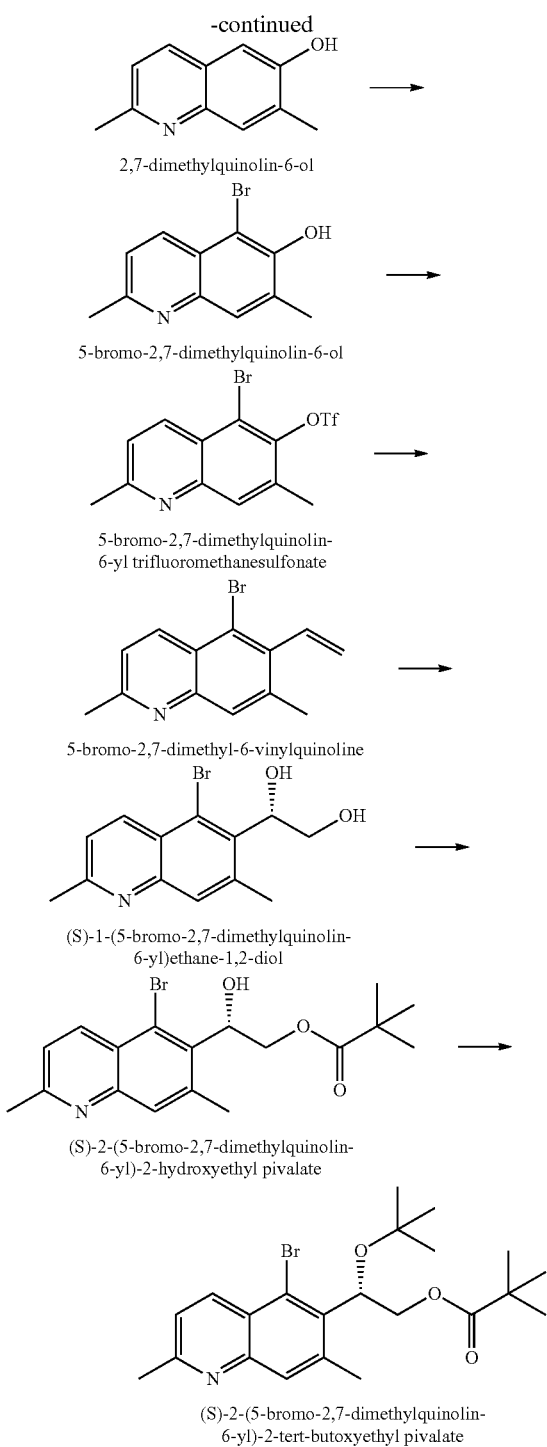

2,7-dimethylquinolin-6-ol 5-bromo-2,7-dimethylquinolin-6-ol 5-bromo-2,7-dimethylquinolin-
6-yl trifluoromethanesulfonate 5-bromo-2,7-dimethyl-6-vinylquinoline (S)-1-(5-bromo-2,7-dimethylquinolin-
6-yl)ethane-1,2-diol (S)-2-(5-bromo-2,7-dimethylquinolin-
6-yl)-2-hydroxyethyl pivalate (S)-2-(5-bromo-2,7-dimethylquinolin-
6-yl)-2-tert-butoxyethyl pivalate Preparation of 2,7-dimethylquinolin-6-ol: To 4-amino-2-methylphenol (5.0 g, 40.6 mmol) was added 6M HCl (100 mL) and heated to 100° C. with stirring. Toluene (30 mL) was added followed with the slowly addition of crotonaldehyde (6.7 mL, 81.2 mmol) at 100° C. The mixture was stirred at 100° C. for 2 hours, cooled to room temperature. The water layer was separated, neutralized by NaHCO$_3$ solution. The solid formed was filtered and collected. LCMS-ESI$^+$: calc'd for C$_{11}$H$_{11}$NO: 174.1 (M+H$^+$); Found: 174.2 (M+H$^+$).

Preparation of 5-bromo-2,7-dimethylquinolin-6-ol: To a stirred solution of 2,7-dimethylquinolin-6-ol (200 mg, 1.2 mmol) in acetic acid (10 mL) was added Br$_2$ (0.062 mL, 1.21 mmol) at ambient temperature. The mixture was stirred at ambient temperature for 0.5 hour. The solid formed was filtered and collected, washed with 2 mL acetic acid to give the product as an HBr salt. LCMS-ESI$^+$: calc'd for C$_{11}$H$_{10}$BrNO: 252.0 (M+H$^+$); Found: 252.2 (M+H$^+$).

Preparation of 5-bromo-2,7-dimethylquinolin-6-yl trifluoromethanesulfonate: To a stirred solution of 5-bromo-2,7-dimethylquinolin-6-ol (1.04 g, 3.1 mmol) in dichloromethane (50 mL) and pyridine (10 mL) was added Tf$_2$O (1.1 mL, 6.2 mmol) at 0° C. The mixture was stirred at room temperature for 2 hours, quenched with slowly addition of NaHCO$_3$ solution at 0° C. The mixture was extracted with dichloromethane. The organic layer was washed with brine, dried and concentrated to give the desired product. Column purification gave pure product. LCMS-ESI$^+$: calc'd for C$_{12}$H$_9$BrF$_3$NO$_3$S: 383.9 (M+H$^+$); Found: 383.9 (M+H$^+$).

Preparation of 5-bromo-2,7-dimethyl-6-vinylquinoline: PdCl$_2$(PPh$_3$)$_2$ (207 mg, 0.30 mmol) were added to a mixture 5-bromo-2,7-dimethylquinolin-6-yl trifluoromethanesulfonate (1.13 g, 2.95 mmol), tributyl-vinyl-stannane (0.95 mL, 3.25 mmol), lithium chloride (375 mg, 8.85 mmol) in DMF (30 mL). The reaction mixture was flushed with nitrogen, heated at 80° C. for 4 hours, cooled to room temperature. The mixture was diluted by ethyl acetate, washed with NaHCO$_3$ solution, water and brine, dried over Na$_2$SO$_4$, filtered and concentrated in vacuo. The obtained residue was purified by flash chromatography to provide the desired product. LCMS-ESI$^+$: calc'd for C$_{13}$H$_{12}$BrN: 262.0 (M+H$^+$); Found: 262.1 (M+H$^+$).

Preparation of (S)-1-(5-bromo-2,7-dimethylquinolin-6-yl)ethane-1,2-diol: AD-mix-α (8 g, excess) was added to a mixed solvent of t-butanol and water (35 mL/35 mL) and stirred at room temperature for 5 min, cooled to 0° C. 5-bromo-2,7-dimethyl-6-vinylquinoline (678 mg, 2.6 mmol) was added and stirred at 0° C. for 16 hrs. The mixture was diluted with ethyl acetate, washed with NaHCO$_3$ solution, water and brine, dried over Na$_2$SO$_4$, filtered and concentrated in vacuo. The obtained residue was purified by flash chromatography to provide the desired product. LCMS-ESI$^+$: calc'd for C$_{13}$H$_{14}$BrNO$_2$: 296.0 (M+H$^+$); Found: 296.1 (M+H$^+$).

Preparation of (S)-2-(5-bromo-2,7-dimethylquinolin-6-yl)-2-hydroxyethyl pivalate: To a stirred solution of (S)-1-(5-bromo-2,7-dimethylquinolin-6-yl)ethane-1,2-diol (290 mg, 0.98 mmol) in dichloromethane (12 mL) and pyridine (2 mL) was added trimethyl acetylchloride (0.24 mL, 1.97 mmol) at 0° C. The mixture was stirred at room temperature for 2 hours, quenched with slowly addition of NaHCO$_3$ solution. The mixture was extracted with ethyl acetate. The organic layer was washed with brine, dried and concentrated in vacuo. The obtained residue was purified by flash chromatography to provide the desired product. LCMS-ESI$^+$: calc'd for C$_{18}$H$_{22}$BrNO$_3$: 380.1 (M+H$^+$); Found: 380.2 (M+H$^+$).

Preparation of (S)-2-(5-bromo-2,7-dimethylquinolin-6-yl)-2-tert-butoxyethyl pivalate: To a stirred solution of (S)-2-(5-bromo-2,7-dimethylquinolin-6-yl)-2-hydroxyethyl pivalate (330 mg, 0.87 mmol) in t-butylacetate (10 mL) was added perchloric acid (0.3 mL, 3.5 mmol) at 0° C. The mixture was stirred at room temperature for 2 hours, quenched with slowly addition of NaHCO$_3$ solution. The mixture was extracted with ethyl acetate. The organic layer was washed with brine, dried and concentrated in vacuo. The residue was purified by flash chromatography to provide the desired product. LCMS-ESI$^+$: calc'd for C$_{22}$H$_{30}$BrNO$_3$: 436.1 (M+H$^+$); Found: 436.2 (M+H$^+$).

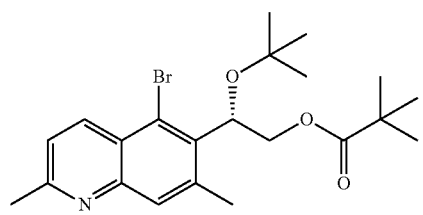

(S)-2-(5-bromo-2,7-dimethylquinolin-6-yl)-2-tert-butoxyethyl pivalate

+

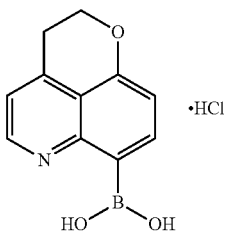

2,3-dihydropyrano[4,3,2-de]quinolin-7-ylboronic acid, monohydrochloride

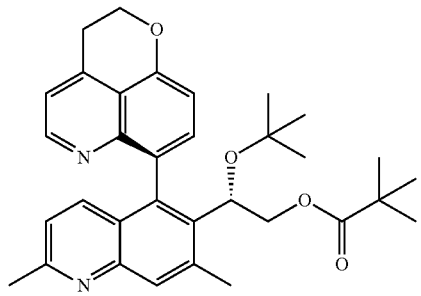

(S)-2-tert-butoxy-2-((R)-5-(2,3-dihydropyrano[4,3,2-de]quinolin-7-yl)-2,7-dimethylquinolin-6-yl)ethyl pivalate (S)-2-tert-Butoxy-2-((R)-5-(2,3-dihydropyrano[4,3,2-de]quinolin-7-yl)-2,7-dimethylquinolin-6-yl)ethyl pivalate was prepared in a similar manner as used to prepare (2S)-ethyl 2-((R)-5-(2,3-dihydropyrano[4,3,2-de]quinolin-7-yl)-2,7-dimethylquinolin-6-yl)-2-(2-methylpentan-2-yloxy)acetate, except using (S)-2-(5-bromo-2,7-dimethylquinolin-6-yl)-2-tert-butoxyethyl pivalate as the starting material. $^1$H NMR (400 MHz, CDCl$_3$) δ 8.63 (d, J=4.3 Hz, 1H), 7.93 (app. s, broad, 1H), 7.51 (d, J=7.8 Hz, 1H), 7.35 (d, J=8.6 Hz, 1H), 7.15 (d, J=7.8 Hz, 1H), 7.07 (d, J=3.9 Hz, 1H), 6.98 (d, J=8.6 Hz, 1H), 4.60-4.48 (m, 1H), 4.34-4.27 (m, 1H), 3.30 (dd, J=5.5, 5.5 Hz, 1H), 2.84 (s, 3H), 2.68 (s, 3H), 0.95 (s, 9H), 0.88 (s, 9H). LCMS-ESI$^+$: calc'd for C$_{33}$H$_{38}$N$_2$O$_4$: 527.3 (M+H$^+$); Found: 527.1 (M+H$^+$).

-continued

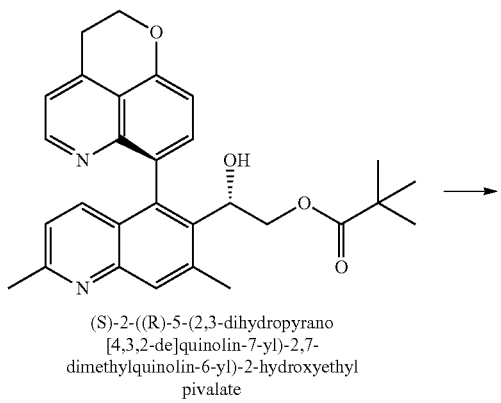

(S)-2-((R)-5-(2,3-dihydropyrano[4,3,2-de]quinolin-7-yl)-2,7-dimethylquinolin-6-yl)-2-hydroxyethyl pivalate

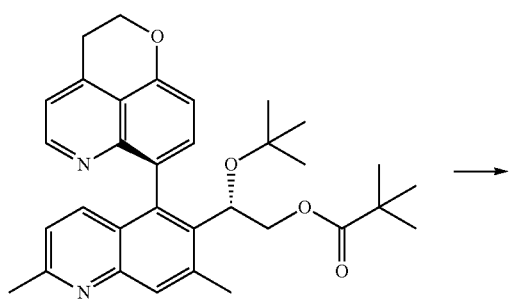

(S)-2-tert-butoxy-2-((R)-5-(2,3-dihydropyrano[4,3,2-de]quinolin-7-yl)-2,7-dimethylquinolin-6-yl)ethyl pivalate

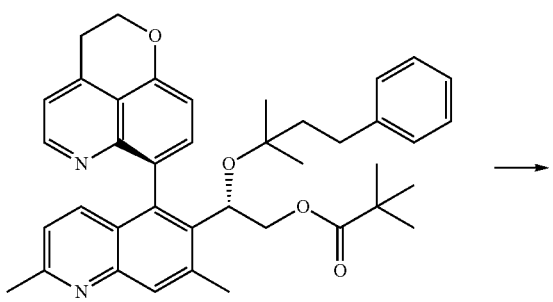

(S)-2-((R)-5-(2,3-dihydropyrano[4,3,2-de]quinolin-7-yl)-2,7-dimethylquinolin-6-yl)-2-(2-methyl-4-phenylbutan-2-yloxy)ethyl pivalate

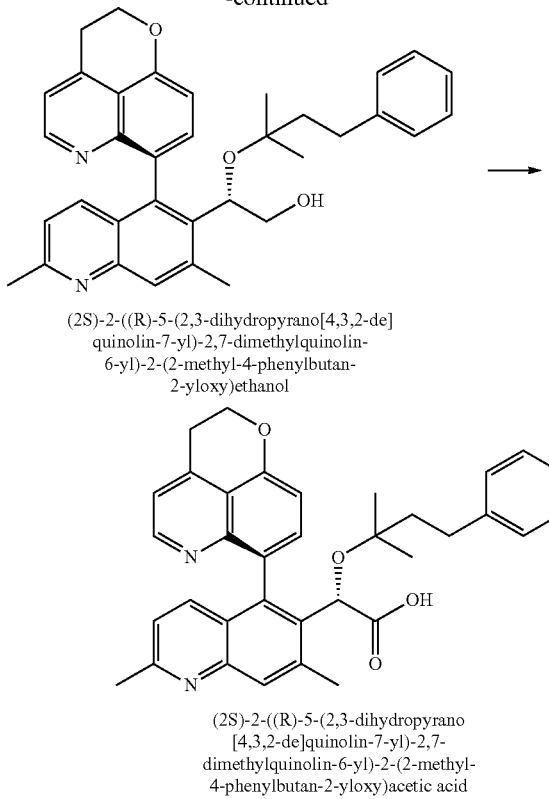

(2S)-2-((R)-5-(2,3-dihydropyrano[4,3,2-de]
quinolin-7-yl)-2,7-dimethylquinolin-
6-yl)-2-(2-methyl-4-phenylbutan-
2-yloxy)ethanol (2S)-2-((R)-5-(2,3-dihydropyrano
[4,3,2-de]quinolin-7-yl)-2,7-
dimethylquinolin-6-yl)-2-(2-methyl-
4-phenylbutan-2-yloxy)acetic acid Preparation of (S)-2-((R)-5-(2,3-dihydropyrano[4,3,2-de]quinolin-7-yl)-2,7-dimethylquinolin-6-yl)-2-hydroxyethyl pivalate: A solution of (S)-2-tert-butoxy-2-((R)-5-(2,3-dihydropyrano[4,3,2-de]quinolin-7-yl)-2,7-dimethylquinolin-6-yl)ethyl pivalate (330 mg, 0.627 mmol) in $CH_2Cl_2$ (3.5 mL) was treated with TFA (2.5 mL) at 23° C. The system was heated to 70° C. for 4 h. After conversion was complete, (indicated by LCMS), the system was cooled to 23° C. and concentrated. More $CH_2Cl_2$ was added, and the system was concentrated again to remove residual TFA. The residue was treated with $CH_2Cl_2$ and purified by flash column chromatography (silica gel, 0 to 20% MeOH/$CH_2Cl_2$) to give (S)-2-((R)-5-(2,3-dihydropyrano[4,3,2-de]quinolin-7-yl)-2,7-dimethylquinolin-6-yl)-2-hydroxyethyl pivalate as a trifluoroacetic acid salt. LCMS-ESI$^+$: calc'd for $C_{29}H_{30}N_2O_4$: 471.2 (M+H$^+$); Found: 471.1 (M+H$^+$).

Preparation of (S)-2-((R)-5-(2,3-dihydropyrano[4,3,2-de]quinolin-7-yl)-2,7-dimethylquinolin-6-yl)-2-(2-methyl-4-phenylbutan-2-yloxy)ethyl pivalate: A slurry of (S)-2-((R)-5-(2,3-dihydropyrano[4,3,2-de]quinolin-7-yl)-2,7-dimethylquinolin-6-yl)-2-hydroxyethyl pivalate (41 mg, 87 µmol) and 2-methyl-4-phenylbutan-2-yl acetate (2.5 mL, excess) was treated at 23° C. with 70% w/v aq HClO$_4$ (20 µL). Conversion was monitored using LCMS. After 2 h, the reaction was not complete, however, it was quenched by adding it dropwise over 5 min to saturated aq NaHCO$_3$ at 23° C. After 10 min, the reaction was extracted with $CH_2Cl_2$ (3×20 mL), and the combined organic layers were dried (Na$_2$SO$_4$), filtered, and concentrated. The residue was treated with $CH_2Cl_2$ and purified by flash column chromatography (silica gel, 0 to 100% EtOAc/hexane) to give (S)-2-((R)-5-(2,3-dihydropyrano[4,3,2-de]quinolin-7-yl)-2,7-dimethylquinolin-6-yl)-2-(2-methyl-4-phenylbutan-2-yloxy)ethyl pivalate. LCMS-ESI$^+$: calc'd for $C_{40}H_{44}N_2O_4$: 617.3 (M+H$^+$); Found: 617.4 (M+H$^+$).

Additionally, starting material ((S)-2-((R)-5-(2,3-dihydropyrano[4,3,2-de]quinolin-7-yl)-2,7-dimethylquinolin-6-yl)-2-hydroxyethyl pivalate) (26 mg) was recovered.

Preparation of (2S)-2-((R)-5-(2,3-dihydropyrano[4,3,2-de]quinolin-7-yl)-2,7-dimethylquinolin-6-yl)-2-(2-methyl-4-phenylbutan-2-yloxy)ethanol: A suspension of (S)-2-((R)-5-(2,3-dihydropyrano[4,3,2-de]quinolin-7-yl)-2,7-dimethylquinolin-6-yl)-2-(2-methyl-4-phenylbutan-2-yloxy)ethyl pivalate (7.0 mg, 11 µmol) in THF (2 mL), EtOH (1 mL), and H$_2$O (1 mL) with LiOH monohydrate (100 mg, excess) was heated to 100° C. for 5 h. The reaction was cooled to 23° C. and diluted with H$_2$O (10 mL). The system was extracted with $CH_2Cl_2$ (3×10 mL). Combined extracts were dried over Na$_2$SO$_4$, filtered, and concentrated giving crude (2S)-2-((R)-5-(2,3-dihydropyrano[4,3,2-de]quinolin-7-yl)-2,7-dimethylquinolin-6-yl)-2-(2-methyl-4-phenylbutan-2-yloxy)ethanol. The material was immediately used in the next reaction. LCMS-ESI$^+$: calc'd for $C_{35}H_{36}N_2O_3$: 533.3 (M+H$^+$); Found: 533.3 (M+H$^+$).

Preparation of (2S)-2-((R)-5-(2,3-dihydropyrano[4,3,2-de]quinolin-7-yl)-2,7-dimethylquinolin-6-yl)-2-(2-methyl-4-phenylbutan-2-yloxy)acetic acid: A solution of (2S)-2-((R)-5-(2,3-dihydropyrano[4,3,2-de]quinolin-7-yl)-2,7-dimethylquinolin-6-yl)-2-(2-methyl-4-phenylbutan-2-yloxy)ethanol (~11 mg, crude from the reaction above) in CH$_3$CN (800 µL) and H$_2$O (200 µL) was treated with H$_5$IO$_6$ (120 mg) at 23° C. immediately followed by CrO$_3$ (10 mg). After 5 min, the reaction was treated with H$_2$O (1.5 mL) followed by CH$_3$CN (500 µL). After 5 min, the system was filtered through a 0.45 micron Teflon filter. The filtrate was directly purified on a C18 Gemini column (Eluent: H$_2$O/CH$_3$CN 95:5→0:100 spiked with 0.1% v/v TFA), giving (2S)-2-((R)-5-(2,3-dihydropyrano[4,3,2-de]quinolin-7-yl)-2,7-dimethylquinolin-6-yl)-2-(2-methyl-4-phenylbutan-2-yloxy)acetic acid as the mono trifluoroacetic acid salt (4.5 mg). $^1$H NMR (400 MHz, CD$_3$OD) δ 8.55 (d, J=4.7 Hz, 1H), 8.06 (s, 1H), 7.90 (d, J=9.4 Hz, 1H), 7.52 (d, J=9.0 Hz, 1H), 7.47 (d, J=7.8 Hz, 1H), 7.38-7.34 (m, 1H), 7.20-7.09 (m, 5H), 6.89 (d, J=7.4 Hz, 1H), 5.27 (s, 1H), 4.58-4.40 (m, 2H), 3.50-3.11 (m, 2H), 2.95 (s, 3H), 2.91 (s, 3H), 2.45-2.20 (m, 2H), 1.40-1.33 (m, 2H), 1.05 (s, 3H), 0.96 (s, 3H). $^{19}$F NMR (377 MHz, CD$_3$OD) δ −77.6. LCMS-ESI$^+$: calc'd for $C_{35}H_{34}N_2O_4$: 547.3 (M+H$^+$); Found: 547.3 (M+H$^+$).

EXAMPLE 39

(2S)-2-((R)-5-(2,3-Dihydropyrano[4,3,2-de]quinolin-7-yl)-2,7-dimethylquinolin-6-yl)-2-(2-methylpentan-2-yloxy)acetic acid

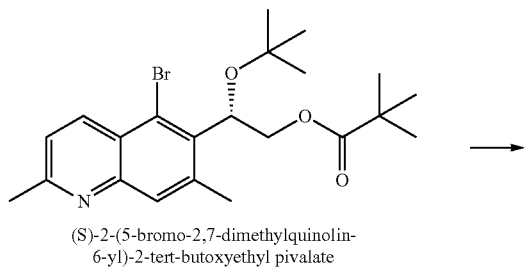

(S)-2-(5-bromo-2,7-dimethylquinolin-
6-yl)-2-tert-butoxyethyl pivalate

-continued

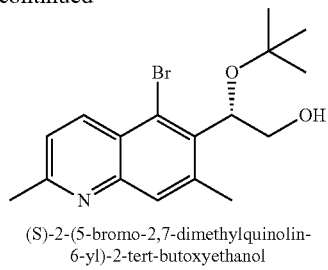

(S)-2-(5-bromo-2,7-dimethylquinolin-6-yl)-2-tert-butoxyethanol

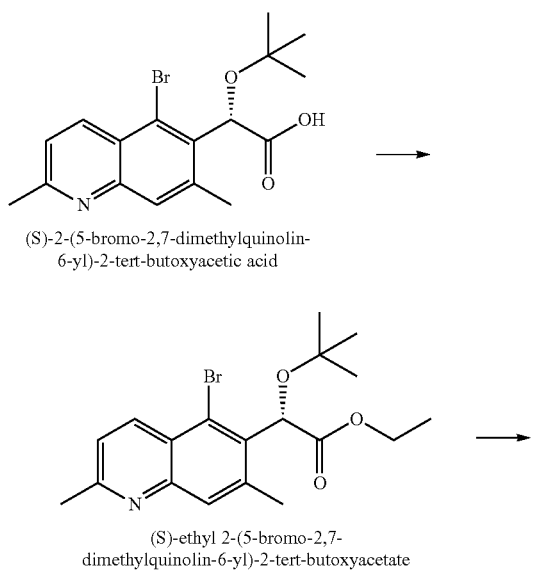

(S)-2-(5-bromo-2,7-dimethylquinolin-6-yl)-2-tert-butoxyacetic acid (S)-ethyl 2-(5-bromo-2,7-dimethylquinolin-6-yl)-2-tert-butoxyacetate

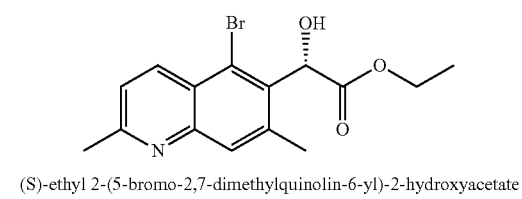

(S)-ethyl 2-(5-bromo-2,7-dimethylquinolin-6-yl)-2-hydroxyacetate

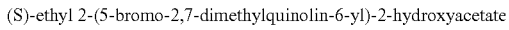

Preparation of (S)-2-(5-bromo-2,7-dimethylquinolin-6-yl)-2-tert-butoxyethanol: To a stirred solution of (S)-2-(5-bromo-2,7-dimethylquinolin-6-yl)-2-tert-butoxyethyl pivalate (50.0 g, 115 mmol) in THF (600 mL) and methanol (200 mL) was added 1M NaOH solution (300 mL, excess) at 0° C. The mixture was stirred at room temperature for 16 hours, diluted with water. The mixture was extracted with ethyl acetate. The organic layer was washed with brine, dried and concentrated in vacuo. The obtained residue was purified by flash chromatography to provide the desired product. LCMS-ESI$^+$: calc'd for $C_{17}H_{22}BrNO_2$: 352.1 (M+H$^+$); Found: 352.1 (M+H$^+$).

Preparation of (S)-2-(5-bromo-2,7-dimethylquinolin-6-yl)-2-tert-butoxyacetic acid: To a stirred solution of (S)-2-(5-bromo-2,7-dimethylquinolin-6-yl)-2-tert-butoxyethanol (38 g, 108 mmol) in acetone (500 mL) was added RuCl$_3$.3H$_2$O (2.83 g, 10.83 mmol) followed by NaIO$_4$ (116 g, 540 mmol) in H$_2$O (400 mL) at 0° C. The mixture was stirred at room temperature for 2 hours. The mixture was extracted with ethyl acetate. The organic layer was washed with brine, dried and concentrated in vacuo. The obtained residue was purified by flash chromatography to provide the desired product. LCMS-ESI$^+$: calc'd for $C_{17}H_{20}BrNO_3$: 366.1 (M+H$^+$); Found: 366.0 (M+H$^+$).

Preparation of (S)-ethyl 2-(5-bromo-2,7-dimethylquinolin-6-yl)-2-tert-butoxyacetate: To a stirred solution of (S)-2-(5-bromo-2,7-dimethylquinolin-6-yl)-2-tert-butoxyacetic acid (17 g, 46.6 mmol) in DMF (200 mL) was added Cs$_2$CO$_3$ (30.4 g, 93.2 mmol), followed with the addition of iodoethane (11 g, 69.9 mmol) at room temperature. The mixture was stirred at room temperature for 2 hours, diluted with water. The mixture was extracted with ethyl acetate. The organic layer was washed with brine, dried and concentrated in vacuo. The obtained residue was purified by flash chromatography to provide the desired product. LCMS-ESI$^+$: calc'd for $C_{19}H_{24}BrNO_3$: 394.1 (M+H$^+$); Found: 394.0 (M+H$^+$).

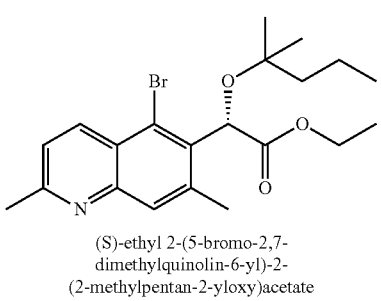

(S)-ethyl 2-(5-bromo-2,7-dimethylquinolin-6-yl)-2-(2-methylpentan-2-yloxy)acetate

+

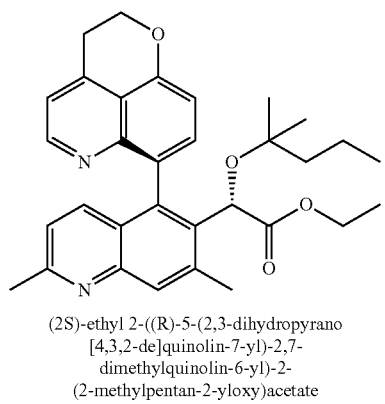

(2S)-ethyl 2-((R)-5-(2,3-dihydropyrano[4,3,2-de]quinolin-7-yl)-2,7-dimethylquinolin-6-yl)-2-(2-methylpentan-2-yloxy)acetate

+

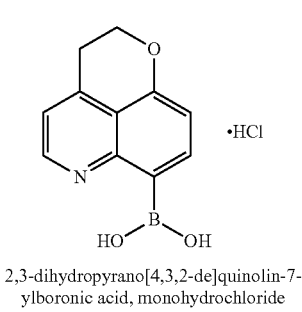

2,3-dihydropyrano[4,3,2-de]quinolin-7-ylboronic acid, monohydrochloride

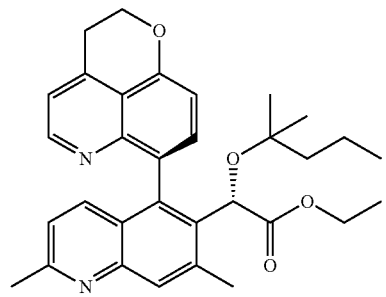

(2S)-ethyl 2-((S)-5-(2,3-dihydropyrano[4,3,2-de]quinolin-7-yl)-2,7-dimethylquinolin-6-yl)-2-(2-methylpentan-2-yloxy)acetate Preparation of (2S)-ethyl 2-((R)-5-(2,3-dihydropyrano[4,3,2-de]quinolin-7-yl)-2,7-dimethylquinolin-6-yl)-2-(2-methylpentan-2-yloxy)acetate: A microwave vial was charged with 2,3-dihydropyrano[4,3,2-de]quinolin-7-ylboronic acid, monohydrochloride (54 mg, 0.22 mmol), Pd(PPh$_3$)$_4$ (41 mg, 36 µmol), and a solution of K$_2$CO$_3$ (119 mg, 0.864 mmol) in H$_2$O (250 µL). A solution of (S)-ethyl 2-(5-bromo-2,7-dimethylquinolin-6-yl)-2-(2-methylpentan-2-yloxy)acetate (76 mg, 0.18 mmol) in 1,2-dimethoxyethane (1.0 mL, distilled from sodium/benzophenone) was added. The vessel was sealed and heated to 120° C. for 1.5 h. The reaction was cooled to 23° C. and added to a mixture of brine (10 mL) and H$_2$O (10 mL). The system was extracted with EtOAc (3×15 mL). Combined organic phases were dried over Na$_2$SO$_4$, filtered, and concentrated. DCM was added, and again the mixture was concentrated to remove residual 1,2-dimethoxyethane. The residue was treated with CH$_2$Cl$_2$ and purified by flash column chromatography (silica gel, 0 to 20% MeOH/CH$_2$Cl$_2$) to give (2S)-ethyl 2-((R)-5-(2,3-dihydropyrano[4,3,2-de]quinolin-7-yl)-2,7-dimethylquinolin-6-yl)-2-(2-methylpentan-2-yloxy)acetate. LCMS-ESI$^+$: calc'd for C$_{32}$H$_{36}$N$_2$O$_4$: 513.3 (M+H$^+$); Found: 513.1 (M+H$^+$). In addition, the other atropdiastereomer, (2S)-ethyl 2-((S)-5-(2,3-dihydropyrano[4,3,2-de]quinolin-7-yl)-2,7-dimethylquinolin-6-yl)-2-(2-methylpentan-2-yloxy)acetate was isolated. LCMS-ESI$^+$: calc'd for C$_{32}$H$_{36}$N$_2$O$_4$: 513.3 (M+H$^+$); Found: 513.1 (M+H$^+$).

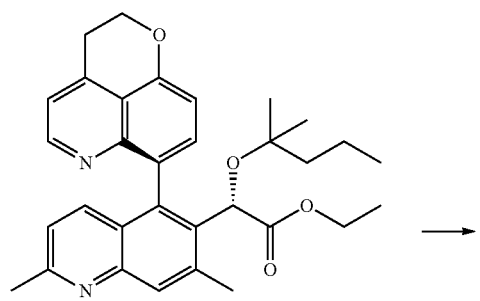

(2S)-ethyl 2-((R)-5-(2,3-dihydropyrano[4,3,2-de]quinolin-7-yl)-2,7-dimethylquinolin-6-yl)-2-(2-methylpentan-2-yloxy)acetate

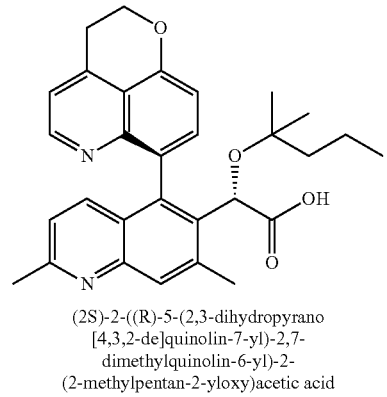

(2S)-2-((R)-5-(2,3-dihydropyrano[4,3,2-de]quinolin-7-yl)-2,7-dimethylquinolin-6-yl)-2-(2-methylpentan-2-yloxy)acetic acid Preparation of (2S)-2-((R)-5-(2,3-dihydropyrano[4,3,2-de]quinolin-7-yl)-2,7-dimethylquinolin-6-yl)-2-(2-methylpentan-2-yloxy)acetic acid: A suspension of (2S)-ethyl 2-((R)-5-(2,3-dihydropyrano[4,3,2-de]quinolin-7-yl)-2,7-dimethylquinolin-6-yl)-2-(2-methylpentan-2-yloxy)acetate (31 mg, 61 µmol), THF (1.0 mL), EtOH (absolute, 500 µL), H$_2$O (500 µL), and LiOH monohydrate (135 mg) was heated to 100° C. for 15 h. The reaction was cooled to 23° C. and filtered through a 0.45 micron Teflon filter. The filtrate was directly purified on a C18 Gemini column (Eluent: H$_2$O/CH$_3$CN 95:5→0:100 spiked with 0.1% v/v TFA), giving (2S)-2-((R)-5-(2,3-dihydropyrano[4,3,2-de]quinolin-7-yl)-2,7-dimethylquinolin-6-yl)-2-(2-methylpentan-2-yloxy)acetic acid as its mono trifluoroacetic acid salt. $^1$H NMR (400 MHz, CD$_3$OD) δ 8.60 (d, J=4.6 Hz, 1H), 8.06 (s, 1H), 7.96 (d, J=9.0 Hz, 1H), 7.68 (d, J=7.8 Hz, 1H), 7.56 (d, J=8.6 Hz, 1H), 7.50 (d, J=4.6 Hz, 1H), 7.30 (d, J=8.2 Hz, 1H), 5.24 (s, 1H), 4.64 (dd, J=5.8, 5.8 Hz, 2H), 3.49 (dd, J=5.8, 5.8 Hz, 2H), 2.92 (app. s, 6H), 1.26-1.00 (m, 4H), 0.93 (s, 3H), 0.89 (s, 3H), 0.74 (t, J=6.6 Hz, 3H). $^{19}$F NMR (377 MHz, CD$_3$OD) δ −77.8. LCMS-ESI$^+$: calc'd for C$_{30}$H$_{32}$N$_2$O$_4$: 485.2 (M+H$^+$); Found: 485.1 (M+H$^+$).

EXAMPLE 40

(2S)-2-((S)-5-(2,3-Dihydropyrano[4,3,2-de]quinolin-7-yl)-2,7-dimethylquinolin-6-yl)-2-(2-methylpentan-2-yloxy)acetic acid

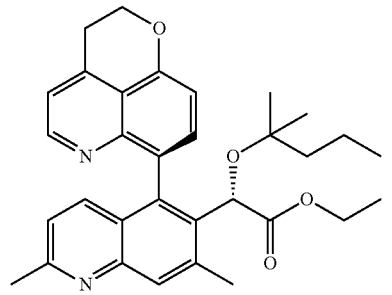

(2S)-ethyl 2-((S)-5-(2,3-dihydropyrano[4,3,2-de]quinolin-7-yl)-2,7-dimethylquinolin-6-yl)-2-(2-methylpentan-2-yloxy)acetate

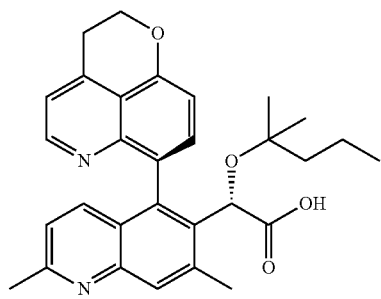

(2S)-2-((S)-5-(2,3-dihydropyrano[4,3,2-de]quinolin-7-yl)-2,7-dimethylquinolin-6-yl)-2-(2-methylpentan-2-yloxy)acetic acid (2S)-2-((S)-5-(2,3-Dihydropyrano[4,3,2-de]quinolin-7-yl)-2,7-dimethylquinolin-6-yl)-2-(2-methylpentan-2-yloxy) acetic acid was prepared in a similar manner as used to prepare (2S)-2-((R)-5-(2,3-dihydropyrano[4,3,2-de]quinolin-7-yl)-2,7-dimethylquinolin-6-yl)-2-(2-methylpentan-2-yloxy) acetic acid, except using (2S)-ethyl 2-((S)-5-(2,3-dihydropyrano[4,3,2-de]quinolin-7-yl)-2,7-dimethylquinolin-6-yl)-2-(2-methylpentan-2-yloxy)acetate as the starting material. $^1$H NMR (400 MHz, CD$_3$OD) δ 8.50 (d, J=4.6 Hz, 1H), 8.00-7.93 (m, 3H), 7.54 (d, J=8.6 Hz, 1H), 7.33 (d, J=4.6 Hz, 1H), 7.26 (d, J=8.2 Hz, 1H), 5.33 (s, 1H), 4.59 (dd, J=5.8, 5.8 Hz, 2H), 3.41 (dd, J=5.8, 5.8 Hz, 2H), 2.93 (s, 3H), 2.83 (s, 3H), 1.15-0.97 (m, 4H), 0.75 (s, 3H), 0.62 (t, J=6.6 Hz, 3H), 0.52 (s, 3H). $^{19}$F NMR (377 MHz, CD$_3$OD) δ −77.8. LCMS-ESI$^+$: calc'd for C$_{30}$H$_{32}$N$_2$O$_4$: 485.2 (M+H$^+$); Found: 485.1 (M+H$^+$).

EXAMPLE 41

(S)-2-((R)-5-(2,3-Dihydropyrano[4,3,2-de]quinolin-7-yl)-2,7-dimethylquinolin-6-yl)-2-(3-methylpentan-3-yloxy)acetic acid

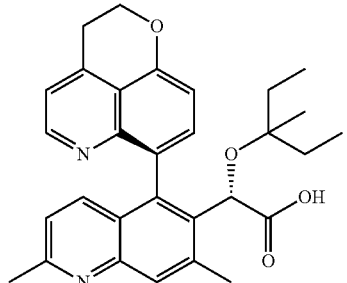

(S)-2-((R)-5-(2,3-dihydropyrano[4,3,2-de]quinolin-7-yl)-2,7-dimethylquinolin-6-yl)-2-(3-methylpentan-3-yloxy)acetic acid (S)-2-((R)-5-(2,3-Dihydropyrano[4,3,2-de]quinolin-7-yl)-2,7-dimethylquinolin-6-yl)-2-(3-methylpentan-3-yloxy) acetic acid was prepared in a similar manner as used to prepare (2S)-2-((R)-5-(2,3-dihydropyrano[4,3,2-de]quinolin-7-yl)-2,7-dimethylquinolin-6-yl)-2-(2-methylpentan-2-yloxy) acetic acid. $^1$H-NMR: 400 MHz, (d$^4$ MeOH): 8.60-8.59 (d, J=4.4 Hz, 1H); 8.06 (s, 1H); 7.714-7.96 (d, J=8.4 Hz, 1H); 7.71-7.69 (m, 1H); 7.58-7.56 (d, J=8.0 Hz, 1H); 7.51-7.49 (m, 1H); 7.34-7.32 (d, J=8.0, 1H); 5.20 (bs, 1H); 4.67-4.64 (m, 2H); 3.52-3.49 (m, 2H); 2.94-2.93 (d, J=6.0 Hz, 6H); 1.34-1.24 (m, 4H); 0.88 (s, 3H); 0.68-0.62 (m, 6H). LCMS-ESI$^+$ (m/z): [M+H]$^+$ calc'd for C$_{30}$H$_{33}$NO$_4$: 485.2; Found: 485.2.

EXAMPLE 42

(S)-2-((S)-5-(2,3-Dihydropyrano[4,3,2-de]quinolin-7-yl)-2,7-dimethylquinolin-6-yl)-2-(3-methylpentan-3-yloxy)acetic acid

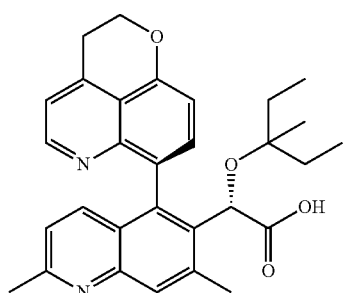

(S)-2-((S)-5-(2,3-dihydropyrano[4,3,2-de]quinolin-7-yl)-2,7-dimethylquinolin-6-yl)-2-(3-methylpentan-3-yloxy)acetic acid (S)-2-((S)-5-(2,3-Dihydropyrano[4,3,2-de]quinolin-7-yl)-2,7-dimethylquinolin-6-yl)-2-(3-methylpentan-3-yloxy)acetic acid was prepared in a similar manner as used to prepare (2S)-2-((S)-5-(2,3-dihydropyrano[4,3,2-de]quinolin-7-yl)-2,7-dimethylquinolin-6-yl)-2-(2-methylpentan-2-yloxy)acetic acid. $^1$H-NMR: 400 MHz, (d$^4$ MeOH): 8.53-8.52 (d, J=4.7 Hz, 1H); 8.00-7.98 (m, 3H); 7.57-7.54 (d, J=9 Hz, 1H); 7.35-7.33 (d, J=4.7 Hz, 1H); 7.28-7.26 (d, J=8.2 Hz, 1H); 5.32 (s, 1H); 4.62-4.59 (m, 2H); 3.44-3.41 (m, 2H); 2.94 (s, 3H); 2.85 (s, 3H); 1.30-1.11 (m, 2H); 0.88-0.78 (m, 2H); 0.67 (t, J=7.4 Hz, 3H); 0.57 (s, 3H), 0.41 (t, J=7.2 Hz, 3H). LCMS-ESI$^+$ (m/z): [M+H]$^+$ calc'd for $C_{30}H_{33}NO_4$: 485.2; Found: 485.2.

EXAMPLE 43

(S)-2-((S)-5-(2,3-Dihydropyrano[4,3,2-de]quinolin-7-yl)-2,7-dimethylquinolin-6-yl)-2-(2-methylheptan-2-yloxy)acetic acid

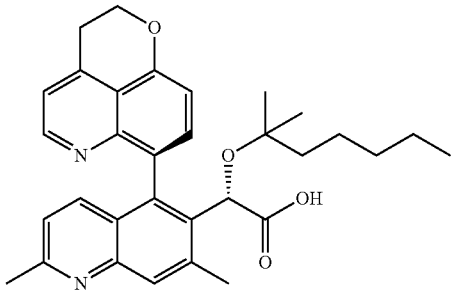

(S)-2-((S)-5-(2,3-dihydropyrano
[4,3,2-de]quinolin-7-yl)-2,7-
dimethylquinolin-6-yl)-2-
(2-methylpentan-2-yloxy)acetic acid (S)-2-((S)-5-(2,3-Dihydropyrano[4,3,2-de]quinolin-7-yl)-2,7-dimethylquinolin-6-yl)-2-(2-methylheptan-2-yloxy)acetic acid was prepared in a similar manner as (2S)-2-((S)-5-(2,3-dihydropyrano[4,3,2-de]quinolin-7-yl)-2,7-dimethylquinolin-6-yl)-2-(2-methylpentan-2-yloxy)acetic acid. $^1$H-NMR: 400 MHz, (d$^6$ DMSO): 8.53-8.52 (d, J=4.4 Hz, 1H); 7.93 (s, 1H); 7.77-7.45 (d, J=7.2 Hz, 1H); 7.68 (bs, 1H); 7.48 (bs, 1H); 7.34-7.33 (d, J=4.0 Hz, 1H); 7.24-7.22 (d, J=7.6 Hz, 1H); 5.11 (s, 1H); 4.58-4.50 (m, 2H); 3.34-3.41 (m, 2H); 2.81 (s, 3H); 2.69 (s, 3H); 1.06-0.95 (m, 4H); 0.87-0.79 (m, 6H); 0.74 (t, J=7.2 Hz, 3H); 0.62 (s, 3H), 0.46 (s, 3H). LCMS-ESI$^+$ (m/z): [M+H]$^+$ calc'd for $C_{32}H_{37}NO_4$: 513.2; Found: 513.28.

EXAMPLE 44

(S)-2-((R)-5-(2,3-Dihydropyrano[4,3,2-de]quinolin-7-yl)-2,7-dimethylquinolin-6-yl)-2-(tert-pentyloxy)acetic acid

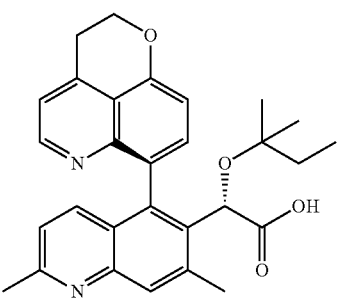

(S)-2-((R)-5-(2,3-dihydropyrano
[4,3,2-de]quinolin-7-yl)-2,7-
dimethylquinolin-6-yl)-2-
(tert-pentyloxy)acetic acid (S)-2-((R)-5-(2,3-Dihydropyrano[4,3,2-de]quinolin-7-yl)-2,7-dimethylquinolin-6-yl)-2-(tert-pentyloxy)acetic acid was prepared in a similar manner as (2S)-2-((R)-5-(2,3-dihydropyrano[4,3,2-de]quinolin-7-yl)-2,7-dimethylquinolin-6-yl)-2-(2-methylpentan-2-yloxy)acetic acid. $^1$H-NMR: 400 MHz, (d$^4$ MeOH): 8.64 (s, 1H); 8.09 (s, 1H); 8.00-8.98 (d, J=9.0 Hz, 1H); 7.73-7.72 (d, J=7.0 Hz, 1H) 7.59-7.57 (m, 2H); 7.35-7.33 (d, J=7.8 Hz, 1H); 5.22 (s, 1H); 4.66(bs, 2H); 3.53 (bs, 2H); 2.93 (s, 6H); 1.29-1.10 (m, 2H); 0.94-0.89 (d, J=12.9 Hz, 6H), 0.66 (bs, 3H) ppm. $^{19}$F-NMR: 400 MHz, (d$^4$ MeOH): −76.374 ppm. LCMS-ESI$^+$ (m/z): [M+H]$^+$ calc'd for $C_{29}H_{31}NO_4$: 471.2; Found: 471.1.

EXAMPLE 45

(S)-2-((S)-5-(2,3-Dihydropyrano[4,3,2-de]quinolin-7-yl)-2,7-dimethylquinolin-6-yl)-2-(tert-pentyloxy) acetic acid

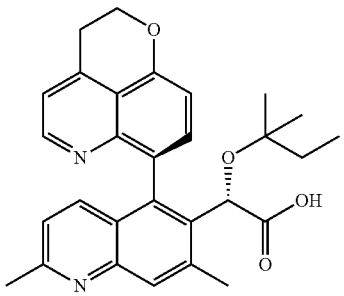

(S)-2-((S)-5-(2,3-dihydropyrano
[4,3,2-de]quinolin-7-yl)-2,7-
dimethylquinolin-6-yl)-2-
(tert-pentyloxy)acetic acid (S)-2-((S)-5-(2,3-Dihydropyrano[4,3,2-de]quinolin-7-yl)-2,7-dimethylquinolin-6-yl)-2-(tert-pentyloxy)acetic acid was prepared in a similar manner as (2S)-2-((S)-5-(2,3-dihydropyrano[4,3,2-de]quinolin-7-yl)-2,7-dimethylquinolin-6-yl)-2-(2-methylpentan-2-yloxy)acetic acid. $^1$H-NMR: 400 MHz, (d$^4$ MeOH): 8.23-8.51 (d, J=4.7 Hz, 1H); 8.00-7.97 (m, 3H); 7.57-7.54 (d, J=8.6 Hz, 1H); 7.35-7.34 (d, J=4.7 Hz, 1H); 7.29-7.27 (d, J=7.6 Hz, 1H); 5.31 (s, 1H); 4.60 (t, J=5.9 Hz, 2H); 3.43 (t, J=5.9 Hz, 2H); 2.94 (s, 3H); 2.84 (s, 3H); 1.15-1.03 (m, 2H); 0.77 (s, 3H); 0.62 (t, J=7.4 Hz, 3H); 0.48 (s, 3H). $^{19}$F-NMR: 400 MHz, (d$^4$ MeOH): −77.81. LCMS-ESI$^+$ (m/z): [M+H]$^+$ calc'd for $C_{29}H_{31}NO_4$: 471.2; Found: 471.1.

EXAMPLE 46

(S)-2-tert-Butoxy-2-((R)-5-(2,3-dihydropyrano[4,3,2-de]quinolin-7-yl)-7-methyl-2-(methylamino) quinolin-6-yl)acetic acid

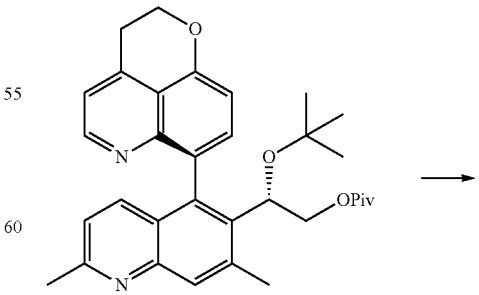

(S)-2-tert-butoxy-2-((R)-5-(2,3-dihydropyrano
[4,3,2-de]quinolin-7-yl)-7-methyl-2-
(trifluoromethylsulfonyloxy)quinolin-
6-yl)ethyl pivalate

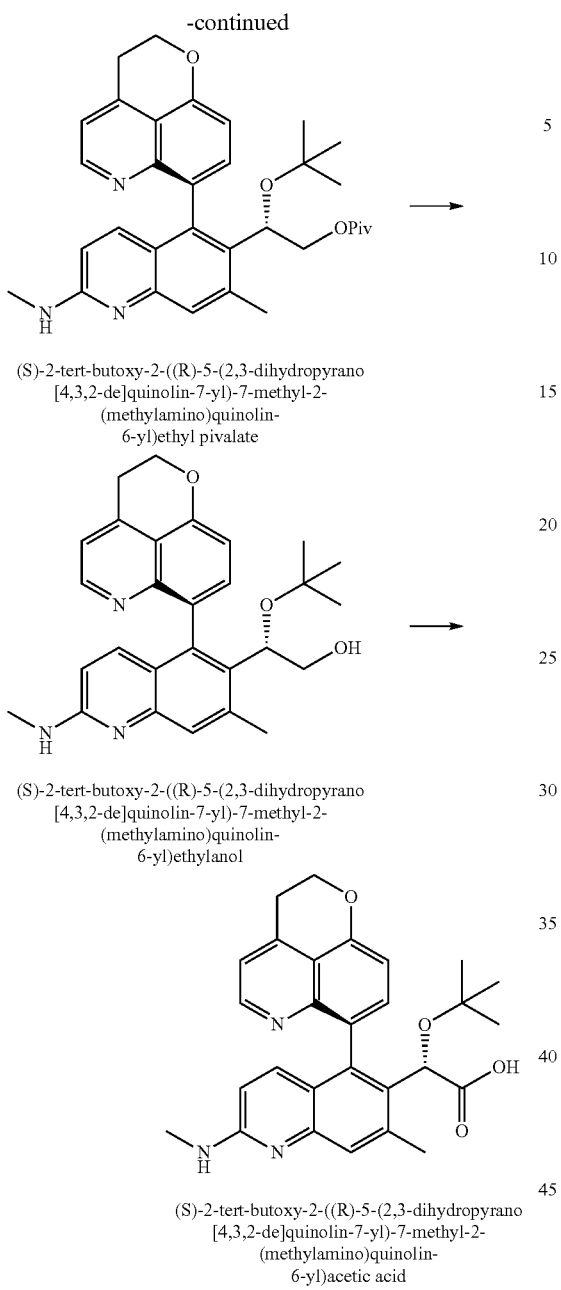

(S)-2-tert-butoxy-2-((R)-5-(2,3-dihydropyrano
[4,3,2-de]quinolin-7-yl)-7-methyl-2-
(methylamino)quinolin-
6-yl)ethyl pivalate (S)-2-tert-butoxy-2-((R)-5-(2,3-dihydropyrano
[4,3,2-de]quinolin-7-yl)-7-methyl-2-
(methylamino)quinolin-
6-yl)ethylanol (S)-2-tert-butoxy-2-((R)-5-(2,3-dihydropyrano
[4,3,2-de]quinolin-7-yl)-7-methyl-2-
(methylamino)quinolin-
6-yl)acetic acid Preparation of (S)-2-tert-butoxy-2-((R)-5-(2,3-dihydropyrano[4,3,2-d]quinolin-7-yl)-7-methyl-2-(methylamino)quinolin-6-yl)ethyl pivalate: (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate (30 mg, 0.04 mol) was dissolved in methylamine (1.0 mL of 2.0 M solution in THF, excess). The reaction mixture was stirred at 40° C. overnight and concentrated and purified by flash column chromatography (silica gel, 0 to 10% methanol/methylene chloride) to give (S)-2-tert-butoxy-2-((R)-5-(2,3-dihydropyrano[4,3,2-de]quinolin-7-yl)-7-methyl-2-(methylamino)quinolin-6-yl)ethyl pivalate. LCMS-ESI$^+$ (m/z): [M+H]$^+$ calc'd for $C_{33}H_{40}N_3O_4$: 541.30; Found: 541.4.

Preparation of (S)-2-tert-butoxy-2-((R)-5-(2,3-dihydropyrano[4,3,2-de]quinolin-7-yl)-7-methyl-2-(methylamino)quinolin-6-yl)ethanol: To a stirred solution of (S)-2-tert-butoxy-2-((R)-5-(2,3-dihydropyrano[4,3,2-de]quinolin-7-yl)-7-methyl-2-(methylamino)quinolin-6-yl)ethyl pivalate (29 mg, 0.05 mmol) in THF (1.0 mL) and methanol (1.0 mL) was added 1 M NaOH solution (1.0 mL, excess). The reaction mixture was stirred at 50° C. overnight. The mixture was diluted with ethyl acetate, washed with water and brine, dried over Na$_2$SO$_4$, filtered and concentrated and purified by flash column chromatography (silica gel, 0 to 100% ethyl acetate/hexanes) to give (S)-2-tert-butoxy-2-((R)-5-(2,3-dihydropyrano[4,3,2-de]quinolin-7-yl)-7-methyl-2-(methylamino)quinolin-6-yl)ethanol. LCMS-ESI$^+$ (m/z): [M+H]$^+$ calc'd for $C_{28}H_{32}N_3O_3$: 458.25; Found: 548.4.

Preparation of (S)-2-tert-butoxy-2-((R)-5-(2,3-dihydropyrano[4,3,2-de]quinolin-7-yl)-7-methyl-2-(methylamino)quinolin-6-yl)acetic acid: To a solution of (S)-2-tert-butoxy-2-((R)-5-(2,3-dihydropyrano[4,3,2-de]quinolin-7-yl)-7-methyl-2-(methylamino)quinolin-6-yl)ethanol (26 mg, 0.05 mmol) in wet acetonitrile (0.75% wt H$_2$O) was added H$_5$IO$_6$/CrO$_3$ (0.439 M stock solution in wet acetonitrile, 1.2 mL) at 0° C. The reaction mixture was stirred at 0° C. for 45 min. The reaction mixture was filtered and purified by reverse phase HPLC (Gemini, 5 to 100% ACN/H$_2$O+0.1% TFA) to give (S)-2-tert-butoxy-2-((R)-5-(2,3-dihydropyrano[4,3,2-de]quinolin-7-yl)-7-methyl-2-(methylamino)quinolin-6-yl)acetic acid as a TFA salt. $^1$H-NMR: 400 MHz, (CD$_3$OD) δ 8.71 (d, J=4.8 Hz, 1H), 7.89 (s, 1H), 7.68 (d, J=7.6 Hz, 1H), 7.63 (d, J=5.2 Hz, 1H), 7.34-7.31 (m, 2H), 6.76 (d, J=7.6 Hz, 1H), 5.15 (s, 1H), 4.68-4.64 (m, 2H), 3.56 (t, J=6.0 Hz, 2H), 3.22 (s, 3H), 2.79 (s, 3H), 0.92 (s, 9H). LCMS-ESI$^+$ (m/z): [M+H]$^+$ calc'd for $C_{28}H_{30}N_3O_4$: 472.23; Found: 472.2.

EXAMPLE 47

(S)-2-((R)-2-Amino-5-(2,3-dihydropyrano[4,3,2-de]quinolin-7-yl)-7-methylquinolin-6-yl)-2-tert-butoxyacetic acid

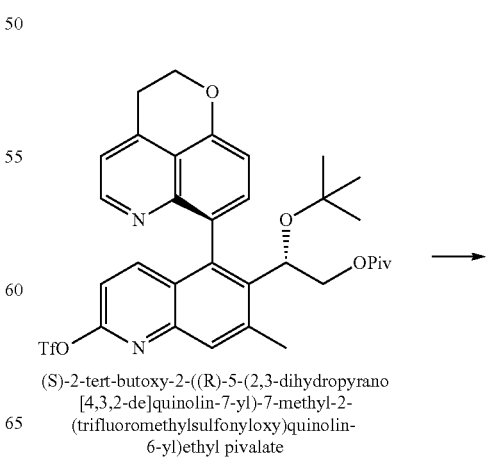

(S)-2-tert-butoxy-2-((R)-5-(2,3-dihydropyrano
[4,3,2-de]quinolin-7-yl)-7-methyl-2-
(trifluoromethylsulfonyloxy)quinolin-
6-yl)ethyl pivalate

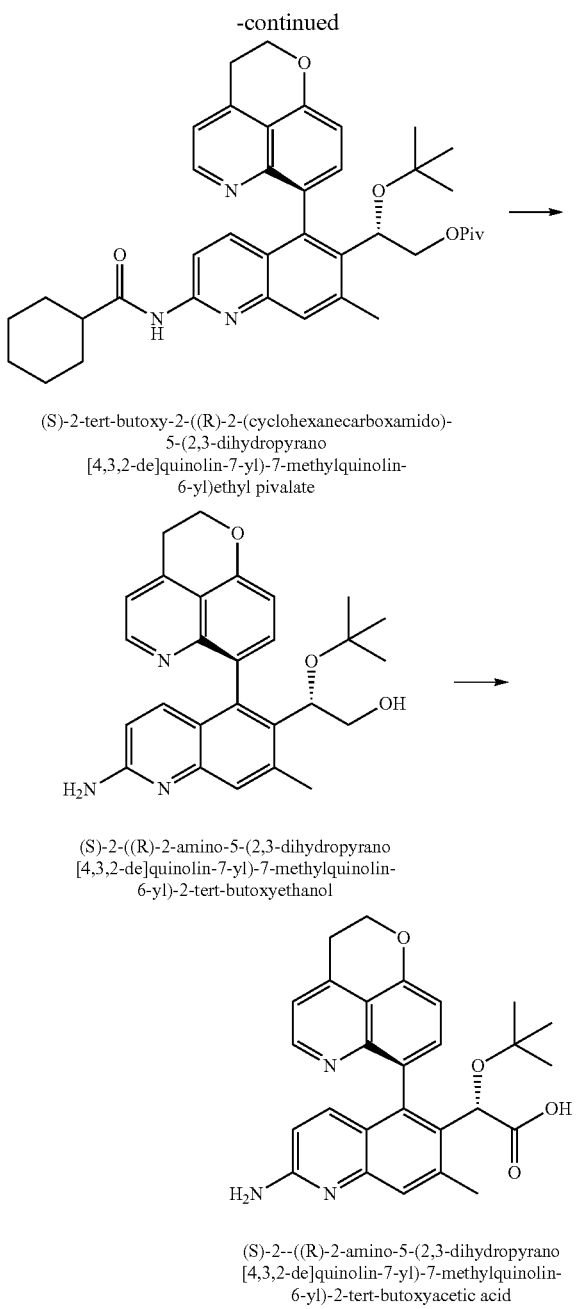

(S)-2-tert-butoxy-2-((R)-2-(cyclohexanecarboxamido)-
5-(2,3-dihydropyrano
[4,3,2-de]quinolin-7-yl)-7-methylquinolin-
6-yl)ethyl pivalate (S)-2-((R)-2-amino-5-(2,3-dihydropyrano
[4,3,2-de]quinolin-7-yl)-7-methylquinolin-
6-yl)-2-tert-butoxyethanol (S)-2-((R)-2-amino-5-(2,3-dihydropyrano
[4,3,2-de]quinolin-7-yl)-7-methylquinolin-
6-yl)-2-tert-butoxyacetic acid Preparation of (S)-2-tert-butoxy-2-((R)-2-(cyclohexanecarboxamido)-5-(2,3-dihydropyrano[4,3,2-de]quinolin-7-yl)-7-methylquinolin-6-yl)ethyl pivalate: To a solution (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate (50 mg, 0.08 mol) in dioxane (1.0 mL) was added cyclohexanecarboxamide (14 mg, 0.11 mmol), $Cs_2CO_3$ (74 mg, 0.23 mmol) and Xantphos (4 mg, $7.6×10^{-3}$ mmol) and $Pd_2(dba)_3$ (3 mg, $3.8×10^{-3}$ mmol). The reaction mixture was stirred at 100° C. for 2 h and then concentrated and purified by flash column chromatography (silica gel, 0 to 50% ethyl acetate/hexanes) to give (S)-2-tert-butoxy-2-((R)-2-(cyclohexanecarboxamido)-5-(2,3-dihydropyrano[4,3,2-de]quinolin-7-yl)-7-methylquinolin-6-yl)ethyl pivalate. LCMS-ESI$^+$ (m/z): [M+H]$^+$ calc'd for $C_{39}H_{48}N_3O_5$: 638.36; Found: 638.4.

Preparation of (S)-2-((R)-2-amino-5-(2,3-dihydropyrano[4,3,2-de]quinolin-7-yl)-7-methylquinolin-6-yl)-2-tert-butoxyethanol: Compound (S)-2-((R)-2-amino-5-(2,3-dihydropyrano[4,3,2-de]quinolin-7-yl)-7-methylquinolin-6-yl)-2-tert-butoxyethanol was prepared following the procedure used to prepare (S)-2-tert-butoxy-2-((R)-5-(2,3-dihydropyrano[4,3,2-de]quinolin-7-yl)-7-methyl-2-(methylamino)quinolin-6-yl)ethanol of Example 46, except that (S)-2-tert-butoxy-2-((R)-2-(cyclohexanecarboxamido)-5-(2,3-dihydropyrano[4,3,2-de]quinolin-7-yl)-7-methylquinolin-6-yl)ethyl pivalate was used instead of (S)-2-tert-butoxy-2-((R)-5-(2,3-dihydropyrano[4,3,2-de]quinolin-7-yl)-7-methyl-2-(methylamino)quinolin-6-yl)ethyl pivalate. LCMS-ESI$^+$ (m/z): [M+H]$^+$ calc'd for $C_{27}H_{30}N_3O_3$: 444.23; Found: 444.3.

Preparation of (S)-2-((R)-2-amino-5-(2,3-dihydropyrano[4,3,2-de]quinolin-7-yl)-7-methylquinolin-6-yl)-2-tert-butoxyacetic acid: Compound (S)-2-((R)-2-amino-5-(2,3-dihydropyrano[4,3,2-de]quinolin-7-yl)-7-methylquinolin-6-yl)-2-tert-butoxyacetic acid was prepared following the procedure used to prepare (S)-2-tert-butoxy-2-((R)-5-(2,3-dihydropyrano[4,3,2-d]quinolin-7-yl)-7-methyl-2-(methylamino)quinolin-6-yl)acetic acid of Example 46, except that (S)-2-((R)-2-amino-5-(2,3-dihydropyrano[4,3,2-de]quinolin-7-yl)-7-methylquinolin-6-yl)-2-tert-butoxyethanol was used instead of (S)-2-tert-butoxy-2-((R)-5-(2,3-dihydropyrano[4,3,2-de]quinolin-7-yl)-7-methyl-2-(methylamino)quinolin-6-yl)ethanol. $^1$H-NMR: 400 MHz, (CD$_3$OD) δ 8.71 (d, J=4.8 Hz, 1H), 7.71-7.68 (m, 2H), 7.62 (d, J=4.8 Hz, 1H), 7.41 (d, J=9.6 Hz, 1H), 7.33 (d, J=8.4 Hz, 1H), 6.79 (d, J=10 Hz, 1H), 5.15 (s, 1H), 4.68-4.64 (m, 2H), 3.56 (t, J=5.6 Hz, 2H), 2.79 (s, 3H), 0.92 (s, 9H). LCMS-ESI$^+$ (m/z): [M+H]$^+$ calc'd for $C_{27}H_{28}N_3O_4$: 458.21; Found: 458.2.

EXAMPLE 48

(S)-2-((R)-2-Acetamido-5-(2,3-dihydropyrano[4,3,2-de]quinolin-7-yl)-7-methylquinolin-6-yl)-2-tert-butoxyacetic acid (S)-2-((R)-2-amino-5-(2,3-dihydropyrano
[4,3,2-de]quinolin-7-yl)-7-methylquinolin-
6-yl)-2-tert-butoxyethanol

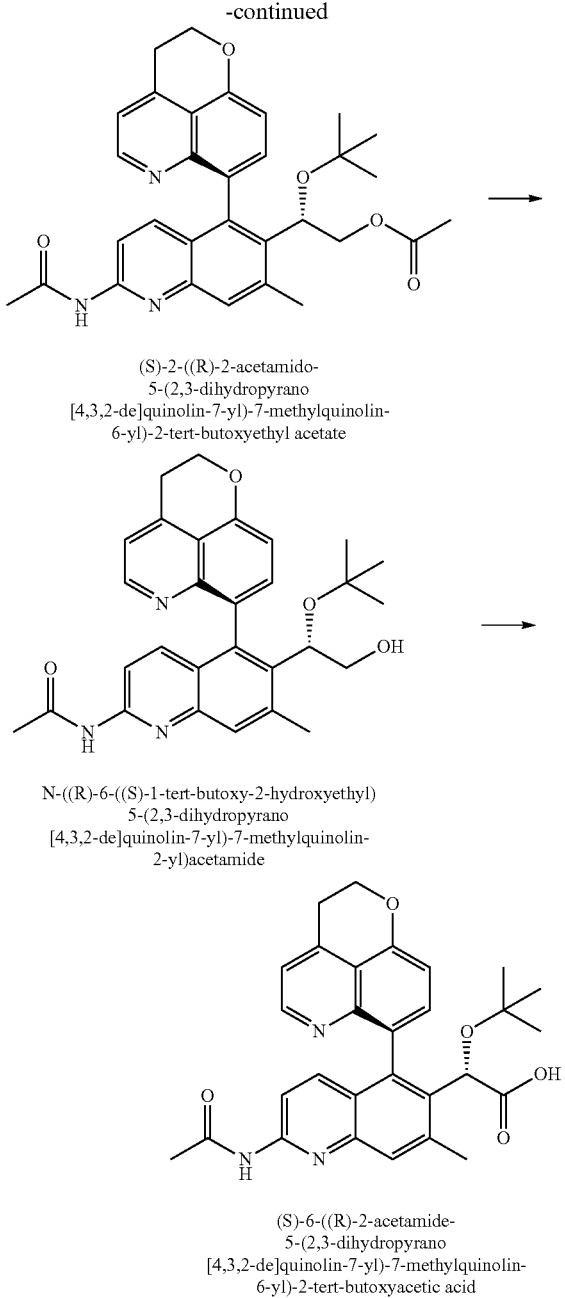

(S)-2-((R)-2-acetamido-
5-(2,3-dihydropyrano
[4,3,2-de]quinolin-7-yl)-7-methylquinolin-
6-yl)-2-tert-butoxyethyl acetate N-((R)-6-((S)-1-tert-butoxy-2-hydroxyethyl)
5-(2,3-dihydropyrano
[4,3,2-de]quinolin-7-yl)-7-methylquinolin-
2-yl)acetamide (S)-6-((R)-2-acetamide-
5-(2,3-dihydropyrano
[4,3,2-de]quinolin-7-yl)-7-methylquinolin-
6-yl)-2-tert-butoxyacetic acid Preparation of (S)-2-((R)-2-acetamido-5-(2,3-dihydropyrano[4,3,2-de]quinolin-7-yl)-7-methylquinolin-6-yl)-2-tert-butoxyethyl acetate: To a solution (S)-2-((R)-2-amino-5-(2,3-dihydropyrano[4,3,2-de]quinolin-7-yl)-7-methylquinolin-6-yl)-2-tert-butoxyethanol (20 mg, 0.04 mmol) in pyridine (0.3 mL) was added acetyl chloride (13 μL, 0.18 mmol). The reaction mixture was stirred at room temperature overnight. The mixture was quenched with water and concentrated and purified by flash column chromatography (silica gel, 0 to 100% ethyl acetate/hexanes) to give (S)-2-((R)-2-acetamido-5-(2,3-dihydropyrano[4,3,2-de]quinolin-7-yl)-7-methylquinolin-6-yl)-2-tert-butoxyethyl acetate. LCMS-ESI$^+$ (m/z): [M+H]$^+$ calc'd for $C_{31}H_{34}N_3O_5$: 528.25; Found: 528.3.

Preparation of N—((R)-6-((S)-1-tert-butoxy-2-hydroxyethyl)-5-(2,3-dihydropyrano[4,3,2-de]quinolin-7-yl)-7-methylquinolin-2-yl)acetamide: To a stirred solution of (S)-2-((R)-2-acetamido-5-(2,3-dihydropyrano[4,3,2-de]quinolin-7-yl)-7-methylquinolin-6-yl)-2-tert-butoxyethyl acetate (15 mg, 0.03 mmol) in THF (0.5 mL) and methanol (0.5 mL) was added 1 M NaOH solution (0.5 mL, excess). The reaction mixture was stirred at room temperature for 1 h. The mixture was diluted with ethyl acetate, washed with water and brine, dried over $Na_2SO_4$, filtered and concentrated and purified by flash column chromatography (silica gel, 15 to 100% ethyl acetate/hexanes) to give N-((R)-6-((S)-1-tert-butoxy-2-hydroxyethyl)-5-(2,3-dihydropyrano[4,3,2-de]quinolin-7-yl)-7-methylquinolin-2-yl)acetamide. LCMS-ESI$^+$ (m/z): [M+H]$^+$ calc'd for $C_{29}H_{32}N_3O_4$: 486.24; Found: 486.3.

Preparation of (S)-2-((R)-2-acetamido-5-(2,3-dihydropyrano[4,3,2-de]quinolin-7-yl)-7-methylquinolin-6-yl)-2-tert-butoxyacetic acid: Compound (S)-2-((R)-2-acetamido-5-(2,3-dihydropyrano[4,3,2-de]quinolin-7-yl)-7-methylquinolin-6-yl)-2-tert-butoxyacetic acid was prepared following the procedure used to prepare the mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid of Example 46, except that N-((R)-6-((S)-1-tert-butoxy-2-hydroxyethyl)-5-(2,3-dihydropyrano[4,3,2-de]quinolin-7-yl)-7-methylquinolin-2-yl)acetamide was used instead of (S)-2-tert-butoxy-2-((R)-5-(2,3-dihydropyrano[4,3,2-de]quinolin-7-yl)-7-methyl-2-(methylamino)quinolin-6-yl)ethanol. $^1$H-NMR: 400 MHz, ($CD_3OD$) δ 8.69 (d, J=5.6 Hz, 1H), 7.99 (s, 1H), 7.81 (t, J=8.4 Hz, 2H), 7.32 (d, J=5.6 Hz, 1H), 7.51 (d, J=9.2 Hz, 1H), 7.41 (d, J=8.4 Hz, 1H), 5.22 (s, 1H), 4.73-4.69 (m, 2H), 3.63 (t, J=5.6 Hz, 2H), 2.81 (s, 3H), 2.26 (s, 3H), 0.92 (s, 9H). LCMS-ESI$^+$ (m/z): [M+H]$^+$ calc'd for $C_{29}H_{30}N_3O_5$: 500.22; Found: 500.1.

EXAMPLE 49

(S)-2-((R)-2-Benzamido-5-(2,3-dihydropyrano[4,3,2-de]quinolin-7-yl)-7-methylquinolin-6-yl)-2-tert-butoxyacetic acid

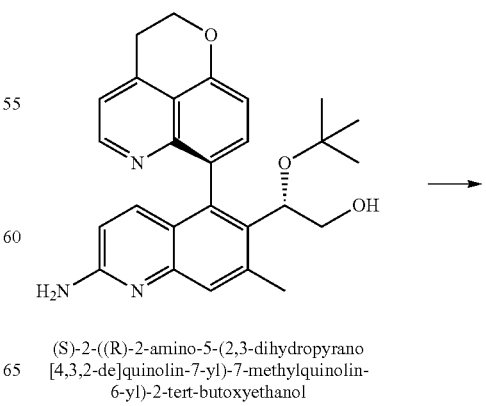

(S)-2-((R)-2-amino-5-(2,3-dihydropyrano
[4,3,2-de]quinolin-7-yl)-7-methylquinolin-
6-yl)-2-tert-butoxyethanol

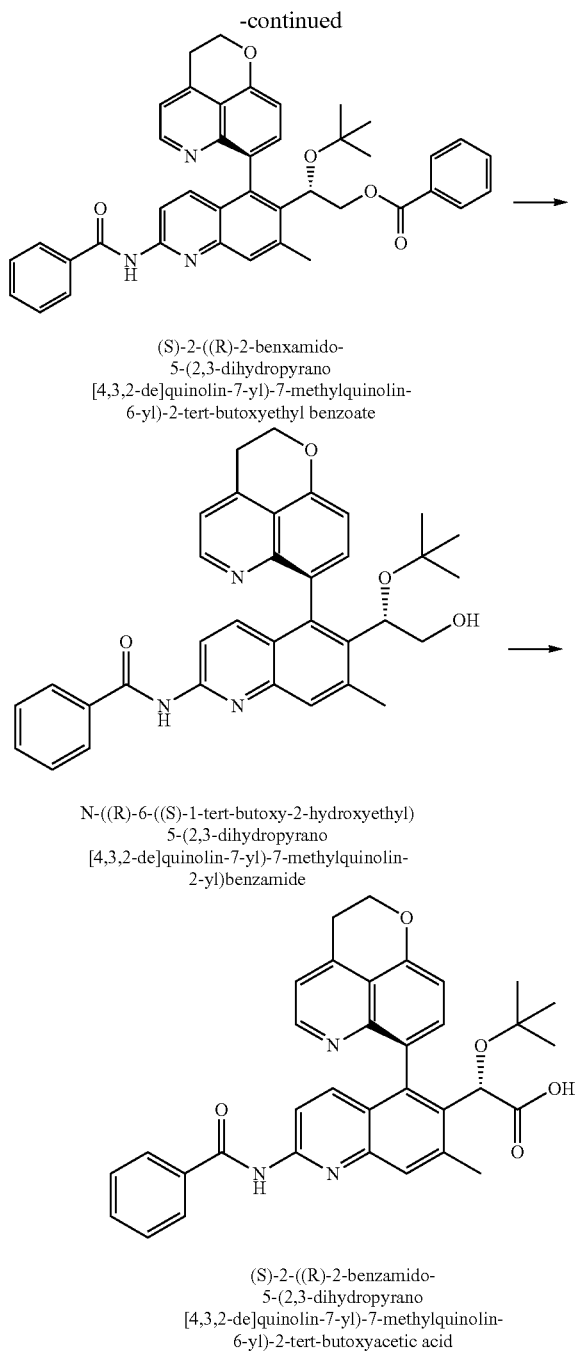

(S)-2-((R)-2-benxamido-
5-(2,3-dihydropyrano
[4,3,2-de]quinolin-7-yl)-7-methylquinolin-
6-yl)-2-tert-butoxyethyl benzoate N-((R)-6-((S)-1-tert-butoxy-2-hydroxyethyl)
5-(2,3-dihydropyrano
[4,3,2-de]quinolin-7-yl)-7-methylquinolin-
2-yl)benzamide (S)-2-((R)-2-benzamido-
5-(2,3-dihydropyrano
[4,3,2-de]quinolin-7-yl)-7-methylquinolin-
6-yl)-2-tert-butoxyacetic acid Preparation of (S)-2-((R)-2-benzamido-5-(2,3-dihydropyrano[4,3,2-de]quinolin-7-yl)-7-methylquinolin-6-yl)-2-tert-butoxyethyl benzoate: To a stirred solution of (S)-2-((R)-2-amino-5-(2,3-dihydropyrano[4,3,2-de]quinolin-7-yl)-7-methylquinolin-6-yl)-2-tert-butoxyethanol (22 mg, 0.05 mmol) and Et$_3$N (16 µL, 0.12 mmol), DMAP (0.1 mg, 9.7× 10$^4$ mmol) in pyridine (0.1 mL), benzoyl chloride (13 µL, 0.12 mmol) was added at 0° C. The reaction mixture was allowed to warm to room temperature overnight. The mixture was diluted with ethyl acetate, washed with water and brine, dried over Na$_2$SO$_4$, filtered and concentrated and purified by flash column chromatography (silica gel, 0 to 90% ethyl acetate/hexanes) to give (S)-2-((R)-2-benzamido-5-(2,3-dihydropyrano[4,3,2-de]quinolin-7-yl)-7-methylquinolin-6-yl)-2-tert-butoxyethyl benzoate. LCMS-ESr (m/z): [M+H]$^+$ calc'd for C$_{41}$H$_{38}$N$_3$O$_5$: 652.28; Found: 652.3.

Preparation of N-((R)-6-((S)-1-tert-butoxy-2-hydroxyethyl)-5-(2,3-dihydropyrano[4,3,2-de]quinolin-7-yl)-7-methylquinolin-2-yl)benzamide: Compound N-((R)-6-((S)-1-tert-butoxy-2-hydroxyethyl)-5-(2,3-dihydropyrano[4,3,2-de]quinolin-7-yl)-7-methylquinolin-2-yl)benzamide was prepared following the procedure used to prepare N-((R)-6-((S)-1-tert-butoxy-2-hydroxyethyl)-5-(2,3-dihydropyrano[4,3,2-de]quinolin-7-yl)-7-methylquinolin-2-yl)acetamide of Example 48, except that (S)-2-((R)-2-benzamido-5-(2,3-dihydropyrano[4,3,2-de]quinolin-7-yl)-7-methylquinolin-6-yl)-2-tert-butoxyethyl benzoate was used instead of (S)-2-((R)-2-acetamido-5-(2,3-dihydropyrano[4,3,2-de]quinolin-7-yl)-7-methylquinolin-6-yl)-2-tert-butoxyethyl acetate. LCMS-ESI$^+$ (m/z): [M+H]$^+$ calc'd for C$_{34}$H$_{34}$N$_3$O$_4$: 548.26; Found: 548.3.

Preparation of (S)-2-((R)-2-benzamido-5-(2,3-dihydropyrano[4,3,2-de]quinolin-7-yl)-7-methylquinolin-6-yl)-2-tert-butoxyacetic acid: Compound (S)-2-((R)-2-benzamido-5-(2,3-dihydropyrano[4,3,2-de]quinolin-7-yl)-7-methylquinolin-6-yl)-2-tert-butoxyacetic acid was prepared following the procedure used to prepare (S)-2-tert-butoxy-2-((R)-5-(2,3-dihydropyrano[4,3,2-de]quinolin-7-yl)-7-methyl-2-(methylamino)quinolin-6-yl)acetic acid of Example 46, except that N-((R)-6-((S)-1-tert-butoxy-2-hydroxyethyl)-5-(2,3-dihydropyrano[4,3,2-de]quinolin-7-yl)-7-methylquinolin-2-yl) benzamide was used instead of (S)-2-tert-butoxy-2-((R)-5-(2,3-dihydropyrano[4,3,2-de]quinolin-7-yl)-7-methyl-2-(methylamino)quinolin-6-yl)ethanol. $^1$H-NMR: 400 MHz, (CD$_3$OD) δ 8.72 (d, J=5.6 Hz, 1H), 8.07-8.01 (m, 4H), 7.85 (d, J=8.0 Hz, 1H), 7.79 (d, J=5.6 Hz, 1H), 7.66 (d, J=7.2 Hz, 1H), 7.62-7.55 (m, 3H), 7.45 (d, J=8.4 Hz, 1H), 5.24 (s, 1H), 4.74-4.69 (m, 2H), 3.66 (t, J=5.6 Hz, 2H), 2.81 (s, 3H), 2.85 (s, 3H), 0.95 (s, 9H). LCMS-ESI$^+$ (m/z): [M+H]$^+$ calc'd for C$_{34}$H$_{32}$N$_3$O$_5$: 562.24; Found: 562.1.

EXAMPLE 50

(S)-2-tert-Butoxy-2-((R)-2-cyano-5-(2,3-dihydropyrano[4,3,2-de]quinolin-7-yl)-7-methylquinolin-6-yl) acetic acid

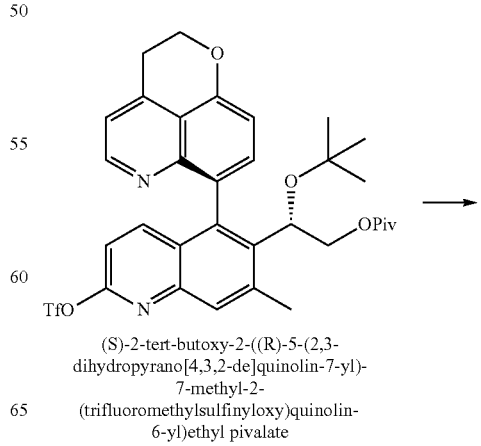

(S)-2-tert-butoxy-2-((R)-5-(2,3-
dihydropyrano[4,3,2-de]quinolin-7-yl)-
7-methyl-2-
(trifluoromethylsulfinyloxy)quinolin-
6-yl)ethyl pivalate

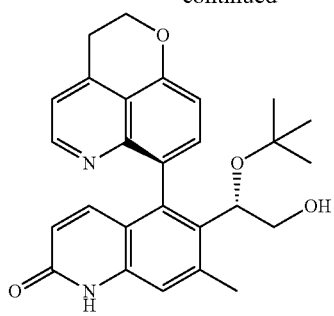

(R)-6-((S)-1-tert-butoxy-2-hydroxyethyl)-
5-(2,3-dihydropyrano[4,3,2-de]quinolin-
7-yl)-7-methylquinolin-
2(1H)-one

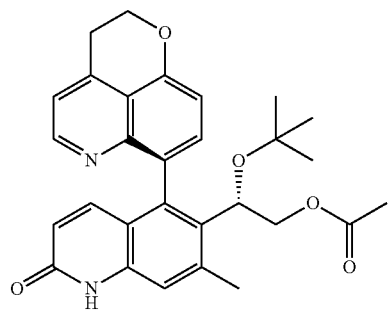

(S)-2-tert-butoxy-2-((R)-5-(2,3-
dihydropyrano[4,3,2-de]quinolin-
7-yl)-7-methyl-2-oxo-1,2-
dihydroquinolin-
6-yl)ethyl acetate

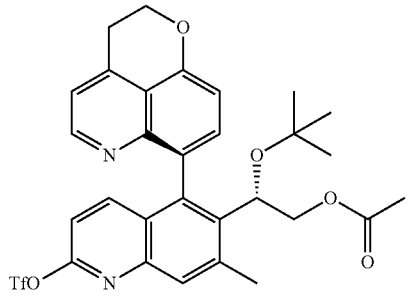

(S)-2-tert-butoxy-2-((R)-5-(2,3-
dihydropyrano[4,3,2-de]quinolin-7-yl)-7-methyl-2-
(trifluoromethylsulfonyloxy)quinolin-
6-yl)ethyl acetate

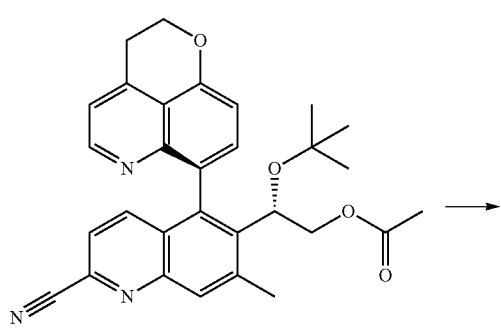

(S)-2-tert-butoxy-2-((R)-2-cyano-5-(2,3-
dihydropyrano[4,3,2-de]quinolin-7-yl)-7-
methylquinolin-6-yl)ethyl acetate

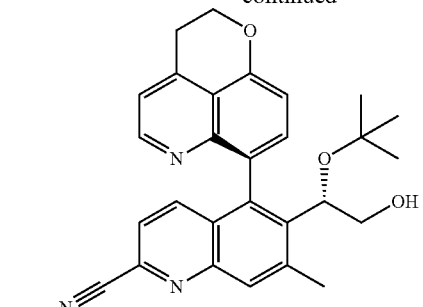

(R)-6-((S)-1-tert-butoxy-2-hydroxyethyl)-5-(2,3-
dihydropyrano[4,3,2-de]quinolin-7-yl)-7-
methylquinolin-2-carbonitrile

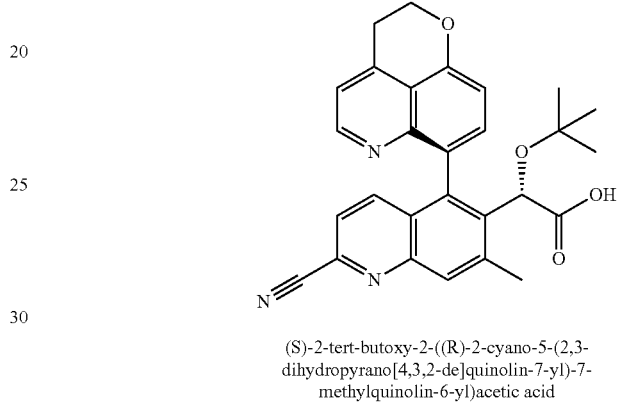

(S)-2-tert-butoxy-2-((R)-2-cyano-5-(2,3-
dihydropyrano[4,3,2-de]quinolin-7-yl)-7-
methylquinolin-6-yl)acetic acid Preparation of (R)-6-((S)-1-tert-butoxy-2-hydroxyethyl)-5-(2,3-dihydropyrano[4,3,2-de]quinolin-7-yl)-7-methylquinolin-2(1H)-one: To a stirred solution of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate (50 mg, 0.08 mmol) in THF (1.1 mL) and methanol (1.1 mL) was added 1 M NaOH solution (1.1 mL, excess). The reaction mixture was stirred at 50° C. overnight. The mixture was diluted with ethyl acetate, washed with water and brine, dried over Na$_2$SO$_4$, filtered and concentrated to give (R)-6-((S)-1-tert-butoxy-2-hydroxyethyl)-5-(2,3-dihydropyrano[4,3,2-de]quinolin-7-yl)-7-methylquinolin-2(1H)-one which was carried over to the next step.

Preparation of (S)-2-tert-butoxy-2-((R)-5-(2,3-dihydropyrano[4,3,2-de]quinolin-7-yl)-7-methyl-2-oxo-1,2-dihydroquinolin-6-yl)ethyl acetate: Compound (S)-2-tert-butoxy-2-((R)-5-(2,3-dihydropyrano[4,3,2-de]quinolin-7-yl)-7-methyl-2-oxo-1,2-dihydroquinolin-6-yl)ethyl acetate was prepared following the procedure used to prepare N-((R)-6-((S)-1-tert-butoxy-2-hydroxyethyl)-5-(2,3-dihydropyrano[4,3,2-de]quinolin-7-yl)-7-methylquinolin-2-yl)acetamide of Example 48, except that (R)-6-((S)-1-tert-butoxy-2-hydroxyethyl)-5-(2,3-dihydropyrano[4,3,2-de]quinolin-7-yl)-7-methylquinolin-2(1H)-one was used instead of (S)-2-((R)-2-acetamido-5-(2,3-dihydropyrano[4,3,2-de]quinolin-7-yl)-7-methylquinolin-6-yl)-2-tert-butoxyethyl acetate. LCMS-ESI$^+$ (m/z): [M+H]$^+$ calc'd for C$_{29}$H$_{31}$N$_2$O$_5$: 487.23; Found: 487.0.

Preparation of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl acetate: To a stirred solution of (S)-2-tert-butoxy-2-((R)-5-(2,3-dihydropyrano[4,3,2-de]quinolin-7-yl)-7-methyl-2-oxo-1,2-dihydroquinolin-6-yl)ethyl acetate (50 mg, 0.10 mmol) in CH$_2$Cl$_2$ (1.5 mL), pyridine (42 μL, 0.51 mmol) and Tf$_2$O (35 μL, 0.21 mmol) at −78° C. The mixture was stirred and warmed to 0° C. over a period of 2 hours. The reaction was quenched with slow addition of NaHCO$_3$ solution. The mixture was extracted with ethyl acetate. The organic layer was washed with brine, dried over sodium sulfate and concentrated to give (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl acetate. LCMS-ESI$^+$ (m/z): [M+H]$^+$ calc'd for C$_{30}$H$_{30}$F$_3$N$_2$O$_7$S: 619.17; Found: 619.0.

Preparation of (S)-2-tert-butoxy-2-((R)-2-cyano-5-(2,3-dihydropyrano[4,3,2-de]quinolin-7-yl)-7-methylquinolin-6-yl)ethyl acetate: To a stirred solution of (S)-2-tert-butoxy-2-((R)-5-(2,3-dihydropyrano[4,3,2-d]quinolin-7-yl)-7-methyl-2-(trifluoromethylsulfonyloxy)quinolin-6-yl)ethyl acetate (58 mg, 0.09 mmol) in DMF (1.4 mL), zinc cyanide (22 mg, 0.19 mmol) and Pd(PPh$_3$)$_4$ (16 mg, 0.01 mmol). The reaction mixture was stirred at 90° C. overnight. The mixture was concentrated and purified by flash column chromatography (silica gel, 0 to 100% ethyl acetate/hexanes) to give (S)-2-tert-butoxy-2-((R)-2-cyano-5-(2,3-dihydropyrano[4,3,2-de]quinolin-7-yl)-7-methylquinolin-6-yl)ethyl acetate. LCMS-ESI$^+$ (m/z): [M+H]$^+$ calc'd for C$_{30}$H$_{30}$N$_3$O$_4$: 496.23; Found: 496.1.

Preparation of (R)-6-((S)-1-tert-butoxy-2-hydroxyethyl)-5-(2,3-dihydropyrano[4,3,2-de]quinolin-7-yl)-7-methylquinoline-2-carbonitrile: To a stirred solution of (S)-2-tert-butoxy-2-((R)-2-cyano-5-(2,3-dihydropyrano[4,3,2-de]quinolin-7-yl)-7-methylquinolin-6-yl)ethyl acetate (15 mg, 0.03 mmol) in THF (0.8 mL) and methanol (0.8 mL) was added 10% K$_2$CO$_3$ solution (0.8 mL, excess). The reaction mixture was stirred at room temperature for 5 h. The mixture was diluted with ethyl acetate, washed with water and brine, dried over Na$_2$SO$_4$, filtered and concentrated and purified by flash column chromatography (silica gel, 10 to 100% ethyl acetate/hexanes) to give (R)-6-((S)-1-tert-butoxy-2-hydroxyethyl)-5-(2,3-dihydropyrano[4,3,2-de]quinolin-7-yl)-7-methylquinoline-2-carbonitrile. LCMS-ESI$^+$ (m/z): [M+H]$^+$ calc'd for C$_{28}$H$_{28}$N$_3$O$_3$: 454.22; Found: 454.0.

Preparation of (S)-2-tert-butoxy-2-((R)-2-cyano-5-(2,3-dihydropyrano[4,3,2-de]quinolin-7-yl)-7-methylquinolin-6-yl)acetic acid: Compound (S)-2-tert-butoxy-2-((R)-2-cyano-5-(2,3-dihydropyrano[4,3,2-de]quinolin-7-yl)-7-methylquinolin-6-yl)acetic acid was prepared following the procedure used to prepare (S)-2-tert-butoxy-2-((R)-5-(2,3-dihydropyrano[4,3,2-de]quinolin-7-yl)-7-methyl-2-(methylamino)quinolin-6-yl)acetic acid of Example 46, except that (R)-6-((S)-1-tert-butoxy-2-hydroxyethyl)-5-(2,3-dihydropyrano[4,3,2-de]quinolin-7-yl)-7-methylquinoline-2-carbonitrile was used instead (S)-2-tert-butoxy-2-((R)-5-(2,3-dihydropyrano[4,3,2-de]quinolin-7-yl)-7-methyl-2-(methylamino)quinolin-6-yl)ethanol. $^1$H-NMR: 400 MHz, (CD$_3$OD) δ 8.71 (d, J=5.2 Hz, 1H), 8.21 (s, 1H), 7.85 (d, J=7.6 Hz, 1H), 7.80 (d, J=5.2 Hz, 1H), 7.65 (s, 2H), 7.45 (d, J=8.4 Hz, 1H), 5.27 (s, 1H), 4.75-4.70 (m, 2H), 3.66 (t, J=5.6 Hz, 2H), 2.87 (s, 3H), 0.95 (s, 9H). LCMS-ESI$^+$ (m/z): [M+H]$^+$ calc'd for C$_{28}$H$_{26}$N$_3$O$_4$: 468.19; Found: 468.1.

EXAMPLE 51

(S)-2-tert-Butoxy-2-((R)-5-(2,3-dihydropyrano[4,3,2-de]quinolin-7-yl)-2-(2-hydroxypropan-2-yl)-7-methylquinolin-6-yl)acetic acid

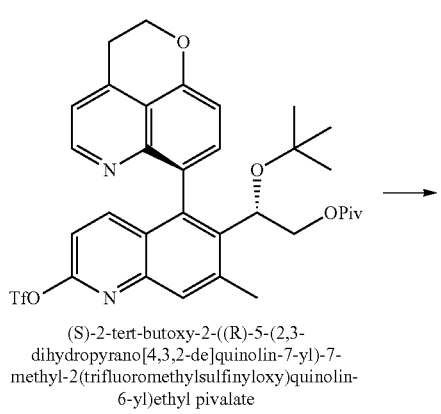

(S)-2-tert-butoxy-2-((R)-5-(2,3-dihydropyrano[4,3,2-de]quinolin-7-yl)-7-methyl-2(trifluoromethylsulfinyloxy)quinolin-6-yl)ethyl pivalate

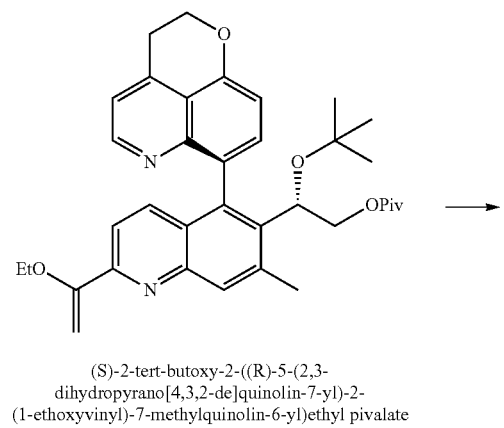

(S)-2-tert-butoxy-2-((R)-5-(2,3-dihydropyrano[4,3,2-de]quinolin-7-yl)-2-(1-ethoxyvinyl)-7-methylquinolin-6-yl)ethyl pivalate

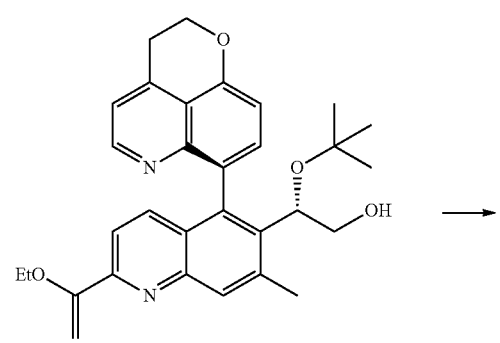

(S)-2-tert-butoxy-2-((R)-5-(2,3-dihydropyrano[4,3,2-de]quinolin-7-yl)-2-(1-ethoxyvinyl)-7-methylquinolin-6-yl)ethylanol

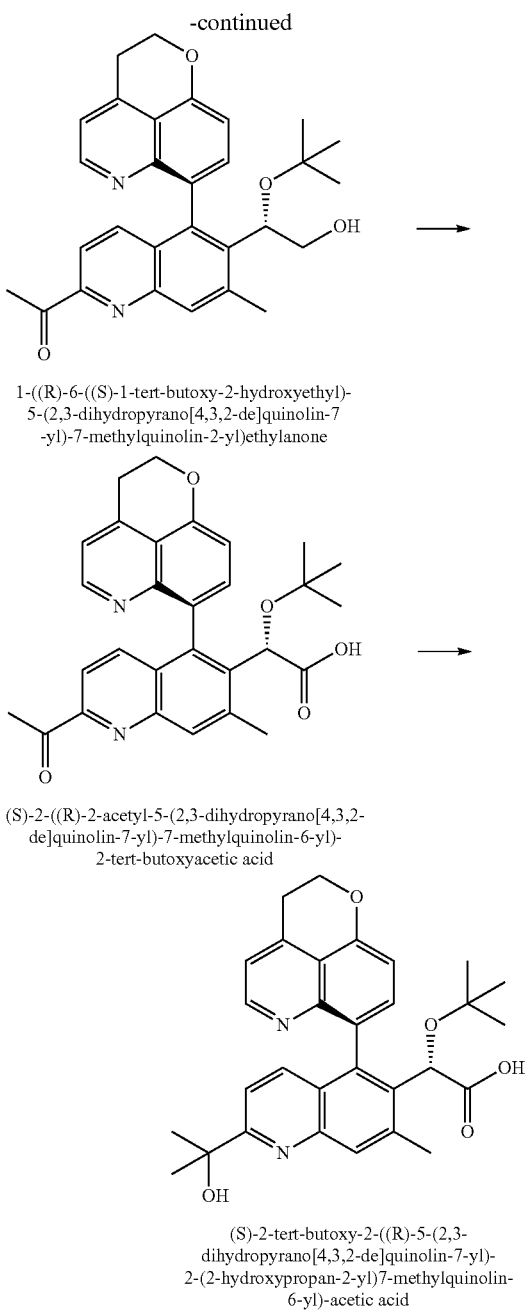

1-((R)-6-((S)-1-tert-butoxy-2-hydroxyethyl)-
5-(2,3-dihydropyrano[4,3,2-de]quinolin-7
-yl)-7-methylquinolin-2-yl)ethylanone (S)-2-((R)-2-acetyl-5-(2,3-dihydropyrano[4,3,2-
de]quinolin-7-yl)-7-methylquinolin-6-yl)-
2-tert-butoxyacetic acid (S)-2-tert-butoxy-2-((R)-5-(2,3-
dihydropyrano[4,3,2-de]quinolin-7-yl)-
2-(2-hydroxypropan-2-yl)7-methylquinolin-
6-yl)-acetic acid Preparation of (S)-2-tert-butoxy-2-((R)-5-(2,3-dihydropyrano[4,3,2-de]quinolin-7-yl)-2-(1-ethoxyvinyl)-7-methylquinolin-6-yl)ethyl pivalate: To a stirred solution of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate (1008 mg, 1.53 mmol) in DMF (23 mL) was added lithium chloride (201 mg, 4.73 mmol), PdCl$_2$(PPh$_3$)$_2$ (107 mg, 0.15 mmol) and tributyl(1-ethoxyvinyl)tin (0.82 mL, 2.44 mmol). The reaction mixture was stirred at 80° C. overnight. The mixture was diluted with ethyl acetate, washed with NaHCO$_3$ and brine, dried over Na$_2$SO$_4$, filtered and concentrated and purified by flash column chromatography (silica gel, 0 to 100% ethyl acetate/hexanes) to give (S)-2-tert-butoxy-2-((R)-5-(2,3-dihydropyrano[4,3,2-de]quinolin-7-yl)-2-(1-ethoxyvinyl)-7-methylquinolin-6-yl) ethyl pivalate. LCMS-ESI$^+$ (m/z): [M+H]$^+$ calc'd for C$_{36}$H$_{43}$N$_2$O$_5$: 583.32; Found: 583.3.

Preparation of (S)-2-tert-butoxy-2-((R)-5-(2,3-dihydropyrano[4,3,2-de]quinolin-7-yl)-2-(1-ethoxyvinyl)-7-methylquinolin-6-yl)ethanol: Compound (S)-2-tert-butoxy-2-((R)-5-(2,3-dihydropyrano[4,3,2-de]quinolin-7-yl)-2-(1-ethoxyvinyl)-7-methylquinolin-6-yl)ethanol was prepared following the procedure used to prepare the mixture of (S)-2-tert-butoxy-2-((R)-5-(2,3-dihydropyrano[4,3,2-de]quinolin-7-yl)-7-methyl-2-(methylamino)quinolin-6-yl)ethanol of Example 46, except that (S)-2-tert-butoxy-2-((R)-5-(2,3-dihydropyrano[4,3,2-de]quinolin-7-yl)-2-(1-ethoxyvinyl)-7-methylquinolin-6-yl)ethyl pivalate was used instead of (S)-2-tert-butoxy-2-((R)-5-(2,3-dihydropyrano[4,3,2-de]quinolin-7-yl)-7-methyl-2-(methylamino)quinolin-6-yl) ethyl pivalate. LCMS-ESI$^+$ (m/z): [M+H]$^+$ calc'd for C$_{31}$H$_{35}$N$_2$O$_4$: 499.26; Found: 499.3.

Preparation of 1-((R)-6-((S)-1-tert-butoxy-2-hydroxyethyl)-5-(2,3-dihydropyrano[4,3,2-de]quinolin-7-yl)-7-methylquinolin-2-yl)ethanone: To a stirred solution of (S)-2-tert-butoxy-2-((R)-5-(2,3-dihydropyrano[4,3,2-de]quinolin-7-yl)-2-(1-ethoxyvinyl)-7-methylquinolin-6-yl)ethanol (431 mg, 0.86 mmol) in acetone (43 mL) was added 2N HCl solution (4.3 mL, 8.65 mmol). The reaction mixture was stirred at room temperature overnight. The solvent was evaporated and the residue was diluted with EtOAc. The organic phase was washed with water, brine, dried over Na$_2$SO$_4$, filtered and concentrated and purified by flash column chromatography (silica gel, 0 to 100% ethyl acetate/hexanes) to give 1-((R)-6-((S)-1-tert-butoxy-2-hydroxyethyl)-5-(2,3-dihydropyrano[4,3,2-de]quinolin-7-yl)-7-methylquinolin-2-yl)ethanone. LCMS-ESI$^+$ (m/z): [M+H]$^+$ calc'd for C$_{29}$H$_{31}$N$_2$O$_4$: 471.23; Found: 471.1.

Preparation of (S)-2-((R)-2-acetyl-5-(2,3-dihydropyrano[4,3,2-de]quinolin-7-yl)-7-methylquinolin-6-yl)-2-tert-butoxyacetic acid: Compound ((S)-2-((R)-2-acetyl-5-(2,3-dihydropyrano[4,3,2-de]quinolin-7-yl)-7-methylquinolin-6-yl)-2-tert-butoxyacetic acid was prepared following the procedure used to prepare (S)-2-tert-butoxy-2-((R)-5-(2,3-dihydropyrano[4,3,2-de]quinolin-7-yl)-7-methyl-2-(methylamino)quinolin-6-yl)acetic acid of Example 46, except that 1-((R)-6-((S)-1-tert-butoxy-2-hydroxyethyl)-5-(2,3-dihydropyrano[4,3,2-de]quinolin-7-yl)-7-methylquinolin-2-yl)ethanone was used instead of (S)-2-tert-butoxy-2-((R)-5-(2,3-dihydropyrano[4,3,2-de]quinolin-7-yl)-7-methyl-2-(methylamino)quinolin-6-yl)ethanol. LCMS-ESI$^+$ (m/z): [M−H]$^+$ calc'd for C$_{29}$H$_{27}$N$_2$O$_5$: 483.2; Found: 483.2.

Preparation of (S)-2-tert-butoxy-2-((R)-5-(2,3-dihydropyrano[4,3,2-de]quinolin-7-yl)-2-(2-hydroxypropan-2-yl)-7-methylquinolin-6-yl)acetic acid: To a stirred solution of (S)-2-((R)-2-acetyl-5-(2,3-dihydropyrano[4,3,2-de]quinolin-7-yl)-7-methylquinolin-6-yl)-2-tert-butoxyacetic acid (15 mg, 0.03 mmol) in THF (0.2 mL) was added MeMgBr (29 μL of 3.2 M solution in 2-MeTHF, 0.09 mmol) at 0° C. The reaction mixture was stirred at room temperature for 3 h. The mixture was quenched with water and concentrated and purified by reverse phase HPLC (Gemini, 5 to 100% ACN/H$_2$O+0.1% TFA) to give (S)-2-tert-butoxy-2-((R)-5-(2,3-dihydropyrano[4,3,2-de]quinolin-7-yl)-2-(2-hydroxypropan-2-yl)-7-methylquinolin-6-yl)acetic acid as TFA salt. $^1$H-NMR: 400 MHz, (CD$_3$OD) δ 8.72 (d, J=5.6 Hz, 1H), 8.44 (s, 1H), 8.03 (d, J=8.8 Hz, 1H), 7.81-7.77 (m, 2H), 7.70 (d, J=5.6 Hz, 1H), 7.39 (d, J=8.0 Hz, 1H), 5.27 (s, 1H), 4.72-4.68 (m, 2H), 3.60 (t, J=6.0

Hz, 2H), 2.91 (s, 3H), 1.69 (s, 3H), 1.68 (s, 3H), 0.92 (s, 9H). LCMS-ESI⁺ (m/z): [M+H]⁺ calc'd for $C_{30}H_{33}N_2O_5$: 501.24; Found: 501.2.

EXAMPLE 52

(S)-2-tert-Butoxy-2-((R)-2-(1,1-difluoroethyl)-5-(2,3-dihydropyrano[4,3,2-de]quinolin-7-yl)-7-methylquinolin-6-yl)acetic acid

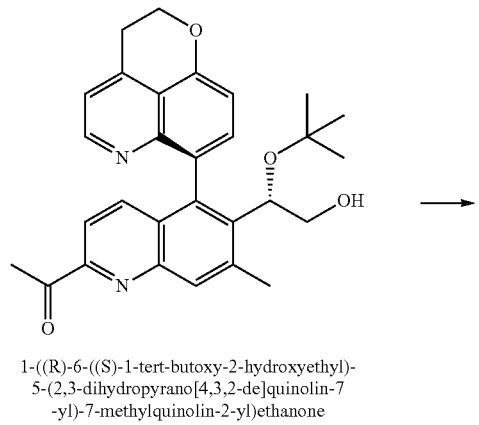

1-((R)-6-((S)-1-tert-butoxy-2-hydroxyethyl)-5-(2,3-dihydropyrano[4,3,2-de]quinolin-7-yl)-7-methylquinolin-2-yl)ethanone

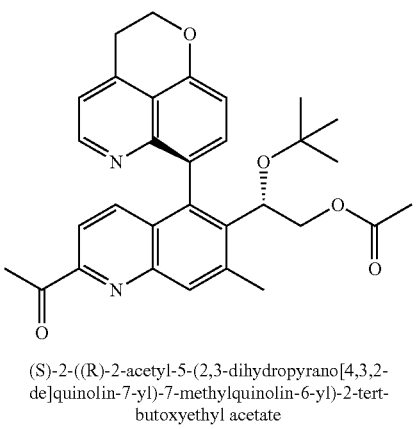

(S)-2-((R)-2-acetyl-5-(2,3-dihydropyrano[4,3,2-de]quinolin-7-yl)-7-methylquinolin-6-yl)-2-tert-butoxyethyl acetate

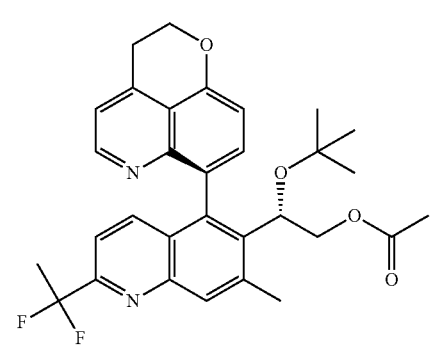

(S)-2-tert-butoxy-2-((R)-2-(1,1-difluoroethyl)-5-(2,3-dihydropyrano[4,3,2-de]quinolin-7-yl)-7-methylquinolin-6-yl)ethyl acetate

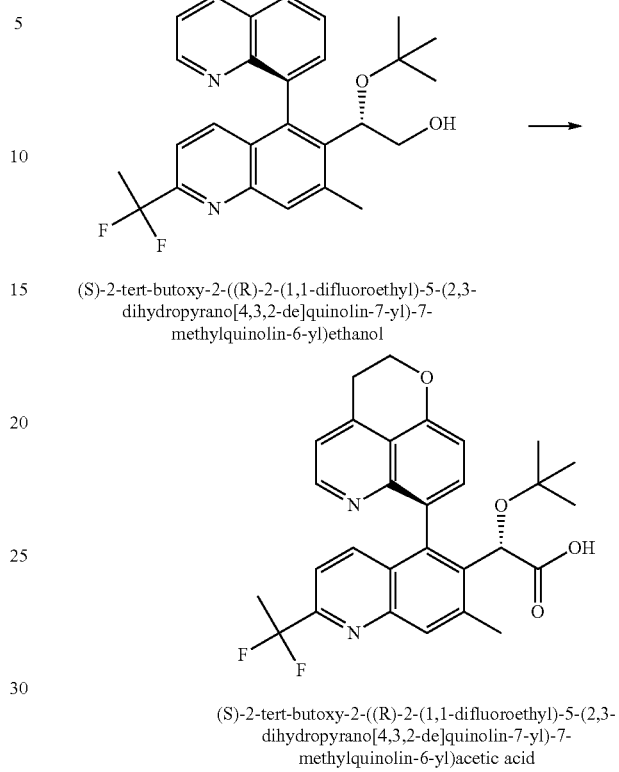

(S)-2-tert-butoxy-2-((R)-2-(1,1-difluoroethyl)-5-(2,3-dihydropyrano[4,3,2-de]quinolin-7-yl)-7-methylquinolin-6-yl)ethanol (S)-2-tert-butoxy-2-((R)-2-(1,1-difluoroethyl)-5-(2,3-dihydropyrano[4,3,2-de]quinolin-7-yl)-7-methylquinolin-6-yl)acetic acid Preparation of (S)-2-((R)-2-acetyl-5-(2,3-dihydropyrano[4,3,2-de]quinolin-7-yl)-7-methylquinolin-6-yl)-2-tert-butoxyethyl acetate: To a stirred solution of 1-((R)-6-((S)-1-tert-butoxy-2-hydroxyethyl)-5-(2,3-dihydropyrano[4,3,2-de]quinolin-7-yl)-7-methylquinolin-2-yl)ethanone (50 mg, 0.11 mmol) in pyridine (0.4 mL) was added acetic anhydride (20 μL, 0.21 mmol). The reaction mixture was stirred at room temperature overnight. The mixture was concentrated and purified by flash column chromatography (silica gel, 0 to 100% ethyl acetate/hexanes) to give (S)-2-((R)-2-acetyl-5-(2,3-dihydropyrano[4,3,2-de]quinolin-7-yl)-7-methylquinolin-6-yl)-2-tert-butoxyethyl acetate as a yellow oil (52 mg, 95%). LCMS-ESI⁺ (m/z): [M+H]⁺ calc'd for $C_{31}H_{33}N_2O_5$: 513.24; Found: 513.1.

Preparation of (S)-2-tert-butoxy-2-((R)-2-(1,1-difluoroethyl)-5-(2,3-dihydropyrano[4,3,2-de]quinolin-7-yl)-7-methylquinolin-6-yl)ethyl acetate: To a stirred solution of (S)-2-((R)-2-acetyl-5-(2,3-dihydropyrano[4,3,2-de]quinolin-7-yl)-7-methylquinolin-6-yl)-2-tert-butoxyethyl acetate (18 mg, 0.04 mmol) in CH₂Cl₂ (0.5 mL) was added (diethylamino)sulfur trifluoride (22 μL, 0.17 mmol) at 0° C. The reaction mixture was allowed to warm to room temperature overnight. The mixture was diluted with CH₂Cl₂, washed with NaHCO₃ and brine, dried over Na₂SO₄, filtered and concentrated and purified by flash column chromatography (silica gel, 0 to 100% ethyl acetate/hexanes) to give (S)-2-tert-butoxy-2-((R)-2-(1,1-difluoroethyl)-5-(2,3-dihydropyrano[4,3,2-de]quinolin-7-yl)-7-methylquinolin-6-yl)ethyl acetate. LCMS-ESI⁺ (m/z): [M+H]⁺ calc'd for $C_{31}H_{33}F_2N_2O_4$: 535.24; Found: 535.1.

Preparation of (S)-2-tert-butoxy-2-((R)-2-(1,1-difluoroethyl)-5-(2,3-dihydropyrano[4,3,2-de]quinolin-7-yl)-7-methylquinolin-6-yl)ethanol: Compound (S)-2-tert-butoxy-2-((R)-2-(1,1-difluoroethyl)-5-(2,3-dihydropyrano[4,3,2-de]quinolin-7-yl)-7-methylquinolin-6-yl)ethanol was prepared following the procedure used to prepare N-((R)-6-((S)-1-tert-butoxy-2-hydroxyethyl)-5-(2,3-dihydropyrano[4,3,2-de]quinolin-7-yl)-7-methylquinolin-2-yl)acetamide of Example 48, except that (S)-2-tert-butoxy-2-((R)-2-(1,1-difluoroethyl)-5-(2,3-dihydropyrano[4,3,2-de]quinolin-7-yl)-7-methylquinolin-6-yl)ethyl acetate was used instead of (S)-2-((R)-2-acetamido-5-(2,3-dihydropyrano[4,3,2-de]quinolin-7-yl)-7-methylquinolin-6-yl)-2-tert-butoxyethyl acetate. LCMS-ESI$^+$ (m/z): [M+H]$^+$ calc'd for $C_{29}H_{31}F_2N_2O_3$: 493.23; Found: 493.1.

Preparation of (S)-2-tert-butoxy-2-((R)-2-(1,1-difluoroethyl)-5-(2,3-dihydropyrano[4,3,2-de]quinolin-7-yl)-7-methylquinolin-6-yl)acetic acid: Compound (S)-2-tert-butoxy-2-((R)-2-(1,1-difluoroethyl)-5-(2,3-dihydropyrano[4,3,2-de]quinolin-7-yl)-7-methylquinolin-6-yl)acetic acid was prepared following the procedure used to prepare (S)-2-tert-butoxy-2-((R)-5-(2,3-dihydropyrano[4,3,2-de]quinolin-7-yl)-7-methyl-2-(methylamino)quinolin-6-yl)acetic acid of Example 46, except that (S)-2-tert-butoxy-2-((R)-2-(1,1-difluoroethyl)-5-(2,3-dihydropyrano[4,3,2-de]quinolin-7-yl)-7-methylquinolin-6-yl)ethanol was used instead of (S)-2-tert-butoxy-2-((R)-5-(2,3-dihydropyrano[4,3,2-de]quinolin-7-yl)-7-methyl-2-(methylamino)quinolin-6-yl)ethanol $^1$H-NMR: 400 MHz, (CD$_3$OD) δ 8.70 (d, J=5.6 Hz, 1H), 8.21 (s, 1H), 8.03 (d, J=8.8 Hz, 1H), 7.81-7.77 (m, 2H), 7.70 (d, J=5.6 Hz, 1H), 7.39 (d, J=8.0 Hz, 1H), 5.27 (s, 1H), 4.72-4.68 (m, 2H), 3.60 (t, J=6.0 Hz, 2H), 2.91 (s, 3H), 1.69 (s, 3H), 1.68 (s, 3H), 0.92 (s, 9H). LCMS-ESI$^+$ (m/z): [M−H]$^+$ calc'd for $C_{29}H_{29}F_2N_2O_4$: 507.21; Found: 507.1.

EXAMPLE 53

(2S)-2-tert-Butoxy-2-((5R)-5-(2,3-dihydropyrano[4,3,2-de]quinolin-7-yl)-2-(1-fluoroethyl)-7-methylquinolin-6-yl)acetic acid

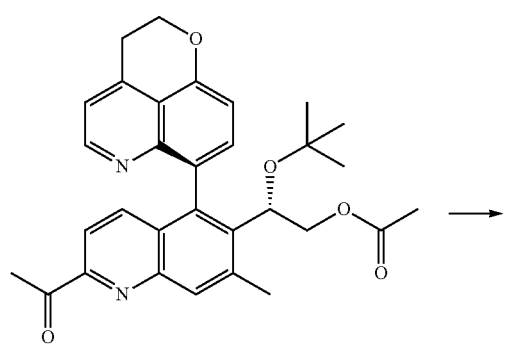

(S)-2-((R)-2-acetyl-5-(2,3-dihydropyrano[4,3,2-de]quinolin-7-yl)-7-methylquinolin-6-yl)-2-tert-butoxyethyl acetate

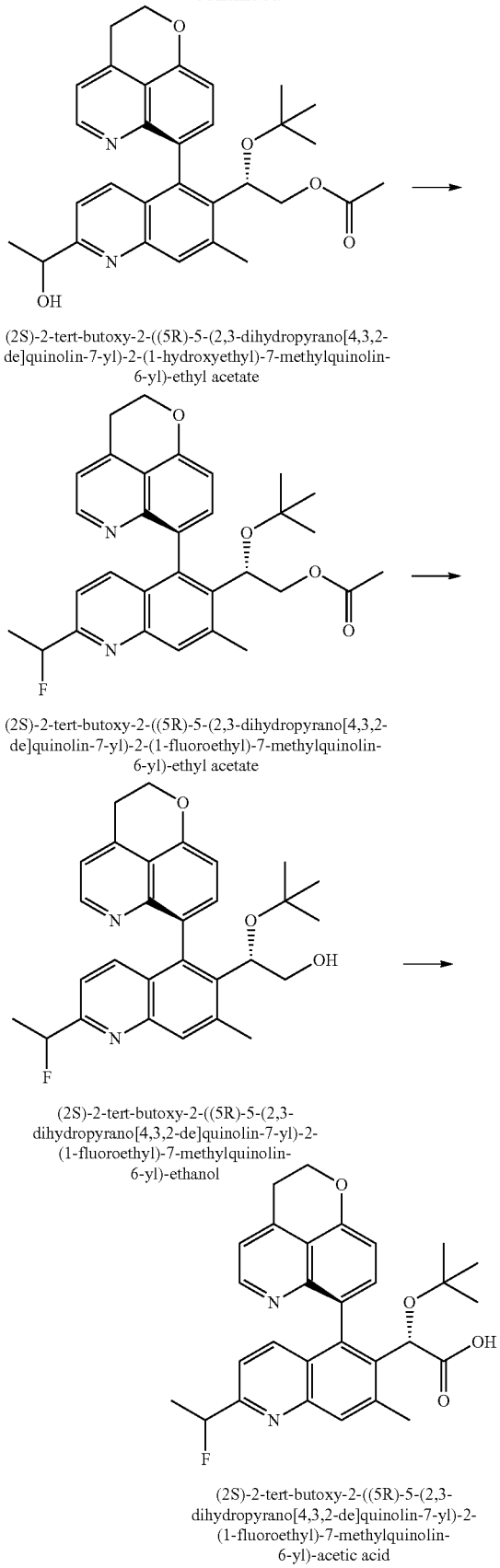

(2S)-2-tert-butoxy-2-((5R)-5-(2,3-dihydropyrano[4,3,2-de]quinolin-7-yl)-2-(1-hydroxyethyl)-7-methylquinolin-6-yl)-ethyl acetate (2S)-2-tert-butoxy-2-((5R)-5-(2,3-dihydropyrano[4,3,2-de]quinolin-7-yl)-2-(1-fluoroethyl)-7-methylquinolin-6-yl)-ethyl acetate (2S)-2-tert-butoxy-2-((5R)-5-(2,3-dihydropyrano[4,3,2-de]quinolin-7-yl)-2-(1-fluoroethyl)-7-methylquinolin-6-yl)-ethanol (2S)-2-tert-butoxy-2-((5R)-5-(2,3-dihydropyrano[4,3,2-de]quinolin-7-yl)-2-(1-fluoroethyl)-7-methylquinolin-6-yl)-acetic acid Preparation of (2S)-2-tert-butoxy-2-((5R)-5-(2,3-dihydropyrano[4,3,2-de]quinolin-7-yl)-2-(1-hydroxyethyl)-7-methylquinolin-6-yl)ethyl acetate: To a stirred solution of (S)-2-((R)-2-acetyl-5-(2,3-dihydropyrano[4,3,2-de]quinolin-7-yl)-7-methylquinolin-6-yl)-2-tert-butoxyethyl acetate (64 mg, 0.12 mmol) in methanol (2.5 mL) was added sodium borohydride (14 mg, 0.37 mmol) at 0° C. The reaction mixture was stirred at 0° C. for 45 min. The mixture was quenched by water and concentrated. The residue was dissolved in CH$_2$Cl$_2$, washed with water and brine, dried over Na$_2$SO$_4$, filtered and concentrated to give (2S)-2-tert-butoxy-2-((5R)-5-(2,3-dihydropyrano[4,3,2-de]quinolin-7-yl)-2-(1-hydroxyethyl)-7-methylquinolin-6-yl)ethyl acetate. LCMS-ESI$^+$ (m/z): [M+H]$^+$ calc'd for C$_{31}$H$_{35}$N$_2$O$_5$: 515.26; Found: 515.3.

Preparation of (2S)-2-tert-butoxy-2-((5R)-5-(2,3-dihydropyrano[4,3,2-de]quinolin-7-yl)-2-(1-fluoroethyl)-7-methylquinolin-6-yl)ethyl acetate: Compound (2S)-2-tert-butoxy-2-((5R)-5-(2,3-dihydropyrano[4,3,2-de]quinolin-7-yl)-2-(1-fluoroethyl)-7-methylquinolin-6-yl)ethyl acetate was prepared following the procedure used to prepare (S)-2-tert-butoxy-2-((R)-2-(1,1-difluoroethyl)-5-(2,3-dihydropyrano[4,3,2-de]quinolin-7-yl)-7-methylquinolin-6-yl)ethyl acetate of Example 52, except (2S)-2-tert-butoxy-2-((5R)-5-(2,3-dihydropyrano[4,3,2-de]quinolin-7-yl)-2-(1-hydroxyethyl)-7-methylquinolin-6-yl)ethyl acetate was used instead of (S)-2-((R)-2-acetyl-5-(2,3-dihydropyrano[4,3,2-de]quinolin-7-yl)-7-methylquinolin-6-yl)-2-tert-butoxyethyl acetate. LCMS-ESI$^+$ (m/z): [M+H]$^+$ calc'd for C$_{31}$H$_{34}$FN$_2$O$_5$: 517.25; Found: 517.2.

Preparation of (2S)-2-tert-butoxy-2-((5R)-5-(2,3-dihydropyrano[4,3,2-de]quinolin-7-yl)-2-(1-fluoroethyl)-7-methylquinolin-6-yl)ethanol: Compound (2S)-2-tert-butoxy-2-((5R)-5-(2,3-dihydropyrano[4,3,2-de]quinolin-7-yl)-2-(1-fluoroethyl)-7-methylquinolin-6-yl)ethanol was prepared following the procedure used to prepare N-((R)-6-((S)-1-tert-butoxy-2-hydroxyethyl)-5-(2,3-dihydropyrano[4,3,2-de]quinolin-7-yl)-7-methylquinolin-2-yl)acetamide of Example 48, except that (2S)-2-tert-butoxy-2-((5R)-5-(2,3-dihydropyrano[4,3,2-de]quinolin-7-yl)-2-(1-fluoroethyl)-7-methylquinolin-6-yl)ethyl acetate was used instead of (S)-2-((R)-2-acetamido-5-(2,3-dihydropyrano[4,3,2-de]quinolin-7-yl)-7-methylquinolin-6-yl)-2-tert-butoxyethyl acetate. LCMS-ESI$^+$ (m/z): [M+H]$^+$ calc'd for C$_{29}$H$_{32}$FN$_2$O$_3$: 475.24; Found: 475.2.

Preparation of (2S)-2-tert-butoxy-2-((5R)-5-(2,3-dihydropyrano[4,3,2-de]quinolin-7-yl)-2-(1-fluoroethyl)-7-methylquinolin-6-yl)acetic acid: Compound (2S)-2-tert-butoxy-2-((5R)-5-(2,3-dihydropyrano[4,3,2-de]quinolin-7-yl)-2-(1-fluoroethyl)-7-methylquinolin-6-yl)acetic acid was prepared following the procedure used to prepare (S)-2-tert-butoxy-2-((R)-5-(2,3-dihydropyrano[4,3,2-de]quinolin-7-yl)-7-methyl-2-(methylamino)quinolin-6-yl)acetic acid of Example 46, except that (2S)-2-tert-butoxy-2-((5R)-5-(2,3-dihydropyrano[4,3,2-de]quinolin-7-yl)-2-(1-fluoroethyl)-7-methylquinolin-6-yl)ethanol was used instead of (S)-2-tert-butoxy-2-((R)-5-(2,3-dihydropyrano[4,3,2-de]quinolin-7-yl)-7-methyl-2-(methylamino)quinolin-6-yl)ethanol. $^1$H-NMR: 400 MHz, (CD$_3$OD) δ 8.70 (d, J=5.2 Hz, 1H), 8.14 (s, 1H), 7.85 (d, J=8.4 Hz, 1H), 7.82 (d, J=5.6 Hz, 1H), 7.57 (d, J=9.2 Hz, 1H), 7.48 (t, J=9.2 Hz, 2H), 5.91-5.76 (m, 1H), 5.25 (s, 1H), 4.77-4.68 (m, 2H), 3.67 (t, J=6.0 Hz, 2H), 2.85 (s, 3H), 1.72 (dt, J=24.4, 6.8 Hz, 3H), 0.94 (s, 9H). LCMS-ESI$^+$ (m/z): [M−H]$^+$ calc'd for C$_{29}$H$_{30}$FN$_2$O$_4$: 489.22; Found: 489.1.

EXAMPLE 54

Mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)acetic acid and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)acetic acid

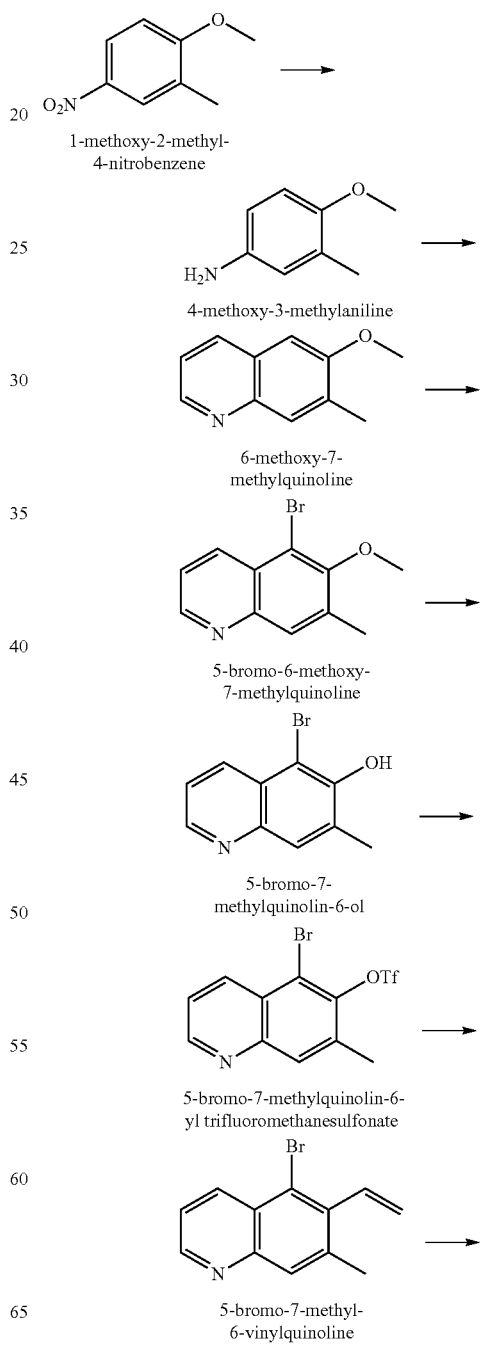

1-methoxy-2-methyl-4-nitrobenzene 4-methoxy-3-methylaniline 6-methoxy-7-methylquinoline 5-bromo-6-methoxy-7-methylquinoline 5-bromo-7-methylquinolin-6-ol 5-bromo-7-methylquinolin-6-yl trifluoromethanesulfonate 5-bromo-7-methyl-6-vinylquinoline

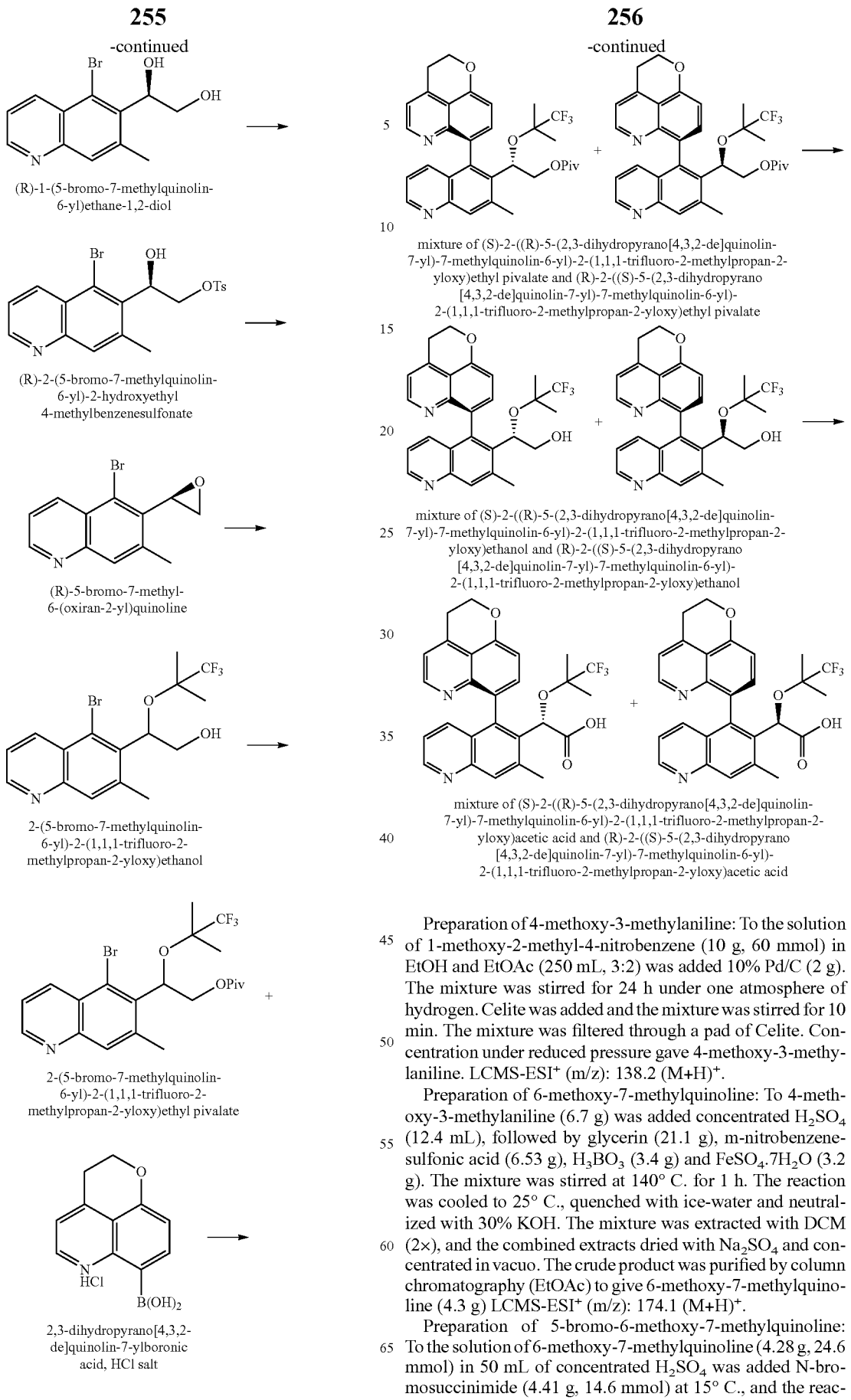

Preparation of 4-methoxy-3-methylaniline: To the solution of 1-methoxy-2-methyl-4-nitrobenzene (10 g, 60 mmol) in EtOH and EtOAc (250 mL, 3:2) was added 10% Pd/C (2 g). The mixture was stirred for 24 h under one atmosphere of hydrogen. Celite was added and the mixture was stirred for 10 min. The mixture was filtered through a pad of Celite. Concentration under reduced pressure gave 4-methoxy-3-methylaniline. LCMS-ESI$^+$ (m/z): 138.2 (M+H)$^+$.

Preparation of 6-methoxy-7-methylquinoline: To 4-methoxy-3-methylaniline (6.7 g) was added concentrated $H_2SO_4$ (12.4 mL), followed by glycerin (21.1 g), m-nitrobenzenesulfonic acid (6.53 g), $H_3BO_3$ (3.4 g) and $FeSO_4 \cdot 7H_2O$ (3.2 g). The mixture was stirred at 140° C. for 1 h. The reaction was cooled to 25° C., quenched with ice-water and neutralized with 30% KOH. The mixture was extracted with DCM (2×), and the combined extracts dried with $Na_2SO_4$ and concentrated in vacuo. The crude product was purified by column chromatography (EtOAc) to give 6-methoxy-7-methylquinoline (4.3 g) LCMS-ESI$^+$ (m/z): 174.1 (M+H)$^+$.

Preparation of 5-bromo-6-methoxy-7-methylquinoline: To the solution of 6-methoxy-7-methylquinoline (4.28 g, 24.6 mmol) in 50 mL of concentrated $H_2SO_4$ was added N-bromosuccinimide (4.41 g, 14.6 mmol) at 15° C., and the reaction was stirred at 15° C. for 3.5 hours. The reaction mixture was poured into ice-water (600 mL). The aqueous mixture was adjusted with a 50% KOH solution to pH ~10, and then extracted with DCM (3×). The combined extract was dried with sodium sulfate. Concentration under reduced pressure gave 5-bromo-6-methoxy-7-methylquinoline. LCMS-ESI$^+$ (m/z): 252.1, 254.1 (M+H)$^+$.

Preparation of 5-bromo-7-methylquinolin-6-ol: To the solution of 5-bromo-6-methoxy-7-methylquinoline (6.5 g, 25.8 mmol) in DCM (150 mL) was added BBr$_3$ slowly (77.3 mL, 1.0 M in DCM, 77.3 mmol). The mixture was stirred for 3 hours and cooled to 0° C. Methanol (40 mL) was added slowly and the mixture was stirred for 20 minutes. The solvents were removed under reduced pressure. The solid was dissolved in methanol (100 mL) and was treated with 1.0 N sodium hydroxide solution (50 mL) (pH ~12). The mixture was stirred for 12 hours and acetic acid was added to adjust pH to between 4-5. The mixture was filtered and washed with water. The gray solid was dried under reduced pressure to give 5-bromo-7-methylquinolin-6-ol. LCMS-ESI$^+$ (m/z): 238.2, 240.1 (M+H)$^+$, 236.1, 238.0 (M−H).

Preparation of 5-bromo-7-methylquinolin-6-yl trifluoromethanesulfonate: To the solution of 5-bromo-7-methylquinolin-6-ol (238 mg, 1.0 mmol) in dichloromethane (10 mL) and pyridine (2 mL) was added Tf$_2$O (0.34 mL, 2.0 mmol) at −30° C. The mixture was stirred and warmed to 0° C. over a period of 2 hours. The reaction was quenched with slow addition of NaHCO$_3$ solution. The mixture was extracted with ethyl acetate. The organic layer was washed with brine, dried over sodium sulfate and concentrated to give 5-bromo-7-methylquinolin-6-yl trifluoromethanesulfonate. LCMS-ESI$^+$ (m/z): 369.9, 371.9 (M+H)$^+$.

Preparation of 5-bromo-7-methyl-6-vinylquinoline: A mixture of 5-bromo-7-methylquinolin-6-yl trifluoromethanesulfonate (230 mg, 0.62 mmol), tributyl(vinyl) stannane (200 µL, 0.68 mmol), lithium chloride (78 mg, 1.86 mmol) and PdCl$_2$(PPh$_3$)$_2$ (43 mg) in DMF (10 mL) was heated at 80° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The residue was purified by flash chromatography (hexanes/EtOAc) to provide 5-bromo-7-methyl-6-vinylquinoline. LCMS-ESI$^+$ (m/z): 248.2, 250.2 (M+H)$^+$.

Preparation of (R)-1-(5-bromo-7-methylquinolin-6-yl) ethane-1,2-diol: A biphasic mixture of AD-mix-β (1.2 g, excess) in tert-butanol (4.5 mL)/H$_2$O (4.5 mL) was cooled to 0° C. and 5-bromo-7-methyl-6-vinylquinoline (210 mg, 0.85 mmol) was added. The reaction mixture was stirred for 2 days at 0° C. The mixture was diluted with ethyl acetate, washed with water and brine, dried over Na$_2$SO$_4$, filtered and concentrated and purified by flash column chromatography (silica gel, 0 to 100% ethyl acetate/hexanes) to give (R)-1-(5-bromo-7-methylquinolin-6-yl)ethane-1,2-diol. $^1$H-NMR: 400 MHz, (CD$_3$OD) δ 8.82 (d, J=4.4 Hz, 1H), 8.76 (d, J=8.8 Hz, 1H), 7.84 (s, 1H), 7.61-7.57 (m, 1H), 5.84 (dd, J=8.8, 4.8 Hz, 1H), 4.00 (dd, J=11.2, 8.8 Hz, 1H), 3.80 (dd, J=11.2, 4.4 Hz, 1H), 2.81 (s, 3 H).

Preparation of (R)-2-(5-bromo-7-methylquinolin-6-yl)-2-hydroxyethyl 4-methylbenzenesulfonate: To a stirred solution of (R)-1-(5-bromo-7-methylquinolin-6-yl)ethane-1,2-diol (197 mg, 0.70 mmol) in CH$_2$Cl$_2$ (97 mL), dibutyltinoxide (3.3 mg, 0.01 mmol), TsCl (150 mg, 0.79 mmol), and Et$_3$N (0.12 mL, 0.83 mmol) were added at 0° C. The reaction mixture was allowed to warm to room temperature overnight. The reaction mixture was quenched with saturated aqueous NH$_4$Cl, and then diluted with CH$_2$Cl$_2$. The organic phase was washed with brine, dried over Na$_2$SO$_4$, filtered and concentrated and purified by flash column chromatography (silica gel, 5 to 100% ethyl acetate/hexanes) to give (R)-2-(5-bromo-7-methylquinolin-6-yl)-2-hydroxyethyl 4-methylbenzenesulfonate. LCMS-ESI$^+$ (m/z): [M+H]$^+$ calc'd for C$_{19}$H$_{19}$BrNO$_4$S: 436.02; Found: 436.1.

Preparation of (R)-5-bromo-7-methyl-6-(oxiran-2-yl) quinoline: To a solution of (R)-2-(5-bromo-7-methylquinolin-6-yl)-2-hydroxyethyl 4-methylbenzenesulfonate (299 mg, 0.69 mmol) in THF (7.5 mL) at 0° C. was added potassium tert-butoxide (0.76 mL of 1.0 M solution in THF, 0.76 mmol). After stirring for 1 h, the reaction mixture was quenched with saturated aqueous NH$_4$Cl, and then diluted with EtOAc. The organic phase was washed with water and brine, dried over Na$_2$SO$_4$, filtered and concentrated and purified by flash column chromatography (silica gel, 0 to 100% ethyl acetate/hexanes) to give (R)-5-bromo-7-methyl-6-(oxiran-2-yl)quinoline. LCMS-ESI$^+$ (m/z): [M+H]$^+$ calc'd for C$_{12}$H$_{11}$BrNO: 264.00; Found: 264.1.

Preparation of 2-(5-bromo-7-methylquinolin-6-yl)-2-(1,1,1-trifluoro-2-methylpropan-2-yloxy)ethanol: To a stirred solution of (R)-5-bromo-7-methyl-6-(oxiran-2-yl)quinoline (52 mg, 0.20 mmol) and 2-trifluoromethyl-2-propanol (0.54 mL, 4.96 mmol) in CH$_2$Cl$_2$ (0.54 mL), boron trifluoride diethyl etherate (0.24 mL, 1.99 mmol) was added at 0° C. The reaction mixture was stirred for 16 h at 0° C. and allowed to warm to room temperature overnight. The mixture was quenched with saturated aqueous NaHCO$_3$, and then diluted with CH$_2$Cl$_2$. The organic phase was washed with brine, dried over Na$_2$SO$_4$, filtered and concentrated and purified by flash column chromatography (silica gel, 0 to 20% ethyl acetate/hexanes) to give 2-(1-chloro-3-methylnaphthalen-2-yl)-2-(1,1,1-trifluoro-2-methylpropan-2-yloxy)ethanol. LCMS-ESI$^+$ (m/z): [M+H]$^+$ calc'd for C$_{16}$H$_{18}$BrF$_3$NO$_2$: 392.05; Found: 392.1.

Preparation of 2-(5-bromo-7-methylquinolin-6-yl)-2-(1,1,1-trifluoro-2-methylpropan-2-yloxy)ethyl pivalate: To a stirred solution of trimethylacetyl chloride (19 µL, 0.15 mmol) in pyridine (0.4 mL, 4.95 mmol) was added 2-(5-bromo-7-methylquinolin-6-yl)-2-(1,1,1-trifluoro-2-methylpropan-2-yloxy)ethanol (29.8 mg, 0.08 mmol) in CH$_2$Cl$_2$ (0.4 mL) at 0° C. The reaction mixture was allowed to warm to room temperature overnight. The mixture was quenched with water and concentrated and purified by flash column chromatography (silica gel, 0 to 20% ethyl acetate/hexanes) to give 2-(5-bromo-7-methylquinolin-6-yl)-2-(1,1,1-trifluoro-2-methylpropan-2-yloxy)ethyl pivalate. LCMS-ESI$^+$ (m/z): [M+H]$^+$ calc'd for C$_{21}$H$_{26}$BrF$_3$NO$_3$: 476.11; Found: 476.2.

Preparation of a mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)ethyl pivalate and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)ethyl pivalate: 2-(5-bromo-7-methylquinolin-6-yl)-2-

(1,1,1-trifluoro-2-methylpropan-2-yloxy)ethyl pivalate (18.7 mg, 0.04 mmol) in freshly distilled DME (1.4 mL) was added to a microwave vial charged with 2,3-dihydropyrano[4,3,2-de]quinolin-7-ylboronic acid, HCl salt (29.6 mg, 0.12 mmol), Sphos precatalyst (Strem, 2.6 mg, 0.004 mmol), and CsF (29.9 mg, 020 mmol). This heterogeneous mixture was then microwaved at 120° C. for 90 minutes. The mixture was then diluted with EtOAc, extracted with saturated NaHCO$_3$, brine, and dried over Na$_2$SO$_4$, filtered and concentrated and purified by flash column chromatography (silica gel, 0 to 100% ethyl acetate/hexanes) to give a mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)ethyl pivalate and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)ethyl pivalate. LCMS-ESI$^+$ (m/z): [M+H]$^+$ calc'd for C$_{32}$H$_{34}$F$_3$N$_2$O$_4$: 567.25; Found: 567.3.

Preparation of a mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)ethanol and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)ethanol: The mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)ethanol and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)ethanol was prepared following the procedure used to prepare (S)-2-tert-butoxy-2-((R)-5-(2,3-dihydropyrano[4,3,2-de]quinolin-7-yl)-7-methyl-2-(methylamino)quinolin-6-yl)ethanol of Example 46, except that the mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)ethyl pivalate and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)ethyl pivalate was used instead of (S)-2-tert-butoxy-2-((R)-5-(2,3-dihydropyrano[4,3,2-de]quinolin-7-yl)-7-methyl-2-(methylamino)quinolin-6-yl)ethyl pivalate. LCMS-ESI$^+$ (m/z): [M+H]$^+$ calc'd for C$_{27}$H$_{26}$F$_3$N$_2$O$_3$: 483.19; Found: 483.2.

Preparation of a mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)acetic acid and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)acetic acid: The mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)acetic acid and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)acetic acid was prepared following the procedure used to prepare (S)-2-tert-butoxy-2-((R)-5-(2,3-dihydropyrano[4,3,2-de]quinolin-7-yl)-7-methyl-2-(methylamino)quinolin-6-yl)acetic acid of Example 46, except that the mixture of (S)-2-((R)-5-(2,3-dihydropyrano[4,3,2-de]quinolin-7-yl)-7-methylquinolin-6-yl)-2-(1,1,1-trifluoro-2-methylpropan-2-yloxy)ethanol and (R)-2-((S)-5-(2,3-dihydropyrano[4,3,2-de]quinolin-7-yl)-7-methylquinolin-6-yl)-2-(1,1,1-trifluoro-2-methylpropan-2-yloxy)ethanol was used instead of (S)-2-tert-butoxy-2-((R)-5-(2,3-dihydropyrano[4,3,2-de]quinolin-7-yl)-7-methyl-2-(methylamino)quinolin-6-yl)ethanol. $^1$H-NMR: 400 MHz, (CD$_3$OD) δ 9.01 (d, J=4.4 Hz, 1H), 8.65 (d, J=5.2 Hz, 1H), 8.20 (s, 1H), 7.90 (d, J=8.4 Hz, 1H), 7.80 (d, J=8.0 Hz, 1H), 7.70 (d, J=5.2 Hz, 1H), 7.58 (dd, J=8.8, 4.8 Hz, 1H), 7.41 (d, J=8.0 Hz, 1H), 5.47 (s, 1H), 4.76-4.65 (m, 2H), 3.60 (t, J=6.0 Hz, 2H), 2.87 (s, 3H), 1.21 (s, 3H), 1.08 (s, 3H). LCMS-ESI$^+$ (m/z): [M+H]$^+$ calc'd for C$_{27}$H$_{24}$F$_3$N$_2$O$_4$: 497.17; Found: 497.2.

EXAMPLE 55

(S)-2-tert-butoxy-2-((R)-6-(2,3-dihydropyrano[4,3,2-de]quinolin-7-yl)-8-methyl-[1,2,3]triazolo[1,5-a]quinolin-7-yl)acetic acid

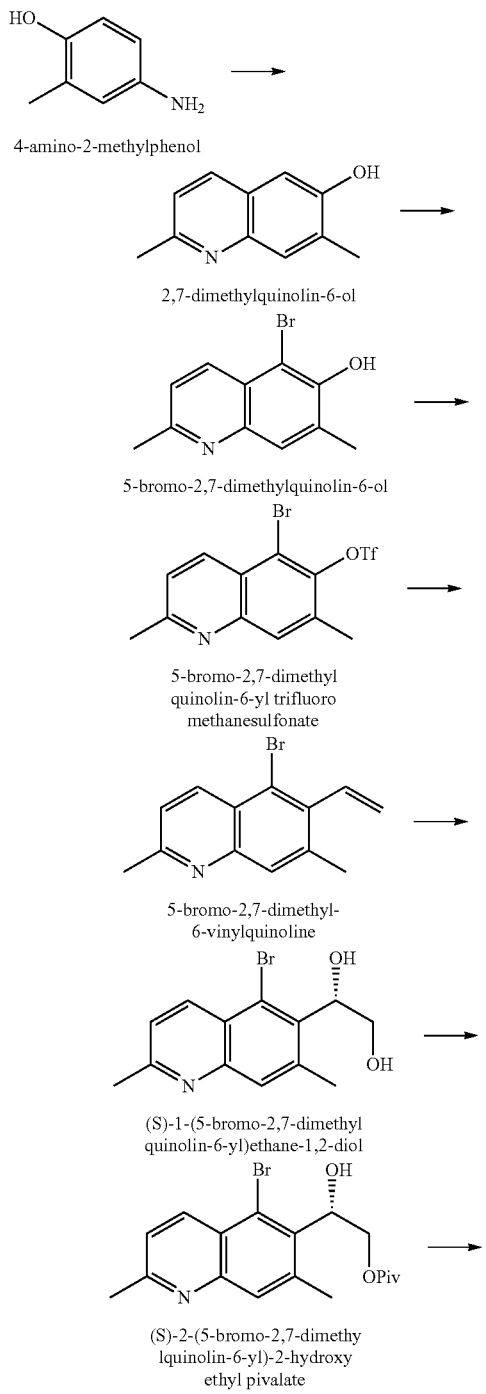

4-amino-2-methylphenol 2,7-dimethylquinolin-6-ol 5-bromo-2,7-dimethylquinolin-6-ol 5-bromo-2,7-dimethyl quinolin-6-yl trifluoro methanesulfonate 5-bromo-2,7-dimethyl-6-vinylquinoline (S)-1-(5-bromo-2,7-dimethyl quinolin-6-yl)ethane-1,2-diol (S)-2-(5-bromo-2,7-dimethyl lquinolin-6-yl)-2-hydroxy ethyl pivalate -continued

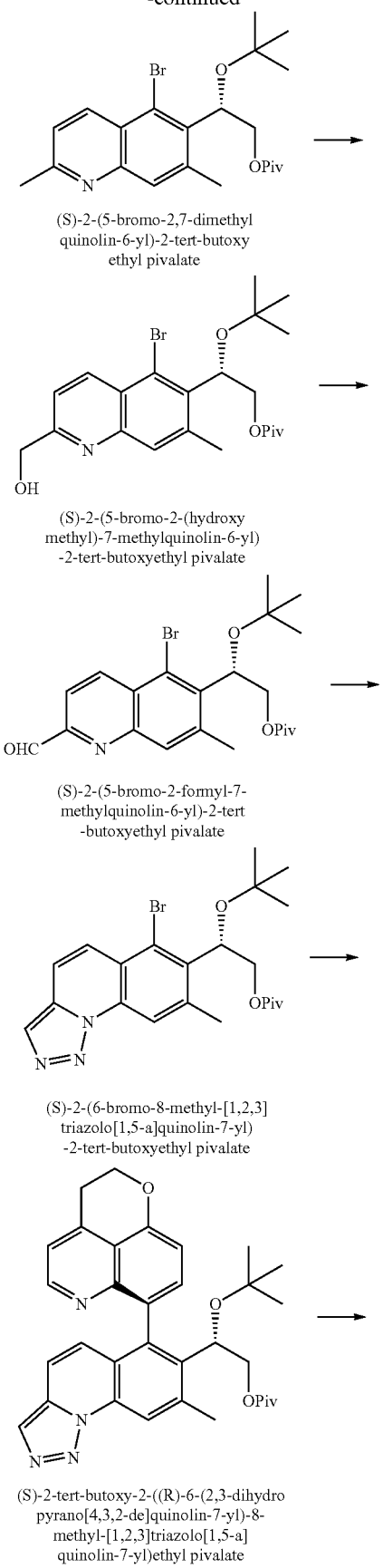

(S)-2-(5-bromo-2,7-dimethyl quinolin-6-yl)-2-tert-butoxy ethyl pivalate (S)-2-(5-bromo-2-(hydroxy methyl)-7-methylquinolin-6-yl)-2-tert-butoxyethyl pivalate (S)-2-(5-bromo-2-formyl-7-methylquinolin-6-yl)-2-tert-butoxyethyl pivalate (S)-2-(6-bromo-8-methyl-[1,2,3]triazolo[1,5-a]quinolin-7-yl)-2-tert-butoxyethyl pivalate (S)-2-tert-butoxy-2-((R)-6-(2,3-dihydro pyrano[4,3,2-de]quinolin-7-yl)-8-methyl-[1,2,3]triazolo[1,5-a]quinolin-7-yl)ethyl pivalate -continued

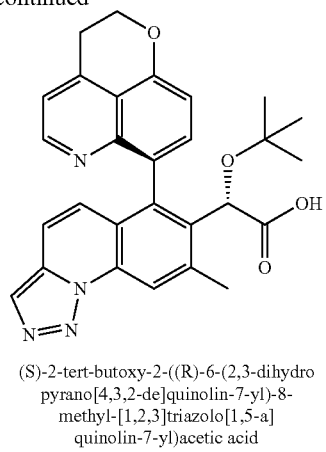

(S)-2-tert-butoxy-2-((R)-6-(2,3-dihydro pyrano[4,3,2-de]quinolin-7-yl)-8-methyl-[1,2,3]triazolo[1,5-a]quinolin-7-yl)acetic acid Preparation of 2,7-dimethylquinolin-6-ol: To 4-amino-2-methylphenol (Aldrich, 5.0 g, 40.6 mmol) was added 6M HCl (100 mL) and heated to 100° C. with stirring. Toluene (30 mL) was added, followed with the slow addition of crotonaldehyde (6.7 mL, 81.2 mmol) at 100° C. The mixture was stirred at 100° C. for 2 additional hours, cooled to room temperature. The water layer was separated, neutralized by NaHCO$_3$ solution. The solid formed was filtered and collected. LCMS-ESI$^+$ (m/z): [M+H]$^+$ calc'd for $C_{11}H_{12}NO$: 174.2; Found: 174.2.

Preparation of 5-bromo-2,7-dimethylquinolin-6-ol: To a stirred solution of 2,7-dimethylquinolin-6-ol (200 mg, 1.2 mmol) in acetic acid (10 mL) was added Br$_2$ (0.062 mL, 1.21 mmol) at ambient temperature. The mixture was stirred at ambient temperature for 0.5 hour. The solid formed was filtered and collected, washed with 2 mL of acetic acid to give 5-bromo-2,7-dimethylquinolin-6-ol as an HBr salt. LCMS-ESI$^+$ (m/z): [M+H]$^+$ calc'd for $C_{11}H_{11}BrNO$: 251.99; Found: 252.2, 254.2.

Preparation of 5-bromo-2,7-dimethylquinolin-6-yl trifluoromethanesulfonate: To a stirred solution of 5-bromo-2,7-dimethylquinolin-6-ol·HBr (1.04 g, 3.1 mmol) in dichloromethane (50 mL) and pyridine (10 mL) was added Tf$_2$O (1.1 mL, 6.2 mmol) at 0° C. The mixture was stirred at room temperature for 2 hours, quenched with slow addition of NaHCO$_3$ solution at 0° C. The mixture was extracted with dichloromethane. The organic layer was washed with brine and dried with Na$_2$SO$_4$. Concentration gave 5-bromo-2,7-dimethylquinolin-6-yl trifluoromethanesulfonate as a brown solid.

Preparation of 5-bromo-2,7-dimethyl-6-vinylquinoline: PdCl$_2$(PPh$_3$)$_2$ (207 mg, 0.30 mmol) was added to a solution of 5-bromo-2,7-dimethylquinolin-6-yl trifluoromethanesulfonate (1.13 g, 2.95 mmol), tributyl-vinyl-stannane (0.95 mL, 3.25 mmol), and lithium chloride (375 mg, 8.85 mmol) in DMF (30 mL). The reaction mixture was flushed with nitrogen, and heated at 80° C. for 4 hours. The mixture was diluted with ethyl acetate, washed with NaHCO$_3$ solution, water and brine, and dried over Na$_2$SO$_4$. Concentration and purification by flash column chromatography yielded 5-bromo-2,7-dimethyl-6-vinylquinoline. LCMS-ESI$^+$ (m/z): [M+H]$^+$ calc'd for $C_{13}H_{13}BrN$: 262.0; Found: 262.1.

Preparation of (S)-1-(5-bromo-2,7-dimethylquinolin-6-yl)ethane-1,2-diol: AD-mix-α (8 g, excess) was added to a mixed solvent of t-butanol and water (35 mL/35 mL) and stirred at room temperature for 5 min, cooled to 0° C. 5-bromo-2,7-dimethyl-6-vinylquinoline (678 mg, 2.6 mmol)

was added and the mixture was stirred at 0° C. for 16 hrs. The mixture was diluted with ethyl acetate, washed with NaHCO$_3$ solution, water and brine, and dried over Na$_2$SO$_4$. Concentration and purification by flash column chromatography yielded (S)-1-(5-bromo-2,7-dimethylquinolin-6-yl)ethane-1,2-diol. LCMS-ESI$^+$ (m/z): [M+H]$^+$ calc'd for C$_{13}$H$_{15}$BrNO$_2$: 296.0; Found: 296.1.

Preparation of (S)-2-(5-bromo-2,7-dimethylquinolin-6-yl)-2-hydroxyethyl pivalate: To a stirred solution of (S)-1-(5-bromo-2,7-dimethylquinolin-6-yl)ethane-1,2-diol (290 mg, 0.98 mmol) in dichloromethane (12 mL) and pyridine (2 mL) was added trimethyl acetylchloride (0.24 mL, 1.97 mmol) at 0° C. The mixture was stirred at room temperature for 2 hours, and quenched with slow addition of NaHCO$_3$ solution. The mixture was extracted with ethyl acetate. The organic layer was washed with brine, dried and concentrated in vacuo. The obtained residue was purified by flash chromatography to provide (S)-2-(5-bromo-2,7-dimethylquinolin-6-yl)-2-hydroxyethyl pivalate. LCMS-ESI$^+$ (m/z): [M+H]$^+$ calc'd for C$_{18}$H$_{23}$BrNO$_3$: 380.1; Found: 380.2.

Preparation of (S)-2-(5-bromo-2,7-dimethylquinolin-6-yl)-2-tert-butoxyethyl pivalate: To a stirred solution of (S)-2-(5-bromo-2,7-dimethylquinolin-6-yl)-2-hydroxyethyl pivalate (330 mg, 0.87 mmol) in t-butylacetate (10 mL) was added perchloric acid (0.3 mL, 3.5 mmol) at 0° C. The mixture was stirred at room temperature for 2 hours, quenched with slow addition of NaHCO$_3$ solution. The mixture was extracted with ethyl acetate. The organic layer was washed with brine, dried and concentrated in vacuo. The obtained residue was purified by flash chromatography to provide (S)-2-(5-bromo-2,7-dimethylquinolin-6-yl)-2-tert-butoxyethyl pivalate. LCMS-ESI$^+$ (m/z): [M+H]$^+$ calc'd for C$_{22}$H$_{31}$BrNO$_3$: 436.1; Found: 436.2.

Preparation of (S)-2-(5-bromo-2-(hydroxymethyl)-7-methylquinolin-6-yl)-2-tert-butoxyethyl pivalate: To a solution of (S)-2-(5-bromo-2,7-dimethylquinolin-6-yl)-2-tert-butoxyethyl pivalate (2.0 g, 4.6 mmol) in dichloromethane (30 ml) was added 3-chloroperoxybenzoic acid (1.4 g, 5.7 mmol). The mixture was stirred for 12 hours and diluted with ethyl acetate. The organic phase was washed with saturated sodium carbonate, water and brine, and was dried over sodium sulfate. Filtration and concentration gave N-oxide intermediate. LCMS-ESI$^+$ (m/z): [M+H]$^+$ calc'd for C$_{22}$H$_{31}$BrNO$_4$: 452.1; Found: 452.2.

The above intermediate (2.3 g) was dissolved in acetic anhydride (20 ml) and was heated at 80° C. for 12 hours. The excess acetic anhydride was removed under reduced pressure. The residue was diluted with ethyl acetate, washed with saturated sodium carbonate solution, water and brine and dried over sodium sulfate. Concentration gave the intermediate acetate. LCMS-ESI$^+$ (m/z): [M+H]$^+$ calc'd for C$_{24}$H$_{33}$BrNO$_5$: 494.1; Found: 494.2.

To the solution of above intermediate (2.0 g) in methanol (20 ml) was added potassium carbonate solution (5 ml, 2 N, 10 mmol). The mixture was stirred for 2 hours, and excess methanol was removed under reduced pressure. The residue was diluted with water, and extracted with ethyl acetate. The organic phase was washed with water and brine, and dried over sodium sulfate. Concentration and purification by flash column chromatography (hexanes/EtOAc) gave (S)-2-(5-bromo-2-(hydroxymethyl)-7-methylquinolin-6-yl)-2-tert-butoxyethyl pivalate. ESI$^+$ (m/z): [M+H]$^+$ calc'd for C$_{22}$H$_{31}$BrNO$_4$: 452.1; Found: 452.2.

Preparation of (S)-2-(5-bromo-2-formyl-7-methylquinolin-6-yl)-2-tert-butoxyethyl pivalate: To a solution of (S)-2-(5-bromo-2-(hydroxymethyl)-7-methylquinolin-6-yl)-2-tert-butoxyethyl pivalate (180 mg, 0.4 mmol) in DCM/DMSO (0.5 ml/0.5 ml) at 0° C. was added triethylamine (192 μl), followed by SO$_3$-pyridine (222 mg). The mixture was stirred for 1 hour, and was quenched with ice-water. The water phase was extracted with ethyl acetate. The organic phase was washed with saturated sodium bicarbonate solution, water and brine, and was dried over sodium sulfate. Concentration gave (S)-2-(5-bromo-2-formyl-7-methylquinolin-6-yl)-2-tert-butoxyethyl pivalate. ESI$^+$ (m/z): [M+H]$^+$ calc'd for C$_{22}$H$_{29}$BrNO$_4$: 450.1; Found: 450.2.

Preparation of (S)-2-(6-bromo-8-methyl-[1,2,3]triazolo[1,5-a]quinolin-7-yl)-2-tert-butoxyethyl pivalate: To a solution of (S)-2-(5-bromo-2-formyl-7-methylquinolin-6-yl)-2-tert-butoxyethyl pivalate (161 mg, 0.4 mmol) in methanol (1 ml) was added hydrazine (24 μl, 0.5 mmol). The mixture was stirred for 2 hours. Concentration gave a solid. ESI$^+$ (m/z): [M+H]$^+$ calc'd for C$_{22}$H$_{31}$BrN$_3$O$_3$: 464.1; Found: 464.3.

To the solution of above solid in chloroform (1 ml) was added manganese oxide (70 mg). The mixture was stirred for 12 hours, and then refluxed for additional hours. Celite was added and the mixture was stirred for 5 minutes. The mixture was filtered and washed with ethyl acetate. Concentration gave (S)-2-(6-bromo-8-methyl-[1,2,3]triazolo[1,5-a]quinolin-7-yl)-2-tert-butoxyethyl pivalate. ESI$^+$ (m/z): [M+H]$^+$ calc'd for C$_{22}$H$_{29}$BrN$_3$O$_3$: 462.1; Found: 462.3.

Preparation of (S)-2-tert-butoxy-2-((R)-6-(2,3-dihydropyrano[4,3,2-de]quinolin-7-yl)-8-methyl-[1,2,3]triazolo[1,5-a]quinolin-7-yl)ethyl pivalate: Pd(PPh$_3$)$_4$ (46 mg, 0.04 mmol) was added to a mixture of (S)-2-(6-bromo-8-methyl-[1,2,3]triazolo[1,5-a]quinolin-7-yl)-2-tert-butoxyethyl pivalate (152 mg, 0.4 mmol), 2,3-dihydro-1-oxa-6-aza-phenalen-7-boronic acid (200 mg, 0.8 mmol), and aqueous K$_2$CO$_3$ (0.9 mL, 2M, 1.8 mmol) in 1,2-dimethoxyethane (8 mL). The reaction mixture was flushed with nitrogen, and heated at 90° C. for 12 hours. The solvent was removed in vacuo. The residue was dissolved in ethyl acetate, washed with NaHCO$_3$ solution, water and brine, dried over Na$_2$SO$_4$. Concentration and purification by flash column chromatography (hexanes/EtOAc) gave (S)-2-tert-butoxy-2-((R)-6-(2,3-dihydropyrano[4,3,2-de]quinolin-7-yl)-8-methyl-[1,2,3]triazolo[1,5-a]quinolin-7-yl)ethyl pivalate. ESI$^+$ (m/z): [M+H]$^+$ calc'd for C$_{33}$H$_{37}$N$_4$O$_4$: 553.3; Found: 553.1.

Preparation of (S)-2-tert-butoxy-2-((R)-6-(2,3-dihydropyrano[4,3,2-de]quinolin-7-yl)-8-methyl-[1,2,3]triazolo[1,5-a]quinolin-7-yl)acetic acid: To the solution of (S)-2-tert-butoxy-2-((R)-6-(2,3-dihydropyrano[4,3,2-de]quinolin-7-yl)-8-methyl-[1,2,3]triazolo[1,5-a]quinolin-7-yl)ethyl pivalate (161 mg) in THF/MeOH (1 ml/1 ml) was added sodium hydroxide solution (1 ml, 1 N, 1 mmol). The mixture was heated at 50° C. for 12 hours. The mixture was diluted with water, and extracted with ethyl acetate. The organic phase was washed with water and brine, and dried over sodium sulfate. Concentration and purification by flash column chromatography (hexanes/EtOAc) gave the intermediate alcohol. ESI$^+$ (m/z): [M+H]$^+$ calc'd for C$_{28}$H$_{29}$N$_4$O$_3$: 469.2; Found: 469.0.

A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. This stock solution (0.70 mL) was added to a solution of above intermediate alcohol (16 mg) in wet acetonitrile (1.0 mL, 0.75% H$_2$O) at 0° C. The reaction mixture was stirred for 30 minutes at 0° C. Filtration and purification by reverse phase HPLC gave (S)-2-tert-butoxy-2-((R)-6-(2,3-dihydropyrano[4,3,2-de]quinolin-7-yl)-8-methyl-[1,2,3]triazolo[1,5-a]quinolin-7-yl)acetic acid as a TFA salt. $^1$H-NMR 400 MHz, (CD$_3$OD) δ 8.87 (s, 1 H), 8.72 (d, J=5.5 Hz, 1 H), 8.19 (s, 1 H), 7.83 (d, J=9.4 Hz, 1 H), 7.75 (d, J=4.7 Hz, 1 H), 7.50

(d, J=9.4 Hz, 1 H), 7.42 (d, J=8.3 Hz, 1 H), 6.82 (d, J=9.4 Hz, 1 H), 5.25 (s, 1 H), 4.70 (m, 2 H), 3.63 (t, J=5.1 Hz, 2 H), 2.90 (s, 3 H), 0.94 (s, 9 H); ESI$^+$ (m/z): [M+H]$^+$ calc'd for $C_{28}H_{27}N_4O_4$: 483.2; Found: 483.3.

EXAMPLE 56

The following illustrate representative pharmaceutical dosage forms, containing a compound described herein ('Compound X'), for therapeutic or prophylactic use in humans.

| | mg/tablet |
|---|---|
| (i) Tablet 1 | |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| | mg/capsule |
|---|---|
| (iii) Capsule | |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| | mg/ml |
|---|---|
| (iv) Injection 1 (1 mg/mL) | |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/ml) | |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| | mg/can |
|---|---|
| (vi) Aerosol | |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:
1. A compound or a pharmaceutically acceptable salt thereof, selected from the group consisting of:
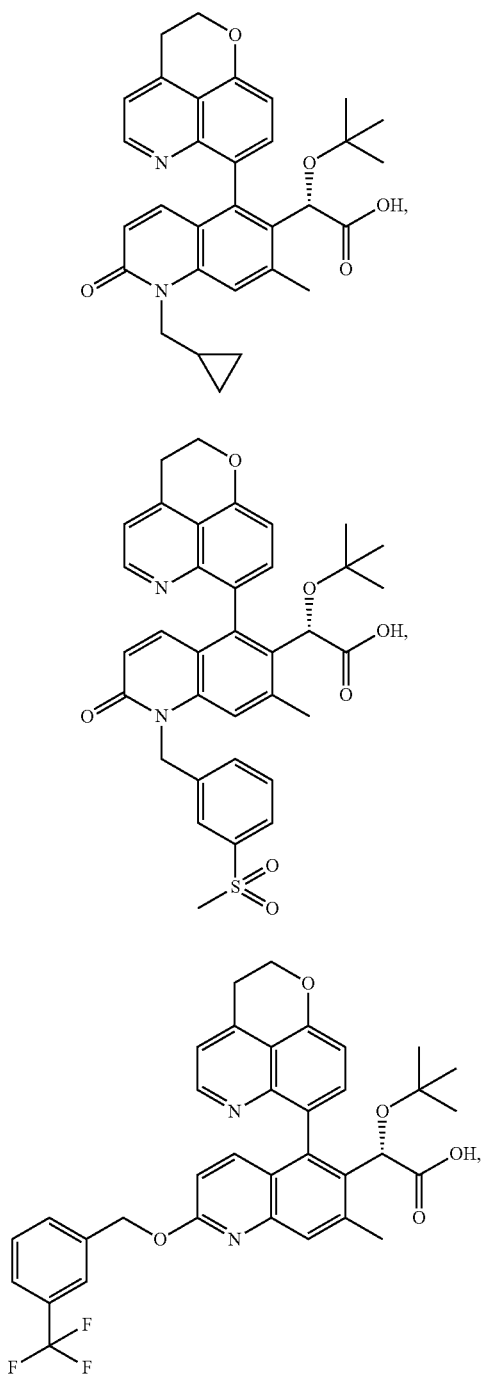
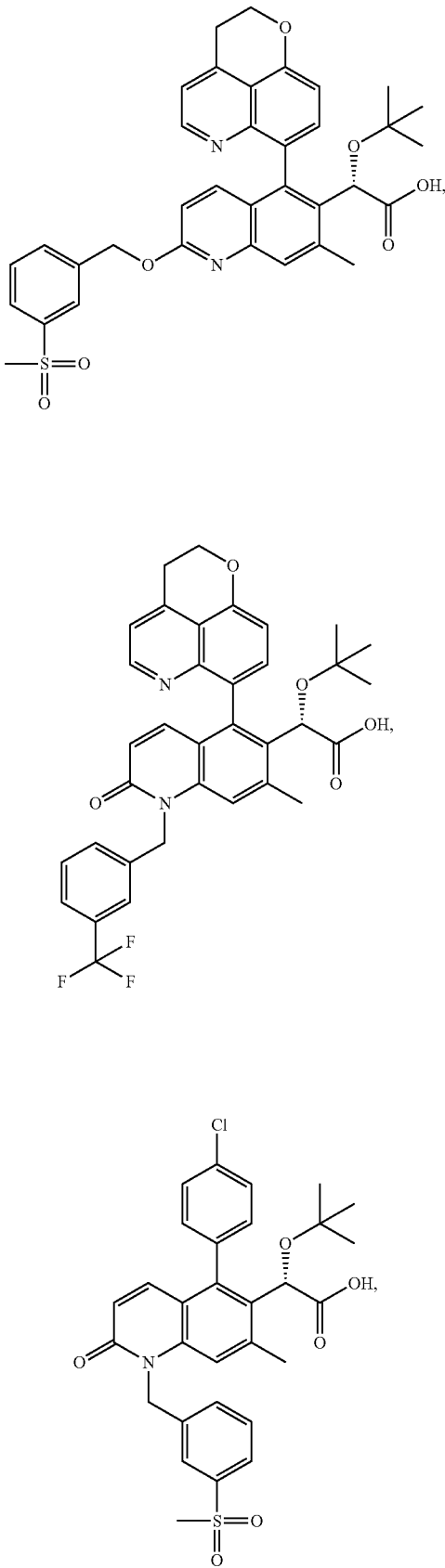

269
-continued
270
-continued
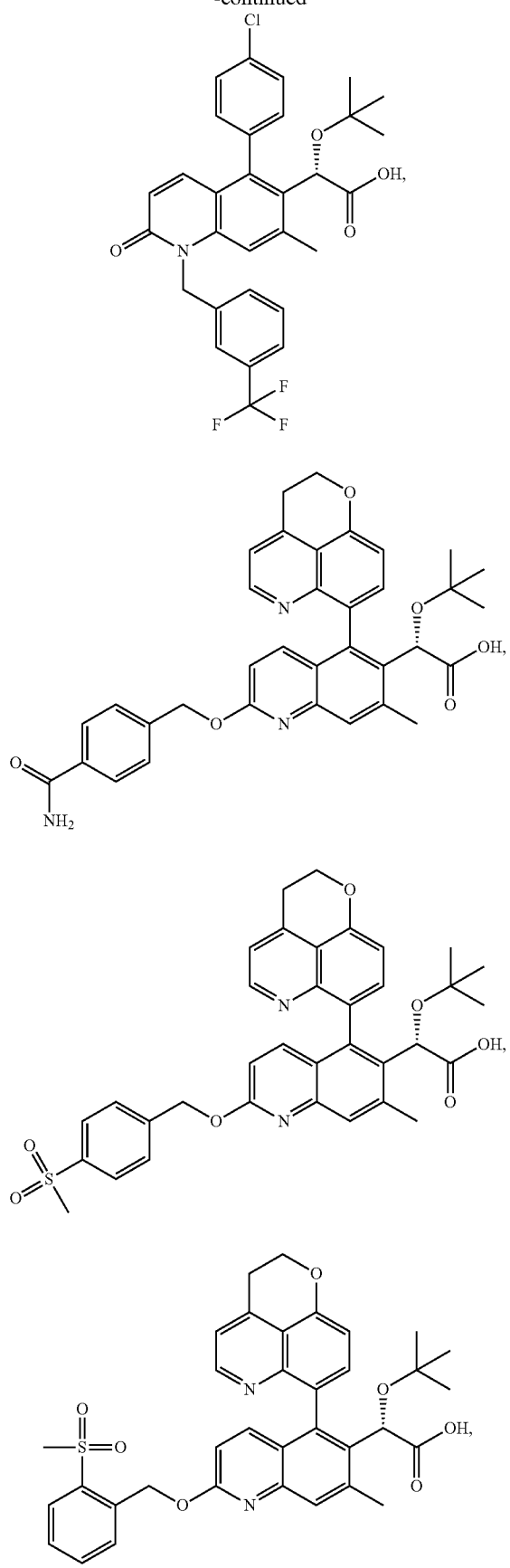
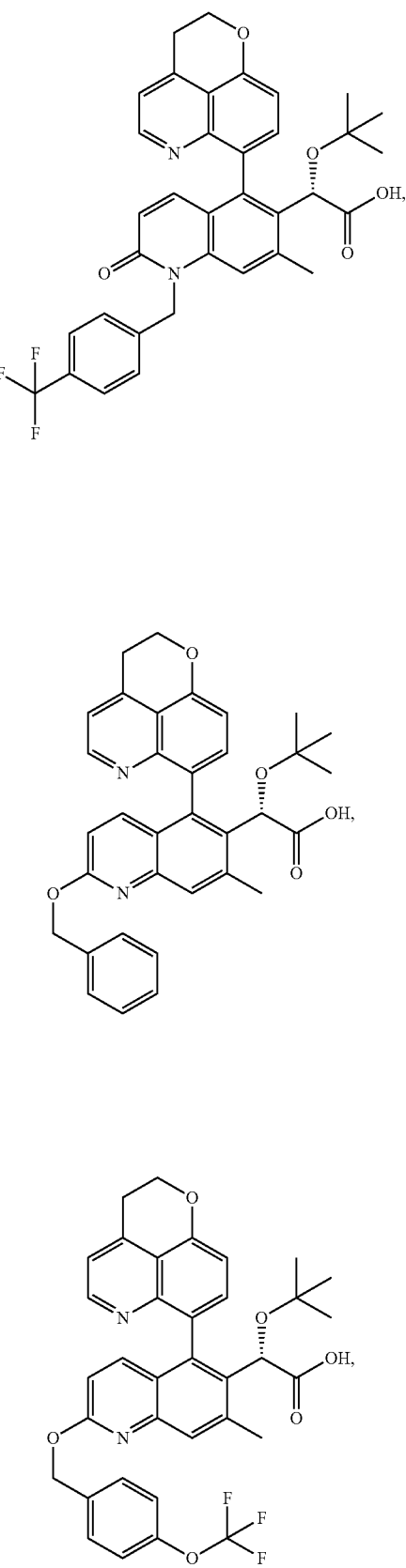

271
-continued
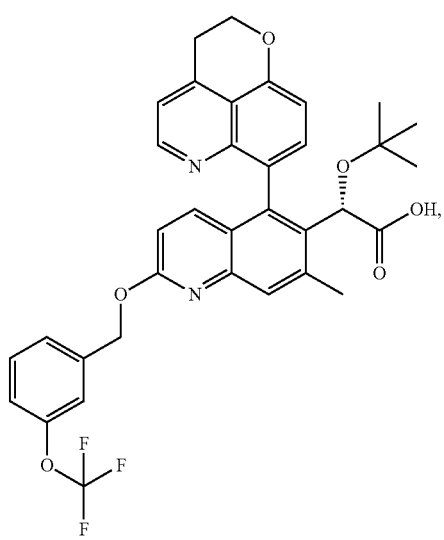
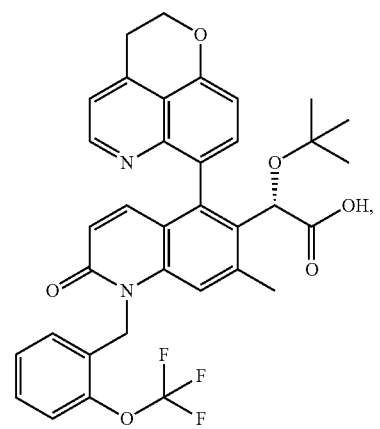
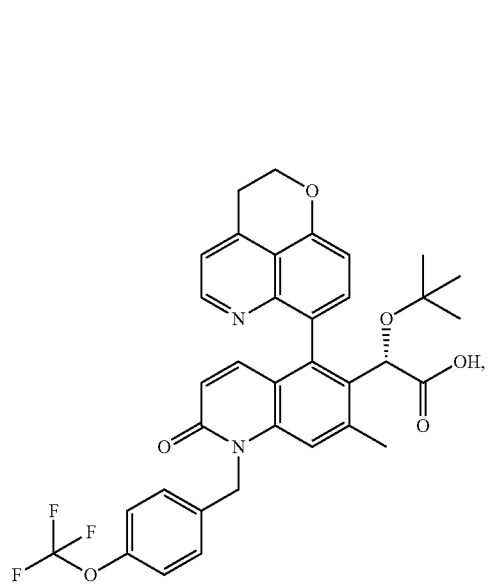
272
-continued
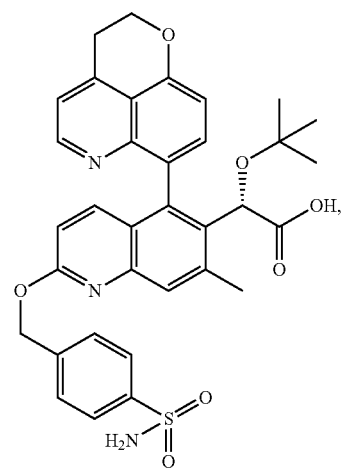
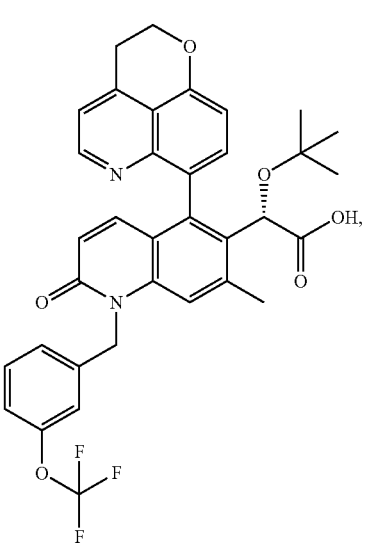
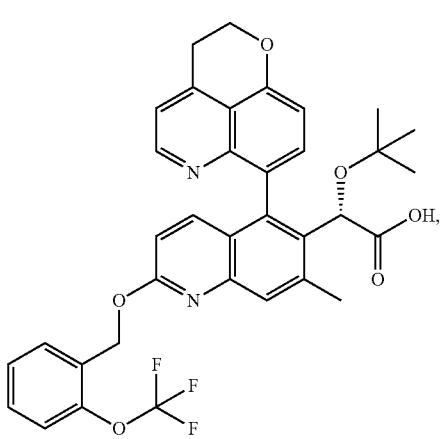

273
-continued
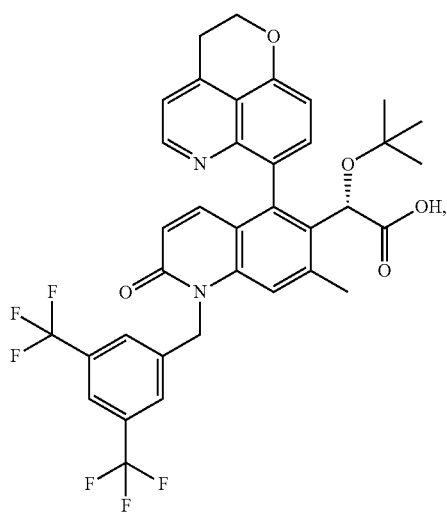
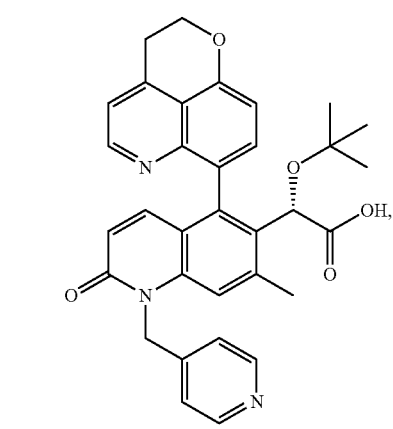
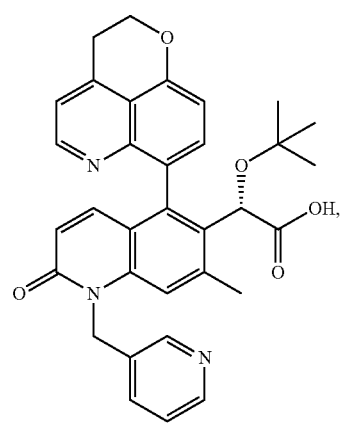
274
-continued
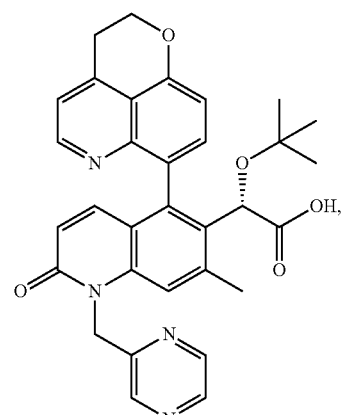
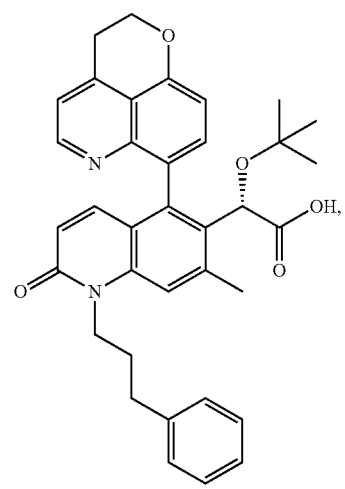
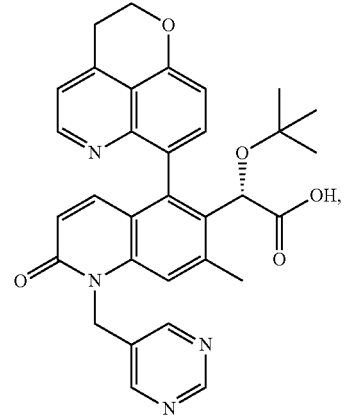

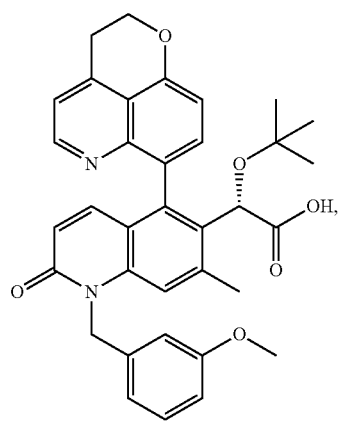
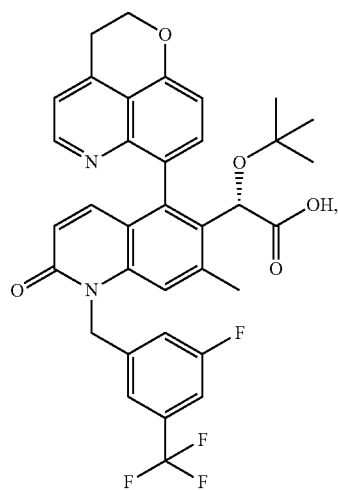
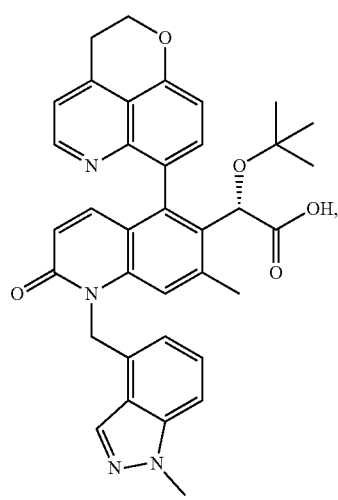
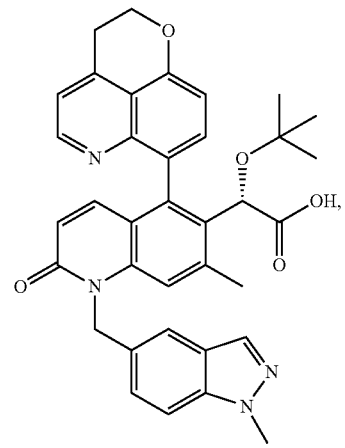
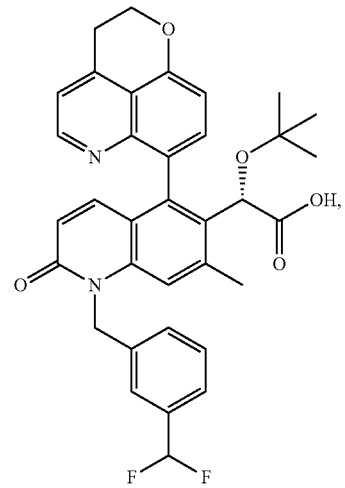
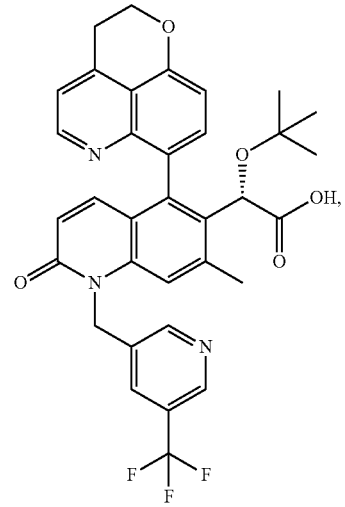

277
-continued
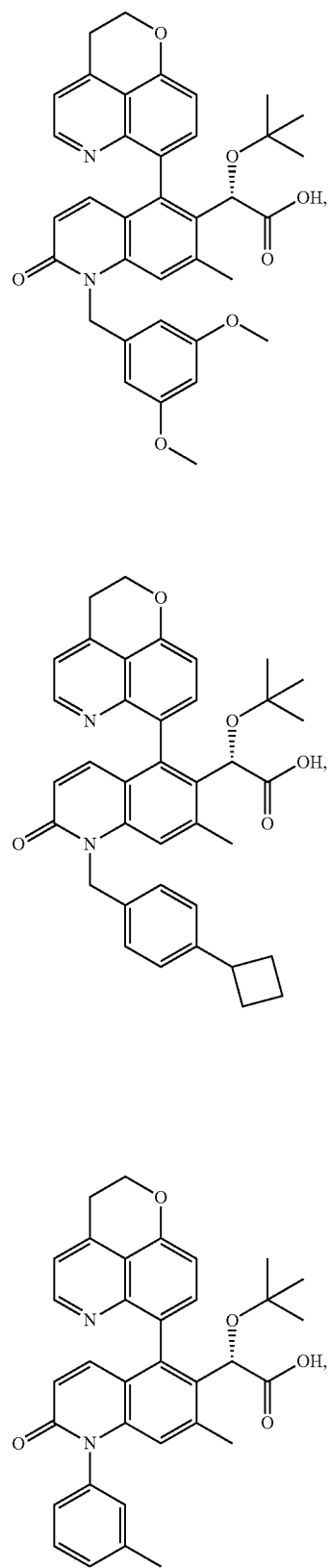
278
-continued
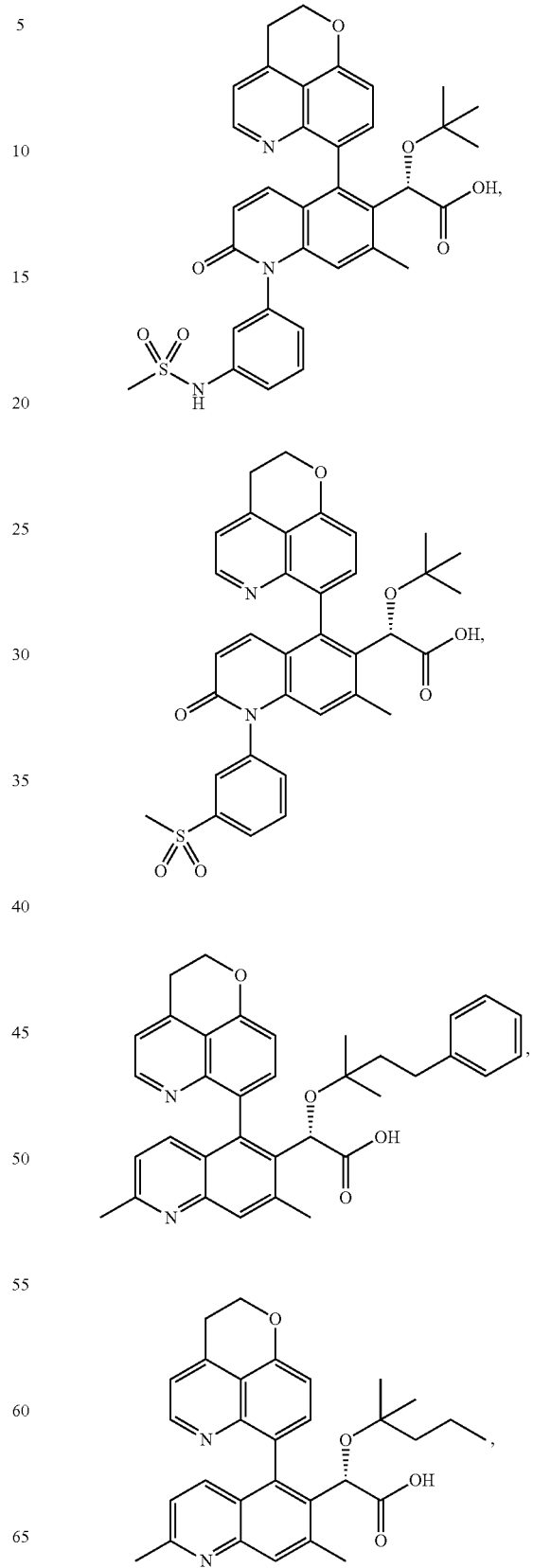

279
-continued
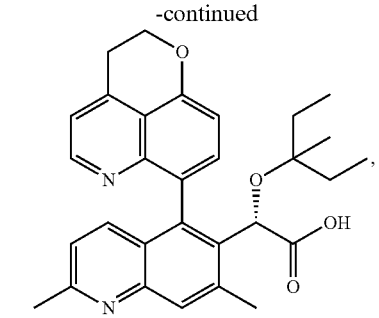
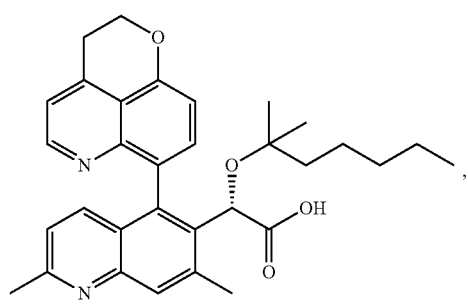
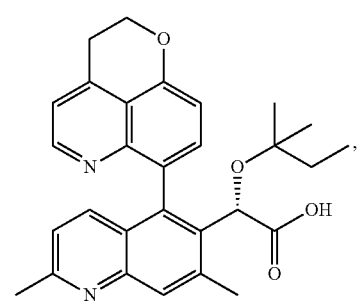
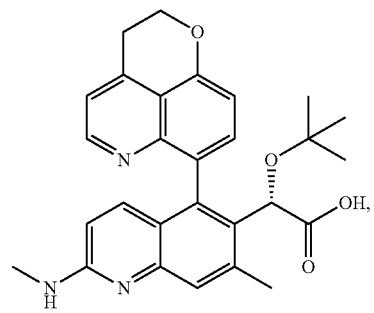
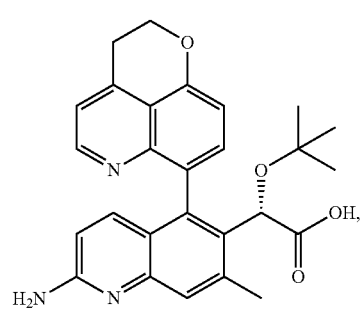
280
-continued
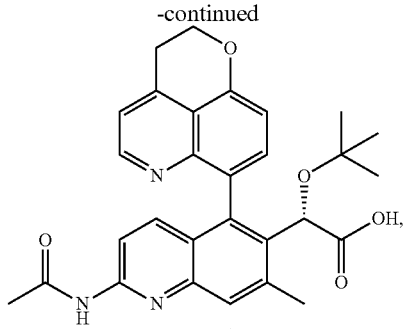
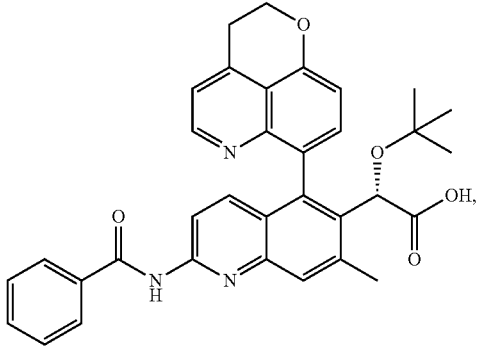
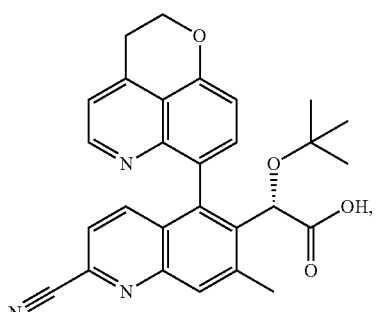
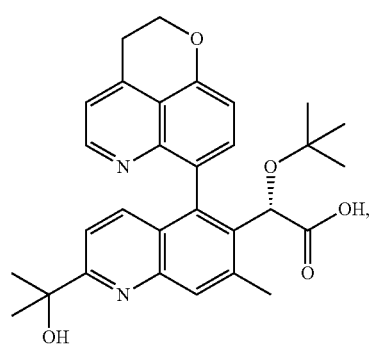
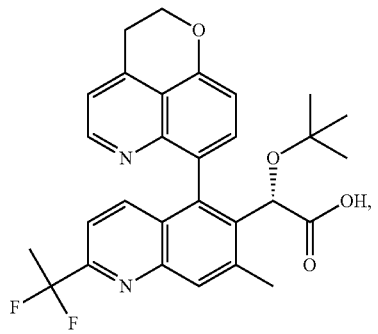

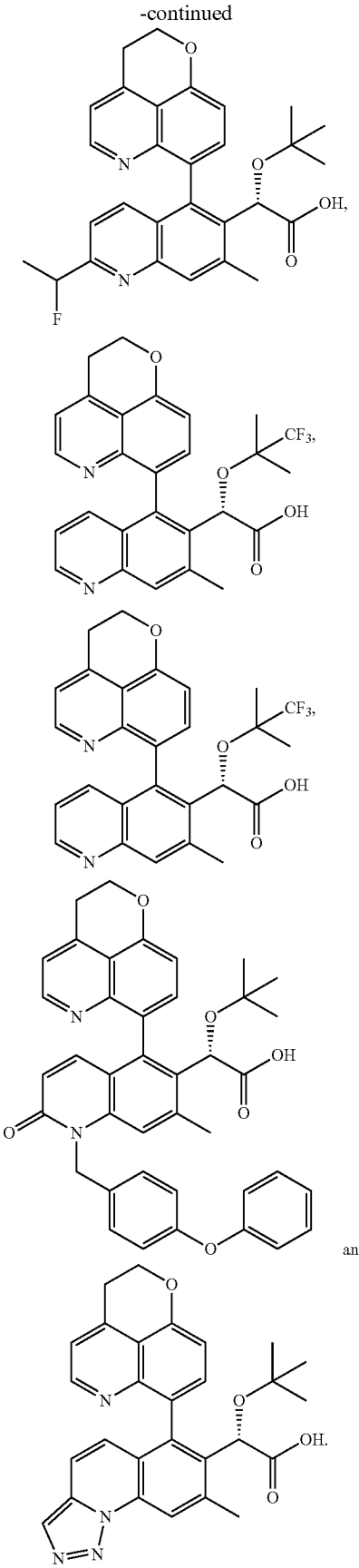
2. The compound of claim 1, or a pharmaceutically acceptable salt thereof, selected from the group consisting of:
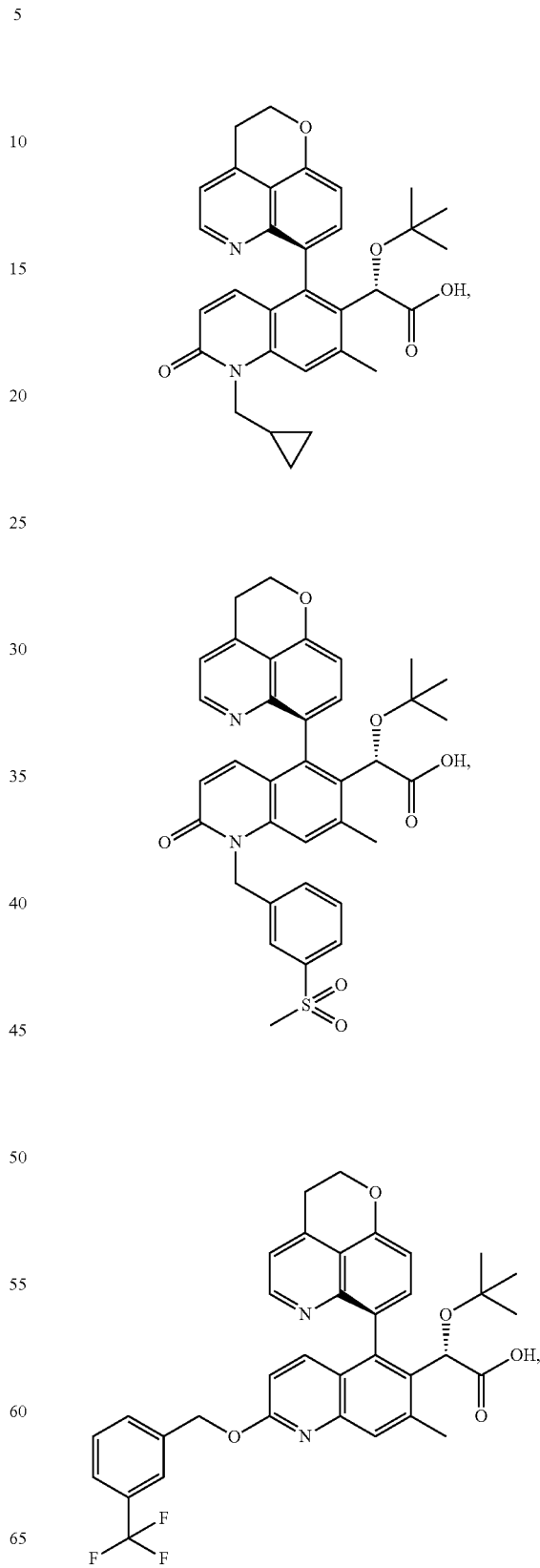

283
-continued
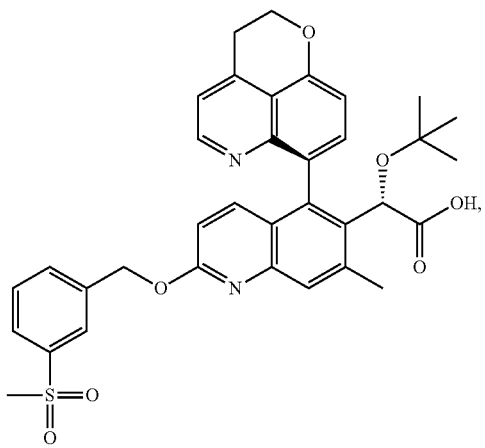
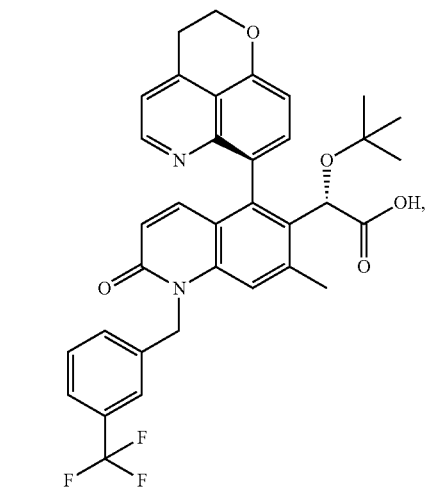
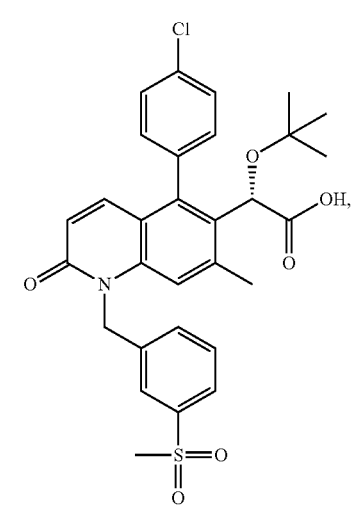
284
-continued
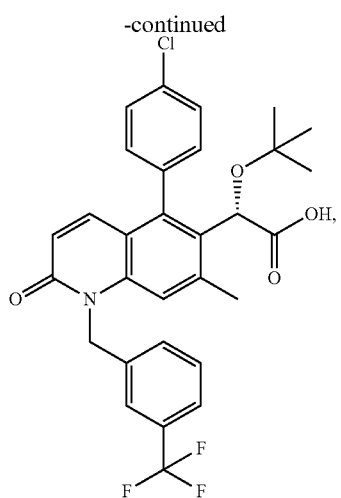
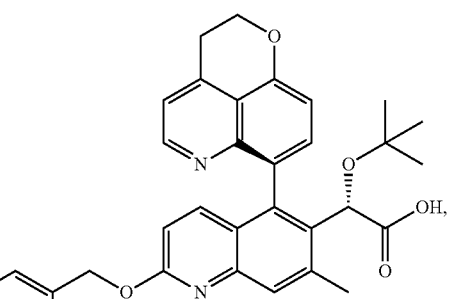
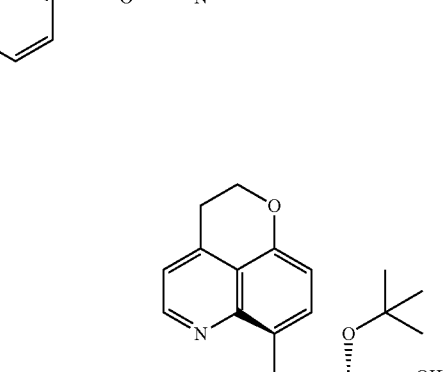
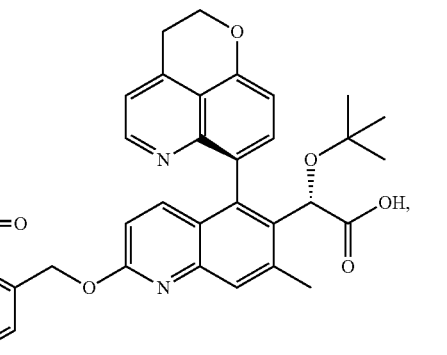

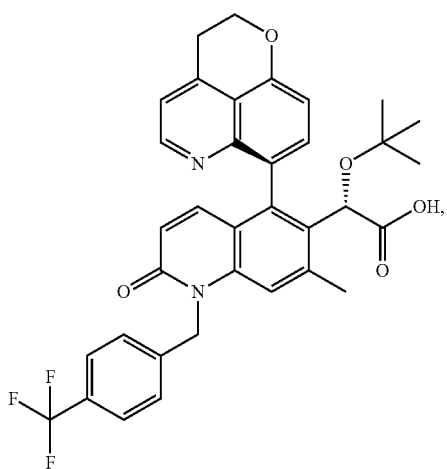
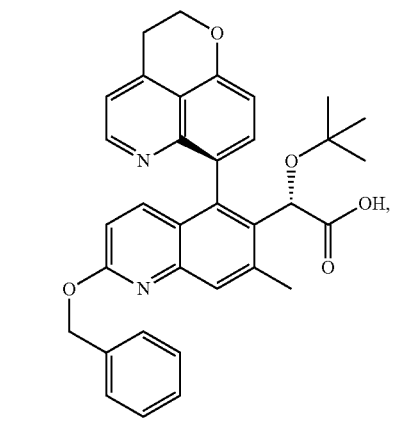
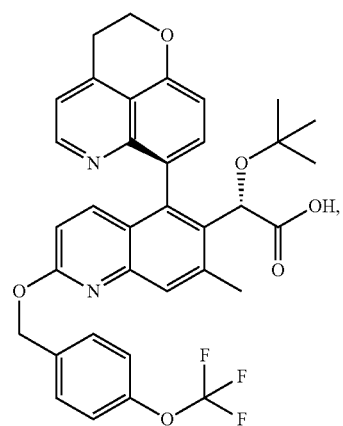
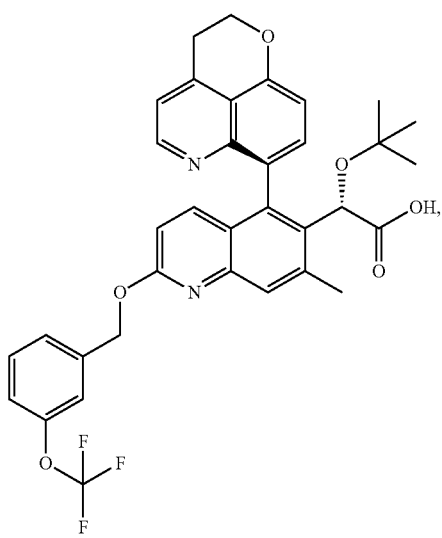
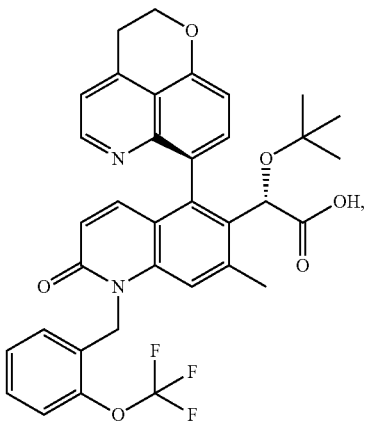
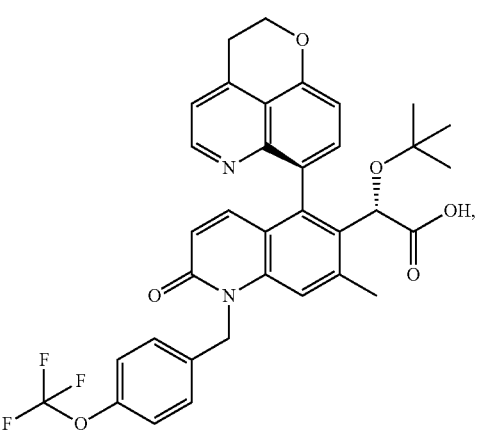

287
-continued
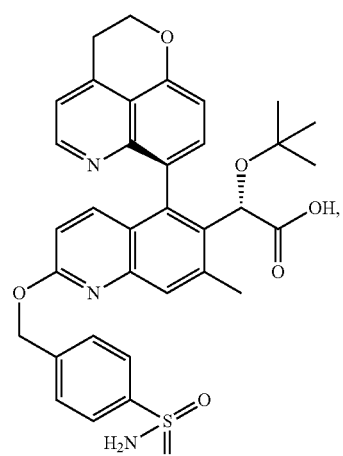
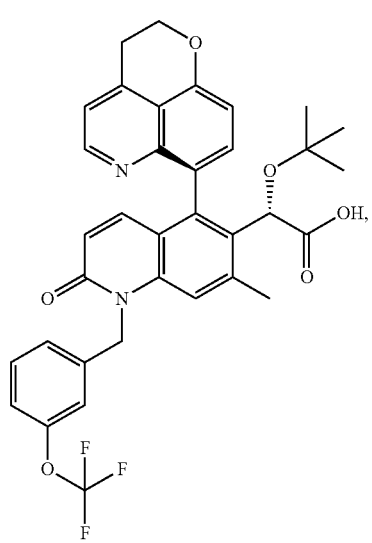
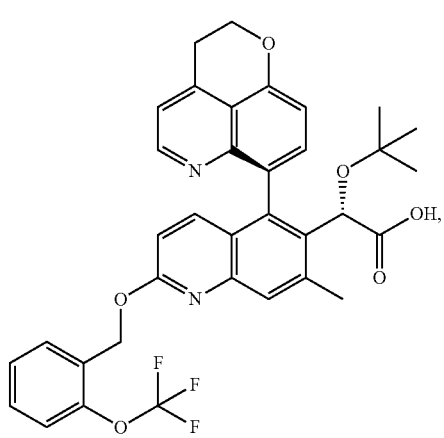
288
-continued
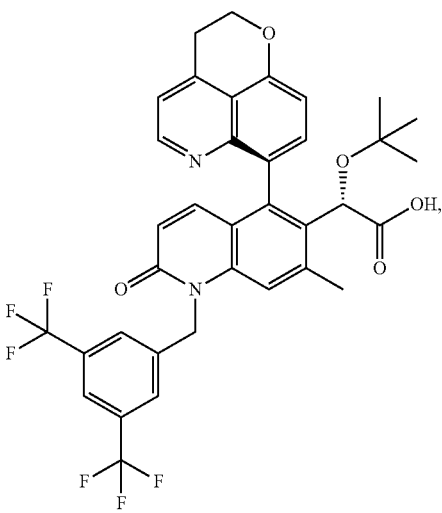
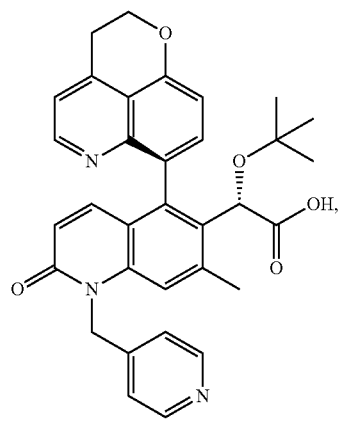
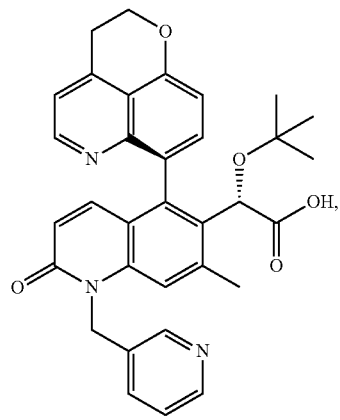

289
-continued
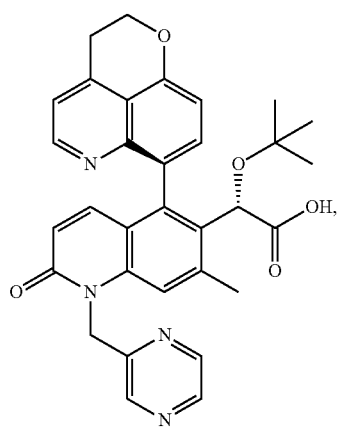
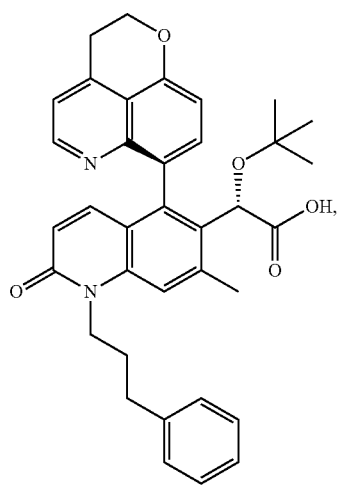
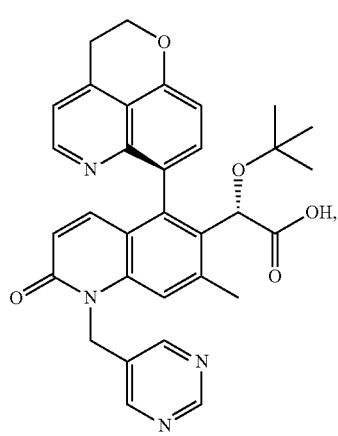
290
-continued
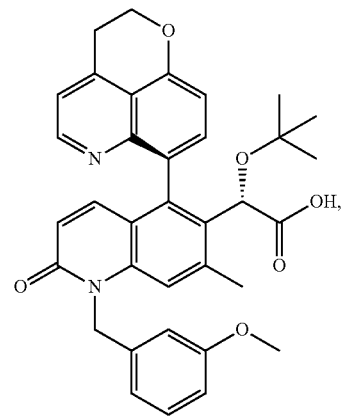
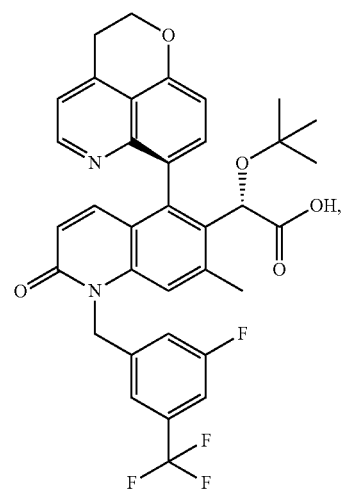
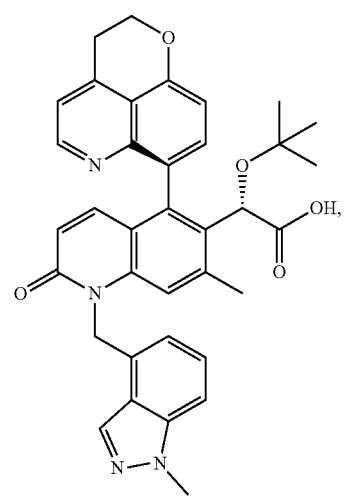

291
-continued
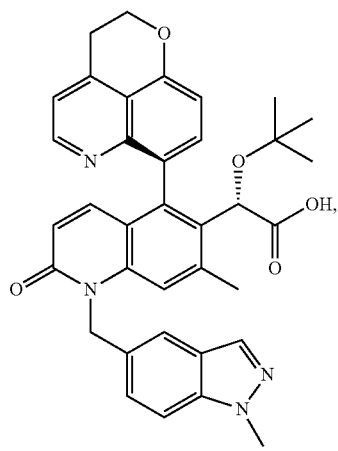
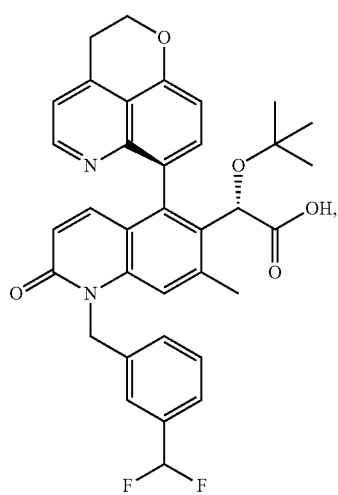
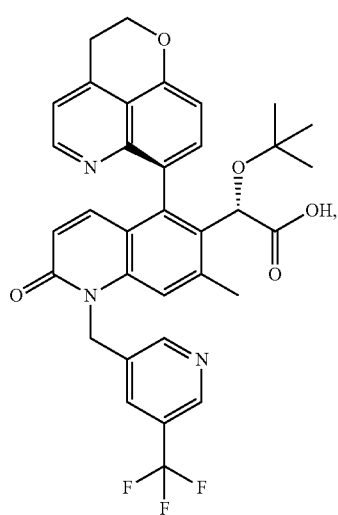
292
-continued
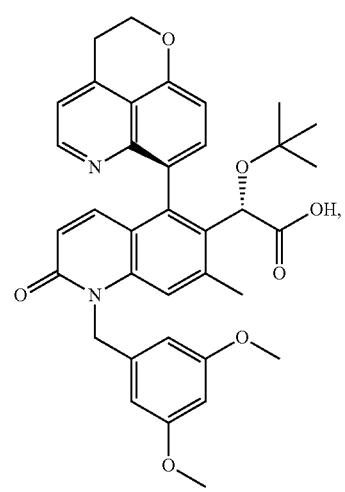
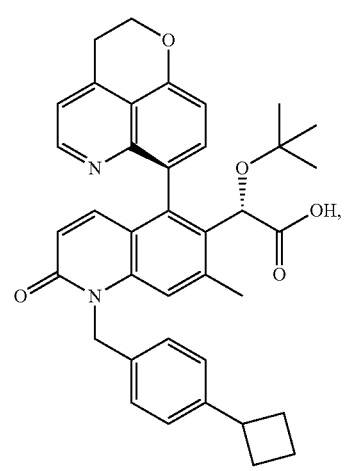
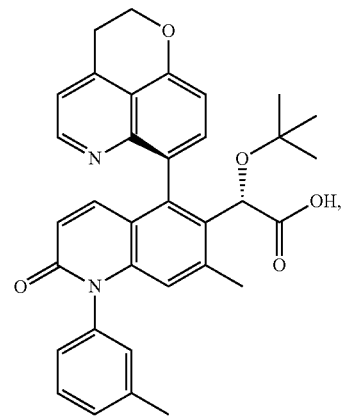

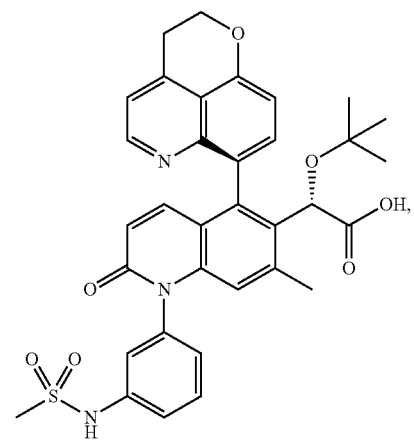
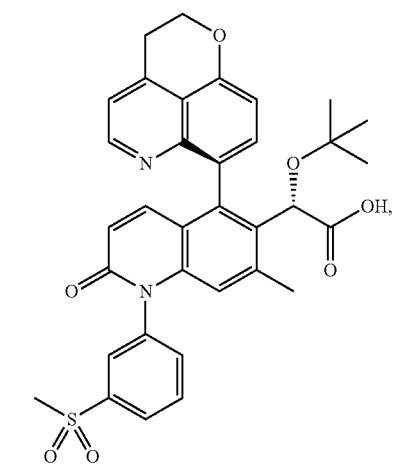
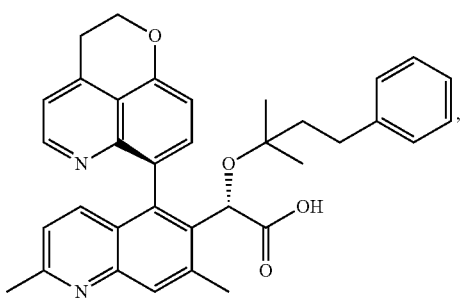
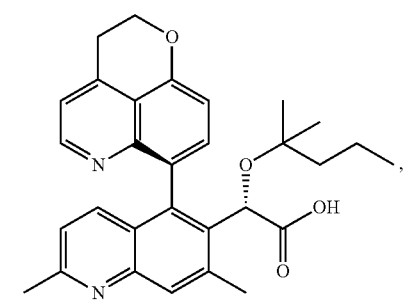
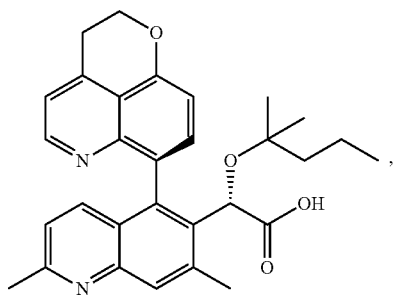
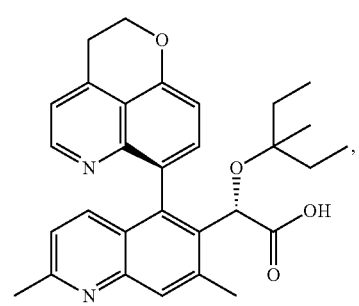
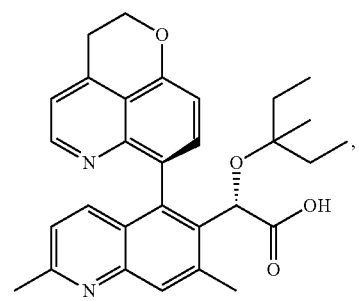
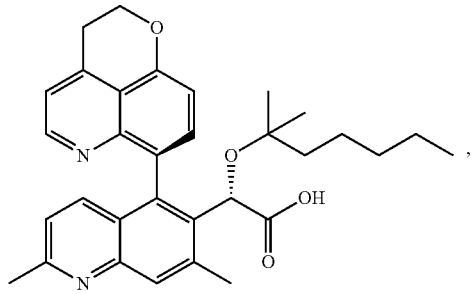
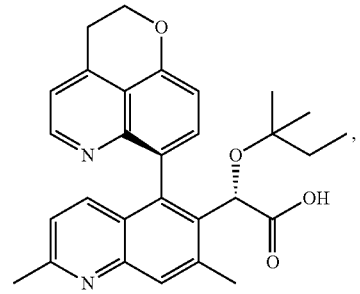

295
-continued
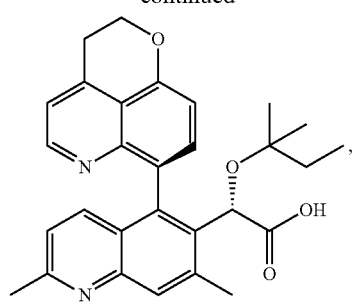
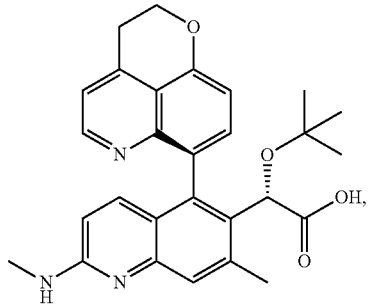
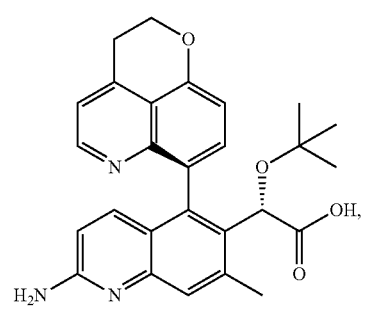
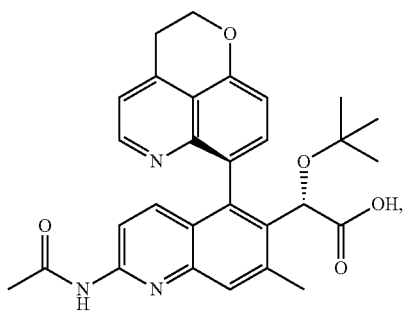
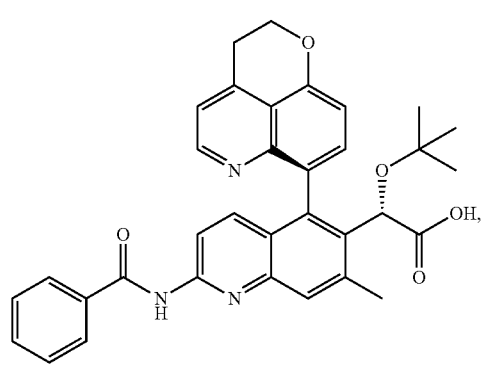
296
-continued
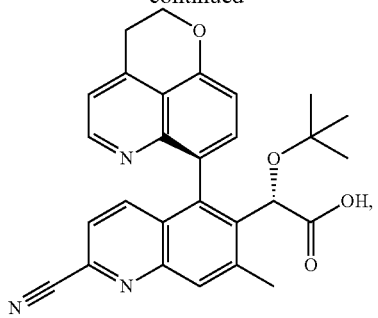
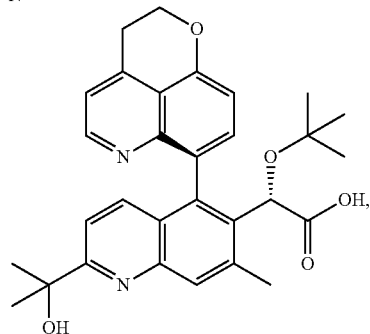
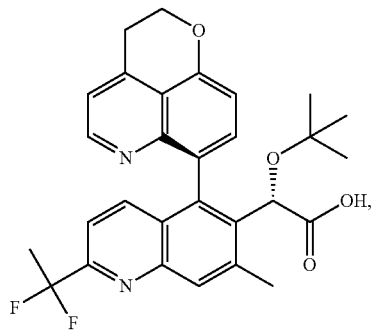
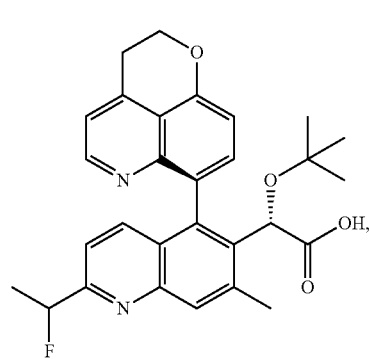
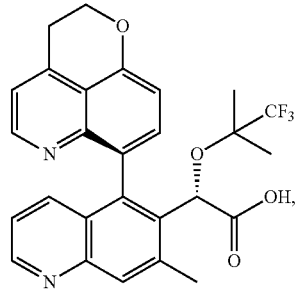

297
-continued
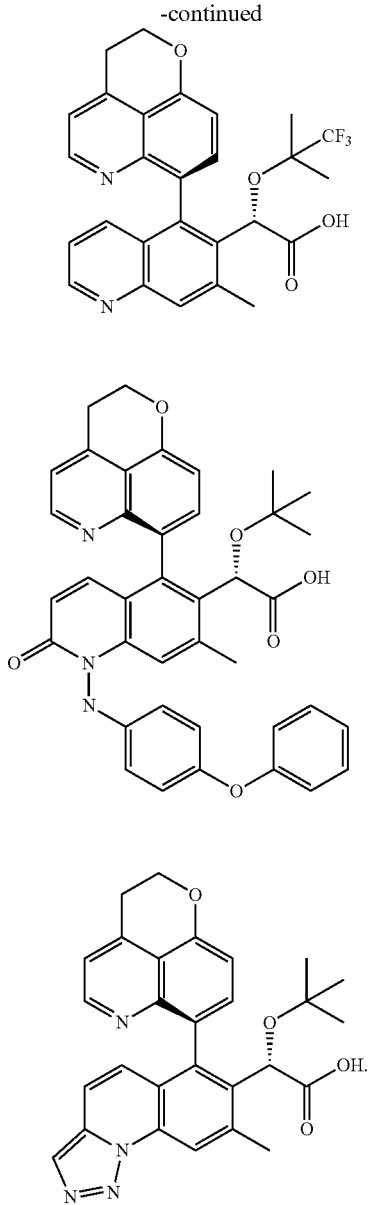
3. The compound of claim 1, or a pharmaceutically acceptable salt thereof, selected from the group consisting of:
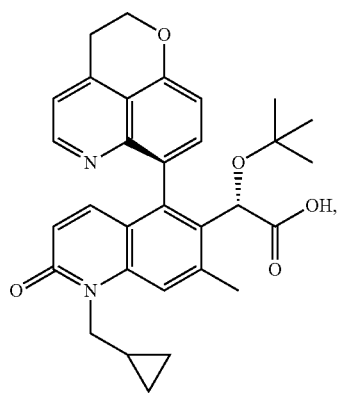
298
-continued
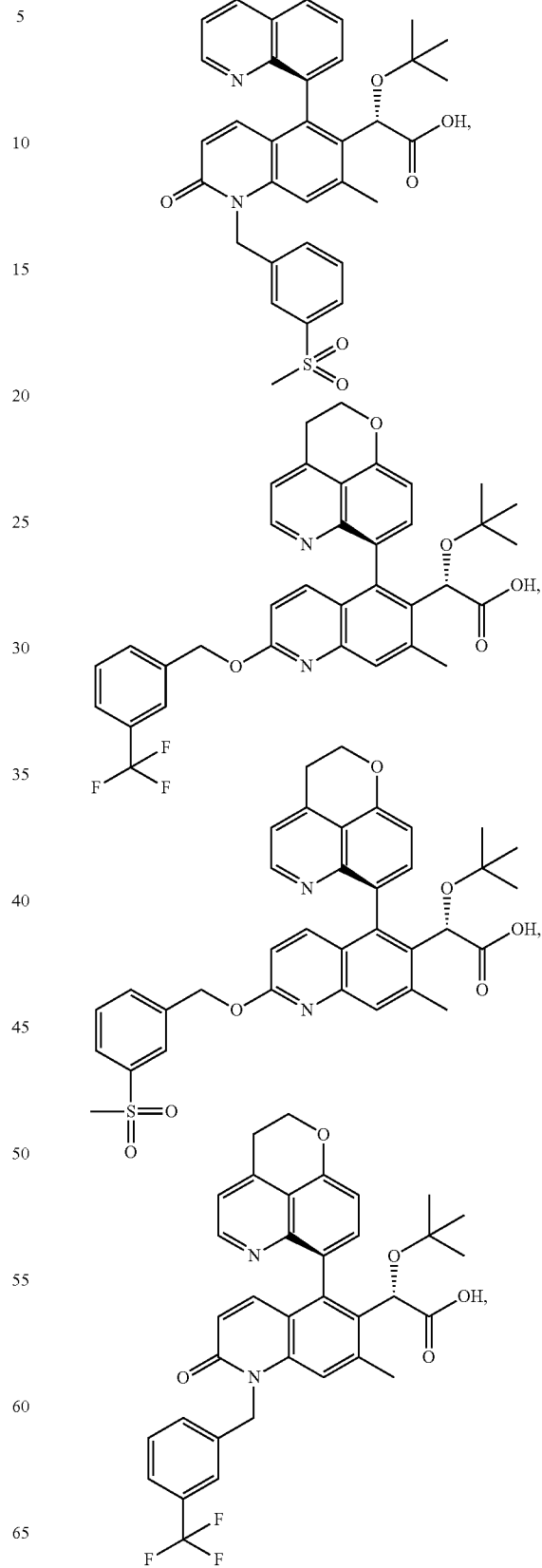
and

299
-continued
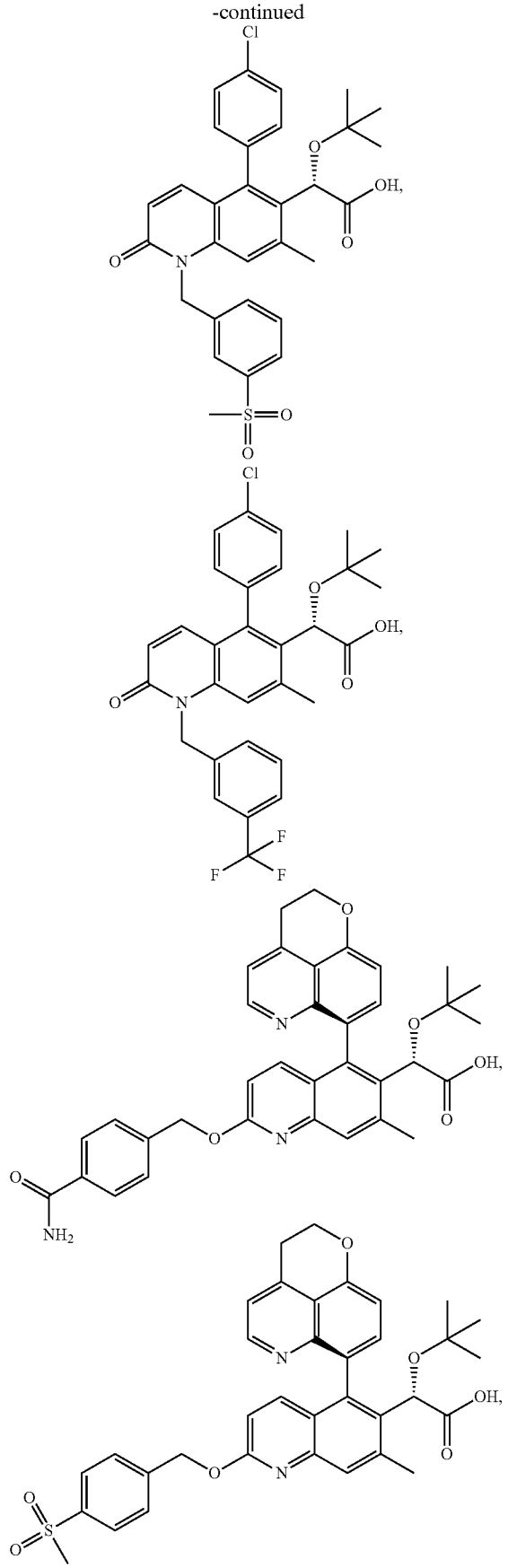
300
-continued
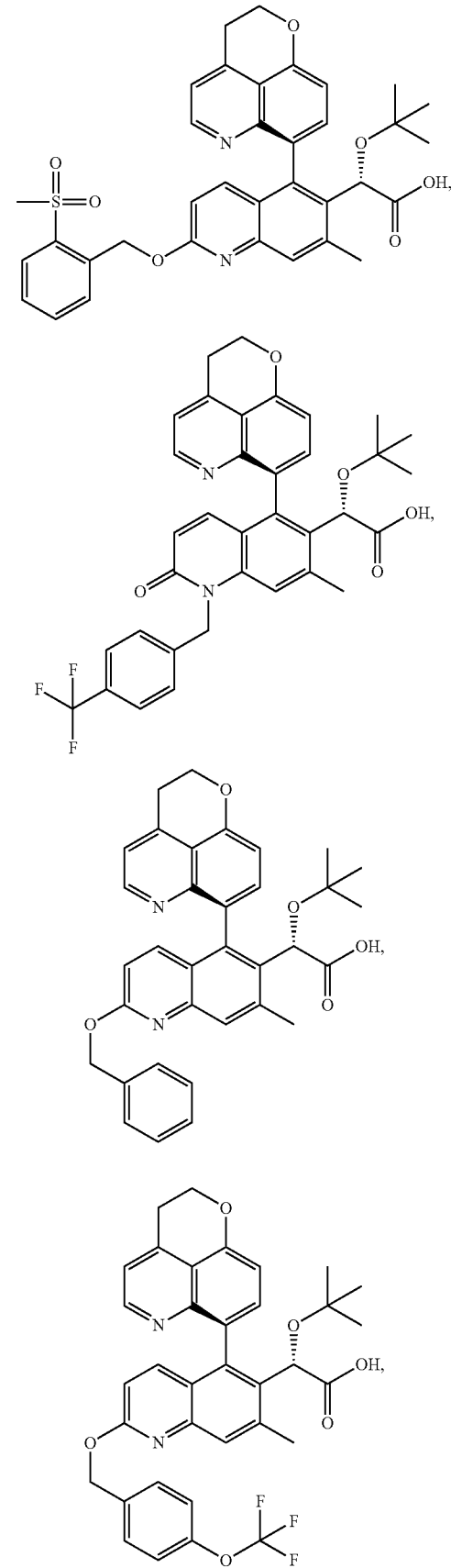

301
-continued
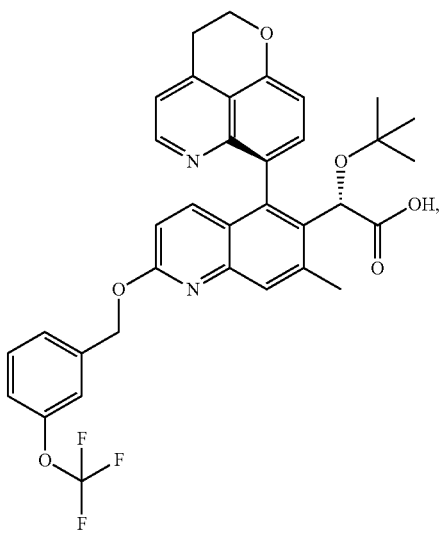
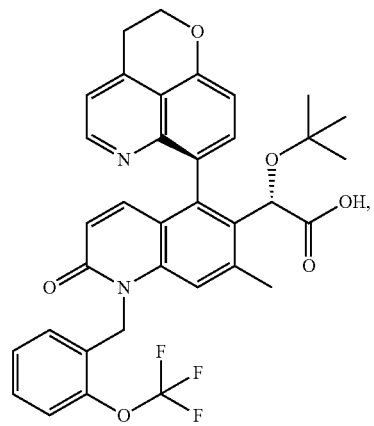
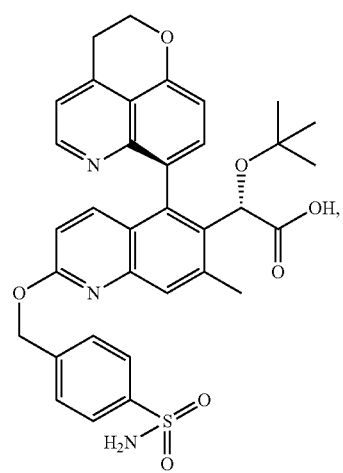
302
-continued
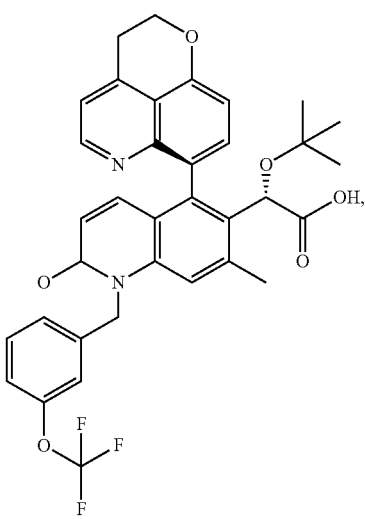
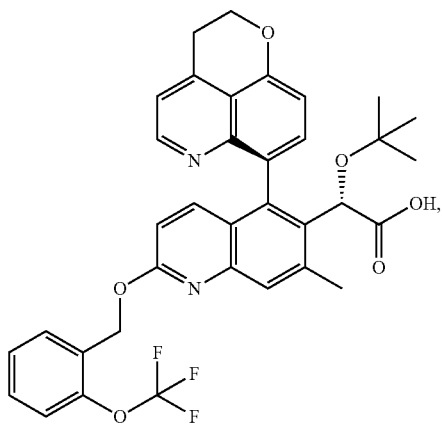
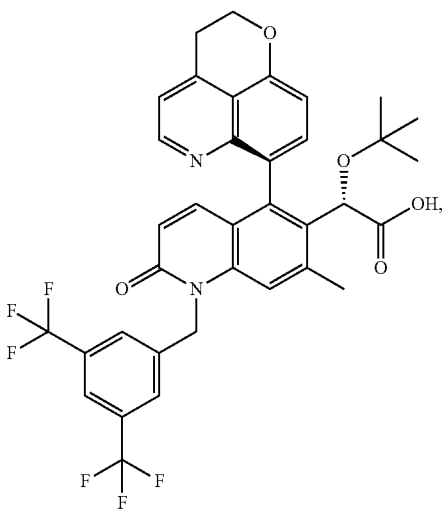

| 303 -continued | 304 -continued |
|---|---|
| 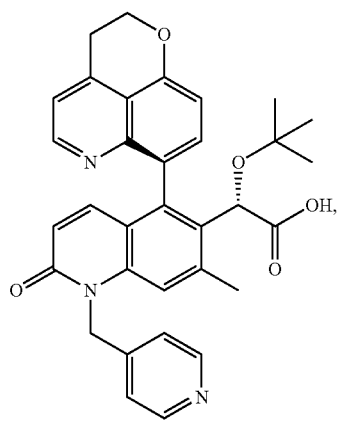 | 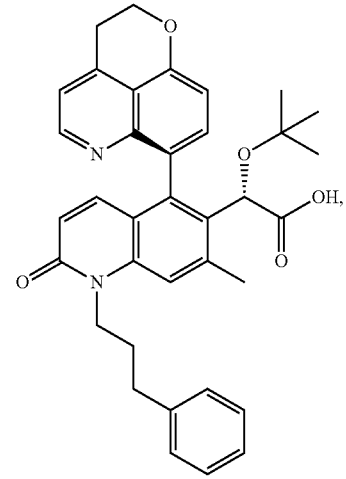 |
| 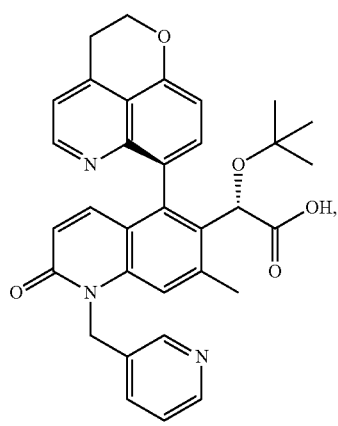 | 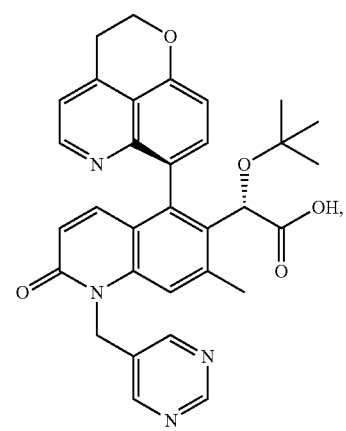 |
| 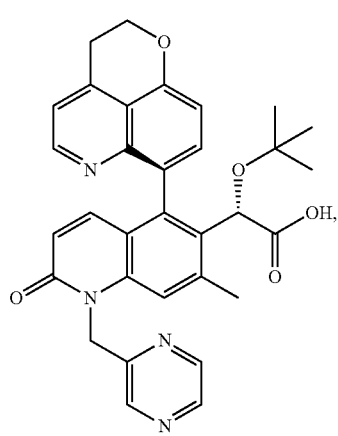 | 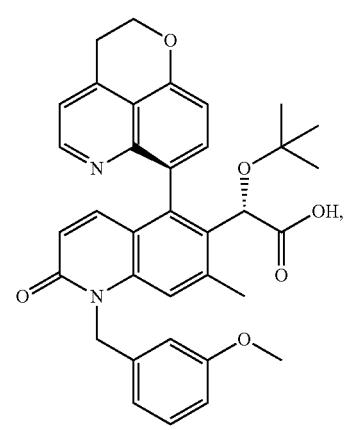 |

305
-continued
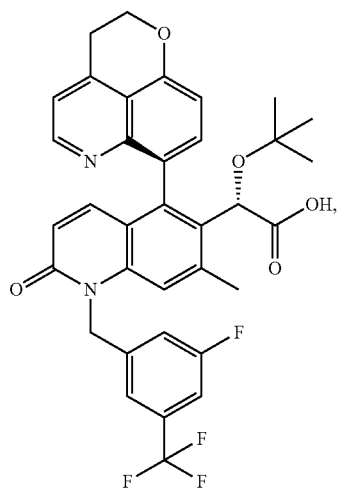
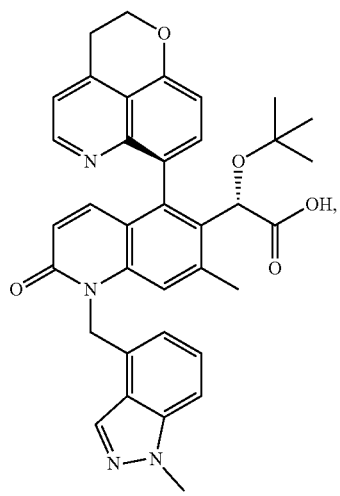
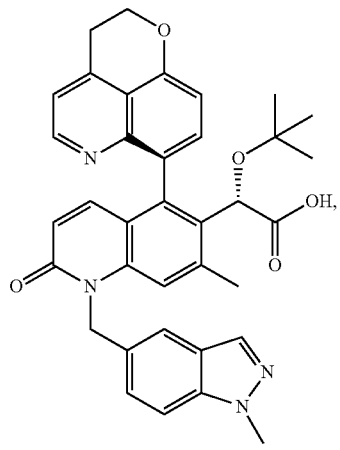
306
-continued
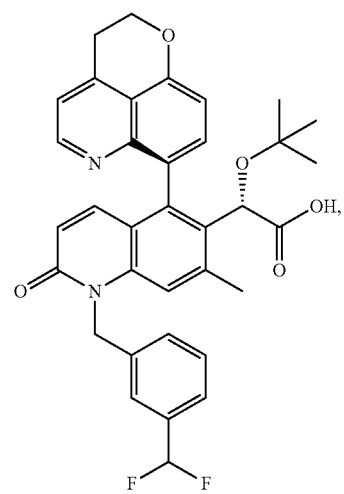
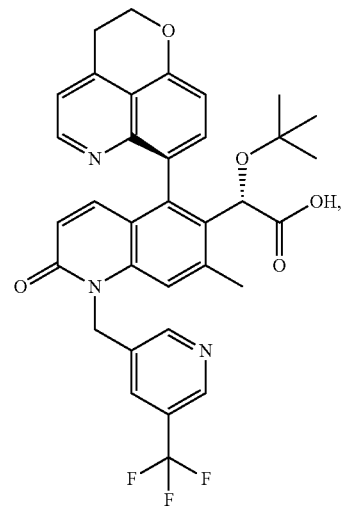
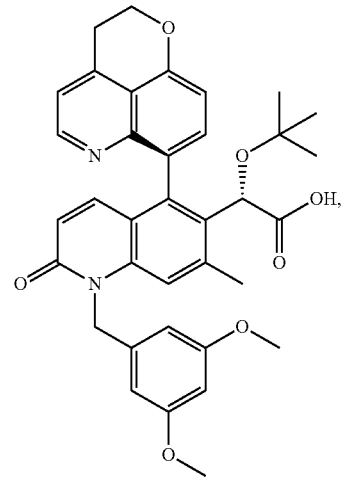

307
-continued
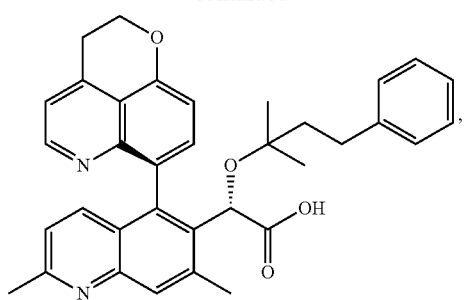
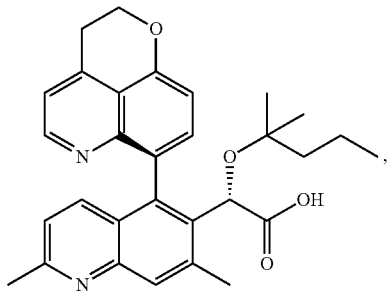
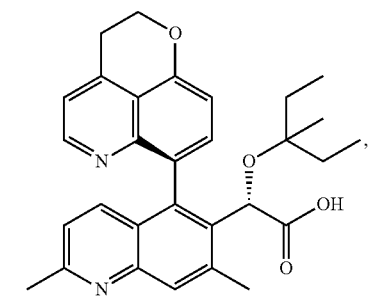
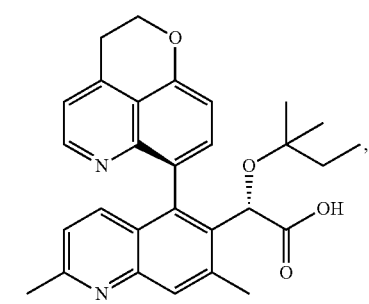
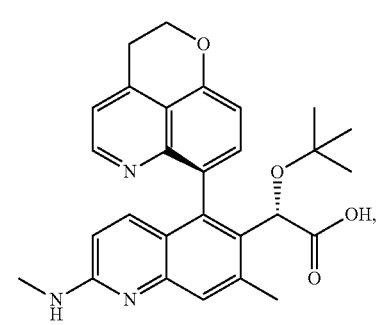
308
-continued
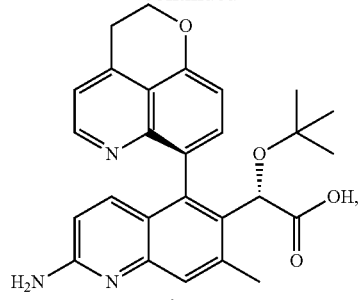
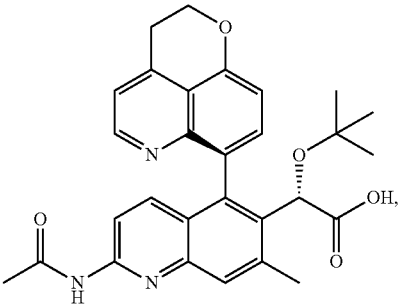
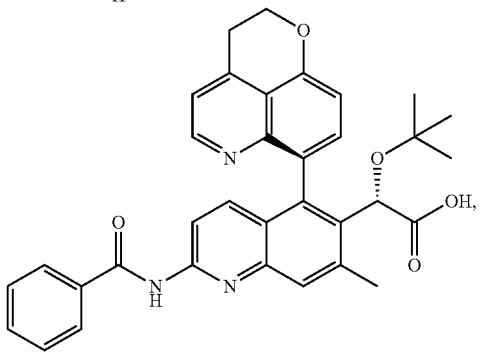
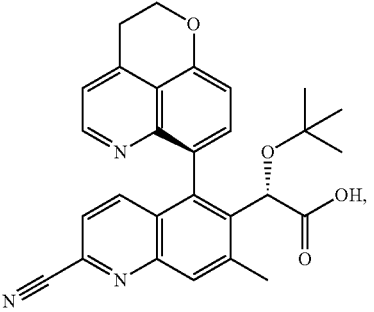
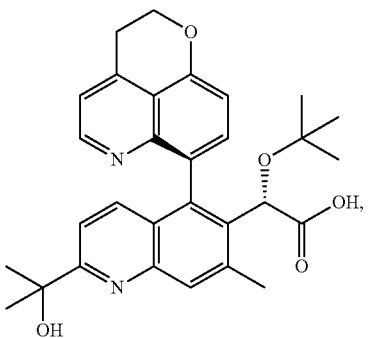

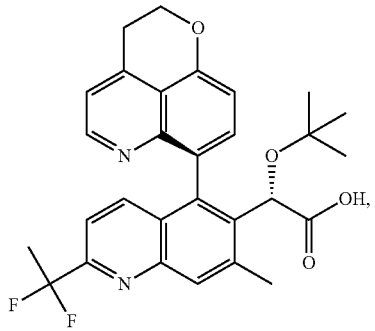
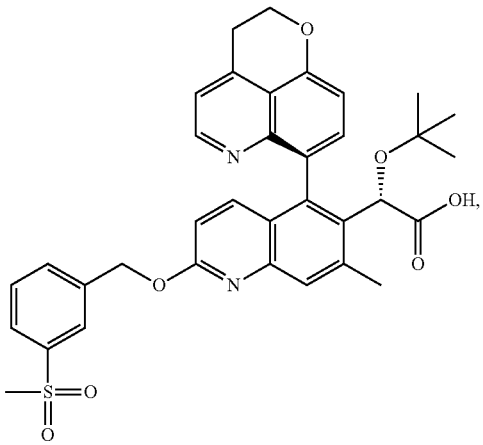
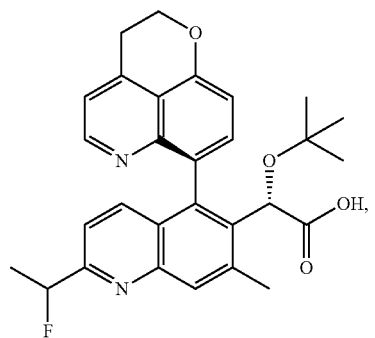
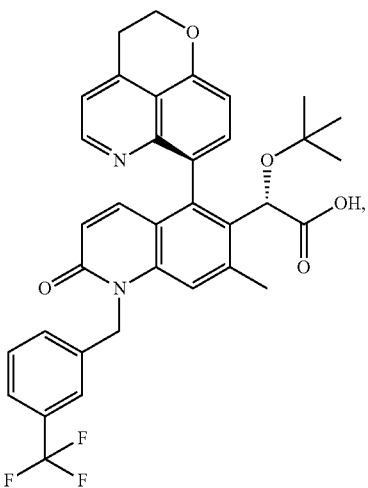
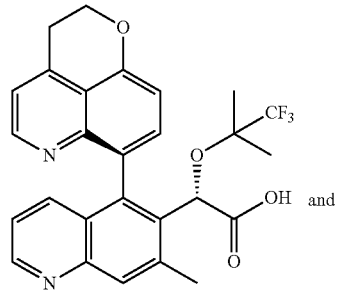
and
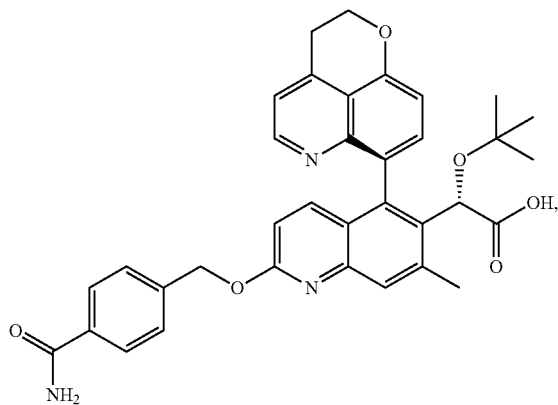
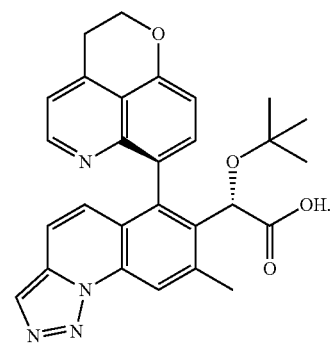
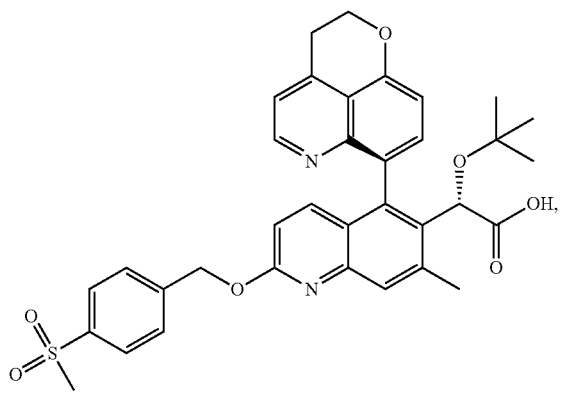
4. The compound of claim 1, or a pharmaceutically acceptable salt thereof, selected from the group consisting of:

| 311 -continued | 312 -continued |
|---|---|
| 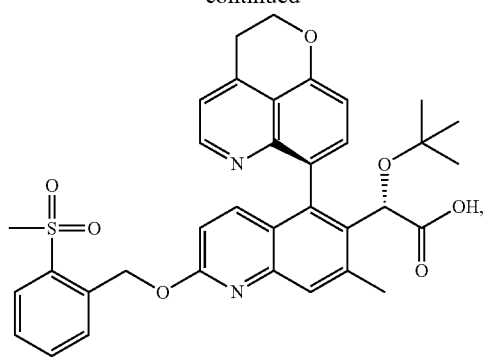 | 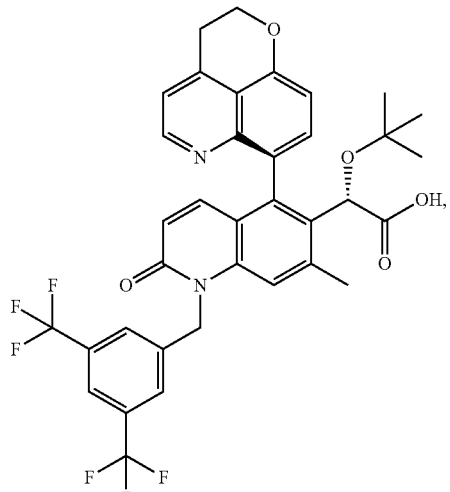 |
| 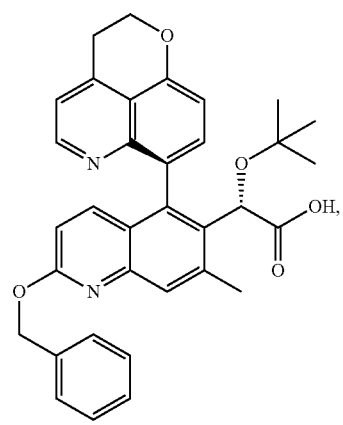 | 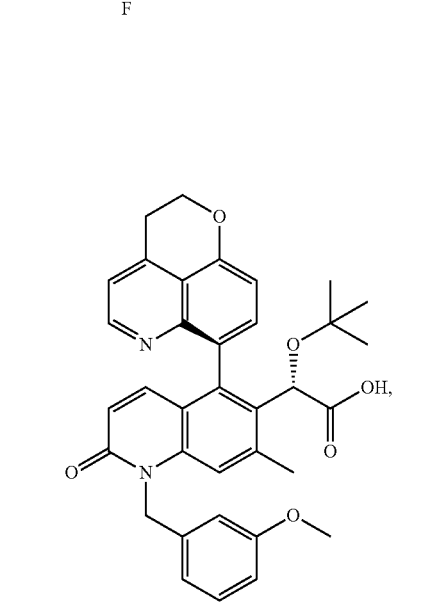 |
| 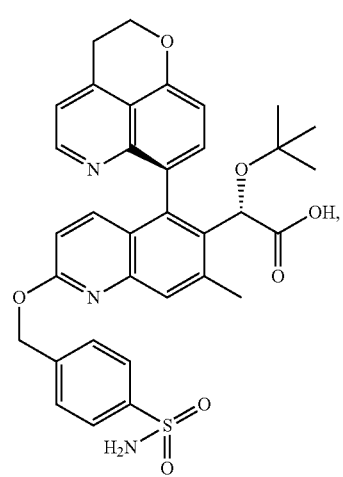 | 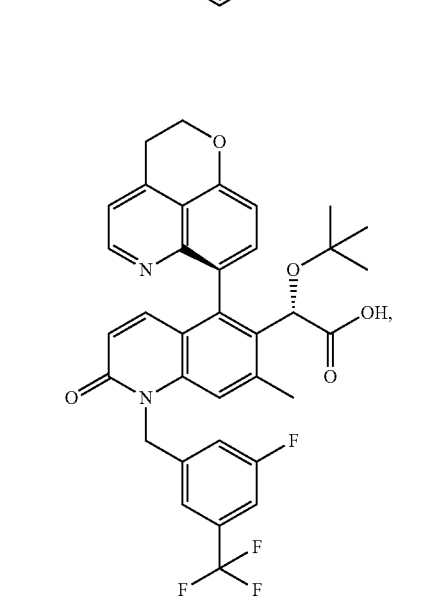 |
| 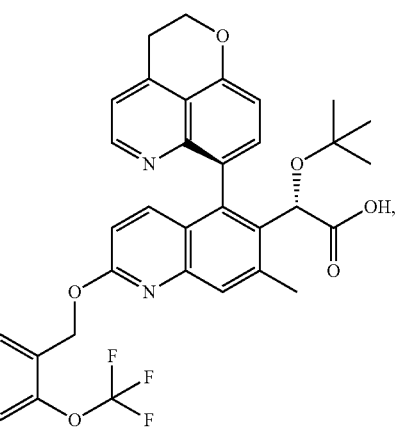 | |

313
-continued
314
-continued
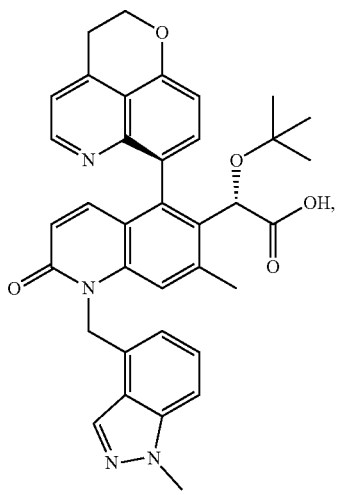
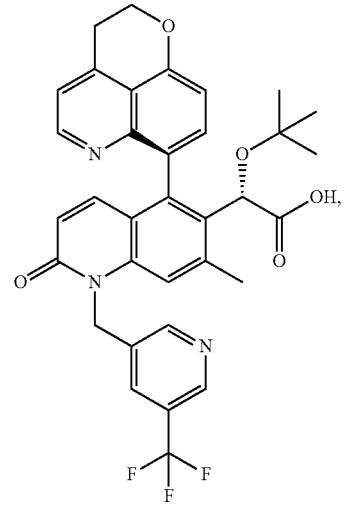
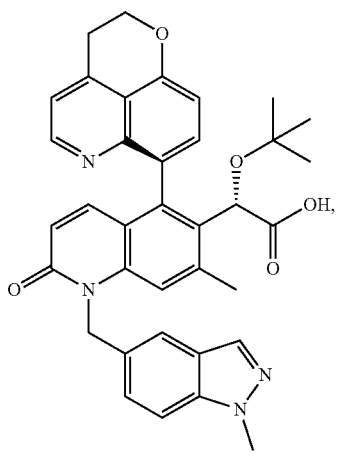
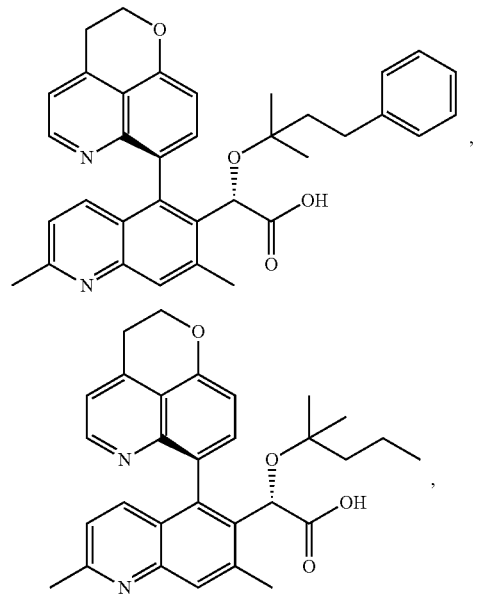
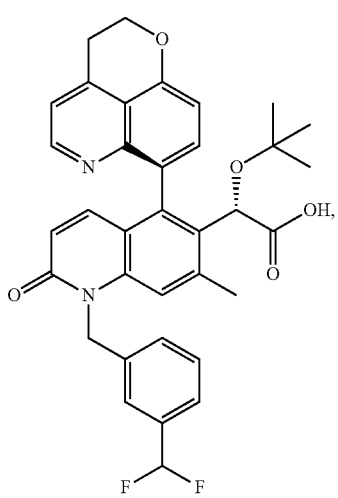
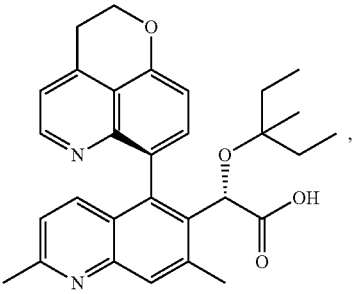
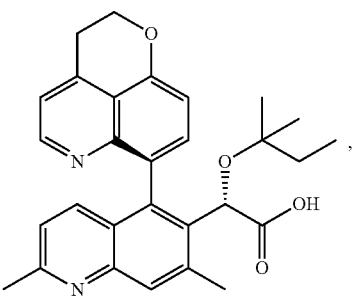

-continued
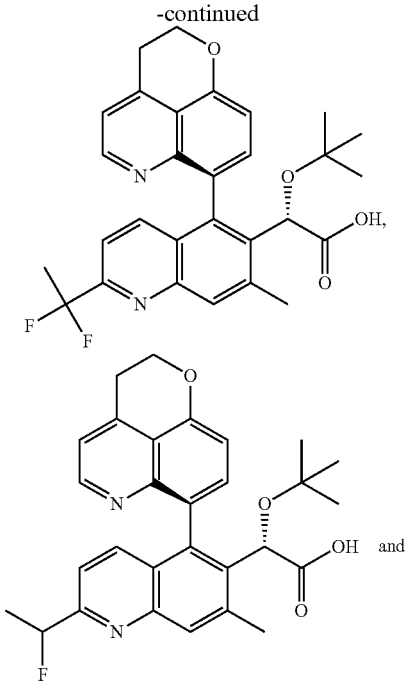
-continued
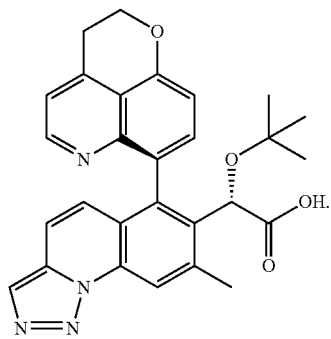
5. A pharmaceutical composition comprising a compound as described in claim 1, or a pharmaceutically acceptable salt thereof, and a pharmaceutically acceptable carrier.
6. A pharmaceutical composition comprising a compound as described in claim 2, or a pharmaceutically acceptable salt thereof, and a pharmaceutically acceptable carrier.
* * * * *